(12) United States Patent
Ogura et al.

(10) Patent No.: US 12,268,672 B2
(45) Date of Patent: Apr. 8, 2025

(54) PPARδ ACTIVATOR

(71) Applicant: JAPAN SCIENCE AND TECHNOLOGY AGENCY, Saitama (JP)

(72) Inventors: Toshihiko Ogura, Sendai (JP); Toshio Hakoshima, Ikoma (JP); Kota Miyasaka, Saitama (JP); Atsushi Kubo, Sendai (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 859 days.

(21) Appl. No.: 17/286,904

(22) PCT Filed: Oct. 23, 2019

(86) PCT No.: PCT/JP2019/041563
§ 371 (c)(1),
(2) Date: Apr. 20, 2021

(87) PCT Pub. No.: WO2020/085393
PCT Pub. Date: Apr. 30, 2020

(65) Prior Publication Data
US 2022/0031666 A1    Feb. 3, 2022

(30) Foreign Application Priority Data
Oct. 23, 2018   (JP) ................. 2018-199523

(51) Int. Cl.
*A61K 31/426*   (2006.01)
*A61K 31/155*   (2006.01)
*A61P 43/00*    (2006.01)

(52) U.S. Cl.
CPC .......... *A61K 31/426* (2013.01); *A61K 31/155* (2013.01); *A61P 43/00* (2018.01)

(58) Field of Classification Search
CPC ...... A61K 31/426; A61K 31/155; A61P 43/00
See application file for complete search history.

(56) References Cited

FOREIGN PATENT DOCUMENTS

| EP | 1500403 A1 | 1/2005 |
|---|---|---|
| JP | 2010-514804 A | 5/2010 |
| JP | 2011-507970 A | 3/2011 |
| WO | 9717333 A1 | 5/1997 |
| WO | 0100603 A1 | 1/2001 |
| WO | 03/090783 A1 | 11/2003 |
| WO | 2006100204 A1 | 9/2006 |
| WO | 2008/083330 A2 | 7/2008 |
| WO | 2009045479 A1 | 4/2009 |
| WO | 2009/086526 A2 | 7/2009 |
| WO | 2009109867 A2 | 9/2009 |
| WO | 2010074588 A2 | 7/2010 |
| WO | 2015122188 A1 | 8/2015 |
| WO | 2016108045 A2 | 7/2016 |
| WO | 2018067860 A1 | 4/2018 |

OTHER PUBLICATIONS

Cheang et al. (Arterioscler Thromb Vasc Biol. 2014; 34(4): Supplementary Information (Year: 2014).*
Jordan et al. (Cell Metab. 2017; 26(1): 243-255). (Year: 2017).*
Wu et al. (PNAS. 2017; 114(13). 2563-2570) (Year: 2017).*
Cheang et al. (Arterioscler Thromb Vasc Biol. 2014; 34(4): 830-836.)). (Year: 2014).*
Of Jordan et al. (Cell Metab. 2017; 26(1): 243-255). (Year: 2017).*
Afzal et al. (Journal for ImmunoTherapy of Cancer. 2018; 6(64): 1-10). (Year: 2018).*
Search Report issued by the European Patent Office for Application No. 19875990.4, Jul. 15, 2022, Europe.
"Unraveling the Effects of PPAR β/δ on Insulin Resistance and Cardiovascular Disease", Manuel Vázquez-Carrera, «Trends in Endocrinology & Metabolism» , vol. 27-5, pp. 1-16.
"CAS: 1003539-44-3, 1252634-96-0", Registry, «STN» , pp. 1.
Wai San Cheang et al., "Metformin Protects Endothelial Function in Diet-Induced Obese Mice by Inhibition of Endoplasmic Reticulum Stress Through 5 Adenosine Monophosphate-Activated Protein Kinase-Peroxisome Proliferator-Activated Receptor δ Pathway", Arterioscler Thromb Vasc Biol, 2014, vol. 34, pp. 830-836.
Zhi Liang Wei et el., "A Short and Efficient Synthesis of the Pharmacological Research Tool GW501516 for the Peroxisome Proliferator-Activated Receptor δ", J. Org. CHem., 9116-9118 vol. 68, pp.
Atsushi Kittaka, Medicinal Science and Medicinal Chemistry 207, p. 142-150.
Satoshi Shuto, Molecular Theory of Organic Medicine, 2nd edition, 2012, p. 218-223.
Edited by C.G.Wermuth, "Latest Medicinal Chemistry vol. 1", Technomic Co., Ltd., Aug. 15, 1998, pp. 235-271, Chapter 13 Transformation of molecules based on equivalent substitution.
Masakatsu Nozaki et al., Medicinal Chemistry, Kagaku Dojin, Jul. 1, 1995, p. 98-99.
Japan Patent Office, "International Search Report for PCT Application No. PCT/JP2019/041563", Japan, Jan. 21, 2020.

(Continued)

*Primary Examiner* — Clinton A Brooks
*Assistant Examiner* — Jerica Katlynn Wilson
(74) *Attorney, Agent, or Firm* — Troutman Pepper Locke LLP; Tim Tingkang Xia, Esq.

(57) ABSTRACT

The present invention provides a PPARδ activator containing a novel PPARδ agonist (peroxisome proliferator-activated receptor δ) as an active ingredient, and an exercise tolerance-improving agent containing the same as an active ingredient. The present invention is a PPARδ activator containing a guanidine derivative or a biguanidine derivative as an active ingredient, wherein the PPARδ activator activates transcriptional activity of PPARδ, and the guanidine derivative and the biguanidine derivative are capable of fitting within a PPARδ ligand binding pocket in a state where a guanidino group or a biguanidino group forms a hydrogen bond with amino acid residues corresponding to each of the 413th histidine, 287th histidine, 253rd threonine and the 437th tyrosine of human PPARδ, among amino acid residues constituting an interior surface of the ligand binding pocket; and is an exercise tolerance-improving agent containing the PPARδ activator as an active ingredient.

6 Claims, 15 Drawing Sheets
Specification includes a Sequence Listing.

(56) References Cited

OTHER PUBLICATIONS

Evans, R. M. et al., "PPARs and the complex journey to obesity", Nature Medicine, Apr. 2004, pp. 355-361, vol. 10, No. 4.

Willson, T. M. et al., "The PPARs: From Orphan Receptors to Drug Discovery", Journal of Medicinal Chemistry, 2000, pp. 527-550, vol. 43, No. 4.

Barish, G. D. et al., "PPARδ: a dagger in the heart of the metabolic syndrome", The Journal of Clinical Investigation, 2006, pp. 590-597, vol. 116, No. 3.

Narkar, V. A. et al., "AMPK and PPARδ Agonists Are Exercise Mimetics", Cell, pp. 405-415, 2008, 134, No. 3.

Palomer, X. et al., "PPARβ/δ attenuates palmitate-induced endoplasmic reticulum stress and induces autophagic markers in human cardiac cells", International Journal of Cardiology, 2014, pp. 110-118, vol. 174.

Iwaisako, K. et al., "Protection from liver fibrosis by a peroxisome proliferator-activated receptor δ agonist", Proceedings of the National Academy of Sciences of the United States of America, 2012, pp. E1369-E1376, vol. 109, No. 21.

Xu, H. E. et al., "Molecular Recognition of Fatty Acids by Peroxisome Proliferator-Activated Receptors", Molecular Cell, 1999, pp. 397-403, vol. 3, No. 3.

Wu, C. C. et al., "Structural basis for specific ligation of the peroxisome proliferator-activated receptor δ", Proceedings of the National Academy of Sciences of the United States of America, 2017, pp. E2563-E2570, vol. 114, No. 13.

Zhou, G. et al., "Role of AMP-activated protein kinase in mechanism of metformin action", The Journal of Clinical Investigation, 2001, pp. 1167-1174, vol. 108, No. 8.

Madiraju, A. K. et al., "Metformin suppresses gluconeogenesis by inhibiting mitochondrial glycerophosphate dehydrogenase", Nature, 2014, pp. 542-546, vol. 510, No. 7506.

Eikawa, S. et al., "Immune-mediated antitumor effect by type 2 diabetes drug, metformin", Proceedings of the National Academy of Sciences of the United States of America, 2015, pp. 1809-1814, vol. 112, No. 6, pp. 1809-1814.

Sugden, M. C. et al., "PPARs and the orchestration of metabolic fuel selectrion", Pharmacological Research, 2009, pp. 141-150, vol. 60.

Vaillancourt, V. A. et al., "Synthesis and biological activity of aminoguanidine and diaminoguanidine analogues of the antidiabetic/antiobesity agent 3-guanidinopropionic acid", J. Med. Chem. 2001, pp. 1231-1248, vol. 44, No. 8.

Takamura, T. et al., "Transgenic mice overexpressing type 2 nitric oxide synthase in pancreatic β cells develop insulin-dependent diabetes without insulitis", J Biol Chem, 1998, pp. 2493-2496, vol. 273, No. 5.

Miyasaka, K. et al., "Mechanomedicine Exercise pill, Potentialities of exercise pill and exercise mimetics", Journal of Clinical and experimental medicine, 2016, pp. 1051-1057, vol. 257, No. 10.

Office Action issued by the State Intellectual Property Office of the Peoples Republic of China for Application No. 201980069412.1, Nov. 6, 2023, China.

Office Action issued by the European Patent Office for Application No. 19875990.4, Dec. 4, 2023.

XP055390154 (Glennon, R.A. et al., "Arylguandine and Arylbiguanide Binding at 5-HT3 Serotonin Receptors: A QSAR Study", Bioorganic & Medicinal Chemistry, vol. 11, No. 20 (2003), p. 4449-4454).

XP093105427 (Stephenson, K. et al., "Developing Inhibitors to Selectively Target Two-Component and Phosphorelay Signal Transduction Systems of Pathogenic Microorganisms" Current medicinal chemistry, vol. 11, No. 6 (2004), p. 765-773).

K Learsi et al., "Metformin improves performance in high-intensity exercise, but not anaerobic capacity in healthy male subjects", «Clin Exp Pharmacol Physiol» , vol. 42, No. 10, pp. 1025-1029, Aug. 7, 2015.

* cited by examiner

FIG. 1

Amino acid residues constituting hPPARδ ligand binding pocket

MEQPQEEAPEVREEEEKEEVAEAEGAPELNGGPQHALPSSSYTDLSRSSSPPSLLDQLQM

GCDGASCGSLNMECRVCGDKASGFHYGVHACEGCKGFFRRTIRMKLEYEKCERSCKIQKK
                                        └─ Ligand binding domain NRNKCQYCRFQKCLALGMSHNAIRFGRMPEAEKRKLVAGLTANEGSQYNPQVADLKAFSK
                                                      ─────────
                                                        Helix1

HIYNAYLKNFNMTKKKARSILTGKASHTAPFVIHDIETLWQAEKGLVWKQLVNGLPPYKE
─────────                                 ───────────
  Helix2                                      Helix3

ISVHVFYRCQCTTVETVRELTEFAKSIPSFSSLFLNDQVTLLKYGVHEAIFAMLASIVNK
─────────────────── ──────                        ───────────
      Helix4          Helix5                         Helix6

DGLLVANGSGFVTREFLRSLRKPFSDIIEPKFEFAVKFNALELDDSDLALFIAAIILGGD
              ──────                                ─────────
               Helix7                                 Helix8

RPGLMNVPRVEAIQDTILRALEFHLQANHPDAQYLFPKLLQKMADLRQLVTEHAQMMQRI
─────────                                          ─────────
  Helix9                                              Helix11

KKTETETSLHPLLQEIYKDMY
─────────────
   Helix12

• Amino acid residue constituting interior surface of ligand binding domain
☐ Amino acid residue forming hydrogen bonding with metformin guanidine group

FIG. 5

Protein sequence coverage: 26%

```
  1  MEQPQEEAPE VREEEEKEEV AEAEGAPELN GGPQHALPSS SYTAIRFGRM
 51  PEAEKRKLVA GLTANEGSQY NPQVADLKAF SKHIYNAYLK NFNMTKKKAR
101  SILTGKASHT APFVIHDIET LWQAEKGLVW KQLVNGLPPY KEISVHVFYR
151  CQCTTVETVR ELTEFAKSIP SFSSLFLNDQ VTLLKYGVHE AIFAMLASIV
201  NKDGLLVANG SGFVTREFLR SLRKPFSDII EPKFEFAVKF NALELDDSDL
251  ALFIAAIILC GDRPGLMNVP RVEAIQDTIL RALEFHLQAN HPDAQYLFPK
301  LLQKMADLRQ LVTEHAQMMQ RIKKTETETS LHPLLQEIYK DMY
```

[underlined] : Amino acid sequence identified by TOF-MF n=3
*p<0.05

SEQUENCE LISTING

```
<160> NUMBER OF SEQ ID NOS: 1

<210> SEQ ID NO 1
<211> LENGTH: 441
<212> TYPE: PRT
<213> ORGANISM: Homo sapiens
<220> FEATURE:
<223> OTHER INFORMATION: PPARdelta

<400> SEQUENCE: 1

Met Glu Gln Pro Gln Glu Glu Ala Pro Glu Val Arg Glu Glu Glu Glu
1               5                   10                  15

Lys Glu Glu Val Ala Glu Ala Glu Gly Ala Pro Glu Leu Asn Gly Gly
            20                  25                  30

Pro Gln His Ala Leu Pro Ser Ser Ser Tyr Thr Asp Leu Ser Arg Ser
        35                  40                  45
```

-continued

```
Ser Ser Pro Pro Ser Leu Leu Asp Gln Leu Gln Met Gly Cys Asp Gly
     50                  55                  60
Ala Ser Cys Gly Ser Leu Asn Met Glu Cys Arg Val Cys Gly Asp Lys
 65                  70                  75                  80
Ala Ser Gly Phe His Tyr Gly Val His Ala Cys Glu Gly Cys Lys Gly
                 85                  90                  95
Phe Phe Arg Arg Thr Ile Arg Met Lys Leu Glu Tyr Glu Lys Cys Glu
            100                 105                 110
Arg Ser Cys Lys Ile Gln Lys Lys Asn Arg Asn Lys Cys Gln Tyr Cys
        115                 120                 125
Arg Phe Gln Lys Cys Leu Ala Leu Gly Met Ser His Asn Ala Ile Arg
130                 135                 140
Phe Gly Arg Met Pro Glu Ala Glu Lys Arg Lys Leu Val Ala Gly Leu
145                 150                 155                 160
Thr Ala Asn Glu Gly Ser Gln Tyr Asn Pro Gln Val Ala Asp Leu Lys
                165                 170                 175
Ala Phe Ser Lys His Ile Tyr Asn Ala Tyr Leu Lys Asn Phe Asn Met
            180                 185                 190
Thr Lys Lys Lys Ala Arg Ser Ile Leu Thr Gly Lys Ala Ser His Thr
        195                 200                 205
Ala Pro Phe Val Ile His Asp Ile Glu Thr Leu Trp Gln Ala Glu Lys
210                 215                 220
Gly Leu Val Trp Lys Gln Leu Val Asn Gly Leu Pro Pro Tyr Lys Glu
225                 230                 235                 240
Ile Ser Val His Val Phe Tyr Arg Cys Gln Cys Thr Thr Val Glu Thr
                245                 250                 255
Val Arg Glu Leu Thr Glu Phe Ala Lys Ser Ile Pro Ser Phe Ser Ser
            260                 265                 270
Leu Phe Leu Asn Asp Gln Val Thr Leu Leu Lys Tyr Gly Val His Glu
        275                 280                 285
Ala Ile Phe Ala Met Leu Ala Ser Ile Val Asn Lys Asp Gly Leu Leu
290                 295                 300
Val Ala Asn Gly Ser Gly Phe Val Thr Arg Glu Phe Leu Arg Ser Leu
305                 310                 315                 320
Arg Lys Pro Phe Ser Asp Ile Ile Glu Pro Lys Phe Glu Phe Ala Val
                325                 330                 335
Lys Phe Asn Ala Leu Glu Leu Asp Asp Ser Asp Leu Ala Leu Phe Ile
            340                 345                 350
Ala Ala Ile Ile Leu Cys Gly Asp Arg Pro Gly Leu Met Asn Val Pro
        355                 360                 365
Arg Val Glu Ala Ile Gln Asp Thr Ile Leu Arg Ala Leu Glu Phe His
370                 375                 380
Leu Gln Ala Asn His Pro Asp Ala Gln Tyr Leu Phe Pro Lys Leu Leu
385                 390                 395                 400
Gln Lys Met Ala Asp Leu Arg Gln Leu Val Thr Glu His Ala Gln Met
                405                 410                 415
Met Gln Arg Ile Lys Lys Thr Glu Thr Glu Thr Ser Leu His Pro Leu
            420                 425                 430
Leu Gln Glu Ile Tyr Lys Asp Met Tyr
        435                 440
```

PPARδ ACTIVATOR

CROSS-REFERENCE TO RELATED PATENT APPLICATION

This application claims priority to Japanese Patent Application No. 2018-199523 filed in Japan on Oct. 23, 2018, the content of which is incorporated herein by reference.

FIELD OF THE INVENTION

The present invention relates to a peroxisome proliferator-activated receptor δ (PPARδ) activator.

BACKGROUND OF THE INVENTION

PPAR is a member of the nuclear hormone receptor superfamily, and is a ligand-activated transcriptional factor. In mammals, PPAR has family members of α, γ and δ. PPARα binds free fatty acids as its endogenous ligands and regulates the expression of various genes regulating lipolysis and is therefore regarded as a target of drug for treatment of hyperlipidemia. PPARγ binds long-chain fatty acids, eicosanoids and their related chemicals like as its endogenous ligands to promote adipocyte differentiation, and is therefore regarded as a target substance for thiazolidine, which is an insulin resistance-improving medicine. PPARδ is widely expressed in various tissues, but the endogenous ligands and its physiological functions have been remained largely unknown, therefore PPARδ can be classified an orphan receptor (see, for example, PTL 1). PPARδ is composed of an N-terminal domain with ligand-independent transcriptional activation ability, a zinc finger domain with a DNA binding ability, and a ligand binding domain (LBD) having a ligand-dependent transcriptional activation ability. The amino acid sequence of LBD of PPARδ has 70% homology (sequence identity) with LBD of PPARα and 68% homology (sequence identity) with LBD of PPARγ (see, for example, NPL 2).

In recent years, PPARδ has been reported to be an important transcriptional regulator of lipid catabolism, transport, accumulation, etc. (see, for example, NPL 3), attracting keen attention as a new molecular target of therapeutic agents for metabolic disorders and the like. For example, it has been reported that ingestion of a PPARδ agonist enhances an exercise-induced effect such as exercise endurance, and that the PPARδ agonist serves as an exercise performance-enhancing medicine (see, for example, PTL 1 and NPL 4). Further, by using the AMPK (5'AMP-activated protein kinase) agonist and the PPARδ agonist in combination, the exercise effect on the subject is further improved (see, for example, PTL 2 and NPL 4). In addition, it has been reported that administration of PPARδ agonist suppresses lipid-induced endoplasmic reticulum (ER) stress, which plays an important role in the development of cardiomyopathy (see, for example, NPL 5), and that a hepatic protective effect and an antifibrotic effect can be obtained in hepatic fibrosis induced by carbon tetrachloride administration (see, for example, NPL 6).

Examples of the PPARδ agonists include a phenoxyacetic acid derivative represented by GW501516 (CAS No.: 317318-70-0). The basic skeleton of the phenoxyacetic acid derivative is a chemical structure, in which a long-chain hydrophobic group such as a non-polar hydrocarbon is bonded to a carboxyl group (—COOH). From the results of structural analysis of a complex of PPARδ and a phenoxyacetic acid derivative that acts as a PPARδ agonist, it has been found that the ligand-binding pocket of PPARδ is a Y-shaped pocket consisting of three tunnel-shaped cavities called arms I, II and III (arm I, arm II and arm III) (see, for example, NPL 7 and NPL 8). As the PPARδ agonist, a medicine having a skeleton in which a hydrophobic group is branched, such as GW2331 (CAS No.: 190844-95-2), has also been developed.

On the other hand, metformin is a biguanide-based medicine widely used as an oral antidiabetic medicine. It is known that metformin enhances sugar uptake in skeletal muscle and fatty acid β-oxidation in the liver by activating AMPK (see, for example, NPL 9). In addition, it has also been reported that metformin suppresses mitochondrial glycerophosphate dehydrogenase in the liver to suppress gluconeogenesis and lower blood glucose (see, for example, NPL 10).

CITATION LIST

Patent Literature

PTL 1: Published Japanese Translation No. 2010-514804 of the PCT International Publication
PTL 2: Published Japanese Translation No. 2011-507970 of the PCT International Publication

Non-Patent Literature

NPL 1: Evans et al., Nature Medicine 2004, vol. 10 (4), p. 355-361
NPL 2: Willson et al., Journal of Medicinal Chemistry, 2000, vol. 43 (4), p. 527-550
NPL 3: Barish et al., The Journal of Clinical Investigation, 2006, vol. 116 (3), p. 590-597
NPL 4: Narkar et al., Cell, 2008, vol. 134 (3), p. 405-415
NPL 5: Palomer et al, International Journal of Cardiology, 2014, Vol. 174, P. 110-118
NPL 6: Iwaisako et al., Proceedings of the National Academy of Sciences of the United States of America, 2012, vol. 109 (21), p. E1369-E1376
NPL 7: Xu et al., Molecular Cell, 1999, vol. 3 (3), p. 397-403
NPL 8: Wu et al, Proceedings of the National Academy of Sciences of the United States of America, 2017, Vol. 114(13), P. E2563-E2570
NPL 9: Zhou et al., Journal of Clinical Investigation, 2001, vol. 108 (8), p. 1167-1174
NPL 10: Madiraju et al., Nature, 2014, vol. 510 (7506), p. 542-546
NPL 11: Eikawa et al., Proceedings of the National Academy of Sciences of the United States of America, 2015, vol. 112 (6), p. 1809-1814
NPL 12: Sugden et al., Pharmacological Research, 2009, vol. 60, p. 141-150

SUMMARY OF THE INVENTION

Technical Problem

A main object of the present invention is to provide a PPARδ activator containing a novel PPARδ agonist as an active ingredient, and an exercise tolerance-improving agent containing the PPARδ agonist as an active ingredient.

Solution to Problem

The present inventors have conducted intensive studies, and as a result, discovered that metformin is a PPARδ agonist and activates the transcriptional activity of PPARδ. Furthermore, from the results of the co-crystal structure analysis of metformin and ligand-binding domain (LBD) of human PPARδ (hPPARδ), it was found that metformin binds to the ligand binding pocket of PPARδ. In this binding mode, the two amino groups of the biguanide skeleton of metformin interact with and bind to the amino acid residues near the entrance of the ligand-binding pocket. As a result, the LBD of PPARδ changes its structure into an active conformation, thereby completing the present invention.

That is, the PPARδ activators and the exercise tolerance-improving agents according to the present invention are as following (1) to (8).

(1) A PPARδ activator comprising a guanidine derivative or a biguanidine derivative as an active ingredient, wherein the PPARδ activator activates transcriptional activity of PPARδ (peroxisome proliferator-activated receptor δ).

(2) The PPARδ activator according to (1), wherein the guanidine derivative and the biguanidine derivative are capable of fitting within a ligand binding pocket of PPARδ, in a state where a guanidino group or a biguanidino group forms a hydrogen bond with amino acid residues of the 413th histidine, 287th histidine, 253rd threonine and the 437th tyrosine of human PPARδ that constitute an interior surface of the ligand binding pocket.

(3) The PPARδ activator according to (1) or (2), wherein the guanidine derivative is a compound represented by the following general formula (1) (excluding the biguanidine derivative), Chemical formula 1:

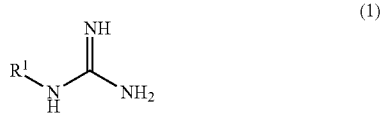

(1)

in formula (1), $R^1$ represents a monovalent organic group.

(4) The PPARδ activator according to [3], wherein the guanidine derivative is a compound represented by any one of the following general formulas (1-1-1) to (1-1-4), Chemical formula 2

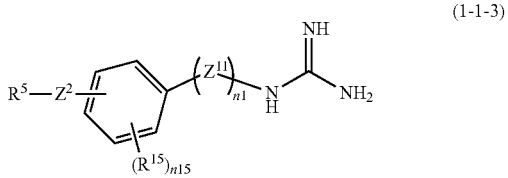

(1-1-1)

(1-1-2)

in formulas (1-1-1) and (1-1-2), $Z^{11}$ represents an oxygen atom or a sulfur atom, n1 represents 0 or 1, $R^{12}$ represents an aliphatic hydrocarbon group having 1 to 6 carbon atoms, n12 represents an integer of 0 to 2, $R^{13}$ represents a hydrogen atom or an aliphatic hydrocarbon group having 1 to 6 carbon atoms, $R^{14}$ represents an optionally substituted aromatic hydrocarbon group, and p1 represents an integer of 1 or more.

Chemical formula 3:

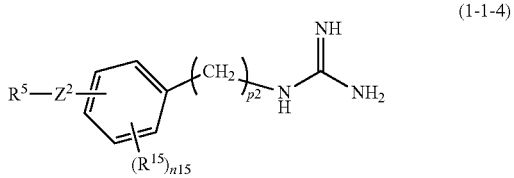

(1-1-3)

(1-1-4)

in formulas (1-1-3) and (1-1-4), $Z^{11}$ represents an oxygen atom or a sulfur atom, n1 represents 0 or 1, $R^{15}$ represents an aliphatic hydrocarbon group having 1 to 6 carbon atoms or an alkoxy group having 1 to 6 carbon atoms, n15 represents an integer of 0 to 2, $Z^2$ represents a divalent linking group, $R^5$ represents an optionally substituted aromatic hydrocarbon group or an optionally substituted cyclic hydrocarbon group, p2 represents an integer of 1 or more.

(5) The PPARδ activator according to (1), wherein the guanidine derivative is a compound represented by any of the following formulas (A-1) to (A-4), (B-1) to (B-3), Chemical formula 4:

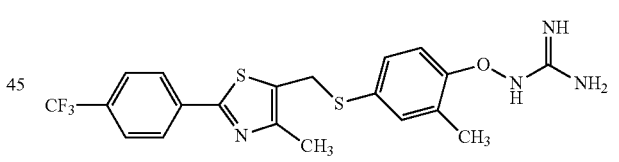

(A-1)

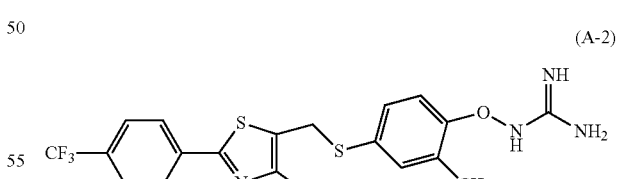

(A-2)

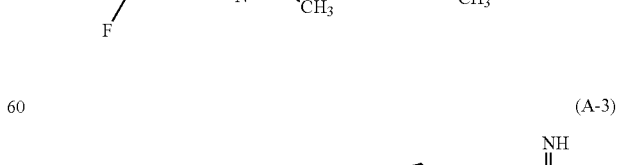

(A-3)

-continued

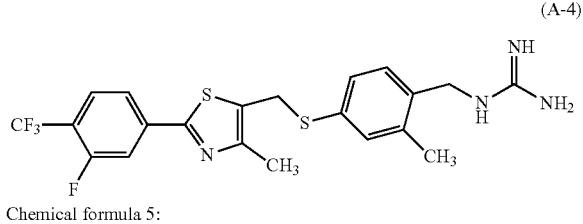

(6) The PPARδ activator according to any one of (1) to (3), wherein the biguanidine derivative is a compound represented by the following general formula (2), Chemical formula 6:

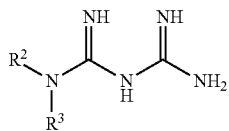

in formula (2), $R^2$ and $R^3$ independently represent a hydrogen atom or a monovalent organic group, when both $R^2$ and $R^3$ are monovalent organic groups, they may be linked to form a ring structure.

(7) The PPARδ activator according to (1), wherein at least one selected from the group consisting of metformin, phenformin and buformin is included as an active ingredient.

(8) An exercise tolerance-improving agent comprising the PPARδ activator defined in any one of (1) to (7) as the active ingredient.

Advantageous Effects of the Invention

The PPARδ activators according to the present invention can activate the transcriptional activity of PPARδ and can affect various physiological actions transcriptionally regulated by PPARδ. Therefore, the PPARδ activators are useful as an active ingredient of an exercise tolerance-improving agent, and can be expected to be useful as an active ingredient of a pharmaceutical composition for treating or preventing metabolic disorders and the like.

BRIEF DESCRIPTION OF DRAWINGS

FIG. 1 is an amino acid sequence of the hPPARδ ligand binding pocket. In the sequence, the amino acid residues with a black circle at the top indicate the amino acid residues constituting the interior surface of the hPPARδ ligand binding pocket, and the amino acid residues surrounded by a square are the amino acid residues forming hydrogen bonds with the guanidino group in the guanidine derivative.

FIG. 5 is a diagram showing the amino acid sequence of PPARδ and the amino acid sequence of the peptide identified by TOF-MS in Example 1.

FIG. 19A shows the results of the control group ("cont" in the figure) and the metformin administration group ("met" in the figure), and FIG. 19B shows the results of the training group ("cont+train" in the figure) and the results of the training+metformin administration group ("met+train" in the figure).

DESCRIPTION OF EMBODIMENTS OF THE INVENTION

Figure 2:
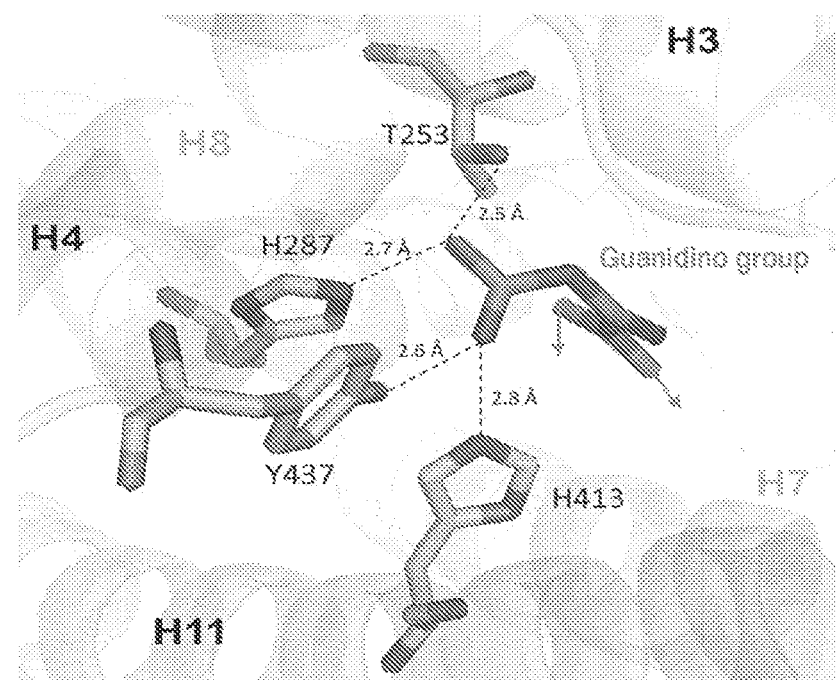
FIG. 2 is a diagram schematically showing the structure of a conjugate of hPPARδ and a compound in which $R^1$ is an organic group branched in the arrow direction among the guanidine derivatives represented by the general formula (1).

PPARδ is composed of an N-terminal domain having ligand-independent transcriptional activation ability, a zinc finger domain as a DNA binding region, and a ligand binding domain (LBD) having a ligand-dependent transcriptional activation ability. The LBD composed of twelve α-helices and three β-sheets, and the 3rd to 8th α-helices form a ligand binding pocket. FIG. 1 shows the amino acid sequence of the ligand binding pocket of hPPARδ. In the amino acid sequence shown in FIG. 1, the following 33 amino acid residues constitute the interior surface of the ligand binding pocket: Asn191, Met192, Ile213, Leu219, Glu223, Trp228, Val245, Phe246, Arg248, Cys249, Gln250, Thr252, Thr253, Glu255, Thr256, Glu259, His287, Ile290, Phe291, Leu294, Ile297, Leu303, Val305, Ala306, Asn307, Val312, Phe316, Leu317, Ile327, Ile328, His413, Met417, Leu433, Tyr437.

From the structural study of the complex of hPPARδ and GW501516, the following was clarified. A phenoxyacetic acid derivative such as GW501516 specifically binds its carboxyl group to an amino acid residue at the entrance (arm I) of the ligand binding pocket of PPARδ by forming a plurality of hydrogen bonds. This binding causes the 12th α-helix (helix-12) of PPARδ to tilt-down to cover the ligand binding pocket, and the remaining hydrophobic groups fit into the non-polar pocket. The tilt-down helix-12 serves as a lid for the ligand-binding pocket, thereby activating the transcriptional activity of PPARδ (NPL 7 and 8).

The PPARδ activators according to the present invention are medicines that activate the transcriptional activity of PPARδ, and contain guanidine derivatives or biguanidine derivatives as active ingredients. The guanidine derivative means a compound having a guanidino group. The biguanidine derivatives mean compounds having a biguanidino group. The active ingredient of the PPARδ activator according to the present invention may be guanidine derivatives having a biguanidino group or biguanidine derivatives having a guanidino group.

The PPARδ activators according to the present invention fit within a ligand binding pocket and forms a plurality of hydrogen bonds by amino acid residues at the entrance (arm I) of the ligand binding pocket of PPARδ and a guanidino group or a biguanidino group, thereby tilting-down the helix-12 to cover the ligand binding pocket. The PPARδ activators according to the present invention can achieve the structural change (tilting-down and immobilization of helix-12) necessary for activating the transcriptional activity of PPARδ by the guanidino group or biguanidino group.

Specifically, the guanidino group or biguanidino group of the PPARδ activators according to the present invention forms hydrogen-bonds with the amino acid residues corresponding to each of the 413th histidine (His413), 287th histidine (His287), 253rd threonine (Thr253), and the 437th tyrosine (Tyr437) of the hPPARδ, among the amino acid residues constituting the interior surface of the ligand binding pocket of PPARδ. Due to these hydrogen bonds, the PPARδ activators according to the present invention are placed at the entrance of the ligand binding pocket of PPARδ. As a result, the helix-12 is tilted down and fixed while covering the ligand binding pocket, thereby the PPARδ is activated.

The guanidino group or biguanidino group of the PPARδ activators according to the present invention also interacts with the amino acid residues corresponding to each of the 246th phenylalanine (Phe246), the 417th methionine (Met417), the 433rd leucine (Leu433) and the 250th glutamine (Gln250) of the hPPARδ, among the amino acid residues constituting the interior surface of the ligand binding pocket of PPARδ. The interaction between the guanidino or biguanidino group with the entrance (arm I) of the ligand binding pocket of PPARδ is more stable than the phenoxyacetic acid derivatives that bind though the carboxyl group, and the helix-12 is efficiently tilted down and fixed. Therefore, it can be expected that the activating action of PPARδ is stronger than that of the phenoxyacetic acid derivative.

The guanidine derivatives as an active ingredient of the PPARδ activator according to the present invention, are not particularly limited as long as they are compounds capable of fitting within the ligand binding pocket of PPARδ in a state where the guanidino group forms hydrogen bonds with His413, His287, Thr253 and Tyr437 of the hPPARδ. Similarly, the biguanidine derivatives as active ingredients of the PPARδ activator according to the present invention, are not particularly limited as long as they are compounds capable of fitting within the ligand binding pocket of PPARδ in a state where the biguanidino group forms hydrogen bonds with His413, His287, Thr253 and Tyr437 of the hPPARδ.

The phrase "the compound fits within the ligand binding pocket" means that the compound may occupy the entire pocket or occupy only a part of the pocket as long as it is contained inside the ligand binding pocket. The active ingredients of the PPARδ activator according to the present invention may be a compound that occupies only a part or all of arm I of PPARδ, or may be a compound that occupies only a part or all of arm I and arm II of PPARδ, or may be a compound that occupies only a part or all of arm I and arm III of PPARδ. Further, it may also be compounds having a branched structure that occupies a part or all of arm I and arm II of PPARδ, and a part or all of arm III.

Examples of the guanidine derivatives as the active ingredient of the PPARδ activator according to the present invention include compounds represented by the following general formula (1) (except for the biguanidine derivative) (hereinafter, referred to as "compound (1)"). Examples of the biguanidine derivatives as the active ingredient of the PPARδ activator according to the present invention include compounds represented by the following general formula (2) (hereinafter, referred to as "compound (2)"). In the general formula (1), $R^1$ represents a monovalent organic group. In the general formula (2), $R^2$ and $R^3$ independently represent a hydrogen atom or a monovalent organic group. Among the compounds (2), the compound in which $R^2$ and $R^3$ are both hydrogen atoms is metformin.

Chemical formula 7:

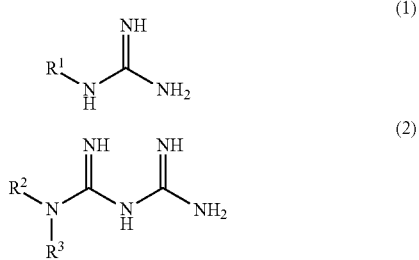

The monovalent organic groups of $R^1$, $R^2$ and $R^3$ are not particularly limited as long as they are organic groups having a size and shape that allow the entire compound to fit within the ligand binding pocket of PPARδ in a state where the guanidino groups or the biguanidino groups form hydrogen bonds with the amino acid residues corresponding to His413, His287, Thr253 and Tyr437 of the hPPARδ. For example, the monovalent organic group may be an acidic group or a basic group. Further, it may be a hydrophilic group or a hydrophobic group.

The monovalent organic group may be linear, may be branched, or may have a cyclic structure. FIG. 2 is a diagram schematically showing the structure of a conjugate of PPARδ and a compound in which $R^1$ is a branched-chain organic group branched in the arrow direction among compounds (1). This branched organic group extends to each of arm II and arm III.

Examples of the monovalent organic group include —($Z^1$)—$R^4$ (wherein, $Z^1$ represents a single bond, oxygen atom, sulfur atom, —NH—, —N=CH—, —CO—, —CO—O—, —O—CO—, —CO—NH—, or —NH—CO—; $R^4$ represents an aliphatic hydrocarbon group, an aromatic hydrocarbon group, or a heterocyclic group), a carboxyl group, nitro group, cyanide group, hydroxy group, amino group and the like.

When $R^4$ is an aliphatic hydrocarbon group, the aliphatic hydrocarbon group is not particularly limited, and examples thereof include saturated or unsaturated hydrocarbon groups having 1 to 20 carbon atoms. The monovalent aliphatic hydrocarbon group may be a chain hydrocarbon group or a cyclic hydrocarbon group. Specific examples of the monovalent chain hydrocarbon group include a methyl group, ethyl group, propyl group, isopropyl group, n-butyl group, t-butyl group, n-pentyl group, isopentyl group, neopentyl group, tert-pentyl group, n-hexyl group, isohexyl group, 2-ethylhexyl group, n-heptyl group, n-octyl group, n-nonyl group, n-decyl group and the like. Examples of the monovalent cyclic hydrocarbon group include a group obtained by removing one hydrogen atom from an alicyclic compound such as a cyclopropane, cyclobutane, cyclopentane, cyclohexane, cycloheptane, cyclooctane, adamantane dicyclopentadiene and the like. These aliphatic hydrocarbon groups may have one or more substituents. Examples of the substituent include a halogen atom (fluorine atom, chlorine atom, bromine atom, iodine atom), trifluoromethyl group, carboxy group, nitro group, cyano group, hydroxy group, amino group, ketone group, alkoxy group, aromatic hydrocarbon group, heterocyclic group, multi-ring linking group and the like. Examples of the aromatic hydrocarbon group and the heterocyclic group include the same groups as those exemplified as $R^4$ later. Examples of the multi-ring linking group include those similar to the multi-ring linking group exemplified as the monovalent organic group later. Specific examples of the alkoxy group include a methoxy group, ethoxy group. propyloxy group, isopropyloxy group, n-butoxy group, t-butoxy group, n-pentyloxy group, isopentyloxy group, neopentyloxy group, tert-pentyloxy group, n-hexyloxy group, isohexyloxy group and the like. When the aliphatic hydrocarbon group has an aromatic hydrocarbon group, a heterocyclic group, or a multi-ring linking group as a substituent, the aliphatic hydrocarbon group preferably has 1 to 6 carbon atoms.

When R4 is an aromatic hydrocarbon group, the aromatic hydrocarbon group is not particularly limited, and examples thereof include a group obtained by removing one hydrogen atom from an aromatic cyclic compound such as a benzene, naphthalene, anthracene, phenanthrene or the like. These aromatic hydrocarbon groups may have one or more substituents. Examples of the substituent include a halogen atom, trifluoromethyl group, carboxy group, nitro group, cyano group, hydroxy group, amino group, ketone group, alkoxy group, aliphatic hydrocarbon group and the like. Examples of the aliphatic hydrocarbon group include the same groups as those exemplified as $R^4$ above. Examples of the alkoxy group include the same groups as those exemplified as the substituent of the aliphatic hydrocarbon group above.

When $R^4$ is a heterocyclic group, the heterocyclic group is not particularly limited, and examples thereof include a group obtained by removing one hydrogen atom from a heterocyclic compound such as 5-membered heterocyclic compounds such as a pyrrolidine, pyrrole, imidazole, pyrazole, imidazoline, triazole, tetrazole, oxazole, thiazole, tetrahydrofuran, furan, dioxolane, tetrahydrothiophene, thiophene or the like; 6-membered heterocyclic compounds such as a piperidine, pyridine, pyrimidine, pyrazine, pyridazine, morpholine, thiazine, oxane, pyririum ion, dioxane, thiane, thiapyran or the like; condensed heterocyclic compounds such as an indol, isoindole, benzimidazole, purine, benzotriazole, quinoline, isoquinoline, quinazoline, quinoxaline, cinnoline, pteridine, chromium, isochromen, xanthene, carbazole, benzo-C-cinnoline or the like; or the like. These heterocyclic groups may have one or more substituents. Examples of the substituent include a halogen atom, trifluoromethyl group, carboxy group, nitro group, cyano group, hydroxy group, amino group, ketone group, alkoxy group, aliphatic hydrocarbon group and the like. Examples of the aliphatic hydrocarbon group include the same groups as those exemplified as $R^4$ above. Examples of the alkoxy group include the same groups as those exemplified as the substituent of the aliphatic hydrocarbon group above.

The monovalent organic group may be a group in which two or more rings are linked by a single bond or a divalent linking group (multi-ring linking group). The rings are not particularly limited, and may be an alicyclic compound, an aromatic cyclic compound, or a heterocyclic compound. Further, the rings to be linked may be the same or different. Specifically, the same alicyclic compound, aromatic cyclic compound, or heterocyclic compound as described above can be used.

Examples of the divalent linking group linking the rings in the multi-ring linking group include a divalent chain aliphatic hydrocarbon group, —O—, —S—, —NH—, —N=CH—, —CO—, and groups in which two or more of these are bonded. The divalent chain aliphatic hydrocarbon group may be linear or branched. Further, it may be a divalent aliphatic hydrocarbon group consisting only of saturated bonds, or it may be a divalent aliphatic hydrocarbon group having one or more unsaturated bonds. As the divalent chain aliphatic hydrocarbon group, an alkylene group having 1 to 10 carbon atoms, an alkenylene group and the like can be used.

Examples of the group in which two or more of a divalent chain aliphatic hydrocarbon group, —O—, —S—, —NH—, —N=CH— and —CO— are bonded include —CO—O—, —O—CO—, —CO—NH—, —NH—CO—, —(CH$_2$)$_n$—O—(CH$_2$)$_m$—, —(CH$_2$)$_n$—S—(CH$_2$)$_m$— (wherein, n and m are each independently an integer of 0 or more satisfying n+m≥1, and —(CH$_2$)$_0$— represents a single bond), and the like.

In the general formula (2), when both $R^2$ and W are monovalent organic groups, they may be linked together to form a ring structure. The ring formed by linking $R^2$ and $R^3$ may be an alicyclic compound, an aromatic ring compound, or a heterocyclic compound. Examples of the alicyclic compound, the aromatic ring compound, and the heterocyclic compound include the same groups as those exemplified as $R^4$ above. Furthermore, these cyclic compounds may have substituents. Examples of the substituent include the same groups as those exemplified as the monovalent organic groups for $R^1$, $R^2$ and $R^3$.

Examples of compound (1) include a compound represented by the following general formula (1-1) (compound (1-1)) and the like.

Chemical formula 8:

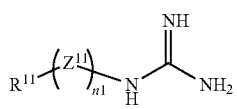

(1-1)

In the general formula (1-1), $Z^{11}$ represents an oxygen atom or a sulfur atom, and n1 represents 0 or 1.

In the general formula (1-1), $R^{11}$ represents an optionally substituted aliphatic hydrocarbon group having 1 to 6 carbon atoms, an optionally substituted aromatic hydrocarbon group, or an optionally substituted multi-ring linking group. Examples of the optionally substituted aliphatic hydrocarbon group having 1 to 6 carbon atoms and the optionally substituted aromatic hydrocarbon group include the same groups as those exemplified as $R^4$ above. Examples of the optionally substituted multi-ring linking group include the same groups as those exemplified as the monovalent organic group.

Examples of compound (1-1) include a compound represented by the following general formula (1-1-1) (compound (1-1-1)) and a compound represented by the general formula (1-1-2) (compound (1-1-2)).

Chemical formula 9:

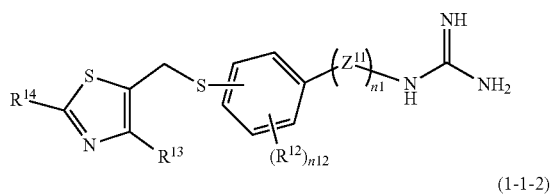

(1-1-1)

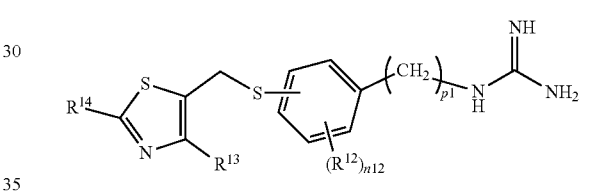

(1-1-2)

In the general formula (1-1-1), $Z^{11}$ and n1 are as defined in the general formula (1-1).

In the general formula (1-1-2), p1 is an integer of 1 or more, preferably an integer of 1 to 6, more preferably an integer of 1 to 3, and particularly preferably 1.

In the general formula (1-1-1) and the general formula (1-1-2), n12 represents an integer of 0 to 2.

In the general formula (1-1-1) and the general formula (1-1-2), $R^{12}$ represents an aliphatic hydrocarbon group having 1 to 6 carbon atoms. Examples of the aliphatic hydrocarbon group include the same groups as those exemplified as $R^4$ above.

In the general formula (1-1-1) and the general formula (1-1-2), $R^{13}$ represents a hydrogen atom or an aliphatic hydrocarbon group having 1 to 6 carbon atoms. Examples of the aliphatic hydrocarbon group include the same groups as those exemplified as R4 above.

In the general formula (1-1-1) and the general formula (1-1-2), $R^{14}$ represents an optionally substituted aromatic hydrocarbon group. Examples of the aromatic hydrocarbon group include the same groups as those exemplified as $R^4$ above.

Compound (1-1-1) is preferably a compound in which $Z^{11}$ is an oxygen atom or a sulfur atom, n1 is 1, n12 is 0 or 1, $R^{12}$ is a methyl group, ethyl group, a propyl group, isopropyl group, n-butyl group, t-butyl group, n-pentyl, iso-pentyl, neopentyl group, tert-pentyl, n-hexyl or isohexyl group, $R^{13}$ is a hydrogen atom, methyl group, ethyl group, propyl group, isopropyl group, n-butyl group, t-butyl group, n-pentyl, iso-pentyl group, neopentyl group, tert-pentyl, n-hexyl or isohexyl group, and $R^{14}$ is an optionally substituted phenyl group. Among the compounds, a compound in which $Z^{11}$ is an oxygen atom or a sulfur atom, n1 is 1, n12 is 0 or 1, $R^{12}$ is a methyl group, ethyl group, propyl group, isopropyl group, n-butyl group or t-butyl group, $R^{13}$ is a hydrogen atom, methyl group, ethyl group, propyl group, isopropyl group, n-butyl group or t-butyl group, and $R^{14}$ is an unsubstituted phenyl group or a phenyl group having one or two substituents selected from the group consisting of a halogen atom, trifluoromethyl group, and methyl group is preferable, and a compound in which $Z^{11}$ is an oxygen atom or a sulfur atom, n1 is 1, n12 is 0 or 1, $R^{12}$ is a methyl group, $R^{13}$ is a hydrogen atom or a methyl group, and $R^{14}$ is an unsubstituted phenyl group or a phenyl group having one or two substituents selected from the group consisting of a halogen atom, trifluoromethyl group, and methyl group is more preferable.

Compound (1-1-2) is preferably a compound in which p1 is 1, n12 is 0 or 1, $R^{12}$ is a methyl group, ethyl group, propyl group, isopropyl group, n-butyl group, t-butyl group, n-pentyl group, iso-pentyl group, neopentyl group, tert-pentyl group, n-hexyl group or an isohexyl group, $R^{13}$ is a hydrogen atom, methyl group, ethyl group, propyl group, isopropyl group, n-butyl group, t-butyl group, n-pentyl group, iso pentyl group, neopentyl group, tert-pentyl group, n-hexyl group or an isohexyl group, and $R^{14}$ is an optionally substituted phenyl group. Among the compounds, a compound in which p1 is 1, n12 is 0 or 1, $R^{12}$ is a methyl group, ethyl group, propyl group, isopropyl group, n-butyl group or a t-butyl group, $R^{13}$ is a hydrogen atom, methyl group, ethyl group, propyl group, isopropyl group, n-butyl group or a t-butyl group, and $R^{14}$ is an unsubstituted phenyl group or a phenyl group having one or two substituents selected from the group consisting of a halogen atom, trifluoromethyl group and a methyl group is preferable, and a compound in which p1 is 1, n12 is 0 or 1, $R^{12}$ is a methyl group, $R^{13}$ is a hydrogen atom or a methyl group, and $R^{14}$ is an unsubstituted phenyl group or a phenyl group having one or two substituents selected from the group consisting of a halogen atom, trifluoromethyl group and a methyl group is more preferable.

Examples of compound (1-1-1) include compounds represented by the following formulas (A-1) to (A-2). Examples of compound (1-1-2) include the compounds represented by the following formulas (A-3) to (A-4).

Chemical formula 10

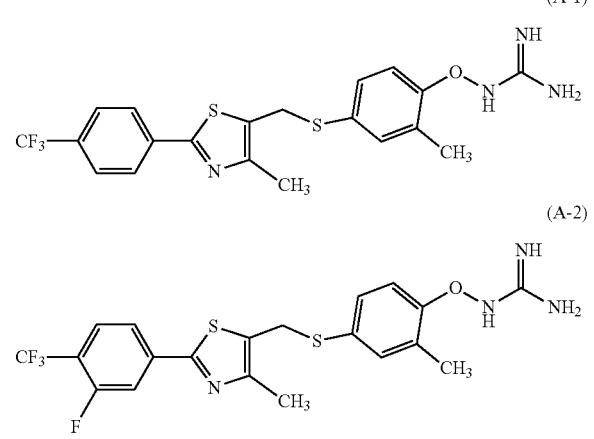

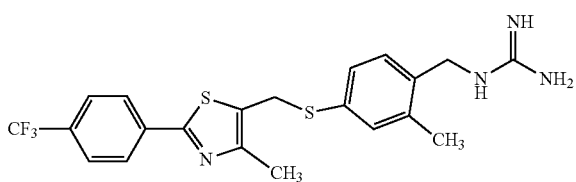

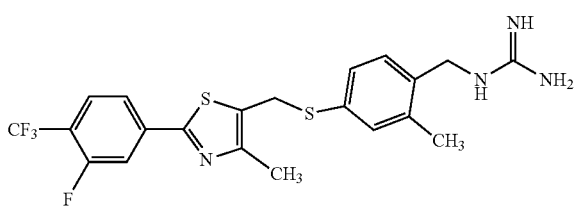

Examples of compound (1-1) include a compound represented by the following general formula (1-1-3) (compound (1-1-3)) and a compound represented by the following general formula (1-1-4) (compounds (1-1-4)).

Chemical formula 11:

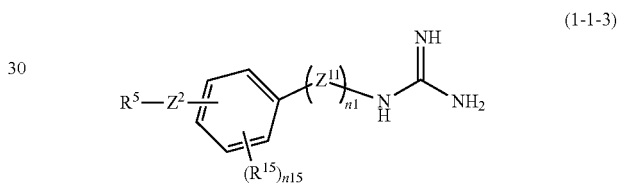

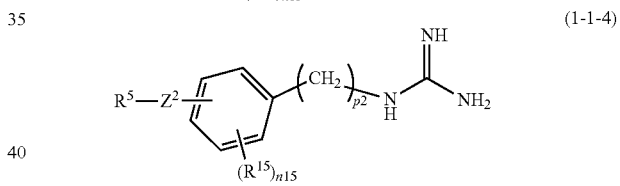

In the general formula (1-1-3), $Z^{11}$ and n1 are as defined in the general formula (1-1).

In the general formula (1-1-4), p2 is an integer of 1 or more, preferably an integer of 1 to 6, more preferably an integer of 1 to 3, and particularly preferably 1.

In the general formula (1-1-3) and the general formula (1-1-4), n15 represents an integer of 0 to 2.

In the general formula (1-1-3) and the general formula (1-1-4), $R^{15}$ represents an aliphatic hydrocarbon group or an alkoxy group having 1 to 6 carbon atoms. Examples of the aliphatic hydrocarbon group include the same groups as those exemplified as $R^4$ above. Examples of the alkoxy group include the same groups as those exemplified as the substituent of the aliphatic hydrocarbon group above.

In the general formula (1-1-3) and the general formula (1-1-4), $Z^2$ is a divalent linking group. Examples of the divalent linking group include the same groups as those exemplified as the divalent linking group linking the rings in the multi-ring linking group. Compound (1-1-3) and compound (1-1-4) are preferably a compound in which $Z^2$ is —(CH$_2$)$_2$—, —(CH$_2$)$_3$—, —O—CH$_2$—, —CH$_2$—O—, —CH$_2$—O—CH$_2$—, —S—CH$_2$—, —CH$_2$—S—, —CH$_2$—S—CH$_2$—, —NH—CH$_2$—, —CH$_2$—NH, or —CH$_2$—NH—CH$_2$—.

In the general formula (1-1-3) and the general formula (1-1-4), $R^5$ is an optionally substituted aromatic hydrocarbon group or an optionally substituted cyclic hydrocarbon group. Examples of the optionally substituted aromatic hydrocarbon group include the same groups as those exemplified as $R^4$ above. Examples of the optionally substituted multi-ring linking group include the same groups as those exemplified as the monovalent organic group. Compound (1-1-3) and compound (1-1-4) are preferably a compound in which $R^5$ is an optionally substituted phenyl group or an optionally substituted cyclohexyl group.

Compound (1-1-3) is preferably a compound in which $Z^{11}$ is an oxygen atom or a sulfur atom, n1 is 1, n15 is 0 or 1, $R^{15}$ is a methyl group, ethyl group, propyl group, isopropyl group, methoxy group, ethoxy group or a propyl group, $Z^2$ is —(CH$_2$)$_2$—, —(CH$_2$)$_3$—, —O—CH$_2$—, —CH$_2$—O—, —CH$_2$—O—CH$_2$—, —S—CH$_2$—, —CH$_2$—S—, —CH$_2$—S—CH$_2$—, —NH—CH$_2$—, —CH$_2$—NH—, or —CH$_2$—NH—CH$_2$—, and $R^5$ is an optionally substituted phenyl group or an optionally substituted cyclohexyl group; and more preferably a compound in which $Z^{11}$ is an oxygen atom or a sulfur atom, n1 is 1, n15 is 0 or 1, $R^{15}$ is a methyl group, ethyl group, propyl group, isopropyl group, methoxy group, ethoxy group or a propyl group, $Z^2$ is —(CH$_2$)$_2$—, —(CH$_2$)$_3$—, —O—CH$_2$—, —CH$_2$—O—, —CH$_2$—O—CH$_2$—, —S—CH$_2$—, —CH$_2$—S—, or —CH$_2$—S—CH$_2$—, and $R^5$ is an unsubstituted cyclohexyl group, an unsubstituted phenyl group or a phenyl group having one or two substituents selected from the group consisting of a halogen atom, trifluoromethyl group and a methyl group. Compound (1-1-3) is particularly preferably a compound in which $Z^{11}$ is a sulfur atom, n1 is 1, n15 is 0 or 1, $R^{15}$ is a methyl group or a methoxy group, and $Z^2$ is —CH—O$_2$—, —CH$_2$—O— or —CH$_2$—O—CH$_2$—, and $R^5$ is an unsubstituted cyclohexyl group or an unsubstituted phenyl group.

Compound (1-1-4) is preferably a compound in which p2 is 1, n15 is 0 or 1, $R^{15}$ is a methyl group, ethyl group, propyl group, isopropyl group, methoxy group, ethoxy group or a propyl group, $Z^2$ is —(CH$_2$)$_2$—, —(CH$_2$)$_3$—, —O—CH$_2$—, —CH$_2$—O—, —CH$_2$—O—CH$_2$—, —S—CH$_2$—, —CH$_2$—S—, —CH$_2$—S—CH$_2$—, —NH—CH$_2$—, —CH$_2$—NH—, or —CH$_2$—NH—CH$_2$—, and $R^5$ is an optionally substituted phenyl group or an optionally substituted cyclohexyl group; and more preferably a compound in which p2 is 1, n15 is 0 or 1, $R^{15}$ is a methyl group, ethyl group, propyl group, isopropyl group, methoxy group, ethoxy group or a propyl group, $Z^2$ is —(CH$_2$)$_2$—, —(CH$_2$)$_3$—, —O—CH$_2$—, —CH$_2$—O—, —CH$_2$—O—CH$_2$—, —S—CH$_2$—, —CH$_2$—S—, or —CH$_2$—S—CH$_2$—, and $R^5$ is an unsubstituted cyclohexyl group, an unsubstituted phenyl group or a phenyl group having one or two substituents selected from the group consisting of a halogen atom, trifluoromethyl group and a methyl group. Compound (1-1-3) is particularly preferably a compound in which p2 is 1, n15 is 0 or 1, $R^{15}$ is a methyl group or a methoxy group, and $Z^2$ is —CH—O$_2$—, —CH$_2$—O— or —CH$_2$—O—CH$_2$—, and $R^5$ is an unsubstituted cyclohexyl group or an unsubstituted phenyl group.

Examples of compound (1-1-4) include N-({4-[(benzyloxy) methyl]phenyl}methyl) guanidine hydrobromide (PubChem CID: 51131487) (hereinafter, referred to as compound (B-1).)), N-({3-[(cyclohexyloxy) methyl]phenyl}methyl) guanidine hydrogen iodide (PubChem CID: 53598567) (hereinafter, referred to as compound (B-2)), and N-{[4-(benzyl) oxy)-3-methoxyphenyl]methyl}guanidine hydrogen iodide (PubChem CID: 16261695) (hereinafter, referred to as compound (B-3)) and the like.

Chemical formula 12:

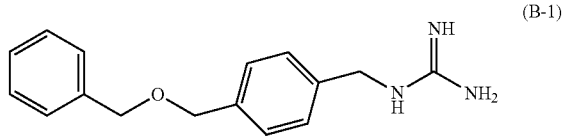

(B-1)

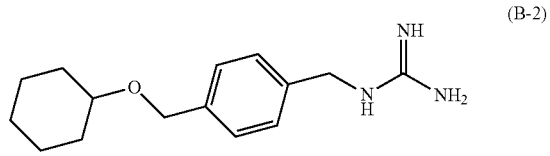

(B-2)

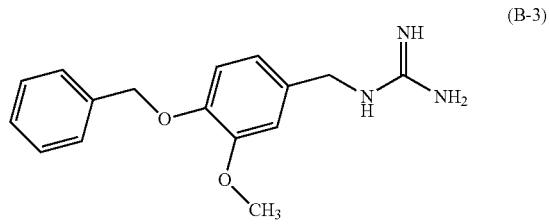

(B-3)

Examples of compound (2) include a compound represented by the following general formula (2-1) (compound (2-1)).

Chemical formula 13:

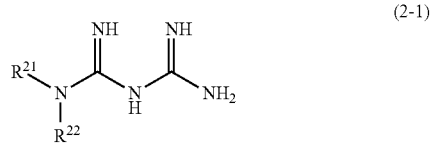

(2-1)

In the general formula (2-1), $R^{21}$ and $R^{22}$ independently represent a hydrogen atom or an optionally substituted aliphatic hydrocarbon group having 1 to 6 carbon atoms. Examples of the aliphatic hydrocarbon group include the same groups as those exemplified as $R^4$ above.

Examples of compound (2-1) include a metformin, buformin, phenformin and the like.

The results of crystal structure analysis of the ligand binding pocket of PPARδ have been published (NPL 7 or 8). Therefore, whether or not compound (1) or compound (2) has a size and shape that can be fitted within the ligand binding pocket of PPARδ, can be determined by using the structural data of the ligand binding pocket of PPARδ. For example, the shape of the ligand binding pocket of hPPARδ is a three-dimensional structure drawn by incorporating the data of Tables 1 to 63 of Example 5 below into the molecular graphics software PyMOL (https://www.pymol.org). That is, a compound having at least one of a guanidino group and a biguanidino group and having a shape that can be included inside the three-dimensional structure can be used as the active ingredient of the PPARδ activator according to the present invention.

By introducing the PPARδ activators according to the present invention into cells expressing PPARδ, the transcriptional activity of PPARδ in the cells can be activated. The cells to be treated with the PPARδ activator according to the present invention may be cells existing in a living body or cells in culture. When the cells to be treated are in a culture vessel, the PPARδ activator can be incorporated into the cells by endocytosis by culturing the cells in a medium containing the PPARδ activator. In addition, the PPARδ activators may also be introduced into the cells by a known introduction method such as a lipofection method, calcium phosphate precipitation method, lithium acetate method, electroporation method or the like.

When the cells to be treated with the PPARδ activator are in a living body of an animal, the administration route for the PPARδ activators to the animal is not particularly limited. Examples of the administration route of the PPARδ activators according to the present invention include oral administration, intravenous administration, intraperitoneal administration, enema administration and the like.

The animal to be administered with the PPARδ activators according to the present invention is not particularly limited, and may be a human or a non-human animal. The non-human animal is preferably a domestic animal or an experimental animal such as cows, pigs, horses, sheep, goats, monkeys, dogs, cats, rabbits, mice, rats, hamsters, guinea pigs or the like.

The PPARδ activators according to the present invention can be formulated into an oral solid agent such as powders, granules, capsules, tablets, chewable agents, sustained-release agents or the like, an oral liquid agent such as solutions, syrups or the like, injections, enema agents, sprays, patches, ointments, and the like. The formulation can be carried out by a conventional method by blending excipients, binders, lubricants, disintegrants, fluidizers, solvents, solubilizers, buffers, suspension agents, emulsifiers, isotonic agents, stabilizers, preservatives, antioxidants, flavoring agents, colorants or the like as necessary for the formulation.

The dose of the PPARδ activator according to the present invention is not limited as long as it is sufficient to make the transcriptional activity of PPARδ in the administered cells stronger than that before administration, and can be appropriately determined in consideration of the species, sex, age, body weight, usage (administration route, dosage form, number of administrations per day, etc.) of the animal to be treated. For example, the daily dose of the active ingredient for an adult (assuming a body weight of 60 kg) is preferably 0.01 mg to 10 g, more preferably 1 mg to 5 mg, and even more preferably 100 mg to 1 g in terms of the active ingredient of the PPARδ activator (guanidine derivative or guanidine derivative). Such a dose can be administered once or in several divided doses.

The PPARδ activators according to the present invention is suitable as an active ingredient of a pharmaceutical composition that can be expected to have therapeutic effects for treating or preventing various diseases by activating the transcriptional activity of PPARδ. Examples of the disease include various metabolic disorders such as diabetes, obesity or the like, diseases caused by ER stress such as cardiomyopathy or the like, liver fibrosis, and the like.

The PPARδ activators according to the present invention, like other PPARδ agonists, is useful as an active ingredient of an exercise tolerance-improving agent. Improving exercise tolerance by activating PPARδ means improving exercise tolerance, suppressing fatigue during exercise, increasing the amount of possible exercise, and increasing the effect of a certain amount of exercise. By taking the exercise tolerance-improving agent, it is possible to perform exercise with the same load for a longer period of time than when not taking the exercise tolerance-improving agent, and the effect of the exercise can be enhanced. As a result, lifestyle-related diseases such as obesity, diabetes or the like are expected to improve. In addition, enhancing the exercise effect can be expected to lead to health promotion. The exercise tolerance-improving agents containing the PPARδ activator according to the present invention preferably also contains AMPK or is preferably used in combination with AMPK.

As the PPARδ activity increases, so does the mitochondrial activity. Therefore, the PPARδ activators according to the present invention are preferable as an active ingredient of a pharmaceutical composition that can be expected to have a therapeutic effect for treating or preventing various diseases by improving mitochondrial activity. For example, when the mitochondrial activity is improved, immune cells are also activated. Therefore, the PPARδ activators according to the present invention are effective as an immunostimulatory agent and can be used as an active ingredient of a pharmaceutical composition for immunotherapy. Further, similarly to metformin (NPL 11), the PPARδ activators according to the present invention are also effective for use in combination with a cancer immunotherapeutic agent such as an immune checkpoint inhibitor.

EXAMPLES

Next, the present invention will be described in more detail with reference to the Examples and the like, but the present invention is not limited to these Examples.

Example 1

A target molecule of metformin in vivo was searched for by an affinity purification method using FG beads (registered trademark), on which metformin was immobilized. A cell extract of human liver cancer-derived cell line HepG2 cells was used to search for a target of metformin.

Met-Bead Production

Figure 3:
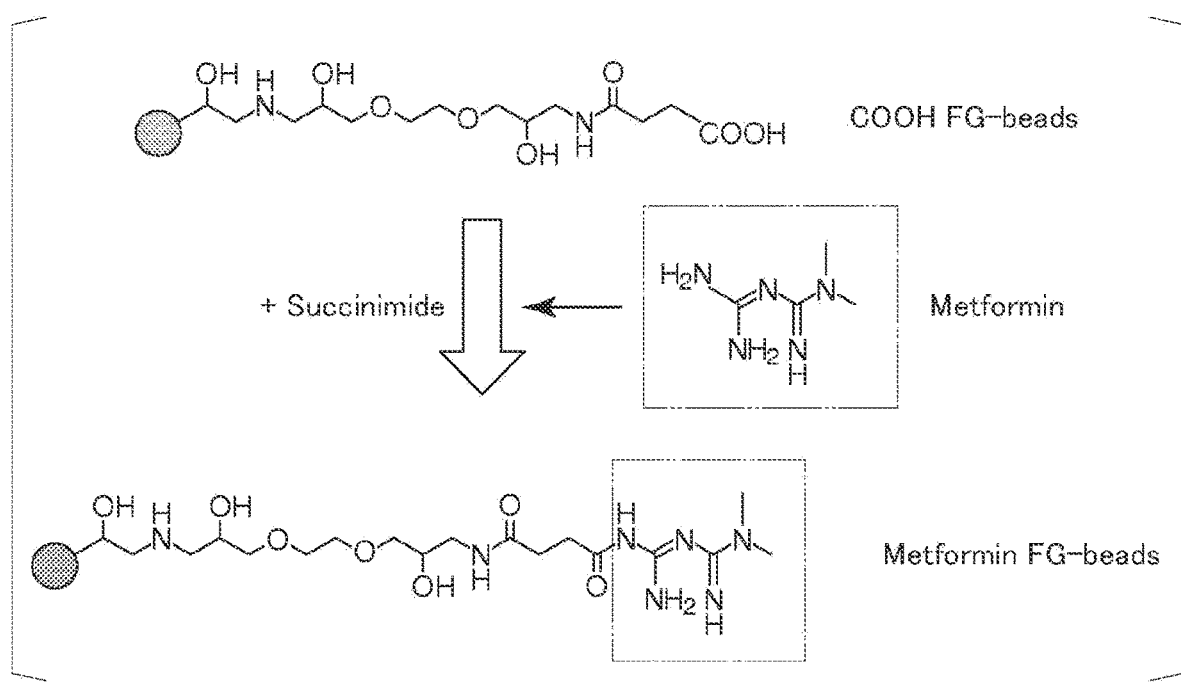
FIG. 3 is a schematic diagram of the reaction of metformin immobilization on COOH FG beads in Example 1.

FG beads on which metformin was immobilized (hereinafter, referred to as "Met-beads") were prepared. The method of immobilization followed a protocol provided by the manufacturer of COOH FG beads. Specifically, first, an N-hydroxysuccinimide (NHS) compound was formed by dehydrating and condensing the linker-terminal carboxylic acid of COOH FG beads (manufactured by Tamagawa Seiki Co., Ltd.) equilibrated with N, N'-dimethylformamide and NHS. Next, metformin was added to the obtained NHS compound, the $NH_2$ group of metformin was reacted with the NHS ester, and the COOH group of COOH FG beads and the $NH_2$ group of metformin were immobilized by amide bonding. FIG. 3 is a schematic diagram of the immobilization reaction of metformin on COOH FG beads. Unbound linker group on the FG beads was masked with aminoethanol. The masked Met-beads were washed and then suspended in 50 volume % methanol-water for use in subsequent experiments.

As a control group, metformin non-immobilized beads (hereinafter, referred to as "NC-beads") obtained by masking COOH FG beads with aminoethanol, followed by washing and suspending in 50 volume % methanol-water, were used in the subsequent experiments.

Affinity Purification Using Met-Beads

The prepared Met-beads were suspended in KCl buffer (100 mM KCl, 0.126 g/mL glycerol, 20 mM HEPES (pH 7.9), 1 mM $MgCl_2$, 200 µM $CaCl_2$, 0.2 mM EDTA, 0.1% NP-40), and then magnetically separated and the supernatant was discarded. Next, a washing process of adding 200 µL of KCl buffer to the Met-beads, dispersing the beads with an ultrasonic disperser, followed by discarding the supernatant by magnetic separation, was repeated 3 times.

Figure 4:
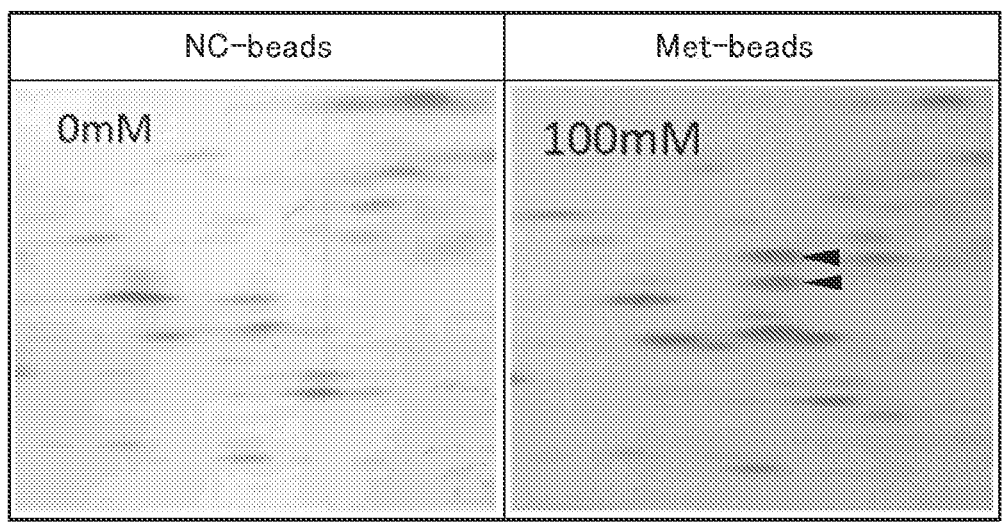
FIG. 4 is a silver-stained image of two-dimensional electrophoresis of eluates isolated from Met-beads (right figure) and NC-beads (left figure) in the affinity purification experiments using Met-beads in Example 1.

The cell extract of the human liver cancer-derived cell line HepG2 cells was diluted with the KCl buffer so that the protein concentration was adjusted to 3 mg/mL, and the obtained diluted solution was centrifuged (15 k rpm/4° C./30 minutes). The insoluble fraction was removed by separating the supernatant. The washed Met-beads were added to 400 μL of the supernatant to disperse, and the resulting mixture was allowed to react by inversion and stirring with a rotator at 4° C. for 4 hours. After the reaction, the supernatant was discarded by magnetic separation, and a washing process of adding 200 μL of KCl buffer to the recovered Met-beads, dispersing the beads with an ultrasonic disperser, followed by discarding the supernatant by magnetic separation, was repeated 4 times. 40 μL of 2D sample buffer (60 mM Tris-HCl (pH 8.8), 7M Urea, 2M Thiourea, 1% CHAPS, 1% Triton X-100, 1× protease inhibitor, 10 mM DTT, 1×BPB) was added to the washed Met-beads, and the resulting mixture was stirred and allowed to stand at room temperature for 10 minutes. Then, 4 μL of an aqueous acrylamide solution (71 mg/mL) was added to suspend, the resulting mixture was allowed to stand at room temperature for 10 minutes, and then magnetically separated to recover the supernatant. The recovered supernatant was subjected to two-dimensional electrophoresis using an agar gel (PI: pH3-10, e-PAGE, manufactured by ATTO CORPORATION), and the gel after electrophoresis was stained with silver to detect the proteins eluted from the Met-beads. Similar experiments were performed on the NC-beads which were non-immobilized with metformin, and the gels after silver staining were compared to visually confirm spots specific to the Met-beads. FIG. 4 shows a silver-stained image of the gel after two-dimensional electrophoresis of the supernatant eluted from the Met-beads (right figure) and the supernatant eluted from the NC-beads (left figure).

In the silver-stained image of the supernatant eluted from the Met-beads, two specific spots (indicated by arrowheads in FIG. 4), which were not found in the silver-stained image of the supernatant eluted from the NC-beads, were observed. The gels of these two spots were cut out and collected, and analyzed by TOF-MS (time-of-flight mass spectrometry). As a result, the proteins in both spots were identified as PPARδ (peroxisome proliferator-activated receptor δ). FIG. 5 shows the amino acid sequence of hPPARδ (SEQ ID NO: 1) and the amino acid sequence of the peptide identified by TOF-MS. In FIG. 5, the underlined region is the peptide identified by TOF-MS. The peptides identified by TOF-MS covered 26% of the total length of hPPARδ.

Metformin and PPARδ binding experiment by immunoprecipitation method:

The binding between PPARγ and metformin was confirmed by co-immunoprecipitation. Affinity-precipitation using the Met-beads was performed on the Myc-hPPARδ that was purified by immunoprecipitation using an anti-Myc antibody (sc-40, manufactured by Santa Cruz Bitechnology, Inc.) from an extract of human embryonic kidney-derived cell line HEK293 overexpressing cell Myc-tagged PPARγ (Myc-hPPARδ) and from a mouse liver extract.

Figure 6:
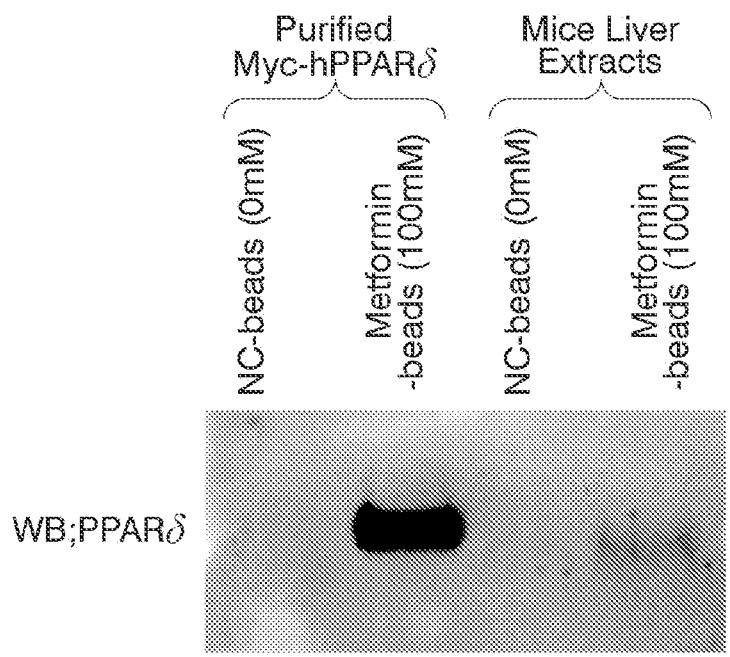
FIG. 6 is a diagram showing the results of Western blotting of eluates affinity-purified by Met-beads from purified Myc-hPPARδ protein and a mouse liver extract in Example 1. An anti-PPARδ antibody was used in this Western blotting experiment.

Specifically, first, the Met-beads were added to each of the purified Myc-hPPARδ and the mouse liver extract, the resulting mixtures were inverted and stirred, and then the Met-beads were recovered by magnetic separation. Western blotting was performed on the protein eluted from the recovered Met-beads using an anti-PPARδ antibody (sc-74517, manufactured by Santa Cruz Biotechnology, Inc.) that recognizes endogenous PPARδ. The result of Western blotting is shown in FIG. 6. As a result, it was confirmed that both the over-expressed Myc-hPPARδ and the endogenous PPARγ in the mouse liver extract bind to metformin.

Verification of Binding Between Metformin and PPARα:

PPARγ is a member of the nuclear receptor superfamily, with PPARα and PPARγ as the other two family members. Affinity purification was performed using the Met-beads and HepG2 cell extract to verify the binding to endogenous PPARα. As a result, the binding between metformin and PPARα was not detected.

Verification of Binding Between Metformin and AMPK:

Metformin is known to regulate the enhancement of sugar uptake in skeletal muscle and fatty acid β-oxidation in the liver by activating AMPK (5'AMP-activated protein kinase). Therefore, affinity purification was performed using the Met-beads and HepG2 cell extract to verify the binding between endogenous AMPK and metformin. As a result, the binding between metformin and AMPK was not detected.

Figure 7:
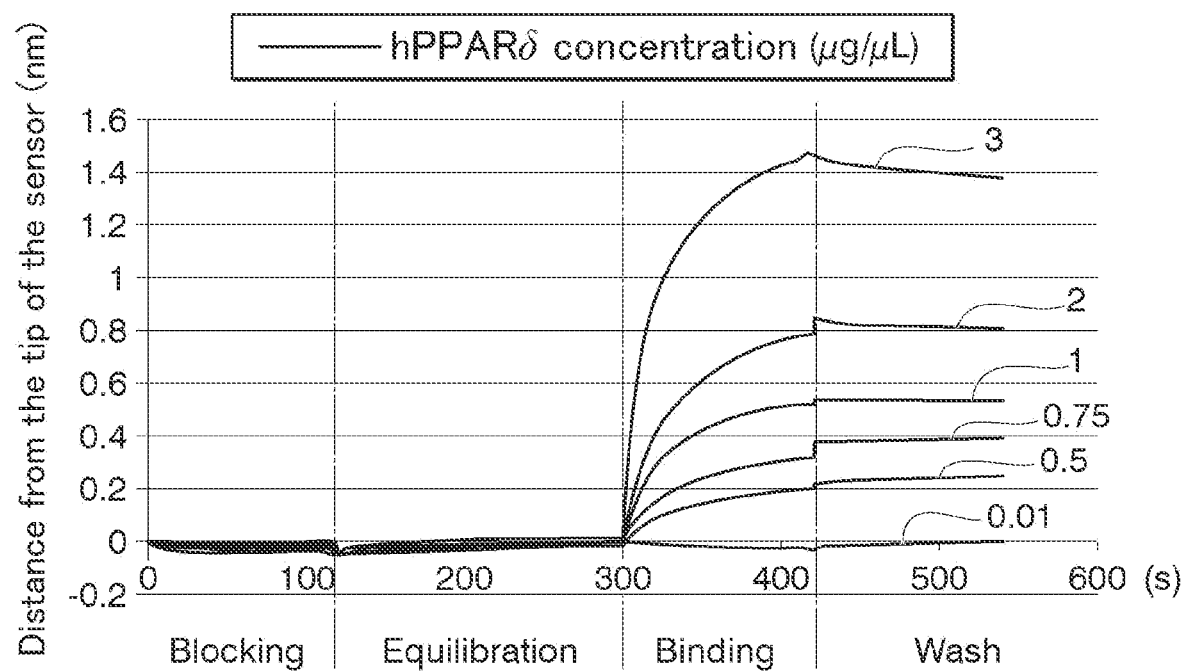
FIG. 7 is a diagram showing a bond dissociation curve between the metformin immobilized on a biosensor and serially diluted purified Myc-hPPARδ in Example 1.

Measurement of Affinity Between Metformin and PPARδ:

The affinity between metformin and PPARδ was measured using an intermolecular interaction-measuring device (product name: BLItz (registered trademark), manufactured by Pall ForteBio Corp.). The intermolecular interaction between metformin and Myc-hPPARδ was measured using the metformin-immobilized biosensor and the purified Myc-hPPARδ. Immobilization of metformin on the biosensor of the intermolecular interaction-measuring device was performed through the $NH_2$ group of metformin. The concentration of Myc-PPARδ was diluted in 6 steps, and the average intermolecular interaction calculated from each concentration was calculated by global fitting. FIG. 7 shows the association/dissociation curve between the metformin immobilized on a biosensor and the serially diluted purified Myc-hPPARδ. In the figure, the vertical axis is the distance (nm) of the Myc-hPPARδ protein from the sensor tip on which metformin was immobilized, and is an index of the amount of the Myc-hPPARδ protein bound to the sensor tip. As a result, the binding association rate constant (ka) was calculated to be $3.40 \times 10^4$ $M^{-1}S^{-1}$, the dissociation rate constant (kd) was calculated to be $1.03 \times 10'S^{-1}$, the dissociation constant (KD) was calculated to be $3.30 \times 10^{-1\circ}$ M, and it was confirmed that PPARδ strongly binds to metformin.

Figure 8:
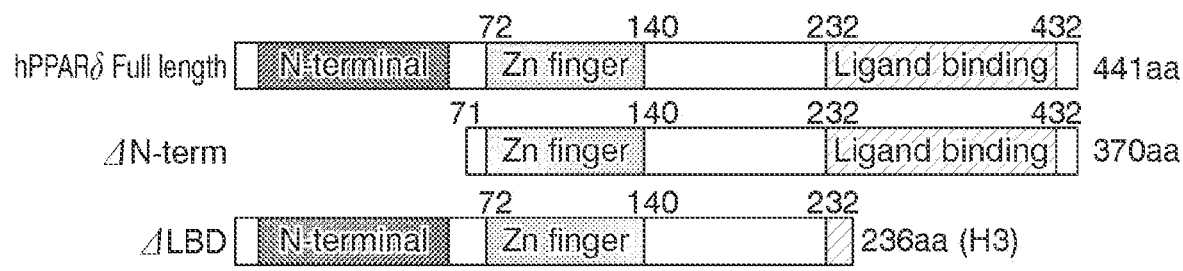
FIG. 8 shows the total length of the PPARδ used in Example 1 and a schematic view of each mutant.

Identification of Binding Site of Metformin in PPARδ:

In order to determine the binding site of metformin in PPARδ, a mutant lacking the N-term domain of PPARδ (ΔN-term: mutant lacking an amino acid region from the 1st amino acid to 70th amino acid) and a mutant having up to the third α-helix of LBD, hence completely lacking the ligand binding pocket (ΔLBD: mutant lacking an amino acid region from the 237th amino acid to the 441st amino acid) were prepared. FIG. 8 shows a schematic diagram of the total length of PPARδ and the structure of each mutant.

Figure 9:
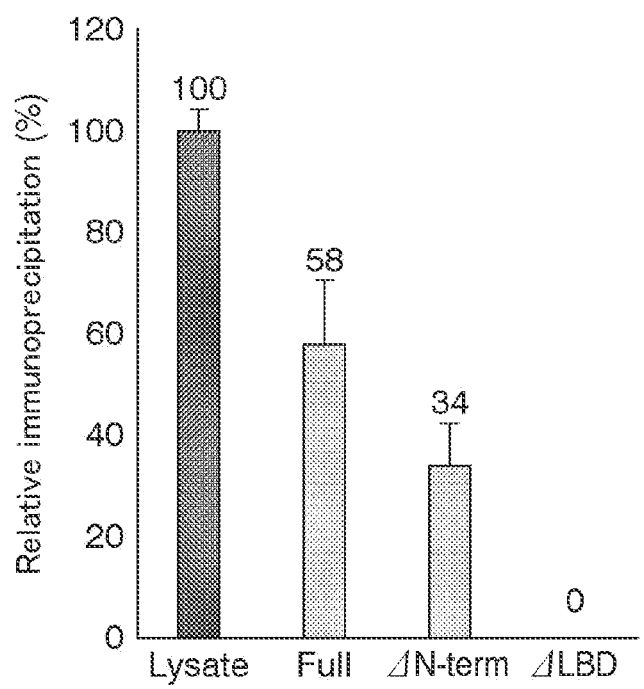
FIG. 9 shows the quantitative results of the relative amount (relative amount where Myc-tagged protein in cell extract is 100%) obtained from the cell extracts of cells overexpressing each of Myc-hPPARδ, Myc-ΔN-term, and Myc-ΔLBD by using Met-beads in Example 1.

Similar to the PPARδ-overexpressing cells that strongly express Myc-hPPARδ, ΔN-term-overexpressing cells that strongly express Myc-tagged ΔN-term (Myc-ΔN-term), and ΔLBD-overexpressing cells that strongly express Myc-tagged ΔLBD (Myc-ΔLBD) were prepared using HEK293 cells. The Met-beads were reacted with each of the cell extracts (Lysate) of these overexpressed cells, and affinity purification was performed. The protein eluted from the recovered Met-beads was subjected to Western blotting using an anti-Myc antibody to quantify the amount of immunoprecipitation. The quantitative results are shown in FIG. 9. As a result, when the amount of Myc-tagged protein in the cell extract was set as 100%, the relative amount (relative immunoprecipitation amount) (%) of the Myc-tagged protein bound to the Met-beads was about 58% for Myc-hPPARδ, about 34% for Myc-ΔN-term, and 0% for Myc-ΔLBD (bands were not confirmed in the Western blotting). From these results, it was found that metformin binds to LBD of PPARδ.

Example 2

PPARδ forms a heterodimer with the nuclear receptor RXR (Retinoid X receptor) in the nucleus, binds to the transcriptional activator PGC1α (peroxisome proliferative activated receptor gamma coactivator-1) in the presence of a ligand for PPARδ, and serves as a positive transcriptional regulator. Therefore, a luciferase assay was performed to verify the effect of metformin on the transcriptional regulation of PPARδ.

Luciferase Assay Using PPRE×2-Tk-Luciferase:

In order to investigate the transcriptional activation of PPARδ by metformin, human PPARδ was overexpressed in human embryonic kidney-derived cultured cell line HEK293 cells together with RXRα and PGC1α. A luciferase assay was performed using a thymidine kinase promoter (tk)/luciferase gene reporter plasmid having two DNA sequences (PPAR-Response Elements) to which the PPARδ/RXRα complex binds as a reporter. As a positive control for PPARδ activation, GW501516 (manufactured by GlaxoSmithKline plc), which is an agonist of PPARδ, was used. The ratio (Relative Light Unit; RLU) of the amount of luminescence of a reaction solution to the amount of luminescence of a reaction solution to which an equal amount of DMSO was added (control) was defined as a relative activity value.

Figure 10A:
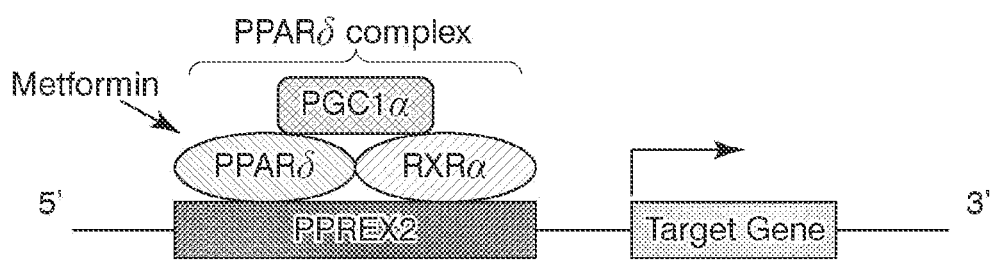
FIG. 10A is a schematic diagram showing the mechanism by which the PPARδ complex (hPPARδ, PGC1α, RXRα) transcriptionally activates PPRE (PPAR-response element), and the relationship between the PPARδ complex and metformin.
Figure 10B:
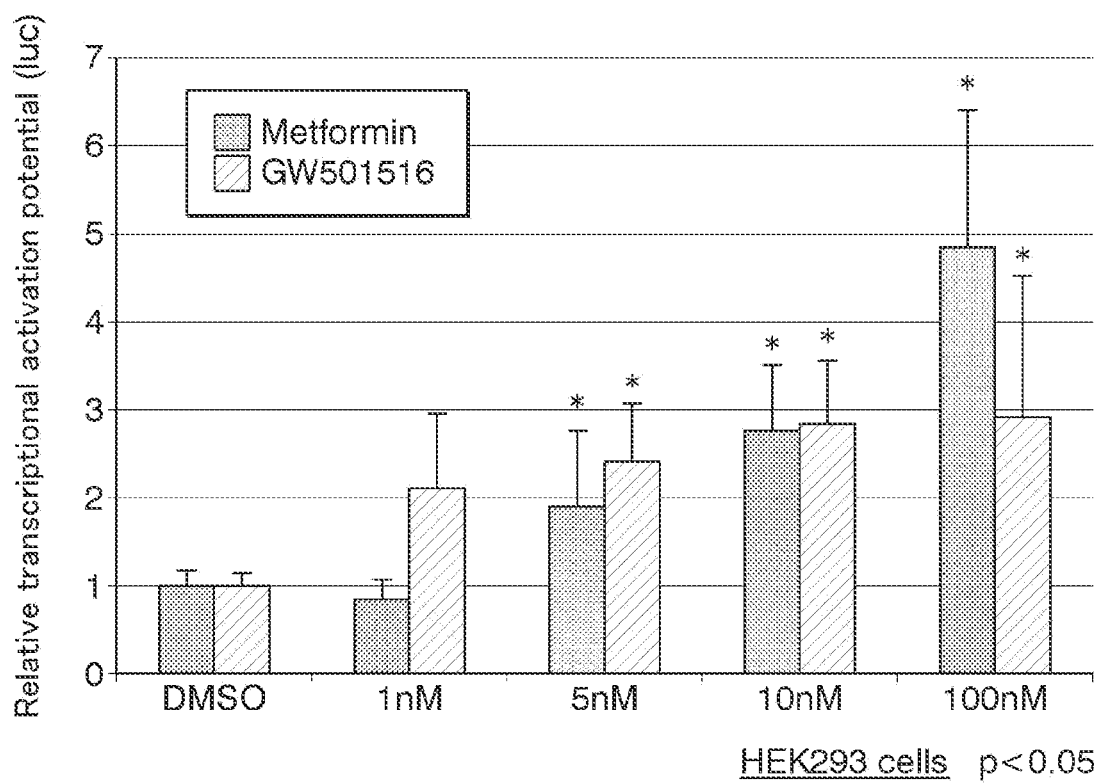
FIG. 10B is a diagram showing the results of a luciferase assay using PPRE×2-tk-luciferase in cells treated with metformin or GW501516 in Example 2.

The results of the luciferase assay are shown in FIG. 10B. In the presence of the PPARδ complex (hPPARδ, PGC1α, RXRα), metformin was able to activate the transcription in a concentration-dependent manner through PPRE (PPAR-Response Element, PPAR response sequence that also has a PPARδ binding sequence) (FIGS. 10A and 10B). Moreover, this activation ability was about the same as that of GW501516. From these results, it was confirmed that metformin activates the transcription by hPPARδ.

Measurement of PPARδ/PGC1α Transcription Complex Formation by Co-Immunoprecipitation Method:

It is known that transcriptional activation by an agonist of PPARδ is caused by binding the agonist to the ligand binding pocket of PPARδ and inducing the formation of a transcriptional complex with PGC1α, which is a transcriptional co-activator. The agonist binds to the ligand binding pocket of PPARδ. Therefore, the amount of the PPARδ/PGC1α transcription complex of the cells treated with metformin or GW501516 was quantified. As a control, DMSO (dimethyl sulfoxide) treatment was performed.

Figure 11:
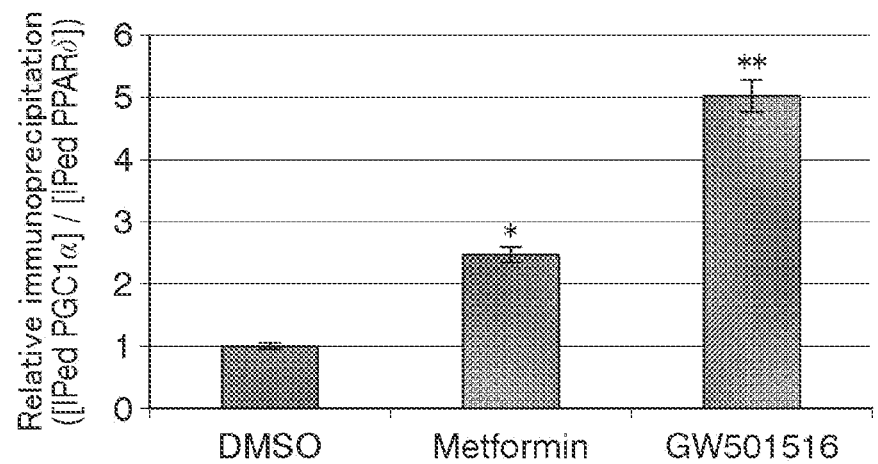
FIG. 11 is a diagram showing the measurement results of the amount of PGC1α co-purifed along with Myc-hPPARδ by an anti-Myc antibody (PGC1α amount relative to Myc-hPPARδ amount in immunoprecipitate: [PGC1α amount]/[Myc-hPPARδ amount]). Immunoprecipitation was carried out on the extracts of cells overexpressing, RXRα, and PGC1α treated with metformin, GW501516, or DMSO in Example 2.

First, overexpressed cells that strongly express Myc-hPPARδ, RXRα, and PGC1α were prepared using HEK293 cells. The overexpressed cells were treated with metformin, GW501516, or DMSO, and then a cell extract was prepared. Immunoprecipitation was performed on the obtained cell extract using an anti-Myc antibody, and Western blotting was performed on the obtained immunoprecipitates using an anti-PGC1α antibody (ab54481, manufactured by Abcam), thereby measuring the relative amount of co-precipitated PGC1α (amount of PGC1α relative to amount of Myc-hPPARδ in the immunoprecipitate (IPed): [amount of PGC1α in the immunoprecipitate]/[amount of Myc-hPPARδ in the immunoprecipitate]). The results are shown in FIG. 11. In metformin-treated cells and GW501516-treated cells, an increase in the amount of co-precipitated PGC1α was observed as compared with DMSO-treated cells. This result showed that metformin binds to the ligand binding pocket of PPARδ and induces the formation of a transcription complex with PGC1α.

Example 3

The effect of metformin on the transcriptional activation by PPARδ in muscle differentiation was investigated.

qPCR Analysis of Target Gene of PPARδ:

Mouse skeletal muscle-derived myoblast cell line C2C12 cells were stimulated by low-serum concentration to induce muscle differentiation and further treated with 100 μM metformin, 1 μM GW501516, or DMSO on day 6 of differentiation. The expression of the target genes of PPARδ was analyzed by qPCR in the treated cells. As the target genes, four genes, namely, the angptl4 gene, pdk4 gene, pin gene, and the ucp3 gene were measured.

Figure 12:
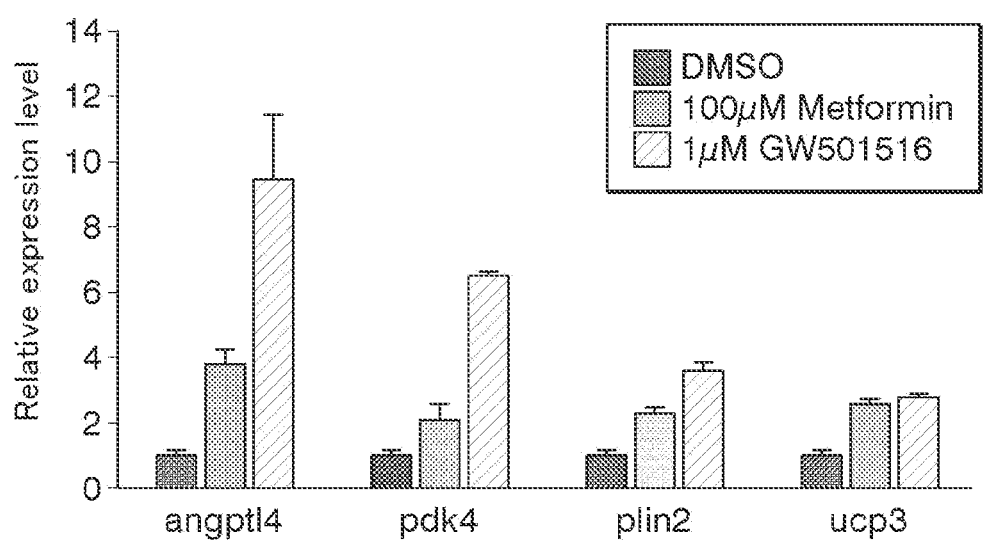
FIG. 12 is a diagram showing the measurement results of the relative expression level of the target genes of PPARδ (the expression level of DMSO-treated cells is set as 1) in C2C12 cells on day 6 of skeletal muscle differentiation induced by low concentration-serum. Cells were treated with metformin, GW501516, or DMSO in Example 3.

FIG. 12 shows the measurement results of the relative expression level when the expression level of the DMSO-treated cells was set as 1. As a result, although the target gene induction efficiency by GW501516 treatment was inferior, metformin was able to induce the expression of the target genes of PPARδ.

Measurement of Effect of Metformin on Recruitment of PPARδ to PPRE:

Investigation of whether the transcription factor PPARδ was recruited to the promoter of the target genes by metformin treatment was carried out.

First, C2C12-PPARδ cells, in which FLAG-tagged PPARδ (FLAG-PPARδ) was constitutively over-expressed in C2C12 cells were prepared. C2C12-PPARδ cells were stimulated by low-serum concentration to induce muscle differentiation and treated with 100 μM metformin, 1 μM GW501516, or DMSO on day 6 of differentiation. The treated cells were subjected to chromatin immunoprecipitation (Conventional ChIP) using an antibody that recognizes the FLAG tag.

Figure 13:
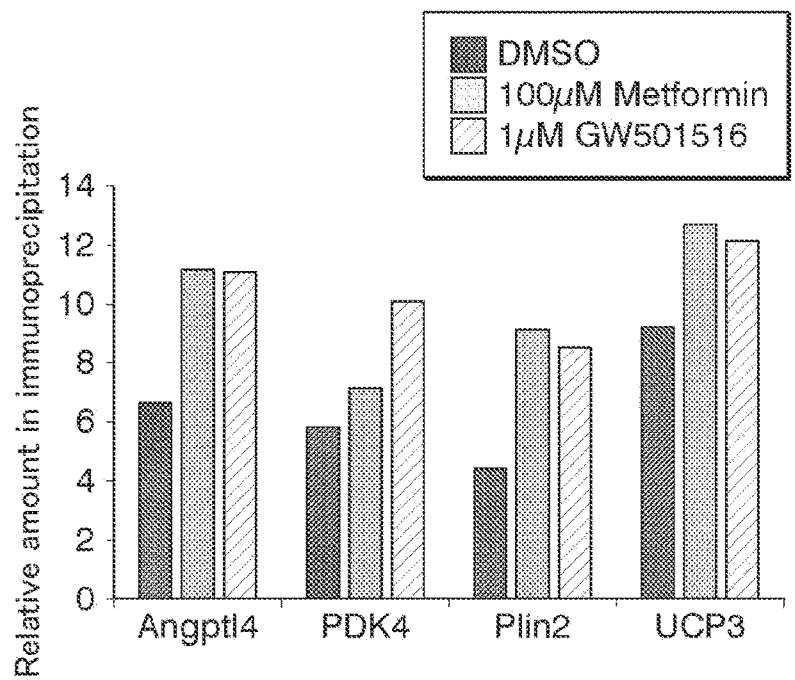
FIG. 13 is a diagram showing the results of chromatin immunoprecipitation using an anti-FLAG antibody on C2C12-Flag-tagged PPARδ expressing cells treated with metformin, GW501516, or DMSO on day 6 of skeletal muscle differentiation induced by low concentration-serum in Example 3.

FIG. 13 shows the measurement results of the relative values of the DNA amounts of the Angptl4 gene, Pdk4 gene, Plin2 gene, and the Ucp3 gene in the chromatin immunoprecipitation (ratio of chromatin amount obtained in each IP to input chromatin amount, the amount of DNA in the IgG control was set as 1). As a result, it was shown that PPARδ was recruited in the vicinity of PPRE (the PPAR response regions) on the promoters of the Angptl4 gene, Pdk4 gene, Plin2 gene, and the Ucp3 gene by metformin treatment or GW501516 treatment, as in the results observed in gene expression.

Example 4

PPARδ is known to induce the expression of lipid metabolism-related genes and enhance β-oxidation of fatty acids, especially in skeletal muscle. The PPARδ agonist is expected to have an effect of increasing mitochondrial activity. Therefore, investigation of the effect of metformin on metabolism, especially mitochondrial activity was carried out. Specifically, using C2C12 cells, the oxygen consumption rate (OCR: Oxygen Consumption Rate) of the cells was measured by a cell metabolism-measuring device (extracellular flux analyzer manufactured by Agilemt Technologies Inc.).

Figure 14:
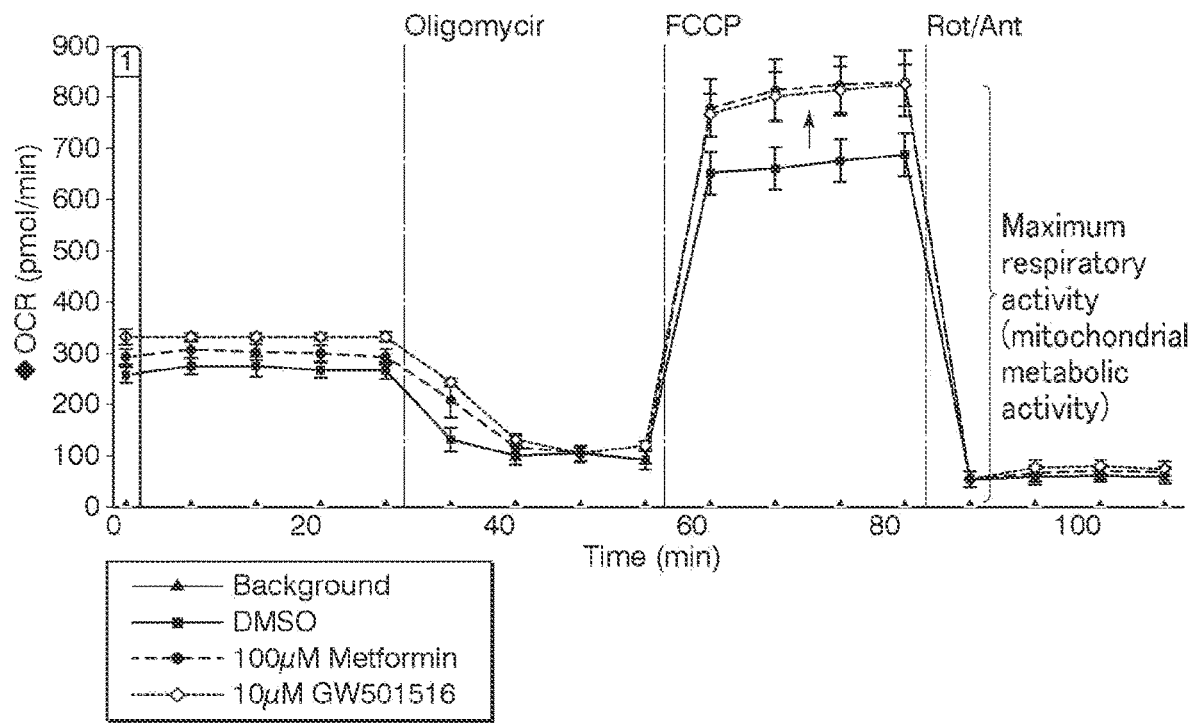
FIG. 14 is a diagram showing the results of measuring the mitochondrial activity of C2C12 cells in the presence of metformin or GW501516 in Example 4.

In this metabolic measurement, four inhibitors were used to force changes in intracellular metabolism (FIG. 14). First, oligomycin, which inhibits Complex V of the electron transport chain, was added. Oligomycin inhibited ATP production and reduced OCR. Next, the uncoupling agent FCCP (Carbonyl cyanide-p-trifluoromethoxyphenylhydrazone) was added. FCCP forcibly discharges hydrogen ions in the mitochondrial membrane to the outside of the membrane to eliminate the proton concentration gradient. Since a proton concentration gradient is required to produce ATP, the TCA cycle and electron transport chain are maximally activated when the gradient is forcibly eliminated by FCCP. This makes it possible to measure the maximum respiration rate of cells. It is known that OCR at this time is further increased in cells in which fatty acid oxidation is enhanced. Finally, rotenone and antimycin were added. Rotenone inhibits the electron transport chain complex I, and antimycin inhibits complex III. With the addition of these inhibitors, the electron transport chain was completely stopped and the OCR of the cells became almost zero.

C2C12 cells were treated with solvent (DMSO), 100 µM metformin, or 10 µM GW501516 for 24 hours, inhibitors were added in the above order, and OCR was measured. The measurement result of OCR is shown in FIG. 14. As a result, the base OCR (pmol/min) before the inhibitor treatment did not change in either the metformin treatment or the GW501516 treatment. After FCCP addition, an increase in OCR was observed in metformin-treated cells and GW501516-treated cells as compared to DMSO-treated cells (FIG. 14, arrow). This indicates that metformin also increased mitochondrial metabolic activity (respiratory activity) in the same manner as GW501516.

Example 5

A series of conventionally developed synthetic agonists of PPARδ (GW agonists) represented by GW501516 are phenoxyacetic acid derivatives and have a basic skeleton of a chemical structure in which a long-chain hydrophobic group such as a non-polar hydrocarbon is bonded to a carboxyl group (—COOH). In contrast, metformin is a biguanide-based medicine having no chemical structural similarity to conventional GW medicines. Metformin does not have either the carboxyl group or the long-chain hydrophobic group that are essential for the specific binding of the ligand-binding pocket of GW medicines and PPARδ. In addition, the physical characteristics of the conventional GW agonists are characterized by being acidic and non-polar, whereas metformin is basic and water-soluble. In addition, the molecular size of the conventional GW agonists corresponds to the size of the ligand binding pocket of PPARδ, but metformin is significantly smaller. For example, the molecular weights of the typical synthetic agonists GW501516 and GW2331 are 453.5 and 490.3, respectively, while metformin is 169.2, which is about one-third. Thus, metformin has no commonality with any conventional medicine targeting PPARδ, and it is not possible to predict how it binds to PPARδ from conventional agonists with known complex structures. Therefore, a crystal of a complex of PPARδ LBD and metformin was prepared, and the three-dimensional structure of the complex was determined by X-ray crystallography.

Production of LBD Polypeptide of PPARδ:

The crystal structure of the complex of the polypeptide (PPARδ-LBD) from the 170th glutamine to the 441st tyrosine (carboxyl terminal, C-terminal) of the amino acid sequence of PPARδ and metformin was analyzed.

PPARδ-LBD was prepared as follows. First, it was expressed in *Escherichia coli* as a His×6-tagged polypeptide, and then lysed to separate an insoluble fraction. The separated insoluble fraction was solubilized with a solubilizing solution (20 mM Tris-Cl (pH 7.5), 2 M urea, 2 mM DTT, 500 mM NaCl, 0.5% Tween 20) and then centrifuged (25,000 rpm, 45 minutes) to separate the supernatant. The obtained supernatant was dialyzed to remove urea and Tween20, purified using a Ni-affinity column (Ni-NTA Agarose, manufactured by QIAGEN, Beverly Inc.), and then the His×6 tag was cleaved with HRV3C. The cleaved polypeptide was concentrated with Amicon (Amicon Ultra tube cutoff molecular weight 10,000, manufactured by Merck Millipore), and purified with an equilibrated Superdex 75 pg gel filtration column (manufactured by GE Healthcare) using a development solution (20 mM TrisCl (pH 7.5), 500 mM NaCl, 0.5 mM Tris (2-carboxyl) phosphate (TCEP)). Fractions containing PPARδ-LBD were concentrated to 10 mg/mL with amicon to prepare crystallization samples. The purified samples were confirmed to be PPARδ-LBD by mass spectrometry (MALDI-TOF MS, manufactured by Bruker Daltonics Inc.), and were instantly frozen in liquid nitrogen and stored at a low temperature of −80° C.

Crystal Preparation:

The complex crystal of PPARδ-LBD and metformin was prepared by a hanging drop type vapor diffusion equilibrium method. Metformin aqueous solution prepared by dissolving metformin hydrochloride (manufactured by LKT Laboratories, Inc.) in purified distilled water to 100 mM was mixed with a purified PPARδ-LBD sample to prepare a sample solution for crystallization (PPARδ-LBD concentration: 0.3 mM, PPARδ-LBD:metformin=1:10 (molar ratio)). For crystallization, 1 µL of the sample solution for crystallization and a reservoir solution (40 mM bis-tris-propylene (pH 6.8), 10 mM DTT, 2.5% EDTA (1,2-propanediol, 1 mM propylenediaminetetraacetic acid), 0.5% HBDG (detergent n-Heptyl-β-D-thioglucoside)), 200 µM KCl, 4% PEG8K) were mixed and vapor equilibrated against the reservoir solution at a temperature of 20° C. to obtain crystals in about 4 days.

Figure 15:
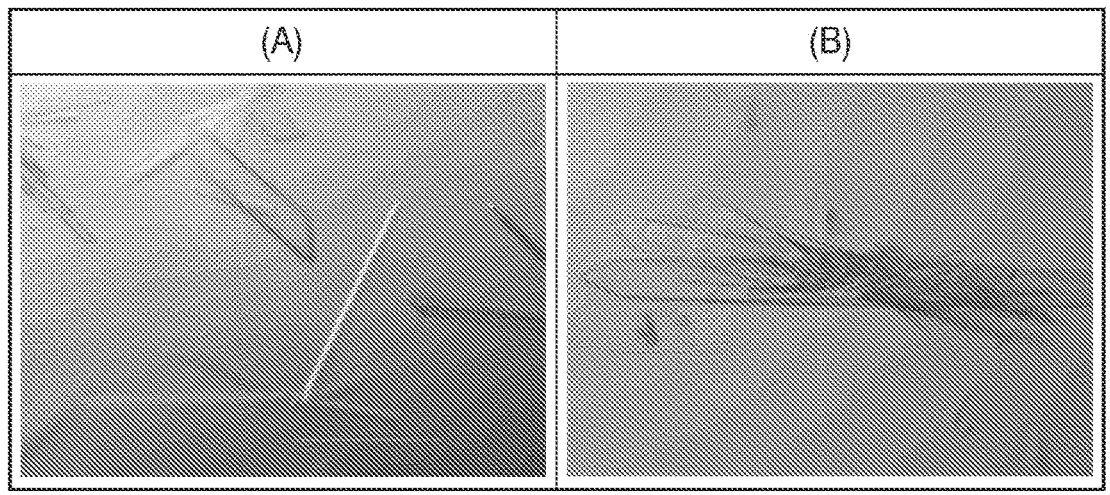
FIG. 15 is a photomicrograph of the complex crystal (A) of PPARδ-LBD and metformin and the complex crystal (B) of PPARδ-LBD and phenformin in Example 5.

A photomicrograph of the obtained complex crystal of metformin-bound PPARδ-LBD is shown in FIG. 15(A). In the figure, the scale bar is 100 µm. The crystal had a unit lattice constant of 49.34 Å for a; 57.88 Å for b; 59.16 Å for c; 98.07° for α; 90.08° for β; 107.02° for γ, and belonged to the triclinic space group P1. The crystals were flash frozen in liquid nitrogen using 30% glycerol as an antifreeze.

Acquisition of Three-Dimensional Structural Coordinates:

X-ray intensity data was collected using a MX300HE detector at the beamline BL41XU of the large radiation facility SPring-8 at a temperature of 100 K° C. The collected X-ray intensity data was subjected to various corrections and the like with software for X-ray diffraction data processing (DENZO/SCALPACK, HKL2000 program) to obtain an X-ray intensity data set (resolution: 2.00 Å) for structural analysis. The structural analysis was based on the published structure (PDB code 5U3Q) of PPARδ-LBD registered in the RCSB Protein Data Bank (Rutgers, UCSD), and the initial phase was determined by the molecular substitution method using a program (PHASER). The structural model was modified and reconstructed using a molecular graphics program (COOT) and refined by a program (PHENIX). By repeating these model modifications and refinements, an atomic model of a complex of 18.4% of R-factor and 21.4% of Free R-factor was obtained.

For the complex of PPARδ-LBD and phenformin, the same experiment as that for metformin was carried out, and crystals (the unit lattice constant was 49.21 Å for a; 57.64 Å for b; 107.82 Å for c; 98.02° for α; 90.03° for β; 107.08° for γ, and belonged to the triclinic space group P1) of almost the same type as the complex of PPARδ-LBD and metformin were obtained. A photomicrograph of the obtained crystal is shown in FIG. 15(B). In the figure, the scale bar is 100 μm.

Furthermore, structural analysis was carried out using the PPARδ-LBD structure in the metformin complex. As a result, an atomic model of a complex having a resolution of 2.29 Å, 19.3% of R-factor, and 22.0% of Free R-factor was obtained.

Figure 16:
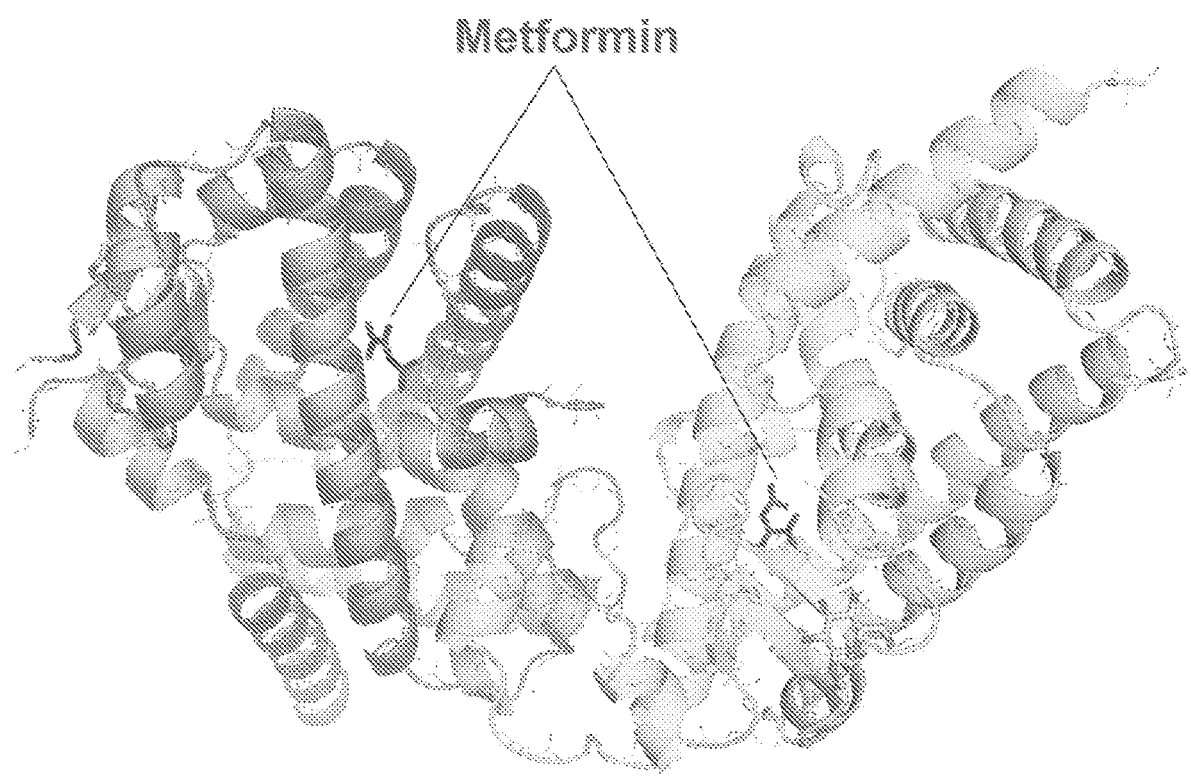
FIG. 16 is a diagram showing the structure of a complex crystal of PPARδ-LBD and metformin in Example 5.

Three-Dimensional Structural Data of Complex Crystal of PPARδ-LBD and Metformin:

The structure of the complex crystal of PPARδ-LBD and metformin is shown in FIG. 16. Two molecules of PPARδ-LBD (molecule A and Molecule B in the figure) having almost the same structure were present in the crystal, and metformin was bound to a ligand-binding pocket in each domain. The surfactant HBDG used for crystallization was bound to the molecular surface of each PPARδ-LBD.

The structure of PPARδ-LBD in the complex crystal was composed of fifteen α-helices H1-H12, H2', H2", H3' and three β-strands S1, S2, S3, and the three β-strands formed one antiparallel β-sheet (FIG. 16). There was a cavity (ligand binding pocket) in the center of the molecule to which a Y-shaped ligand could bind. This overall structure was almost the same as the basic structure of PPARδ-LBD reported so far (NPL 7 and 8). It was also similar to the structure of LBD of PPARα and LBD of PPARγ.

Figure 17:
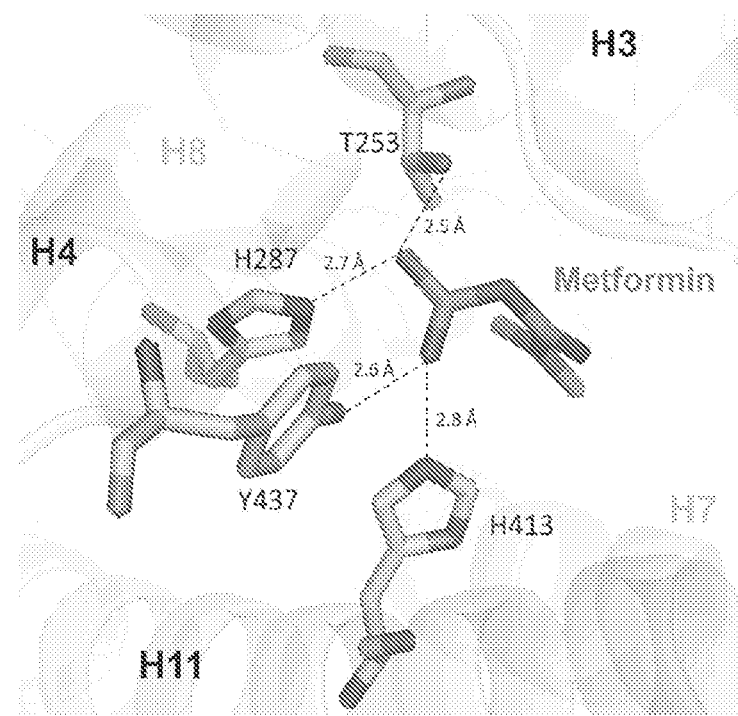
FIG. 17 is a diagram showing a metformin molecule in a ligand-binding pocket of PPARδ-LBD in a complex crystal of PPARδ-LBD and metformin in Example 5.

FIG. 17 shows the metformin molecule in the ligand binding pocket in the complex crystal. In the figure, the broken line indicates the hydrogen bond, and the attached numerical value indicates the distance. H3, H4, H11 and the like represent α-helices that form ligand binding pockets. This ligand-binding pocket was Y-shaped and had three tunnel-like cavities called arms I, II, and III. The metformin molecule was bound to arm I formed from the α-helices H3, H4, H11, and H12, and the two amino groups of the biguanide skeleton of metformin were immobilized by forming direct hydrogen bonds with residues of each α-helix, Thr253 (α-helix H3), His287 (α-helix H4), His413 (α-helix H11) and Tyr437 (α-helix H12). A peptide region (Leu429-Med441) called the AF-2 fragment (activation function-2 segment), which is essential for PPAR activation, was bound to the LBD by forming α-helix H12 so as to cover the ligand-binding pocket. This means that the LBD of PPARδ bound to metformin has an active conformation. Since the formation of this α-helix H12 was induced by the direct interaction with metformin described above, it corresponds well to metformin being an agonist of PPARδ.

In addition to the polar interactions such as hydrogen bonds mentioned above, by fitting metformin within the narrow space at the tip of arm I, all the atoms were in contact with the atoms of PPARδ-LBD in addition to the hydrogen bond, and the bond was stabilized. The biguanide skeleton of metformin was in non-polar contact with Leu433, Phe246, and Met417. The two methyl groups of metformin were in non-polar contact with Thr253, Ph291, Cys249 and Ile327. Metformin is a small molecule and is not large enough to fill all the ligand binding pockets of PPARδ-LBD. The tips of the two methyl groups of metformin were connected to the cavities of arm II and arm III, but these arms remained empty.

Figure 18:
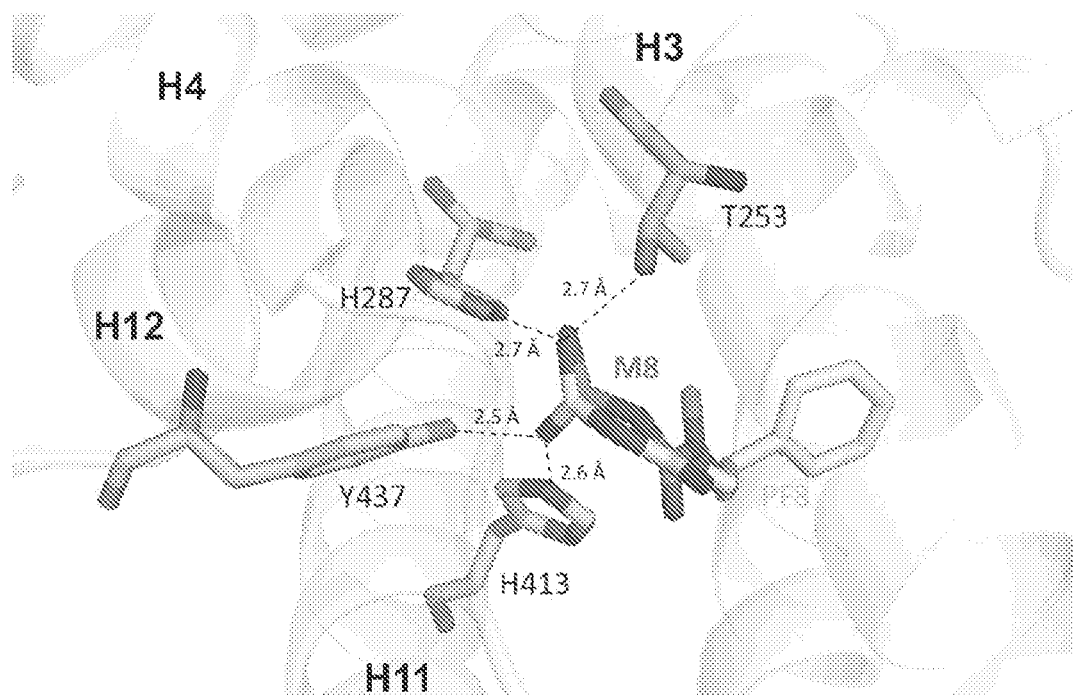
FIG. 18 is a diagram comparing the structures of metformin bound to PPARδ-LBD and phenformin in Example 5.

The above interaction characteristics were also observed in the structure of the complex of phenformin and PPARδ-LBD. FIG. 18 is a diagram in which the structure of the complex crystal of metformin and PPARδ-LBD and the structure of the complex crystal of phenformin and PPARδ-LBD are superimposed. In the figure, the broken line indicates the hydrogen bond, and the attached numerical value indicates the distance. H3, H4, H11, and H12 indicate α-helices that form ligand-binding pockets. The biguanide skeleton of phenformin overlapped well with the biguanide skeleton of metformin, and phenformin also formed hydrogen bonds similar to the four hydrogen bonds of metformin. The phenyl group of phenformin protruded into the large space behind the hydrophobic ligand-binding pocket, but there was no close non-polar contact with PPARδ.

The shape of the ligand binding pocket of hPPARδ can be drawn by incorporating the data of Tables 1 to 63 into the molecular graphics software PyMOL.

TABLE 1

| ATOM | 1 | N | VAL | A | 172 | −76.185 | 38.759 | 23.431 | 1.00 | 52.70 | N |
|---|---|---|---|---|---|---|---|---|---|---|---|
| ATOM | 2 | CA | VAL | A | 172 | −77.335 | 39.035 | 22.492 | 1.00 | 50.01 | C |
| ATOM | 3 | C | VAL | A | 172 | −78.505 | 39.589 | 23.289 | 1.00 | 50.21 | C |
| ATOM | 4 | O | VAL | A | 172 | −79.014 | 40.651 | 22.934 | 1.00 | 46.42 | O |
| ATOM | 5 | CB | VAL | A | 172 | −77.751 | 37.772 | 21.675 | 1.00 | 59.23 | C |
| ATOM | 6 | CG1 | VAL | A | 172 | −79.149 | 37.894 | 21.007 | 1.00 | 56.55 | C |
| ATOM | 7 | CG2 | VAL | A | 172 | −76.677 | 37.483 | 20.631 | 1.00 | 61.76 | C |
| ATOM | 8 | N | ALA | A | 173 | −78.916 | 38.880 | 24.351 | 1.00 | 42.75 | N |
| ATOM | 9 | CA | ALA | A | 173 | −80.048 | 39.296 | 25.221 | 1.00 | 44.81 | C |
| ATOM | 10 | C | ALA | A | 173 | −80.006 | 40.762 | 25.699 | 1.00 | 49.28 | C |
| ATOM | 11 | O | ALA | A | 173 | −81.047 | 41.447 | 25.653 | 1.00 | 43.42 | O |
| ATOM | 12 | CB | ALA | A | 173 | −80.197 | 38.379 | 26.433 | 1.00 | 44.28 | C |
| ATOM | 13 | N | ASP | A | 174 | −78.834 | 41.202 | 26.186 | 1.00 | 40.11 | N |
| ATOM | 14 | CA | ASP | A | 174 | −78.687 | 42.529 | 26.733 | 1.00 | 42.61 | C |
| ATOM | 15 | C | ASP | A | 174 | −78.667 | 43.604 | 25.625 | 1.00 | 31.66 | C |
| ATOM | 16 | O | ASP | A | 174 | −79.182 | 44.676 | 25.837 | 1.00 | 32.54 | O |
| ATOM | 17 | CB | ASP | A | 174 | −77.467 | 42.622 | 27.621 | 1.00 | 48.17 | C |
| ATOM | 18 | CG | ASP | A | 174 | −77.573 | 41.709 | 28.833 | 1.00 | 51.88 | C |
| ATOM | 19 | OD1 | ASP | A | 174 | −78.571 | 41.792 | 29.570 | 1.00 | 58.12 | O |
| ATOM | 20 | OD2 | ASP | A | 174 | −76.667 | 40.885 | 29.031 | 1.00 | 54.26 | O1− |
| ATOM | 21 | N | LEU | A | 175 | −78.102 | 43.295 | 24.479 | 1.00 | 29.50 | N |
| ATOM | 22 | CA | LEU | A | 175 | −78.105 | 44.220 | 23.355 | 1.00 | 35.50 | C |
| ATOM | 23 | C | LEU | A | 175 | −79.527 | 44.345 | 22.747 | 1.00 | 33.52 | C |
| ATOM | 24 | O | LEU | A | 175 | −79.900 | 45.381 | 22.183 | 1.00 | 25.39 | O |
| ATOM | 25 | CB | LEU | A | 175 | −77.110 | 43.795 | 22.290 | 1.00 | 35.60 | C |
| ATOM | 26 | CG | LEU | A | 175 | −75.606 | 43.968 | 22.595 | 1.00 | 39.37 | C |
| ATOM | 27 | CD1 | LEU | A | 175 | −74.788 | 43.137 | 21.631 | 1.00 | 36.52 | C |
| ATOM | 28 | CD2 | LEU | A | 175 | −75.140 | 45.403 | 22.529 | 1.00 | 40.09 | C |
| ATOM | 29 | N | LYS | A | 176 | −80.272 | 43.253 | 22.793 | 1.00 | 30.78 | N |
| ATOM | 30 | CA | LYS | A | 176 | −81.667 | 43.264 | 22.342 | 1.00 | 30.46 | C |
| ATOM | 31 | C | LYS | A | 176 | −82.485 | 44.083 | 23.317 | 1.00 | 24.09 | C |

TABLE 1-continued

| ATOM | 32 | O | LYS | A | 176 | −83.309 | 44.931 | 22.903 | 1.00 | 28.28 | O |
| --- | --- | --- | --- | --- | --- | --- | --- | --- | --- | --- | --- |
| ATOM | 33 | CB | LYS | A | 176 | −82.187 | 41.821 | 22.156 | 1.00 | 32.44 | C |
| ATOM | 34 | CG | LYS | A | 176 | −83.358 | 41.701 | 21.224 | 1.00 | 46.17 | C |
| ATOM | 35 | CD | LYS | A | 176 | −83.949 | 40.281 | 21.175 | 1.00 | 48.50 | C |

TABLE 2

| ATOM | 36 | CE | LYS | A | 176 | −85.386 | 40.271 | 21.683 | 1.00 | 53.08 | C |
| --- | --- | --- | --- | --- | --- | --- | --- | --- | --- | --- | --- |
| ATOM | 37 | NZ | LYS | A | 176 | −85.892 | 38.878 | 21.847 | 1.00 | 55.95 | N1+ |
| ATOM | 38 | N | ALA | A | 177 | −82.295 | 43.889 | 24.604 | 1.00 | 20.61 | N |
| ATOM | 39 | CA | ALA | A | 177 | −82.997 | 44.685 | 25.563 | 1.00 | 24.27 | C |
| ATOM | 40 | C | ALA | A | 177 | −82.707 | 46.175 | 25.514 | 1.00 | 23.29 | C |
| ATOM | 41 | O | ALA | A | 177 | −83.559 | 46.976 | 25.845 | 1.00 | 24.10 | O |
| ATOM | 42 | CB | ALA | A | 177 | −82.779 | 44.202 | 27.003 | 1.00 | 26.55 | C |
| ATOM | 43 | N | PHE | A | 178 | −81.454 | 46.630 | 25.294 | 1.00 | 28.53 | N |
| ATOM | 44 | CA | PHE | A | 178 | −81.050 | 47.934 | 25.261 | 1.00 | 27.37 | C |
| ATOM | 45 | C | PHE | A | 178 | −81.719 | 48.583 | 24.054 | 1.00 | 24.62 | C |
| ATOM | 46 | O | PHE | A | 178 | −82.253 | 49.682 | 24.168 | 1.00 | 25.13 | O |
| ATOM | 47 | CB | PHE | A | 178 | −79.509 | 48.020 | 25.140 | 1.00 | 27.11 | C |
| ATOM | 48 | CG | PHE | A | 178 | −78.961 | 49.415 | 25.227 | 1.00 | 26.79 | C |
| ATOM | 49 | CD1 | PHE | A | 178 | −78.863 | 50.205 | 24.085 | 1.00 | 26.67 | C |
| ATOM | 50 | CD2 | PHE | A | 178 | −78.513 | 49.932 | 26.436 | 1.00 | 28.08 | C |
| ATOM | 51 | CE1 | PHE | A | 178 | −78.334 | 51.526 | 24.127 | 1.00 | 26.61 | C |
| ATOM | 52 | CE2 | PHE | A | 178 | −78.010 | 51.241 | 26.496 | 1.00 | 29.20 | C |
| ATOM | 53 | CZ | PHE | A | 178 | −77.887 | 52.025 | 25.339 | 1.00 | 27.65 | C |
| ATOM | 54 | N | SER | A | 179 | −81.587 | 47.940 | 22.897 | 1.00 | 24.32 | N |
| ATOM | 55 | CA | SER | A | 179 | −82.240 | 48.400 | 21.691 | 1.00 | 25.78 | C |
| ATOM | 56 | C | SER | A | 179 | −83.748 | 48.636 | 21.790 | 1.00 | 26.17 | C |
| ATOM | 57 | O | SER | A | 179 | −84.258 | 49.609 | 21.227 | 1.00 | 28.31 | O |
| ATOM | 58 | CB | SER | A | 179 | −82.027 | 47.458 | 20.554 | 1.00 | 25.46 | C |
| ATOM | 59 | OG | SER | A | 179 | −80.652 | 47.358 | 20.287 | 1.00 | 27.99 | O |
| ATOM | 60 | N | LYS | A | 180 | −84.446 | 47.677 | 22.370 | 1.00 | 26.41 | N |
| ATOM | 61 | CA | LYS | A | 180 | −85.881 | 47.773 | 22.647 | 1.00 | 26.93 | C |
| ATOM | 62 | C | LYS | A | 180 | −86.184 | 48.894 | 23.598 | 1.00 | 26.62 | C |
| ATOM | 63 | O | LYS | A | 180 | −87.176 | 49.597 | 23.425 | 1.00 | 22.77 | O |
| ATOM | 64 | CB | LYS | A | 180 | −86.401 | 46.433 | 23.233 | 1.00 | 28.63 | C |
| ATOM | 65 | CG | LYS | A | 180 | −87.914 | 46.349 | 23.412 | 1.00 | 31.99 | C |
| ATOM | 66 | CD | LYS | A | 180 | −88.584 | 46.557 | 22.076 | 1.00 | 38.19 | C |
| ATOM | 67 | CE | LYS | A | 180 | −88.228 | 45.451 | 21.094 | 1.00 | 40.17 | C |
| ATOM | 68 | NZ | LYS | A | 180 | −88.587 | 44.089 | 21.621 | 1.00 | 45.48 | N1+ |
| ATOM | 69 | N | HIS | A | 181 | −85.324 | 49.108 | 24.606 | 1.00 | 23.61 | N |
| ATOM | 70 | CA | HIS | A | 181 | −85.570 | 50.177 | 25.502 | 1.00 | 24.20 | C |

TABLE 3

| ATOM | 71 | C | HIS | A | 181 | −85.507 | 51.590 | 24.810 | 1.00 | 21.61 | C |
| --- | --- | --- | --- | --- | --- | --- | --- | --- | --- | --- | --- |
| ATOM | 72 | O | HIS | A | 181 | −86.349 | 52.440 | 24.987 | 1.00 | 20.60 | O |
| ATOM | 73 | CB | HIS | A | 181 | −84.564 | 50.083 | 26.652 | 1.00 | 27.72 | C |
| ATOM | 74 | CG | HIS | A | 181 | −84.624 | 51.236 | 27.574 | 1.00 | 29.34 | C |
| ATOM | 75 | CD2 | HIS | A | 181 | −83.963 | 52.421 | 27.566 | 1.00 | 30.58 | C |
| ATOM | 76 | ND1 | HIS | A | 181 | −85.508 | 51.290 | 28.626 | 1.00 | 33.01 | N |
| ATOM | 77 | CE1 | HIS | A | 181 | −85.343 | 52.428 | 29.274 | 1.00 | 34.58 | C |
| ATOM | 78 | NE2 | HIS | A | 181 | −84.425 | 53.142 | 28.647 | 1.00 | 32.87 | N |
| ATOM | 79 | N | ILE | A | 182 | −84.510 | 51.778 | 23.978 | 1.00 | 24.67 | N |
| ATOM | 80 | CA | ILE | A | 182 | −84.369 | 52.999 | 23.222 | 1.00 | 26.38 | C |
| ATOM | 81 | C | ILE | A | 182 | −85.564 | 53.147 | 22.227 | 1.00 | 22.03 | C |
| ATOM | 82 | O | ILE | A | 182 | −86.101 | 54.243 | 22.039 | 1.00 | 23.94 | O |
| ATOM | 83 | CB | ILE | A | 182 | −82.992 | 53.011 | 22.516 | 1.00 | 24.35 | C |
| ATOM | 84 | CG1 | ILE | A | 182 | −81.797 | 53.039 | 23.528 | 1.00 | 25.44 | C |
| ATOM | 85 | CG2 | ILE | A | 182 | −82.858 | 54.181 | 21.579 | 1.00 | 22.74 | C |
| ATOM | 86 | CD1 | ILE | A | 182 | −81.825 | 54.167 | 24.530 | 1.00 | 29.44 | C |
| ATOM | 87 | N | TYR | A | 183 | −85.969 | 52.059 | 21.615 | 1.00 | 23.11 | N |
| ATOM | 88 | CA | TYR | A | 183 | −87.124 | 52.120 | 20.632 | 1.00 | 25.83 | C |
| ATOM | 89 | C | TYR | A | 183 | −88.388 | 52.482 | 21.376 | 1.00 | 25.20 | C |
| ATOM | 90 | O | TYR | A | 183 | −89.053 | 53.417 | 20.978 | 1.00 | 24.99 | O |
| ATOM | 91 | CB | TYR | A | 183 | −87.265 | 50.826 | 19.881 | 1.00 | 25.77 | C |
| ATOM | 92 | CG | TYR | A | 183 | −88.375 | 50.749 | 18.873 | 1.00 | 27.56 | C |
| ATOM | 93 | CD1 | TYR | A | 183 | −88.736 | 51.833 | 18.117 | 1.00 | 25.51 | C |
| ATOM | 94 | CD2 | TYR | A | 183 | −89.016 | 49.548 | 18.656 | 1.00 | 29.78 | C |
| ATOM | 95 | CE1 | TYR | A | 183 | −89.729 | 51.750 | 17.163 | 1.00 | 29.45 | C |
| ATOM | 96 | CE2 | TYR | A | 183 | −90.031 | 49.433 | 17.712 | 1.00 | 33.07 | C |
| ATOM | 97 | CZ | TYR | A | 183 | −90.388 | 50.545 | 16.966 | 1.00 | 32.67 | C |
| ATOM | 98 | OH | TYR | A | 183 | −91.405 | 50.438 | 16.055 | 1.00 | 32.23 | O |
| ATOM | 99 | N | ASN | A | 184 | −88.610 | 51.884 | 22.558 | 1.00 | 26.33 | N |
| ATOM | 100 | CA | ASN | A | 184 | −89.697 | 52.319 | 23.413 | 1.00 | 25.07 | C |

TABLE 3-continued

| ATOM | 101 | C | ASN | A | 184 | −89.716 | 53.770 | 23.731 | 1.00 | 27.45 | C |
| --- | --- | --- | --- | --- | --- | --- | --- | --- | --- | --- | --- |
| ATOM | 102 | O | ASN | A | 184 | −90.805 | 54.394 | 23.663 | 1.00 | 26.57 | O |
| ATOM | 103 | CB | ASN | A | 184 | −89.769 | 51.559 | 24.744 | 1.00 | 28.54 | C |
| ATOM | 104 | CG | ASN | A | 184 | −90.248 | 50.151 | 24.562 | 1.00 | 33.01 | C |
| ATOM | 105 | ND2 | ASN | A | 184 | −89.860 | 49.296 | 25.498 | 1.00 | 35.70 | N |

TABLE 4

| ATOM | 106 | OD1 | ASN | A | 184 | −90.869 | 49.798 | 23.531 | 1.00 | 32.82 | O |
| --- | --- | --- | --- | --- | --- | --- | --- | --- | --- | --- | --- |
| ATOM | 107 | N | ALA | A | 185 | −88.559 | 54.309 | 24.134 | 1.00 | 25.16 | N |
| ATOM | 108 | CA | ALA | A | 185 | −88.461 | 55.727 | 24.489 | 1.00 | 24.60 | C |
| ATOM | 109 | C | ALA | A | 185 | −88.822 | 56.613 | 23.283 | 1.00 | 21.27 | C |
| ATOM | 110 | O | ALA | A | 185 | −89.439 | 57.648 | 23.440 | 1.00 | 23.34 | O |
| ATOM | 111 | CB | ALA | A | 185 | −87.071 | 56.086 | 24.982 | 1.00 | 27.11 | C |
| ATOM | 112 | N | TYR | A | 186 | −88.327 | 56.237 | 22.112 | 1.00 | 22.27 | N |
| ATOM | 113 | CA | TYR | A | 186 | −88.597 | 56.943 | 20.889 | 1.00 | 21.03 | C |
| ATOM | 114 | C | TYR | A | 186 | −90.119 | 57.000 | 20.635 | 1.00 | 24.36 | C |
| ATOM | 115 | O | TYR | A | 186 | −90.715 | 58.061 | 20.386 | 1.00 | 23.47 | O |
| ATOM | 116 | CB | TYR | A | 186 | −87.867 | 56.270 | 19.779 | 1.00 | 21.85 | C |
| ATOM | 117 | CG | TYR | A | 186 | −88.076 | 56.707 | 18.346 | 1.00 | 22.41 | C |
| ATOM | 118 | CD1 | TYR | A | 186 | −89.070 | 56.126 | 17.589 | 1.00 | 26.35 | C |
| ATOM | 119 | CD2 | TYR | A | 186 | −87.187 | 57.548 | 17.704 | 1.00 | 24.76 | C |
| ATOM | 120 | CE1 | TYR | A | 186 | −89.241 | 56.422 | 16.230 | 1.00 | 28.94 | C |
| ATOM | 121 | CE2 | TYR | A | 186 | −87.333 | 57.847 | 16.344 | 1.00 | 26.27 | C |
| ATOM | 122 | CZ | TYR | A | 186 | −88.389 | 57.297 | 15.623 | 1.00 | 28.95 | C |
| ATOM | 123 | OH | TYR | A | 186 | −88.556 | 57.498 | 14.260 | 1.00 | 28.54 | O |
| ATOM | 124 | N | LEU | A | 187 | −90.745 | 55.859 | 20.734 | 1.00 | 25.86 | N |
| ATOM | 125 | CA | LEU | A | 187 | −92.198 | 55.777 | 20.565 | 1.00 | 25.87 | C |
| ATOM | 126 | C | LEU | A | 187 | −92.983 | 56.530 | 21.571 | 1.00 | 26.59 | C |
| ATOM | 127 | O | LEU | A | 187 | −94.066 | 57.036 | 21.241 | 1.00 | 26.00 | O |
| ATOM | 128 | CB | LEU | A | 187 | −92.689 | 54.326 | 20.516 | 1.00 | 24.38 | C |
| ATOM | 129 | CG | LEU | A | 187 | −92.192 | 53.544 | 19.352 | 1.00 | 22.73 | C |
| ATOM | 130 | CD1 | LEU | A | 187 | −92.515 | 52.061 | 19.564 | 1.00 | 27.08 | C |
| ATOM | 131 | CD2 | LEU | A | 187 | −92.786 | 54.020 | 18.054 | 1.00 | 26.39 | C |
| ATOM | 132 | N | LYS | A | 188 | −92.461 | 56.646 | 22.784 | 1.00 | 24.71 | N |
| ATOM | 133 | CA | LYS | A | 188 | −93.120 | 57.426 | 23.769 | 1.00 | 30.26 | C |
| ATOM | 134 | C | LYS | A | 188 | −92.996 | 58.925 | 23.536 | 1.00 | 31.07 | C |
| ATOM | 135 | O | LYS | A | 188 | −93.787 | 59.690 | 24.091 | 1.00 | 33.85 | O |
| ATOM | 136 | CB | LYS | A | 188 | −92.590 | 57.124 | 25.197 | 1.00 | 34.62 | C |
| ATOM | 137 | CG | LYS | A | 188 | −93.579 | 56.325 | 26.004 | 1.00 | 38.65 | C |
| ATOM | 138 | CD | LYS | A | 188 | −93.032 | 55.886 | 27.367 | 1.00 | 41.52 | C |
| ATOM | 139 | CE | LYS | A | 188 | −93.446 | 54.445 | 27.638 | 1.00 | 45.53 | C |
| ATOM | 140 | NZ | LYS | A | 188 | −92.983 | 54.006 | 28.975 | 1.00 | 49.87 | N1+ |

TABLE 5

| ATOM | 141 | N | ASN | A | 189 | −91.974 | 59.378 | 22.809 | 1.00 | 26.38 | N |
| --- | --- | --- | --- | --- | --- | --- | --- | --- | --- | --- | --- |
| ATOM | 142 | CA | ASN | A | 189 | −91.663 | 60.818 | 22.804 | 1.00 | 25.85 | C |
| ATOM | 143 | C | ASN | A | 189 | −91.933 | 61.497 | 21.494 | 1.00 | 26.44 | C |
| ATOM | 144 | O | ASN | A | 189 | −92.064 | 62.694 | 21.479 | 1.00 | 29.96 | O |
| ATOM | 145 | CB | ASN | A | 189 | −90.206 | 61.007 | 23.244 | 1.00 | 26.95 | C |
| ATOM | 146 | CG | ASN | A | 189 | −90.054 | 60.856 | 24.742 | 1.00 | 28.25 | C |
| ATOM | 147 | ND2 | ASN | A | 189 | −89.518 | 59.749 | 25.204 | 1.00 | 26.96 | N |
| ATOM | 148 | OD1 | ASN | A | 189 | −90.485 | 61.721 | 25.462 | 1.00 | 24.74 | O |
| ATOM | 149 | N | PHE | A | 190 | −91.959 | 60.767 | 20.387 | 1.00 | 24.89 | N |
| ATOM | 150 | CA | PHE | A | 190 | −92.113 | 61.397 | 19.069 | 1.00 | 28.46 | C |
| ATOM | 151 | C | PHE | A | 190 | −93.489 | 61.145 | 18.488 | 1.00 | 33.62 | C |
| ATOM | 152 | O | PHE | A | 190 | −93.987 | 60.031 | 18.564 | 1.00 | 36.21 | O |
| ATOM | 153 | CB | PHE | A | 190 | −90.991 | 60.998 | 18.112 | 1.00 | 25.42 | C |
| ATOM | 154 | CG | PHE | A | 190 | −89.666 | 61.313 | 18.676 | 1.00 | 27.59 | C |
| ATOM | 155 | CD1 | PHE | A | 190 | −89.340 | 62.651 | 18.939 | 1.00 | 28.25 | C |
| ATOM | 156 | CD2 | PHE | A | 190 | −88.786 | 60.308 | 19.065 | 1.00 | 24.59 | C |
| ATOM | 157 | CE1 | PHE | A | 190 | −88.137 | 63.003 | 19.541 | 1.00 | 28.57 | C |
| ATOM | 158 | CE2 | PHE | A | 190 | −87.559 | 60.662 | 19.656 | 1.00 | 28.38 | C |
| ATOM | 159 | CZ | PHE | A | 190 | −87.258 | 62.004 | 19.916 | 1.00 | 28.52 | C |
| ATOM | 160 | N | ASN | A | 191 | −94.100 | 62.197 | 17.939 | 1.00 | 35.72 | N |
| ATOM | 161 | CA | ASN | A | 191 | −95.480 | 62.070 | 17.499 | 1.00 | 44.39 | C |
| ATOM | 162 | C | ASN | A | 191 | −95.609 | 61.499 | 16.099 | 1.00 | 39.01 | C |
| ATOM | 163 | O | ASN | A | 191 | −96.577 | 60.866 | 15.814 | 1.00 | 48.11 | O |
| ATOM | 164 | CB | ASN | A | 191 | −96.261 | 63.378 | 17.626 | 1.00 | 54.13 | C |
| ATOM | 165 | CG | ASN | A | 191 | −97.708 | 63.124 | 18.050 | 1.00 | 65.01 | C |
| ATOM | 166 | ND2 | ASN | A | 191 | −98.173 | 63.868 | 19.049 | 1.00 | 70.35 | N |
| ATOM | 167 | OD1 | ASN | A | 191 | −98.388 | 62.237 | 17.510 | 1.00 | 70.56 | O |
| ATOM | 168 | N | MET | A | 192 | −94.640 | 61.677 | 15.242 | 1.00 | 33.14 | N |
| ATOM | 169 | CA | MET | A | 192 | −94.737 | 61.141 | 13.882 | 1.00 | 35.43 | C |

TABLE 5-continued

| ATOM | 170 | C  | MET | A | 192 | −93.640 | 60.107 | 13.682 | 1.00 | 34.11 | C |
| --- | --- | --- | --- | --- | --- | --- | --- | --- | --- | --- | --- |
| ATOM | 171 | O  | MET | A | 192 | −92.504 | 60.438 | 13.788 | 1.00 | 38.98 | O |
| ATOM | 172 | CB | MET | A | 192 | −94.523 | 62.310 | 12.939 | 1.00 | 35.95 | C |
| ATOM | 173 | CG | MET | A | 192 | −94.571 | 61.990 | 11.451 | 1.00 | 39.68 | C |
| ATOM | 174 | SD | MET | A | 192 | −96.067 | 61.093 | 11.033 | 1.00 | 43.83 | S |
| ATOM | 175 | CE | MET | A | 192 | −97.212 | 62.454 | 11.103 | 1.00 | 42.08 | C |

TABLE 6

| ATOM | 176 | N   | THR | A | 193 | −93.969  | 58.863 | 13.425 | 1.00 | 29.64 | N   |
| --- | --- | --- | --- | --- | --- | --- | --- | --- | --- | --- | --- |
| ATOM | 177 | CA  | THR | A | 193 | −92.972  | 57.856 | 13.147 | 1.00 | 29.54 | C   |
| ATOM | 178 | C   | THR | A | 193 | −92.826  | 57.686 | 11.660 | 1.00 | 32.16 | C   |
| ATOM | 179 | O   | THR | A | 193 | −93.731  | 58.066 | 10.878 | 1.00 | 30.21 | O   |
| ATOM | 180 | CB  | THR | A | 193 | −93.392  | 55.545 | 13.752 | 1.00 | 28.89 | C   |
| ATOM | 181 | CG2 | THR | A | 193 | −93.542  | 56.732 | 15.265 | 1.00 | 29.71 | C   |
| ATOM | 182 | OG1 | THR | A | 193 | −94.644  | 56.151 | 13.196 | 1.00 | 27.83 | O   |
| ATOM | 183 | N   | LYS | A | 194 | −91.709  | 57.212 | 11.279 | 1.00 | 25.68 | N   |
| ATOM | 184 | CA  | LYS | A | 194 | −92.463  | 56.815 | 9.919  | 1.00 | 29.45 | C   |
| ATOM | 185 | C   | LYS | A | 194 | −92.523  | 55.844 | 9.368  | 1.00 | 33.65 | C   |
| ATOM | 186 | O   | LYS | A | 194 | −92.911  | 55.942 | 8.200  | 1.00 | 29.84 | O   |
| ATOM | 187 | CB  | LYS | A | 194 | −90.084  | 56.188 | 9.751  | 1.00 | 27.21 | C   |
| ATOM | 188 | CG  | LYS | A | 194 | −89.759  | 56.048 | 8.311  | 1.00 | 25.95 | C   |
| ATOM | 189 | CD  | LYS | A | 194 | −88.290  | 55.769 | 8.013  | 1.00 | 27.58 | C   |
| ATOM | 190 | CE  | LYS | A | 194 | −88.063  | 55.739 | 5.522  | 1.00 | 25.56 | C   |
| ATOM | 191 | NZ  | LYS | A | 194 | −86.718  | 55.308 | 6.129  | 1.00 | 26.53 | N1+ |
| ATOM | 192 | N   | LYS | A | 195 | −92.939  | 54.905 | 10.206 | 1.00 | 31.19 | N   |
| ATOM | 193 | CA  | LYS | A | 195 | −93.996  | 53.954 | 9.846  | 1.00 | 35.70 | C   |
| ATOM | 194 | C   | LYS | A | 195 | −95.294  | 54.660 | 9.475  | 1.00 | 32.58 | C   |
| ATOM | 195 | O   | LYS | A | 195 | −95.896  | 54.369 | 8.424  | 1.00 | 29.06 | O   |
| ATOM | 196 | CE  | LYS | A | 195 | −94.258  | 52.976 | 10.998 | 1.00 | 36.70 | C   |
| ATOM | 197 | CG  | LYS | A | 195 | −95.420  | 52.028 | 10.740 | 1.00 | 45.84 | C   |
| ATOM | 198 | CD  | LYS | A | 195 | −95.641  | 51.070 | 11.901 | 1.00 | 48.59 | C   |
| ATOM | 199 | CE  | LYS | A | 195 | −94.658  | 49.924 | 11.848 | 1.00 | 60.77 | C   |
| ATOM | 200 | NZ  | LYS | A | 195 | −95.288  | 48.672 | 12.385 | 1.00 | 69.98 | N1+ |
| ATOM | 201 | N   | LYS | A | 196 | −95.702  | 55.583 | 10.319 | 1.00 | 32.50 | N   |
| ATOM | 202 | CA  | LYS | A | 196 | −96.904  | 56.377 | 10.038 | 1.00 | 34.50 | C   |
| ATOM | 203 | C   | LYS | A | 196 | −96.677  | 57.229 | 8.772  | 1.00 | 34.61 | C   |
| ATOM | 204 | O   | LYS | A | 196 | −97.494  | 57.165 | 7.854  | 1.00 | 30.35 | O   |
| ATOM | 205 | CB  | LYS | A | 196 | −97.300  | 57.258 | 11.213 | 1.00 | 40.01 | C   |
| ATOM | 206 | CG  | LYS | A | 196 | −98.443  | 58.194 | 10.860 | 1.00 | 48.30 | C   |
| ATOM | 207 | CD  | LYS | A | 196 | −99.127  | 58.814 | 12.059 | 1.00 | 50.20 | C   |
| ATOM | 208 | CE  | LYS | A | 196 | −100.277 | 57.888 | 12.664 | 1.00 | 56.16 | C   |
| ATOM | 209 | NZ  | LYS | A | 196 | −101.237 | 58.717 | 13.308 | 1.00 | 61.35 | N1+ |
| ATOM | 210 | N   | ALA | A | 197 | −95.570  | 57.985 | 8.702  | 1.00 | 25.18 | N   |

TABLE 7

| ATOM | 211 | CA  | ALA | A | 197 | −95.312  | 58.847 | 7.547 | 1.00 | 29.66 | C   |
| --- | --- | --- | --- | --- | --- | --- | --- | --- | --- | --- | --- |
| ATOM | 212 | C   | ALA | A | 197 | −95.347  | 58.115 | 6.211 | 1.00 | 32.31 | C   |
| ATOM | 213 | O   | ALA | A | 197 | −95.981  | 58.621 | 5.231 | 1.00 | 31.92 | O   |
| ATOM | 214 | CB  | ALA | A | 197 | −94.009  | 59.581 | 7.710 | 1.00 | 32.70 | C   |
| ATOM | 215 | N   | ARG | A | 198 | −94.713  | 56.941 | 6.154 | 1.00 | 31.55 | N   |
| ATOM | 216 | CA  | ARG | A | 198 | −94.635  | 55.151 | 4.923 | 1.00 | 36.68 | C   |
| ATOM | 217 | C   | ARG | A | 198 | −95.992  | 55.615 | 4.513 | 1.00 | 40.95 | C   |
| ATOM | 218 | O   | ARG | A | 198 | −96.284  | 55.571 | 3.319 | 1.00 | 40.04 | O   |
| ATOM | 219 | CB  | ARG | A | 198 | −93.666  | 54.982 | 5.017 | 1.00 | 40.12 | C   |
| ATOM | 220 | CG  | ARG | A | 198 | −92.196  | 55.397 | 5.078 | 1.00 | 47.18 | C   |
| ATOM | 221 | CD  | ARG | A | 198 | −91.670  | 56.059 | 3.783 | 1.00 | 57.47 | C   |
| ATOM | 222 | NE  | ARG | A | 198 | −91.036  | 57.334 | 4.140 | 1.00 | 68.80 | N   |
| ATOM | 223 | CZ  | ARG | A | 198 | −90.732  | 58.335 | 3.313 | 1.00 | 68.29 | C   |
| ATOM | 224 | NH1 | ARG | A | 198 | −90.952  | 58.264 | 2.003 | 1.00 | 69.84 | N1+ |
| ATOM | 225 | NH2 | ARG | A | 128 | −90.191  | 59.431 | 3.822 | 1.00 | 63.73 | N   |
| ATOM | 226 | N   | SER | A | 199 | −96.818  | 55.216 | 5.479 | 1.00 | 37.94 | N   |
| ATOM | 227 | CA  | SER | A | 199 | −98.134  | 54.718 | 5.132 | 1.00 | 42.22 | C   |
| ATOM | 228 | C   | SER | A | 199 | −99.048  | 55.847 | 4.579 | 1.00 | 47.84 | C   |
| ATOM | 229 | O   | SER | A | 199 | −99.856  | 55.607 | 3.652 | 1.00 | 49.67 | O   |
| ATOM | 230 | CB  | SER | A | 199 | −98.778  | 54.057 | 6.319 | 1.00 | 41.34 | C   |
| ATOM | 231 | OG  | SER | A | 199 | −99.263  | 55.088 | 7.142 | 1.00 | 53.26 | O   |
| ATOM | 232 | N   | ILE | A | 200 | −98.916  | 57.059 | 5.133 | 1.00 | 42.42 | N   |
| ATOM | 233 | CA  | ILE | A | 200 | −99.624  | 58.240 | 4.600 | 1.00 | 39.98 | C   |
| ATOM | 234 | C   | ILE | A | 200 | −99.047  | 58.587 | 3.241 | 1.00 | 40.57 | C   |
| ATOM | 235 | O   | ILE | A | 200 | −99.790  | 58.795 | 2.319 | 1.00 | 47.87 | O   |
| ATOM | 236 | CB  | ILE | A | 200 | −99.476  | 59.454 | 5.506 | 1.00 | 34.95 | C   |
| ATOM | 237 | CG1 | ILE | A | 200 | −100.161 | 59.193 | 6.831 | 1.00 | 37.25 | C   |
| ATOM | 238 | CG2 | ILE | A | 200 | −100.062 | 60.720 | 4.862 | 1.00 | 36.32 | C   |

TABLE 7-continued

| | | | | | | | | | | |
|---|---|---|---|---|---|---|---|---|---|---|
| ATOM | 239 | CD1 | ILE | A | 200 | −99.742 | 60.182 | 7.903 | 1.00 | 37.05 C |
| ATOM | 240 | N | LEU | A | 201 | −97.727 | 58.636 | 3.114 | 1.00 | 38.24 N |
| ATOM | 241 | CA | LEU | A | 201 | −97.064 | 59.066 | 1.864 | 1.00 | 39.20 C |
| ATOM | 242 | C | LEU | A | 201 | −97.270 | 58.151 | 0.675 | 1.00 | 50.00 C |
| ATOM | 243 | O | LEU | A | 201 | −97.123 | 58.604 | −0.464 | 1.00 | 55.84 O |
| ATOM | 244 | CB | LEU | A | 201 | −95.536 | 59.283 | 2.038 | 1.00 | 35.38 C |
| ATOM | 245 | CG | LEU | A | 201 | −95.097 | 60.600 | 2.704 | 1.00 | 37.94 C |

TABLE 8

| | | | | | | | | | | |
|---|---|---|---|---|---|---|---|---|---|---|
| ATOM | 246 | CD1 | LEU | A | 201 | −93.635 | 60.616 | 3.159 | 1.00 | 36.58 C |
| ATOM | 247 | CD2 | LEU | A | 201 | −95.377 | 61.804 | 1.797 | 1.00 | 40.74 C |
| ATOM | 248 | N | THR | A | 202 | −97.561 | 56.871 | 0.920 | 1.00 | 51.78 N |
| ATOM | 249 | CA | THR | A | 202 | −97.797 | 55.910 | −0.149 | 1.00 | 54.02 C |
| ATOM | 250 | C | THR | A | 202 | −99.267 | 55.481 | −0.295 | 1.00 | 55.85 C |
| ATOM | 251 | O | THR | A | 202 | −99.544 | 54.582 | −1.066 | 1.00 | 51.84 O |
| ATOM | 252 | CB | THR | A | 202 | −96.931 | 54.650 | 0.040 | 1.00 | 50.12 C |
| ATOM | 253 | CG2 | THR | A | 202 | −95.472 | 54.994 | 0.007 | 1.00 | 51.23 C |
| ATOM | 254 | OG1 | THR | A | 202 | −97.278 | 54.018 | 1.281 | 1.00 | 47.02 O |
| ATOM | 255 | N | GLY | A | 203 | −100.190 | 56.085 | 0.454 | 1.00 | 59.43 N |
| ATOM | 256 | CA | GLY | A | 203 | −101.616 | 55.902 | 0.209 | 1.00 | 64.43 C |
| ATOM | 257 | C | GLY | A | 203 | −102.318 | 54.911 | 1.118 | 1.00 | 67.48 C |
| ATOM | 258 | O | GLY | A | 203 | −103.543 | 54.878 | 1.149 | 1.00 | 74.08 O |
| ATOM | 259 | N | LYS | A | 204 | −101.553 | 54.108 | 1.853 | 1.00 | 69.89 N |
| ATOM | 260 | CA | LYS | A | 204 | −102.098 | 53.112 | 2.773 | 1.00 | 66.42 C |
| ATOM | 261 | C | LYS | A | 204 | −102.657 | 53.794 | 4.027 | 1.00 | 74.34 C |
| ATOM | 262 | O | LYS | A | 204 | −103.770 | 53.498 | 4.466 | 1.00 | 84.31 O |
| ATOM | 263 | CB | LYS | A | 204 | −100.999 | 52.118 | 3.153 | 1.00 | 56.83 C |
| TER | 264 | | LYS | A | 204 | | | | | |
| ATOM | 265 | N | ALA | A | 209 | −106.293 | 61.454 | 1.202 | 1.00 | 55.53 N |
| ATOM | 266 | CA | ALA | A | 209 | −105.038 | 62.090 | 0.830 | 1.00 | 54.52 C |
| ATOM | 267 | C | ALA | A | 209 | −104.730 | 63.270 | 1.774 | 1.00 | 54.60 C |
| ATOM | 268 | O | ALA | A | 209 | −105.668 | 63.879 | 2.320 | 1.00 | 53.35 O |
| ATOM | 269 | CB | ALA | A | 209 | −105.092 | 62.568 | −0.604 | 1.00 | 51.75 C |
| ATOM | 270 | N | PRO | A | 210 | −103.421 | 63.601 | 1.978 | 1.00 | 48.56 N |
| ATOM | 271 | CA | PRO | A | 210 | −103.097 | 64.868 | 2.681 | 1.00 | 40.74 C |
| ATOM | 272 | C | PRO | A | 210 | −103.422 | 66.082 | 1.785 | 1.00 | 33.37 C |
| ATOM | 273 | O | PRO | A | 210 | −103.268 | 66.021 | 0.596 | 1.00 | 31.34 O |
| ATOM | 274 | CB | PRO | A | 210 | −101.566 | 64.760 | 2.915 | 1.00 | 40.59 C |
| ATOM | 275 | CG | PRO | A | 210 | −101.259 | 63.307 | 2.695 | 1.00 | 44.72 C |
| ATOM | 276 | CD | PRO | A | 210 | −102.175 | 62.925 | 1.560 | 1.00 | 44.48 C |
| ATOM | 277 | N | PHE | A | 211 | −103.832 | 67.175 | 2.376 | 1.00 | 32.36 N |
| ATOM | 278 | CA | PHE | A | 211 | −104.097 | 68.420 | 1.635 | 1.00 | 33.25 C |
| ATOM | 279 | C | PHE | A | 211 | −102.803 | 68.977 | 1.101 | 1.00 | 32.20 C |
| ATOM | 280 | O | PHE | A | 211 | −101.881 | 69.176 | 1.870 | 1.00 | 31.71 O |

TABLE 9

| | | | | | | | | | | |
|---|---|---|---|---|---|---|---|---|---|---|
| ATOM | 281 | CB | PHE | A | 211 | −104.716 | 69.440 | 2.595 | 1.00 | 32.28 C |
| ATOM | 282 | CG | PHE | A | 211 | −105.018 | 70.763 | 1.941 | 1.00 | 37.76 C |
| ATOM | 283 | CD1 | PHE | A | 211 | −105.996 | 70.851 | 0.938 | 1.00 | 38.37 C |
| ATOM | 284 | CD2 | PHE | A | 211 | −104.278 | 71.905 | 2.253 | 1.00 | 37.26 C |
| ATOM | 285 | CE1 | PHE | A | 211 | −106.278 | 72.059 | 0.321 | 1.00 | 38.29 C |
| ATOM | 286 | CE2 | PHE | A | 211 | −104.558 | 73.114 | 1.632 | 1.00 | 37.21 C |
| ATOM | 287 | CZ | PHE | A | 211 | −105.579 | 73.205 | 0.689 | 1.00 | 35.97 C |
| ATOM | 288 | N | VAL | A | 212 | −102.731 | 69.267 | −0.195 | 1.00 | 33.46 N |
| ATOM | 289 | CA | VAL | A | 212 | −101.490 | 69.702 | −0.822 | 1.00 | 32.40 C |
| ATOM | 290 | C | VAL | A | 212 | −101.333 | 71.250 | −0.788 | 1.00 | 32.85 C |
| ATOM | 291 | O | VAL | A | 212 | −102.205 | 72.005 | −1.239 | 1.00 | 31.47 O |
| ATOM | 292 | CB | VAL | A | 212 | −101.361 | 69.147 | −2.267 | 1.00 | 34.62 C |
| ATOM | 293 | CG1 | VAL | A | 212 | −100.081 | 69.657 | −2.906 | 1.00 | 37.02 C |
| ATOM | 294 | CG2 | VAL | A | 212 | −101.352 | 67.650 | −2.280 | 1.00 | 37.32 C |
| ATOM | 295 | N | ILE | A | 213 | −100.206 | 71.703 | −0.259 | 1.00 | 28.76 N |
| ATOM | 296 | CA | ILE | A | 213 | −98.851 | 73.094 | −0.168 | 1.00 | 28.25 C |
| ATOM | 297 | C | ILE | A | 213 | −98.799 | 73.363 | −1.237 | 1.00 | 30.12 C |
| ATOM | 298 | O | ILE | A | 213 | −97.661 | 72.906 | −1.127 | 1.00 | 27.80 O |
| ATOM | 299 | CB | ILE | A | 213 | −99.293 | 73.430 | 1.210 | 1.00 | 27.64 C |
| ATOM | 300 | CG1 | ILE | A | 213 | −100.384 | 73.300 | 2.253 | 1.00 | 31.93 C |
| ATOM | 301 | CG2 | ILE | A | 213 | −98.777 | 74.851 | 1.290 | 1.00 | 28.09 C |
| ATOM | 302 | CD1 | ILE | A | 213 | −99.769 | 73.030 | 3.628 | 1.00 | 35.50 C |
| ATOM | 303 | N | HIS | A | 214 | −99.177 | 74.128 | −2.253 | 1.00 | 26.14 N |
| ATOM | 304 | CA | HIS | A | 214 | −98.297 | 74.401 | −3.353 | 1.00 | 31.25 C |
| ATOM | 305 | C | HIS | A | 214 | −98.249 | 75.866 | −3.781 | 1.00 | 30.04 C |
| ATOM | 306 | O | HIS | A | 214 | −97.569 | 76.202 | −4.735 | 1.00 | 33.51 O |
| ATOM | 307 | CB | HIS | A | 214 | −98.630 | 73.466 | −4.542 | 1.00 | 31.14 C |

TABLE 9-continued

| | | | | | | | | | | |
|---|---|---|---|---|---|---|---|---|---|---|
| ATOM | 308 | CG | HIS | A | 214 | −100.037 | 73.559 | −5.012 | 1.00 | 37.86 C |
| ATOM | 309 | CD2 | HIS | A | 214 | −100.872 | 72.640 | −5.533 | 1.00 | 42.12 C |
| ATOM | 310 | ND1 | HIS | A | 214 | −100.742 | 74.738 | −4.989 | 1.00 | 43.19 N |
| ATOM | 311 | CE1 | HIS | A | 214 | −101.952 | 74.540 | −5.447 | 1.00 | 38.08 C |
| ATOM | 312 | NE2 | HIS | A | 214 | −102.073 | 73.267 | −5.749 | 1.00 | 39.03 N |
| ATOM | 313 | N | ASP | A | 215 | −98.958 | 76.736 | −3.081 | 1.00 | 29.01 N |
| ATOM | 314 | CA | ASP | A | 215 | −99.014 | 78.156 | −3.387 | 1.00 | 29.06 C |
| ATOM | 315 | C | ASP | A | 215 | −99.573 | 78.935 | −2.191 | 1.00 | 27.03 C |

TABLE 10

| | | | | | | | | | | |
|---|---|---|---|---|---|---|---|---|---|---|
| ATOM | 316 | O | ASP | A | 215 | −99.911 | 78.345 | −1.164 | 1.00 | 25.52 O |
| ATOM | 317 | CB | ASP | A | 215 | −99.858 | 78.384 | −4.653 | 1.00 | 31.06 C |
| ATOM | 318 | CG | ASP | A | 215 | −101.351 | 78.135 | −4.444 | 1.00 | 36.19 C |
| ATOM | 319 | OD1 | ASP | A | 215 | −101.803 | 77.450 | −3.520 | 1.00 | 35.10 O |
| ATOM | 320 | OD2 | ASP | A | 215 | −102.117 | 78.632 | −5.291 | 1.00 | 44.50 O1− |
| ATOM | 321 | N | ILE | A | 216 | −99.598 | 80.243 | −2.333 | 1.00 | 26.54 N |
| ATOM | 322 | CA | ILE | A | 216 | −100.082 | 81.140 | −1.310 | 1.00 | 28.71 C |
| ATOM | 323 | C | ILE | A | 216 | −101.464 | 80.833 | −0.850 | 1.00 | 29.59 C |
| ATOM | 324 | O | ILE | A | 216 | −101.742 | 80.776 | 0.352 | 1.00 | 27.49 O |
| ATOM | 325 | CB | ILE | A | 216 | −99.957 | 82.645 | −1.714 | 1.00 | 33.33 C |
| ATOM | 326 | CG1 | ILE | A | 216 | −100.482 | 83.559 | −0.587 | 1.00 | 34.01 C |
| ATOM | 327 | CG2 | ILE | A | 216 | −100.744 | 83.041 | −2.984 | 1.00 | 35.34 C |
| ATOM | 328 | CD1 | ILE | A | 216 | −99.969 | 84.996 | −0.741 | 1.00 | 39.78 C |
| ATOM | 329 | N | GLU | A | 217 | −102.361 | 80.626 | −1.796 | 1.00 | 28.92 N |
| ATOM | 330 | CA | GLU | A | 217 | −103.750 | 80.381 | −1.456 | 1.00 | 31.25 C |
| ATOM | 331 | C | GLU | A | 217 | −103.926 | 79.093 | −0.662 | 1.00 | 28.15 C |
| ATOM | 332 | O | GLU | A | 217 | −104.615 | 79.086 | 0.344 | 1.00 | 29.20 O |
| ATOM | 333 | CB | GLU | A | 217 | −104.599 | 80.367 | −2.742 | 1.00 | 35.18 C |
| ATOM | 334 | CG | GLU | A | 217 | −106.058 | 80.016 | −2.482 | 1.00 | 47.47 C |
| ATOM | 335 | CD | GLU | A | 217 | −106.948 | 80.155 | −3.732 | 1.00 | 57.20 C |
| ATOM | 336 | OE1 | GLU | A | 217 | −108.039 | 79.550 | −3.715 | 1.00 | 70.21 O |
| ATOM | 337 | OE2 | GLU | A | 217 | −106.581 | 80.878 | −4.698 | 1.00 | 58.40 O1− |
| ATOM | 338 | N | THR | A | 218 | −103.329 | 77.998 | −1.110 | 1.00 | 26.55 N |
| ATOM | 339 | CA | THR | A | 218 | −103.449 | 76.745 | −0.398 | 1.00 | 25.93 C |
| ATOM | 340 | C | THR | A | 218 | −102.689 | 76.826 | 0.970 | 1.00 | 27.70 C |
| ATOM | 341 | O | THR | A | 218 | −103.139 | 76.271 | 1.945 | 1.00 | 26.11 O |
| ATOM | 342 | CB | THR | A | 218 | −102.958 | 75.536 | −1.214 | 1.00 | 27.44 C |
| ATOM | 343 | CG2 | THR | A | 218 | −103.834 | 75.360 | −2.518 | 1.00 | 32.83 C |
| ATOM | 344 | OG1 | THR | A | 218 | −101.567 | 75.667 | −1.522 | 1.00 | 24.38 O |
| ATOM | 345 | N | LEU | A | 219 | −101.619 | 77.605 | 1.041 | 1.00 | 26.88 N |
| ATOM | 346 | CA | LEU | A | 219 | −100.909 | 77.798 | 2.329 | 1.00 | 28.99 C |
| ATOM | 347 | C | LEU | A | 219 | −101.810 | 78.453 | 3.366 | 1.00 | 28.45 C |
| ATOM | 348 | O | LEU | A | 219 | −101.833 | 78.029 | 4.526 | 1.00 | 27.21 O |
| ATOM | 349 | CB | LEU | A | 219 | −99.670 | 78.668 | 2.140 | 1.00 | 26.14 C |
| ATOM | 350 | CG | LEU | A | 219 | −98.844 | 79.045 | 3.403 | 1.00 | 27.90 C |

TABLE 11

| | | | | | | | | | | |
|---|---|---|---|---|---|---|---|---|---|---|
| ATOM | 351 | CD1 | LEU | A | 219 | −98.059 | 77.854 | 3.974 | 1.00 | 28.82 C |
| ATOM | 352 | CD2 | LEU | A | 219 | −97.849 | 80.127 | 3.039 | 1.00 | 25.88 C |
| ATOM | 353 | N | TRP | A | 220 | −102.483 | 79.544 | 2.969 | 1.00 | 26.01 N |
| ATOM | 354 | CA | TRP | A | 220 | −103.385 | 80.225 | 3.882 | 1.00 | 27.72 C |
| ATOM | 355 | C | TRP | A | 220 | −104.581 | 79.350 | 4.254 | 1.00 | 30.97 C |
| ATOM | 356 | O | TRP | A | 220 | −104.984 | 79.286 | 5.430 | 1.00 | 28.16 O |
| ATOM | 357 | CB | TRP | A | 220 | −103.865 | 81.591 | 3.332 | 1.00 | 27.25 C |
| ATOM | 358 | CG | TRP | A | 220 | −103.464 | 82.718 | 4.139 | 1.00 | 25.20 C |
| ATOM | 359 | CD1 | TRP | A | 220 | −104.249 | 83.772 | 4.520 | 1.00 | 27.15 C |
| ATOM | 360 | CD2 | TRP | A | 220 | −102.140 | 82.964 | 4.694 | 1.00 | 24.07 C |
| ATOM | 361 | CE2 | TRP | A | 220 | −102.213 | 84.206 | 5.382 | 1.00 | 24.73 C |
| ATOM | 362 | CE3 | TRP | A | 220 | −100.926 | 82.284 | 4.642 | 1.00 | 22.88 C |
| ATOM | 363 | NE1 | TRP | A | 220 | −103.502 | 84.669 | 5.267 | 1.00 | 25.61 N |
| ATOM | 364 | CZ2 | TRP | A | 220 | −101.095 | 84.772 | 6.039 | 1.00 | 24.36 C |
| ATOM | 365 | CZ3 | TRP | A | 220 | −99.826 | 82.822 | 5.354 | 1.00 | 24.87 C |
| ATOM | 366 | CH2 | TRP | A | 220 | −99.914 | 84.081 | 5.987 | 1.00 | 24.01 C |
| ATOM | 367 | N | GLN | A | 221 | −105.085 | 78.631 | 3.270 | 1.00 | 31.28 N |
| ATOM | 368 | CA | GLN | A | 221 | −106.223 | 77.726 | 3.469 | 1.00 | 35.33 C |
| ATOM | 369 | C | GLN | A | 221 | −105.943 | 76.582 | 4.450 | 1.00 | 32.72 C |
| ATOM | 370 | O | GLN | A | 221 | −106.837 | 76.150 | 5.182 | 1.00 | 32.09 O |
| ATOM | 371 | CB | GLN | A | 221 | −106.592 | 77.221 | 2.103 | 1.00 | 40.68 C |
| ATOM | 372 | CG | GLN | A | 221 | −107.866 | 76.499 | 1.946 | 1.00 | 49.08 C |
| ATOM | 373 | CD | GLN | A | 221 | −108.041 | 76.052 | 0.484 | 1.00 | 55.49 C |
| ATOM | 374 | NE2 | GLN | A | 221 | −109.051 | 75.214 | 0.269 | 1.00 | 61.19 N |
| ATOM | 375 | OE1 | GLN | A | 221 | −107.248 | 76.417 | −0.431 | 1.00 | 47.72 O |
| ATOM | 376 | N | ALA | A | 222 | −104.705 | 76.096 | 4.478 | 1.00 | 31.67 N |

TABLE 11-continued

| ATOM | 377 | CA | ALA | A | 222 | −104.353 | 75.014 | 5.390 | 1.00 | 31.76 | C |
|---|---|---|---|---|---|---|---|---|---|---|---|
| ATOM | 378 | C | ALA | A | 222 | −104.401 | 75.464 | 6.871 | 1.00 | 33.22 | C |
| ATOM | 379 | O | ALA | A | 222 | −104.444 | 74.631 | 7.757 | 1.00 | 37.17 | O |
| ATOM | 380 | CB | ALA | A | 222 | −102.984 | 74.459 | 5.058 | 1.00 | 32.29 | C |
| ATOM | 381 | N | GLU | A | 223 | −104.385 | 76.765 | 7.164 | 1.00 | 30.55 | N |
| ATOM | 382 | CA | GLU | A | 223 | −104.313 | 77.185 | 8.585 | 1.00 | 28.25 | C |
| ATOM | 383 | C | GLU | A | 223 | −105.737 | 77.197 | 9.173 | 1.00 | 30.28 | C |
| ATOM | 384 | O | GLU | A | 223 | −106.596 | 77.924 | 8.681 | 1.00 | 31.72 | O |
| ATOM | 385 | CB | GLU | A | 223 | −103.704 | 78.582 | 8.679 | 1.00 | 32.89 | C |

TABLE 12

| ATOM | 386 | CG | GLU | A | 223 | −102.186 | 78.675 | 8.474 | 1.00 | 38.82 | C |
|---|---|---|---|---|---|---|---|---|---|---|---|
| ATOM | 387 | CD | GLU | A | 223 | −101.356 | 77.917 | 9.542 | 1.00 | 39.25 | C |
| ATOM | 388 | OE1 | GLU | A | 223 | −101.881 | 77.591 | 10.664 | 1.00 | 42.27 | O |
| ATOM | 389 | OE2 | GLU | A | 223 | −100.161 | 77.644 | 9.244 | 1.00 | 41.46 | O1− |
| ATOM | 390 | N | LYS | A | 224 | −105.975 | 76.438 | 10.227 | 1.00 | 30.44 | N |
| ATOM | 391 | CA | LYS | A | 224 | −107.327 | 76.273 | 10.784 | 1.00 | 32.21 | C |
| ATOM | 392 | C | LYS | A | 224 | −107.403 | 76.659 | 12.267 | 1.00 | 29.82 | C |
| ATOM | 393 | O | LYS | A | 224 | −108.402 | 76.411 | 12.919 | 1.00 | 27.58 | O |
| ATOM | 394 | CB | LYS | A | 224 | −107.753 | 74.831 | 10.579 | 1.00 | 43.59 | C |
| ATOM | 395 | CG | LYS | A | 224 | −107.842 | 74.447 | 9.084 | 1.00 | 44.22 | C |
| ATOM | 396 | CD | LYS | A | 224 | −108.768 | 73.274 | 8.865 | 1.00 | 54.69 | C |
| ATOM | 397 | CE | LYS | A | 224 | −110.055 | 73.717 | 8.205 | 1.00 | 61.58 | C |
| ATOM | 398 | NZ | LYS | A | 224 | −109.791 | 74.233 | 6.826 | 1.00 | 61.34 | N1+ |
| ATOM | 399 | N | GLY | A | 225 | −106.411 | 77.369 | 12.771 | 1.00 | 28.25 | N |
| ATOM | 400 | CA | GLY | A | 225 | −106.477 | 77.807 | 14.165 | 1.00 | 30.48 | C |
| ATOM | 401 | C | GLY | A | 225 | −107.680 | 78.702 | 14.401 | 1.00 | 28.06 | C |
| ATOM | 402 | O | GLY | A | 225 | −108.175 | 79.389 | 13.500 | 1.00 | 25.43 | O |
| ATOM | 403 | N | LEU | A | 226 | −108.183 | 78.678 | 15.633 | 1.00 | 30.00 | N |
| ATOM | 404 | CA | LEU | A | 226 | −109.372 | 79.429 | 15.954 | 1.00 | 28.45 | C |
| ATOM | 405 | C | LEU | A | 226 | −109.153 | 80.958 | 16.023 | 1.00 | 25.19 | C |
| ATOM | 406 | O | LEU | A | 226 | −109.975 | 81.699 | 15.561 | 1.00 | 26.61 | O |
| ATOM | 407 | CB | LEU | A | 226 | −110.037 | 78.883 | 17.220 | 1.00 | 31.57 | C |
| ATOM | 408 | CG | LEU | A | 226 | −110.466 | 77.405 | 17.202 | 1.00 | 32.24 | C |
| ATOM | 409 | CD1 | LEU | A | 226 | −110.867 | 77.008 | 18.645 | 1.00 | 35.09 | C |
| ATOM | 410 | CD2 | LEU | A | 226 | −111.654 | 77.197 | 16.252 | 1.00 | 36.04 | C |
| ATOM | 411 | N | VAL | A | 227 | −108.037 | 81.427 | 16.565 | 1.00 | 23.49 | N |
| ATOM | 412 | CA | VAL | A | 227 | −107.781 | 82.837 | 16.586 | 1.00 | 25.44 | C |
| ATOM | 413 | C | VAL | A | 227 | −107.507 | 83.303 | 15.105 | 1.00 | 25.27 | C |
| ATOM | 414 | O | VAL | A | 227 | −107.988 | 84.344 | 14.646 | 1.00 | 26.27 | O |
| ATOM | 415 | CB | VAL | A | 227 | −106.661 | 83.145 | 17.568 | 1.00 | 27.09 | C |
| ATOM | 416 | CG1 | VAL | A | 227 | −106.369 | 84.618 | 17.523 | 1.00 | 27.54 | C |
| ATOM | 417 | CG2 | VAL | A | 227 | −107.098 | 82.781 | 18.983 | 1.00 | 26.25 | C |
| ATOM | 418 | N | TRP | A | 228 | −106.697 | 82.539 | 14.418 | 1.00 | 23.62 | N |
| ATOM | 419 | CA | TRP | A | 228 | −106.385 | 82.794 | 13.014 | 1.00 | 26.38 | C |
| ATOM | 420 | C | TRP | A | 228 | −107.653 | 83.023 | 12.212 | 1.00 | 23.20 | C |

TABLE 13

| ATOM | 421 | O | TRP | A | 228 | −107.776 | 84.060 | 11.527 | 1.00 | 25.18 | O |
|---|---|---|---|---|---|---|---|---|---|---|---|
| ATOM | 422 | CB | TRP | A | 228 | −105.622 | 81.599 | 12.444 | 1.00 | 25.18 | C |
| ATOM | 423 | CG | TRP | A | 228 | −105.316 | 81.692 | 10.961 | 1.00 | 23.48 | C |
| ATOM | 424 | CD1 | TRP | A | 228 | −106.172 | 81.470 | 9.929 | 1.00 | 25.70 | C |
| ATOM | 425 | CD2 | TRP | A | 228 | −104.060 | 81.988 | 10.387 | 1.00 | 23.62 | C |
| ATOM | 426 | CE2 | TRP | A | 228 | −104.224 | 81.941 | 8.974 | 1.00 | 25.23 | C |
| ATOM | 427 | CE3 | TRP | A | 228 | −102.813 | 82.301 | 10.912 | 1.00 | 23.99 | C |
| ATOM | 428 | NE1 | TRP | A | 228 | −105.534 | 81.654 | 8.730 | 1.00 | 24.36 | N |
| ATOM | 429 | CZ2 | TRP | A | 228 | −103.179 | 82.164 | 8.096 | 1.00 | 25.75 | C |
| ATOM | 430 | CZ3 | TRP | A | 228 | −101.766 | 82.511 | 10.041 | 1.00 | 27.72 | C |
| ATOM | 431 | CH2 | TRP | A | 228 | −101.966 | 82.477 | 8.645 | 1.00 | 29.61 | C |
| ATOM | 432 | N | LYS | A | 229 | −108.610 | 82.111 | 12.348 | 1.00 | 28.40 | N |
| ATOM | 433 | CA | LYS | A | 229 | −109.904 | 82.239 | 11.613 | 1.00 | 27.35 | C |
| ATOM | 434 | C | LYS | A | 229 | −110.716 | 83.486 | 11.916 | 1.00 | 27.34 | C |
| ATOM | 435 | O | LYS | A | 229 | −111.341 | 84.042 | 11.021 | 1.00 | 24.15 | O |
| ATOM | 436 | CB | LYS | A | 229 | −110.739 | 80.955 | 11.719 | 1.00 | 34.49 | C |
| ATOM | 437 | CG | LYS | A | 229 | −110.199 | 79.862 | 10.814 | 1.00 | 42.23 | C |
| ATOM | 438 | CD | LYS | A | 229 | −110.501 | 80.213 | 9.335 | 1.00 | 50.98 | C |
| ATOM | 439 | CE | LYS | A | 229 | −109.668 | 79.455 | 8.298 | 1.00 | 51.88 | C |
| ATOM | 440 | NZ | LYS | A | 229 | −109.962 | 78.008 | 8.382 | 1.00 | 55.83 | N1+ |
| ATOM | 441 | N | GLN | A | 230 | −110.646 | 83.988 | 13.163 | 1.00 | 22.13 | N |
| ATOM | 442 | CA | GLN | A | 230 | −111.308 | 85.169 | 13.499 | 1.00 | 23.23 | C |
| ATOM | 443 | C | GLN | A | 230 | −110.559 | 86.376 | 12.914 | 1.00 | 26.53 | C |
| ATOM | 444 | O | GLN | A | 230 | −111.172 | 87.342 | 12.530 | 1.00 | 28.96 | O |
| ATOM | 445 | CB | GLN | A | 230 | −111.530 | 85.244 | 15.041 | 1.00 | 28.25 | C |

TABLE 13-continued

| ATOM | 446 | CG  | GLN | A | 230 | −112.576 | 86.265 | 15.474 | 1.00 | 31.72 | C |
|------|-----|-----|-----|---|-----|----------|--------|--------|------|-------|---|
| ATOM | 447 | CD  | GLN | A | 230 | −112.625 | 86.472 | 17.007 | 1.00 | 33.18 | C |
| ATOM | 448 | NE2 | GLN | A | 230 | −113.091 | 87.665 | 17.433 | 1.00 | 29.89 | N |
| ATOM | 449 | OE1 | GLN | A | 230 | −112.288 | 85.555 | 17.776 | 1.00 | 31.36 | O |
| ATOM | 450 | N   | LEU | A | 231 | −109.245 | 86.284 | 12.742 | 1.00 | 25.55 | N |
| ATOM | 451 | CA  | LEU | A | 231 | −108.451 | 87.359 | 12.171 | 1.00 | 23.69 | C |
| ATOM | 452 | C   | LEU | A | 231 | −108.307 | 87.445 | 10.627 | 1.00 | 28.39 | C |
| ATOM | 453 | O   | LEU | A | 231 | −108.149 | 88.537 | 10.062 | 1.00 | 27.36 | O |
| ATOM | 454 | CB  | LEU | A | 231 | −107.033 | 87.265 | 12.748 | 1.00 | 23.92 | C |
| ATOM | 455 | CG  | LEU | A | 231 | −107.009 | 87.610 | 14.255 | 1.00 | 23.15 | C |

TABLE 14

| ATOM | 456 | CD1 | LEU | A | 231 | −105.611 | 87.391 | 14.789 | 1.00 | 24.33 | C |
|------|-----|-----|-----|---|-----|----------|--------|--------|------|-------|---|
| ATOM | 457 | CD2 | LEU | A | 231 | −107.454 | 89.041 | 14.526 | 1.00 | 26.45 | C |
| ATOM | 458 | N   | VAL | A | 232 | −108.246 | 86.293 | 10.001 | 1.00 | 27.90 | N |
| ATOM | 459 | CA  | VAL | A | 232 | −107.851 | 86.215 | 8.615  | 1.00 | 31.48 | C |
| ATOM | 460 | C   | VAL | A | 232 | −108.803 | 87.040 | 7.747  | 1.00 | 33.91 | C |
| ATOM | 461 | O   | VAL | A | 232 | −110.005 | 86.973 | 7.957  | 1.00 | 30.37 | O |
| ATOM | 462 | CB  | VAL | A | 232 | −107.714 | 84.773 | 8.150  | 1.00 | 27.87 | C |
| ATOM | 463 | CG1 | VAL | A | 232 | −109.030 | 84.025 | 8.160  | 1.00 | 29.47 | C |
| ATOM | 464 | CG2 | VAL | A | 232 | −107.050 | 84.696 | 6.783  | 1.00 | 30.88 | C |
| ATOM | 465 | N   | ASN | A | 233 | −108.221 | 87.833 | 6.838  | 1.00 | 35.16 | N |
| ATOM | 466 | CA  | ASN | A | 233 | −108.945 | 88.690 | 5.860  | 1.00 | 37.19 | C |
| ATOM | 467 | C   | ASN | A | 233 | −108.160 | 88.790 | 4.536  | 1.00 | 36.25 | C |
| ATOM | 468 | O   | ASN | A | 233 | −107.350 | 89.715 | 4.316  | 1.00 | 42.41 | O |
| ATOM | 469 | CB  | ASN | A | 233 | −109.134 | 90.071 | 6.479  | 1.00 | 45.16 | C |
| ATOM | 470 | CG  | ASN | A | 233 | −109.772 | 91.051 | 5.526  | 1.00 | 51.93 | C |
| ATOM | 471 | ND2 | ASN | A | 233 | −109.249 | 92.287 | 5.479  | 1.00 | 56.58 | N |
| ATOM | 472 | OD1 | ASN | A | 233 | −110.706 | 90.693 | 4.819  | 1.00 | 50.78 | O |
| ATOM | 473 | N   | GLY | A | 234 | −108.364 | 87.818 | 3.668  | 1.00 | 33.18 | N |
| ATOM | 474 | CA  | GLY | A | 234 | −107.680 | 87.803 | 2.378  | 1.00 | 36.80 | C |
| ATOM | 475 | C   | GLY | A | 234 | −106.224 | 87.294 | 2.444  | 1.00 | 39.73 | C |
| ATOM | 476 | O   | GLY | A | 234 | −105.660 | 87.016 | 3.510  | 1.00 | 35.01 | O |
| ATOM | 477 | N   | LEU | A | 235 | −105.620 | 87.199 | 1.274  | 1.00 | 34.38 | N |
| ATOM | 478 | CA  | LEU | A | 235 | −104.260 | 86.704 | 1.114  | 1.00 | 30.03 | C |
| ATOM | 479 | C   | LEU | A | 235 | −103.306 | 87.700 | 1.654  | 1.00 | 31.66 | C |
| ATOM | 480 | O   | LEU | A | 235 | −103.575 | 88.894 | 1.638  | 1.00 | 33.19 | O |
| ATOM | 481 | CB  | LEU | A | 235 | −103.970 | 86.477 | −0.365 | 1.00 | 33.48 | C |
| ATOM | 482 | CG  | LEU | A | 235 | −104.871 | 85.423 | −0.998 | 1.00 | 36.37 | C |
| ATOM | 483 | CD1 | LEU | A | 235 | −104.533 | 85.326 | −2.508 | 1.00 | 40.42 | C |
| ATOM | 484 | CD2 | LEU | A | 235 | −104.764 | 84.087 | −0.280 | 1.00 | 36.84 | C |
| ATOM | 485 | N   | PRO | A | 236 | −102.191 | 87.243 | 2.194  | 1.00 | 28.44 | N |
| ATOM | 486 | CA  | PRO | A | 236 | −101.250 | 88.187 | 2.765  | 1.00 | 29.55 | C |
| ATOM | 487 | C   | PRO | A | 236 | −100.332 | 88.751 | 1.654  | 1.00 | 33.40 | C |
| ATOM | 488 | O   | PRO | A | 236 | −100.176 | 88.109 | 0.614  | 1.00 | 27.71 | O |
| ATOM | 489 | CB  | PRO | A | 236 | −100.406 | 87.271 | 3.642  | 1.00 | 29.57 | C |
| ATOM | 490 | CG  | PRO | A | 236 | −100.374 | 85.996 | 2.917  | 1.00 | 26.53 | C |

TABLE 15

| ATOM | 491 | CD  | PRO | A | 236 | −101.769 | 85.853 | 2.402  | 1.00 | 31.12 | C |
|------|-----|-----|-----|---|-----|----------|--------|--------|------|-------|---|
| ATOM | 492 | N   | PRO | A | 237 | −99.623  | 89.839 | 1.947  | 1.00 | 37.59 | N |
| ATOM | 493 | CA  | PRO | A | 237 | −98.528  | 90.215 | 1.033  | 1.00 | 39.69 | C |
| ATOM | 494 | C   | PRO | A | 237 | −97.493  | 89.095 | 0.834  | 1.00 | 44.89 | C |
| ATOM | 495 | O   | PRO | A | 237 | −97.217  | 88.309 | 1.770  | 1.00 | 37.55 | O |
| ATOM | 496 | CB  | PRO | A | 237 | −97.898  | 91.457 | 1.709  | 1.00 | 42.96 | C |
| ATOM | 497 | CG  | PRO | A | 237 | −98.639  | 91.688 | 2.995  | 1.00 | 42.18 | C |
| ATOM | 498 | CD  | PRO | A | 237 | −99.841  | 90.810 | 3.042  | 1.00 | 38.98 | C |
| ATOM | 499 | N   | TYR | A | 238 | −96.930  | 89.015 | −0.372 | 1.00 | 40.75 | N |
| ATOM | 500 | CA  | TYR | A | 238 | −95.859  | 88.071 | −0.668 | 1.00 | 40.80 | C |
| ATOM | 501 | C   | TYR | A | 238 | −94.695  | 88.111 | 0.344  | 1.00 | 33.52 | C |
| ATOM | 502 | O   | TYR | A | 238 | −94.179  | 87.083 | 0.659  | 1.00 | 32.36 | O |
| ATOM | 503 | CB  | TYR | A | 238 | −95.272  | 88.274 | −2.094 | 1.00 | 46.05 | C |
| ATOM | 504 | CG  | TYR | A | 238 | −94.080  | 87.365 | −2.470 | 1.00 | 51.13 | C |
| ATOM | 505 | CD1 | TYR | A | 238 | −94.268  | 86.008 | −2.812 | 1.00 | 55.84 | C |
| ATOM | 506 | CD2 | TYR | A | 238 | −92.749  | 87.880 | −2.494 | 1.00 | 59.32 | C |
| ATOM | 507 | CE1 | TYR | A | 238 | −93.177  | 85.192 | −3.137 | 1.00 | 56.49 | C |
| ATOM | 508 | CE2 | TYR | A | 238 | −91.638  | 87.077 | −2.829 | 1.00 | 61.40 | C |
| ATOM | 509 | CZ  | TYR | A | 238 | −91.844  | 85.736 | −3.153 | 1.00 | 65.15 | C |
| ATOM | 510 | OH  | TYR | A | 238 | −90.727  | 84.948 | −3.480 | 1.00 | 63.19 | O |
| ATOM | 511 | N   | LYS | A | 239 | −94.263  | 89.284 | 0.764  | 1.00 | 31.44 | N |
| ATOM | 512 | CA  | LYS | A | 239 | −93.214  | 89.435 | 1.780  | 1.00 | 32.68 | C |
| ATOM | 513 | C   | LYS | A | 239 | −93.479  | 88.548 | 3.006  | 1.00 | 30.12 | C |
| ATOM | 514 | O   | LYS | A | 239 | −92.579  | 87.958 | 3.561  | 1.00 | 29.08 | O |

TABLE 15-continued

| | | | | | | | | | | |
|---|---|---|---|---|---|---|---|---|---|---|
| ATOM | 515 | CB | LYS | A | 239 | −93.170 | 90.916 | 2.113 | 1.00 | 41.84 C |
| ATOM | 516 | CG | LYS | A | 239 | −92.178 | 91.459 | 3.105 | 1.00 | 48.30 C |
| ATOM | 517 | CD | LYS | A | 239 | −92.088 | 92.986 | 2.936 | 1.00 | 51.72 C |
| ATOM | 518 | CE | LYS | A | 239 | −91.803 | 93.740 | 4.221 | 1.00 | 55.22 C |
| ATOM | 519 | NZ | LYS | A | 239 | −92.859 | 93.440 | 5.244 | 1.00 | 55.94 N1+ |
| ATOM | 520 | N | GLU | A | 240 | −94.737 | 88.390 | 3.368 | 1.00 | 26.04 N |
| ATOM | 521 | CA | GLU | A | 240 | −95.117 | 87.664 | 4.570 | 1.00 | 27.60 C |
| ATOM | 522 | C | GLU | A | 240 | −94.995 | 86.168 | 4.421 | 1.00 | 29.20 C |
| ATOM | 523 | O | GLU | A | 240 | −94.785 | 85.484 | 5.420 | 1.00 | 23.45 O |
| ATOM | 524 | CB | GLU | A | 240 | −96.527 | 88.036 | 5.030 | 1.00 | 25.48 C |
| ATOM | 525 | CG | GLU | A | 240 | −97.052 | 87.235 | 6.239 | 1.00 | 27.90 C |

TABLE 16

| | | | | | | | | | | |
|---|---|---|---|---|---|---|---|---|---|---|
| ATOM | 526 | CD | GLU | A | 240 | −98.372 | 87.776 | 6.836 | 1.00 | 29.26 C |
| ATOM | 527 | OE1 | GLU | A | 240 | −98.778 | 88.875 | 6.510 | 1.00 | 31.53 O |
| ATOM | 528 | OE2 | GLU | A | 240 | −99.053 | 87.054 | 7.558 | 1.00 | 32.36 O1− |
| ATOM | 529 | N | ILE | A | 241 | −95.168 | 85.635 | 3.203 | 1.00 | 25.20 N |
| ATOM | 530 | CA | ILE | A | 241 | −95.136 | 84.194 | 3.027 | 1.00 | 29.06 C |
| ATOM | 531 | C | ILE | A | 241 | −93.857 | 83.564 | 3.538 | 1.00 | 24.96 C |
| ATOM | 532 | O | ILE | A | 241 | −93.894 | 82.530 | 4.174 | 1.00 | 24.40 O |
| ATOM | 533 | CB | ILE | A | 241 | −95.339 | 83.840 | 1.521 | 1.00 | 36.65 C |
| ATOM | 534 | CG1 | ILE | A | 241 | −96.739 | 84.273 | 1.041 | 1.00 | 42.81 C |
| ATOM | 535 | CG2 | ILE | A | 241 | −95.166 | 82.377 | 1.263 | 1.00 | 39.69 C |
| ATOM | 536 | CD1 | ILE | A | 241 | −97.869 | 83.936 | 2.003 | 1.00 | 46.32 C |
| ATOM | 537 | N | SER | A | 242 | −92.717 | 84.147 | 3.205 | 1.00 | 26.29 N |
| ATOM | 538 | CA | SER | A | 242 | −91.438 | 83.579 | 3.592 | 1.00 | 26.86 C |
| ATOM | 539 | C | SER | A | 242 | −91.229 | 83.569 | 5.094 | 1.00 | 25.88 C |
| ATOM | 540 | O | SER | A | 242 | −90.669 | 82.611 | 5.663 | 1.00 | 23.72 O |
| ATOM | 541 | CB | SER | A | 242 | −90.279 | 84.346 | 2.952 | 1.00 | 29.75 C |
| ATOM | 542 | OG | SER | A | 242 | −90.254 | 84.036 | 1.578 | 1.00 | 34.97 O |
| ATOM | 543 | N | VAL | A | 243 | −91.635 | 84.653 | 5.725 | 1.00 | 22.47 N |
| ATOM | 544 | CA | VAL | A | 243 | −91.489 | 84.745 | 7.171 | 1.00 | 24.78 C |
| ATOM | 545 | C | VAL | A | 243 | −92.425 | 83.761 | 7.834 | 1.00 | 24.92 C |
| ATOM | 546 | O | VAL | A | 243 | −92.061 | 83.141 | 8.857 | 1.00 | 24.19 O |
| ATOM | 547 | CB | VAL | A | 243 | −91.808 | 86.144 | 7.696 | 1.00 | 26.22 C |
| ATOM | 548 | CG1 | VAL | A | 243 | −91.725 | 86.160 | 9.205 | 1.00 | 28.40 C |
| ATOM | 549 | CG2 | VAL | A | 243 | −90.894 | 87.156 | 7.038 | 1.00 | 29.51 C |
| ATOM | 550 | N | HIS | A | 244 | −93.624 | 83.616 | 7.264 | 1.00 | 21.78 N |
| ATOM | 551 | CA | HIS | A | 244 | −94.631 | 82.676 | 7.764 | 1.00 | 21.33 C |
| ATOM | 552 | C | HIS | A | 244 | −94.086 | 81.259 | 7.755 | 1.00 | 21.60 C |
| ATOM | 553 | O | HIS | A | 244 | −94.242 | 80.500 | 8.726 | 1.00 | 21.80 O |
| ATOM | 554 | CB | HIS | A | 244 | −95.921 | 82.745 | 6.911 | 1.00 | 20.84 C |
| ATOM | 555 | CG | HIS | A | 244 | −96.969 | 81.778 | 7.330 | 1.00 | 21.23 C |
| ATOM | 556 | CD2 | HIS | A | 244 | −97.973 | 81.896 | 8.242 | 1.00 | 22.30 C |
| ATOM | 557 | ND1 | HIS | A | 244 | −97.051 | 80.489 | 6.838 | 1.00 | 26.16 N |
| ATOM | 558 | CE1 | HIS | A | 244 | −98.068 | 79.863 | 7.420 | 1.00 | 25.54 C |
| ATOM | 559 | NE2 | HIS | A | 244 | −98.623 | 80.681 | 8.289 | 1.00 | 24.70 N |
| ATOM | 560 | N | VAL | A | 245 | −93.458 | 80.861 | 6.653 | 1.00 | 21.27 N |

TABLE 17

| | | | | | | | | | | |
|---|---|---|---|---|---|---|---|---|---|---|
| ATOM | 561 | CA | VAL | A | 245 | −92.901 | 79.506 | 6.559 | 1.00 | 20.74 C |
| ATOM | 562 | C | VAL | A | 245 | −91.775 | 79.348 | 7.527 | 1.00 | 19.82 C |
| ATOM | 563 | O | VAL | A | 245 | −91.657 | 78.299 | 8.178 | 1.00 | 21.82 O |
| ATOM | 564 | CB | VAL | A | 245 | −92.439 | 79.172 | 5.125 | 1.00 | 23.52 C |
| ATOM | 565 | CG1 | VAL | A | 245 | −91.772 | 77.835 | 5.109 | 1.00 | 24.69 C |
| ATOM | 566 | CG2 | VAL | A | 245 | −93.621 | 79.122 | 4.191 | 1.00 | 25.48 C |
| ATOM | 567 | N | PHE | A | 246 | −90.983 | 80.396 | 7.685 | 1.00 | 20.67 N |
| ATOM | 568 | CA | PHE | A | 246 | −89.858 | 80.378 | 8.608 | 1.00 | 22.33 C |
| ATOM | 569 | C | PHE | A | 246 | −90.310 | 80.194 | 10.049 | 1.00 | 23.48 C |
| ATOM | 570 | O | PHE | A | 246 | −89.739 | 79.380 | 10.839 | 1.00 | 20.99 O |
| ATOM | 571 | CB | PHE | A | 246 | −89.054 | 81.701 | 8.524 | 1.00 | 23.13 C |
| ATOM | 572 | CG | PHE | A | 246 | −87.771 | 81.715 | 9.327 | 1.00 | 24.64 C |
| ATOM | 573 | CD1 | PHE | A | 246 | −86.838 | 80.682 | 9.214 | 1.00 | 25.20 C |
| ATOM | 574 | CD2 | PHE | A | 246 | −87.454 | 82.790 | 10.135 | 1.00 | 27.56 C |
| ATOM | 575 | CE1 | PHE | A | 246 | −85.631 | 80.750 | 9.914 | 1.00 | 29.06 C |
| ATOM | 576 | CE2 | PHE | A | 246 | −86.251 | 82.847 | 10.841 | 1.00 | 28.22 C |
| ATOM | 577 | CZ | PHE | A | 246 | −85.356 | 81.823 | 10.764 | 1.00 | 26.60 C |
| ATOM | 578 | N | TYR | A | 247 | −91.366 | 80.907 | 10.360 | 1.00 | 23.58 N |
| ATOM | 579 | CA | TYR | A | 247 | −92.075 | 80.744 | 11.687 | 1.00 | 23.11 C |
| ATOM | 580 | C | TYR | A | 247 | −92.576 | 79.331 | 11.937 | 1.00 | 23.49 C |
| ATOM | 581 | O | TYR | A | 247 | −92.460 | 78.803 | 13.086 | 1.60 | 20.33 O |
| ATOM | 582 | CB | TYR | A | 247 | −93.236 | 81.739 | 11.835 | 1.00 | 23.83 C |
| ATOM | 583 | CG | TYR | A | 247 | −94.094 | 81.552 | 13.083 | 1.00 | 24.06 C |

TABLE 17-continued

| ATOM | 584 | CD1 | TYR | A | 247 | −93.611 | 81.908 | 14.330 | 1.00 | 25.10 | C |
| ATOM | 585 | CD2 | TYR | A | 247 | −95.364 | 80.997 | 12.994 | 1.00 | 29.89 | C |
| ATOM | 586 | CE1 | TYR | A | 247 | −94.383 | 81.692 | 15.473 | 1.00 | 24.45 | C |
| ATOM | 587 | CE2 | TYR | A | 247 | −96.141 | 80.783 | 14.135 | 1.00 | 28.98 | C |
| ATOM | 588 | CZ | TYR | A | 247 | −95.622 | 81.159 | 15.354 | 1.00 | 27.55 | C |
| ATOM | 589 | OH | TYR | A | 247 | −96.383 | 81.002 | 16.474 | 1.00 | 30.95 | O |
| ATOM | 390 | N | ARG | A | 248 | −93.197 | 78.743 | 10.927 | 1.00 | 20.10 | N |
| ATOM | 591 | CA | ARG | A | 248 | −93.674 | 77.348 | 11.074 | 1.00 | 23.57 | C |
| ATOM | 592 | C | ARG | A | 248 | −92.524 | 76.328 | 11.238 | 1.00 | 23.70 | C |
| ATOM | 593 | O | ARG | A | 248 | −92.692 | 75.403 | 12.038 | 1.00 | 24.41 | O |
| ATOM | 594 | CB | ARG | A | 248 | −94.537 | 76.897 | 9.907 | 1.00 | 26.30 | C |
| ATOM | 595 | CG | ARG | A | 248 | −95.919 | 77.522 | 9.857 | 1.00 | 32.93 | C |

TABLE 18

| ATOM | 596 | CD | ARG | A | 248 | −97.095 | 76.574 | 10.166 | 1.00 | 47.80 | C |
| ATOM | 597 | NE | ARG | A | 248 | −98.235 | 77.430 | 10.576 | 1.00 | 53.35 | N |
| ATOM | 598 | CZ | ARG | A | 248 | −98.489 | 77.878 | 11.821 | 1.00 | 58.22 | C |
| ATOM | 599 | NH1 | ARG | A | 248 | −97.759 | 77.472 | 12.881 | 1.00 | 59.96 | N1+ |
| ATOM | 600 | NH2 | ARG | A | 248 | −99.518 | 78.731 | 12.021 | 1.00 | 52.67 | N |
| ATOM | 601 | N | CYS | A | 249 | −91.401 | 76.508 | 10.502 | 1.00 | 21.92 | N |
| ATOM | 602 | CA | CYS | A | 249 | −90.154 | 75.797 | 10.809 | 1.00 | 24.49 | C |
| ATOM | 603 | C | CYS | A | 248 | −89.676 | 75.856 | 12.274 | 1.00 | 23.26 | C |
| ATOM | 604 | O | CYS | A | 249 | −89.389 | 74.818 | 12.898 | 1.00 | 19.87 | O |
| ATOM | 605 | CB | CYS | A | 249 | −89.027 | 76.301 | 9.913 | 1.00 | 24.21 | C |
| ATOM | 606 | SG | CYS | A | 249 | −89.353 | 75.925 | 8.148 | 1.00 | 31.53 | S |
| ATOM | 607 | N | GLN | A | 250 | −89.604 | 77.056 | 12.799 | 1.00 | 21.07 | N |
| ATOM | 608 | CA | GLN | A | 250 | −89.245 | 77.255 | 14.213 | 1.00 | 24.78 | C |
| ATOM | 609 | C | GLN | A | 250 | −90.230 | 76.542 | 15.167 | 1.00 | 25.50 | C |
| ATOM | 610 | O | GLN | A | 250 | −89.794 | 75.912 | 16.104 | 1.00 | 24.08 | O |
| ATOM | 611 | CB | GLN | A | 250 | −89.205 | 78.726 | 14.544 | 1.00 | 24.55 | C |
| ATOM | 612 | CG | GLN | A | 250 | −88.047 | 79.484 | 13.934 | 1.00 | 26.53 | C |
| ATOM | 613 | CD | GLN | A | 250 | −87.925 | 80.855 | 14.528 | 1.00 | 28.68 | C |
| ATOM | 614 | NE2 | GLN | A | 250 | −87.750 | 81.844 | 13.684 | 1.00 | 28.49 | N |
| ATOM | 615 | OE1 | GLN | A | 250 | −87.953 | 81.016 | 15.767 | 1.00 | 28.35 | O |
| ATOM | 616 | N | CYS | A | 251 | −91.550 | 76.640 | 14.930 | 1.00 | 25.99 | N |
| ATOM | 817 | CA | CYS | A | 251 | −92.559 | 75.993 | 15.833 | 1.00 | 26.11 | C |
| ATOM | 618 | C | CYS | A | 251 | −92.270 | 74.482 | 15.874 | 1.00 | 25.63 | C |
| ATOM | 619 | O | CYS | A | 251 | −92.275 | 73.888 | 16.923 | 1.00 | 25.19 | O |
| ATOM | 620 | CB | CYS | A | 251 | −93.994 | 76.233 | 15.319 | 1.00 | 29.43 | C |
| ATOM | 621 | SG | CYS | A | 251 | −94.481 | 77.978 | 15.469 | 1.00 | 34.43 | S |
| ATOM | 622 | N | THR | A | 252 | −91.979 | 73.874 | 14.727 | 1.00 | 23.31 | N |
| ATOM | 623 | CA | THR | A | 252 | −91.750 | 72.473 | 14.672 | 1.00 | 24.92 | C |
| ATOM | 624 | C | THR | A | 252 | −90.428 | 72.029 | 15.308 | 1.00 | 25.51 | C |
| ATOM | 625 | O | THR | A | 252 | −90.401 | 71.018 | 16.019 | 1.00 | 25.21 | O |
| ATOM | 626 | CB | THR | A | 252 | −91.634 | 72.044 | 13.218 | 1.00 | 30.78 | C |
| ATOM | 627 | CG2 | THR | A | 252 | −91.499 | 70.507 | 13.083 | 1.00 | 28.82 | C |
| ATOM | 628 | OG1 | THR | A | 252 | −92.811 | 72.498 | 12.576 | 1.00 | 38.00 | O |
| ATOM | 629 | N | THR | A | 253 | −89.347 | 72.774 | 15.060 | 1.00 | 23.95 | N |
| ATOM | 630 | CA | THR | A | 253 | −88.046 | 72.441 | 15.656 | 1.00 | 24.48 | C |

TABLE 19

| ATOM | 631 | C | THR | A | 253 | −88.086 | 72.666 | 17.181 | 1.00 | 24.75 | C |
| ATOM | 632 | O | THR | A | 253 | −87.534 | 71.853 | 17.940 | 1.00 | 24.55 | O |
| ATOM | 633 | CB | THR | A | 253 | −86.820 | 73.151 | 14.980 | 1.00 | 28.62 | C |
| ATOM | 634 | CG2 | THR | A | 253 | −86.800 | 72.915 | 13.548 | 1.00 | 29.89 | C |
| ATOM | 635 | OG1 | THR | A | 253 | −86.870 | 74.547 | 15.222 | 1.00 | 29.20 | O |
| ATOM | 636 | N | VAL | A | 254 | −88.755 | 73.723 | 17.645 | 1.00 | 22.78 | N |
| ATOM | 637 | CA | VAL | A | 254 | −88.919 | 73.948 | 19.118 | 1.00 | 25.70 | C |
| ATOM | 638 | C | VAL | A | 254 | −89.613 | 72.727 | 19.793 | 1.00 | 26.72 | C |
| ATOM | 639 | O | VAL | A | 254 | −89.096 | 72.150 | 20.810 | 1.00 | 25.27 | O |
| ATOM | 640 | CB | VAL | A | 254 | −89.708 | 75.250 | 19.376 | 1.00 | 27.37 | C |
| ATOM | 641 | CG1 | VAL | A | 254 | −90.315 | 75.319 | 20.805 | 1.00 | 29.63 | C |
| ATOM | 642 | CG2 | VAL | A | 254 | −88.820 | 76.431 | 19.047 | 1.00 | 25.01 | C |
| ATOM | 643 | N | GLU | A | 255 | −90.723 | 72.281 | 19.204 | 1.00 | 29.93 | N |
| ATOM | 644 | CA | GLU | A | 255 | −91.460 | 71.180 | 19.779 | 1.00 | 32.48 | C |
| ATOM | 645 | C | GLU | A | 255 | −90.592 | 69.876 | 19.738 | 1.00 | 28.29 | C |
| ATOM | 646 | O | GLU | A | 255 | −90.632 | 69.093 | 20.660 | 1.00 | 28.79 | O |
| ATOM | 647 | CB | GLU | A | 255 | −92.817 | 70.959 | 19.078 | 1.00 | 38.57 | C |
| ATOM | 648 | CG | GLU | A | 255 | −93.470 | 69.575 | 19.331 | 1.00 | 46.15 | C |
| ATOM | 649 | CD | GLU | A | 255 | −93.851 | 69.184 | 20.795 | 1.00 | 54.90 | C |
| ATOM | 650 | OE1 | GLU | A | 255 | −93.224 | 69.606 | 21.829 | 1.00 | 52.64 | O |
| ATOM | 651 | OE2 | GLU | A | 255 | −94.822 | 68.375 | 20.922 | 1.00 | 62.08 | O1− |
| ATOM | 652 | N | THR | A | 256 | −89.850 | 69.651 | 18.668 | 1.00 | 26.33 | N |

TABLE 19-continued

| ATOM | 653 | CA  | THR | A | 256 | −88.992 | 68.486 | 18.605 | 1.00 | 27.86 | C  |
|------|-----|-----|-----|---|-----|---------|--------|--------|------|-------|----|
| ATOM | 654 | C   | THR | A | 256 | −87.810 | 68.521 | 19.540 | 1.00 | 25.69 | C  |
| ATOM | 655 | O   | THR | A | 256 | −87.359 | 67.474 | 20.028 | 1.00 | 21.71 | O  |
| ATOM | 656 | CB  | THR | A | 256 | −88.462 | 68.263 | 17.208 | 1.00 | 26.98 | C  |
| ATOM | 657 | CG2 | THR | A | 256 | −87.836 | 66.890 | 17.081 | 1.00 | 26.68 | C  |
| ATOM | 658 | OG1 | THR | A | 256 | −89.568 | 69.396 | 16.339 | 1.00 | 26.38 | O  |
| ATOM | 659 | N   | VAL | A | 257 | −87.257 | 69.692 | 19.716 | 1.00 | 20.54 | N  |
| ATOM | 660 | CA  | VAL | A | 257 | −86.212 | 69.861 | 20.718 | 1.00 | 22.72 | C  |
| ATOM | 661 | C   | VAL | A | 257 | −86.696 | 69.451 | 22.107 | 1.00 | 24.68 | C  |
| ATOM | 662 | O   | VAL | A | 257 | −85.966 | 68.767 | 22.866 | 1.00 | 22.82 | O  |
| ATOM | 663 | CB  | VAL | A | 257 | −85.678 | 71.329 | 20.734 | 1.00 | 21.52 | C  |
| ATOM | 664 | CG1 | VAL | A | 257 | −84.841 | 71.640 | 21.961 | 1.00 | 22.71 | C  |
| ATOM | 665 | CG2 | VAL | A | 257 | −84.870 | 71.630 | 19.450 | 1.00 | 22.77 | C  |

TABLE 20

| ATOM | 666 | N   | ARG | A | 258 | −87.922 | 69.867 | 22.455 | 1.00 | 23.96 | N   |
|------|-----|-----|-----|---|-----|---------|--------|--------|------|-------|-----|
| ATOM | 667 | CA  | ARG | A | 258 | −88.506 | 69.491 | 23.762 | 1.00 | 27.75 | C   |
| ATOM | 668 | C   | ARG | A | 258 | −88.687 | 67.984 | 23.876 | 1.00 | 25.70 | C   |
| ATOM | 669 | O   | ARG | A | 258 | −88.484 | 67.379 | 24.939 | 1.00 | 19.96 | O   |
| ATOM | 670 | CB  | ARG | A | 258 | −89.827 | 70.215 | 24.006 | 1.00 | 29.54 | C   |
| ATOM | 671 | CG  | ARG | A | 258 | −89.598 | 71.694 | 24.303 | 1.00 | 36.50 | C   |
| ATOM | 672 | CD  | ARG | A | 258 | −90.907 | 72.457 | 24.122 | 1.00 | 42.37 | C   |
| ATOM | 673 | NE  | ARG | A | 258 | −90.762 | 73.853 | 24.447 | 1.00 | 45.82 | N   |
| ATOM | 674 | CZ  | ARG | A | 258 | −91.566 | 74.824 | 24.040 | 1.00 | 44.79 | C   |
| ATOM | 675 | NH1 | ARG | A | 258 | −92.605 | 74.570 | 23.234 | 1.00 | 49.04 | N1+ |
| ATOM | 676 | NH2 | ARG | A | 258 | −91.297 | 76.058 | 24.441 | 1.00 | 39.28 | N   |
| ATOM | 677 | N   | GLU | A | 259 | −89.059 | 67.369 | 22.758 | 1.00 | 22.49 | N   |
| ATOM | 678 | CA  | GLU | A | 259 | −89.266 | 65.934 | 22.723 | 1.00 | 23.47 | C   |
| ATOM | 679 | C   | GLU | A | 259 | −87.945 | 65.165 | 22.850 | 1.00 | 23.30 | C   |
| ATOM | 680 | O   | GLU | A | 259 | −87.900 | 64.162 | 23.516 | 1.00 | 21.31 | O   |
| ATOM | 681 | CB  | GLU | A | 259 | −89.944 | 65.554 | 21.413 | 1.00 | 23.94 | C   |
| ATOM | 682 | CG  | GLU | A | 259 | −91.415 | 65.918 | 21.391 | 1.00 | 28.57 | C   |
| ATOM | 683 | CD  | GLU | A | 259 | −92.009 | 65.642 | 19.990 | 1.00 | 31.69 | C   |
| ATOM | 684 | OE1 | GLU | A | 259 | −91.236 | 65.458 | 18.994 | 1.00 | 33.72 | O   |
| ATOM | 685 | OE2 | GLU | A | 259 | −93.247 | 65.550 | 19.930 | 1.00 | 39.03 | O1− |
| ATOM | 686 | N   | LEU | A | 260 | −86.927 | 65.610 | 22.114 | 1.00 | 20.99 | N   |
| ATOM | 687 | CA  | LEU | A | 260 | −85.543 | 65.124 | 22.241 | 1.00 | 22.23 | C   |
| ATOM | 688 | C   | LEU | A | 260 | −84.964 | 65.185 | 23.644 | 1.00 | 19.81 | C   |
| ATOM | 689 | O   | LEU | A | 260 | −84.330 | 64.230 | 24.085 | 1.00 | 21.52 | O   |
| ATOM | 690 | CB  | LEU | A | 260 | −84.655 | 65.866 | 21.244 | 1.00 | 20.41 | C   |
| ATOM | 691 | CG  | LEU | A | 260 | −84.813 | 65.354 | 19.789 | 1.00 | 21.07 | C   |
| ATOM | 692 | CD1 | LEU | A | 260 | −84.187 | 66.403 | 18.867 | 1.00 | 21.47 | C   |
| ATOM | 693 | CD2 | LEU | A | 260 | −84.180 | 63.987 | 19.597 | 1.00 | 22.68 | C   |
| ATOM | 694 | N   | THR | A | 261 | −85.197 | 66.291 | 24.303 | 1.00 | 20.33 | N   |
| ATOM | 695 | CA  | THR | A | 261 | −84.839 | 66.484 | 25.703 | 1.00 | 23.03 | C   |
| ATOM | 696 | C   | THR | A | 261 | −85.505 | 65.411 | 26.581 | 1.00 | 27.17 | C   |
| ATOM | 697 | O   | THR | A | 261 | −84.793 | 64.774 | 27.404 | 1.00 | 28.62 | O   |
| ATOM | 698 | CB  | THR | A | 261 | −85.184 | 67.888 | 26.172 | 1.00 | 22.70 | C   |
| ATOM | 699 | CG2 | THR | A | 261 | −84.713 | 68.139 | 27.590 | 1.00 | 27.27 | C   |
| ATOM | 700 | OG1 | THR | A | 261 | −84.555 | 68.867 | 25.346 | 1.00 | 23.21 | O   |

TABLE 21

| ATOM | 701 | N   | GLU | A | 262 | −86.813 | 65.129 | 26.366 | 1.00 | 26.54 | N   |
|------|-----|-----|-----|---|-----|---------|--------|--------|------|-------|-----|
| ATOM | 702 | CA  | GLU | A | 262 | −87.505 | 64.117 | 27.142 | 1.00 | 28.98 | C   |
| ATOM | 703 | C   | GLU | A | 262 | −86.952 | 62.764 | 26.755 | 1.00 | 25.16 | C   |
| ATOM | 704 | O   | GLU | A | 262 | −86.681 | 61.935 | 27.616 | 1.00 | 25.51 | O   |
| ATOM | 705 | CB  | GLU | A | 262 | −89.065 | 64.096 | 26.996 | 1.00 | 29.46 | C   |
| ATOM | 706 | CG  | GLU | A | 262 | −89.804 | 65.206 | 27.688 | 1.00 | 37.91 | C   |
| ATOM | 707 | CD  | GLU | A | 262 | −89.393 | 65.458 | 29.156 | 1.00 | 38.92 | C   |
| ATOM | 708 | OE1 | GLU | A | 262 | −89.343 | 64.509 | 29.907 | 1.00 | 46.37 | O   |
| ATOM | 709 | OE2 | GLU | A | 262 | −89.117 | 66.616 | 29.537 | 1.00 | 41.43 | O1− |
| ATOM | 710 | N   | PHE | A | 263 | −86.753 | 62.537 | 25.471 | 1.00 | 22.12 | N   |
| ATOM | 711 | CA  | PHE | A | 263 | −86.199 | 61.274 | 25.021 | 1.90 | 22.19 | C   |
| ATOM | 712 | C   | PHE | A | 263 | −84.832 | 60.945 | 25.683 | 1.00 | 21.53 | C   |
| ATOM | 713 | O   | PHE | A | 263 | −84.511 | 59.736 | 26.031 | 1.00 | 21.92 | O   |
| ATOM | 714 | CB  | PHE | A | 263 | −86.126 | 61.290 | 23.465 | 1.00 | 20.77 | C   |
| ATOM | 715 | CG  | PHE | A | 263 | −85.332 | 60.189 | 22.847 | 1.00 | 22.53 | C   |
| ATOM | 716 | CD1 | PHE | A | 263 | −85.879 | 58.886 | 22.695 | 1.00 | 23.74 | C   |
| ATOM | 717 | CD2 | PHE | A | 263 | −84.037 | 60.443 | 22.322 | 1.00 | 21.36 | C   |
| ATOM | 713 | CE1 | PHE | A | 263 | −85.157 | 57.855 | 22.082 | 1.00 | 23.16 | C   |
| ATOM | 719 | CE2 | PHE | A | 263 | −83.323 | 59.420 | 21.713 | 1.00 | 22.52 | C   |
| ATOM | 720 | CZ  | PHE | A | 263 | −83.872 | 58.113 | 21.590 | 1.00 | 23.87 | C   |
| ATOM | 721 | N   | ALA | A | 264 | −84.013 | 61.973 | 25.761 | 1.00 | 20.57 | N   |

TABLE 21-continued

| ATOM | 722 | CA | ALA | A | 264 | −82.630 | 61.832 | 26.257 | 1.00 | 20.84 | C |
| --- | --- | --- | --- | --- | --- | --- | --- | --- | --- | --- | --- |
| ATOM | 723 | C | ALA | A | 264 | −82.643 | 61.333 | 27.684 | 1.00 | 22.31 | C |
| ATOM | 724 | O | ALA | A | 264 | −81.772 | 60.590 | 28.063 | 1.00 | 23.76 | O |
| ATOM | 725 | CB | ALA | A | 264 | −81.857 | 63.111 | 26.183 | 1.00 | 19.54 | C |
| ATOM | 726 | N | LYS | A | 265 | −83.656 | 61.698 | 28.448 | 1.00 | 25.83 | N |
| ATOM | 727 | CA | LYS | A | 265 | −83.764 | 61.250 | 29.843 | 1.00 | 26.84 | C |
| ATOM | 728 | C | LYS | A | 265 | −83.900 | 59.725 | 29.954 | 1.00 | 27.47 | C |
| ATOM | 729 | O | LYS | A | 265 | −83.539 | 59.154 | 30.995 | 1.00 | 23.98 | O |
| ATOM | 730 | CB | LYS | A | 265 | −84.939 | 61.903 | 30.514 | 1.00 | 29.97 | C |
| ATOM | 731 | CG | LYS | A | 265 | −84.858 | 63.418 | 30.681 | 1.00 | 31.35 | C |
| ATOM | 732 | CD | LYS | A | 265 | −86.149 | 63.869 | 31.323 | 1.00 | 33.74 | C |
| ATOM | 733 | CE | LYS | A | 265 | −86.202 | 65.355 | 31.504 | 1.00 | 35.36 | C |
| ATOM | 734 | NZ | LYS | A | 265 | −87.484 | 65.759 | 32.106 | 1.00 | 37.19 | N1+ |
| ATOM | 735 | N | SER | A | 266 | −84.391 | 59.074 | 28.906 | 1.00 | 23.06 | N |

TABLE 22

| ATOM | 736 | CA | SER | A | 266 | −84.514 | 57.605 | 28.866 | 1.00 | 23.53 | C |
| --- | --- | --- | --- | --- | --- | --- | --- | --- | --- | --- | --- |
| ATOM | 737 | C | SER | A | 266 | −83.317 | 56.846 | 28.324 | 1.00 | 22.93 | C |
| ATOM | 738 | O | SER | A | 266 | −83.305 | 55.613 | 28.389 | 1.00 | 23.34 | O |
| ATOM | 739 | CB | SER | A | 266 | −85.783 | 57.165 | 28.097 | 1.00 | 23.51 | C |
| ATOM | 740 | OG | SER | A | 266 | −86.917 | 57.659 | 28.781 | 1.00 | 27.04 | O |
| ATOM | 741 | N | ILE | A | 267 | −82.292 | 57.558 | 27.839 | 1.00 | 21.32 | N |
| ATOM | 742 | CA | ILE | A | 267 | −81.043 | 56.965 | 27.365 | 1.00 | 20.33 | C |
| ATOM | 743 | C | ILE | A | 267 | −80.297 | 56.593 | 28.641 | 1.00 | 24.01 | C |
| ATOM | 744 | O | ILE | A | 267 | −80.084 | 57.462 | 29.493 | 1.00 | 26.38 | O |
| ATOM | 745 | CB | ILE | A | 267 | −80.212 | 57.907 | 26.560 | 1.00 | 21.56 | C |
| ATOM | 746 | CG1 | ILE | A | 267 | −80.948 | 58.246 | 25.253 | 1.00 | 24.08 | C |
| ATOM | 747 | CG2 | ILE | A | 267 | −78.852 | 57.273 | 26.220 | 1.00 | 24.45 | C |
| ATOM | 748 | CD1 | ILE | A | 267 | −80.390 | 59.479 | 24.606 | 1.00 | 23.72 | C |
| ATOM | 749 | N | PRO | A | 268 | −80.036 | 55.298 | 28.835 | 1.00 | 27.46 | N |
| ATOM | 750 | CA | PRO | A | 268 | −79.385 | 54.876 | 30.078 | 1.00 | 27.50 | C |
| ATOM | 751 | C | PRO | A | 268 | −78.088 | 55.633 | 30.323 | 1.00 | 26.85 | C |
| ATOM | 752 | O | PRO | A | 268 | −77.247 | 55.797 | 29.403 | 1.00 | 24.54 | O |
| ATOM | 753 | CB | PRO | A | 268 | −79.095 | 53.375 | 29.833 | 1.00 | 31.30 | C |
| ATOM | 754 | CG | PRO | A | 268 | −80.077 | 52.961 | 28.765 | 1.00 | 31.63 | C |
| ATOM | 755 | CD | PRO | A | 268 | −80.177 | 54.180 | 27.875 | 1.00 | 27.41 | C |
| ATOM | 756 | N | SER | A | 268 | −77.965 | 56.117 | 31.552 | 1.00 | 25.73 | N |
| ATOM | 757 | CA | SER | A | 269 | −76.825 | 56.875 | 32.071 | 1.00 | 26.29 | C |
| ATOM | 758 | C | SER | A | 269 | −76.777 | 58.364 | 31.676 | 1.00 | 26.88 | C |
| ATOM | 759 | O | SER | A | 269 | −75.985 | 59.116 | 32.270 | 1.00 | 22.24 | O |
| ATOM | 760 | CB | SER | A | 269 | −75.481 | 56.213 | 31.806 | 1.00 | 27.32 | C |
| ATOM | 761 | OG | SER | A | 269 | −75.460 | 54.962 | 32.435 | 1.00 | 38.88 | O |
| ATOM | 762 | N | PHE | A | 270 | −77.598 | 58.807 | 30.708 | 1.00 | 25.22 | N |
| ATOM | 763 | CA | PHE | A | 270 | −77.627 | 60.232 | 30.358 | 1.00 | 23.82 | C |
| ATOM | 764 | C | PHE | A | 270 | −77.924 | 61.093 | 31.588 | 1.00 | 23.99 | C |
| ATOM | 765 | O | PHE | A | 270 | −77.283 | 62.106 | 31.804 | 1.00 | 25.71 | O |
| ATOM | 766 | CB | PHE | A | 270 | −78.728 | 60.481 | 29.313 | 1.00 | 22.96 | C |
| ATOM | 767 | CG | PHE | A | 270 | −78.826 | 61.896 | 28.883 | 1.00 | 23.60 | C |
| ATOM | 768 | CD1 | PHE | A | 270 | −77.966 | 62.384 | 27.883 | 1.00 | 22.76 | C |
| ATOM | 769 | CD2 | PHE | A | 270 | −79.740 | 62.747 | 29.436 | 1.00 | 22.64 | C |
| ATOM | 770 | CE1 | PHE | A | 270 | −78.058 | 63.692 | 27.451 | 1.00 | 20.70 | C |

TABLE 23

| ATOM | 771 | CE2 | PHE | A | 270 | −79.819 | 64.070 | 29.014 | 1.00 | 22.58 | C |
| --- | --- | --- | --- | --- | --- | --- | --- | --- | --- | --- | --- |
| ATOM | 772 | CZ | PHE | A | 270 | −78.955 | 64.542 | 28.023 | 1.00 | 20.60 | C |
| ATOM | 773 | N | SER | A | 271 | −78.915 | 60.709 | 32.370 | 1.00 | 24.16 | N |
| ATOM | 774 | CA | SER | A | 271 | −79.327 | 61.473 | 33.554 | 1.00 | 25.56 | C |
| ATOM | 775 | C | SER | A | 271 | −78.318 | 61.460 | 34.729 | 1.00 | 25.23 | C |
| ATOM | 776 | O | SER | A | 271 | −78.500 | 62.205 | 35.657 | 1.00 | 29.47 | O |
| ATOM | 777 | CB | SER | A | 271 | −80.715 | 61.092 | 34.035 | 1.00 | 28.81 | C |
| ATOM | 778 | OG | SER | A | 271 | −81.690 | 61.513 | 33.082 | 1.00 | 30.33 | O |
| ATOM | 779 | N | SER | A | 272 | −77.281 | 60.663 | 34.638 | 1.00 | 26.56 | N |
| ATOM | 780 | CA | SER | A | 272 | −76.201 | 60.569 | 35.617 | 1.00 | 30.69 | C |
| ATOM | 781 | C | SER | A | 272 | −75.068 | 61.522 | 35.254 | 1.00 | 29.88 | C |
| ATOM | 782 | O | SER | A | 272 | −74.169 | 61.744 | 36.060 | 1.00 | 24.66 | O |
| ATOM | 783 | CB | SER | A | 272 | −75.664 | 59.122 | 35.651 | 1.00 | 28.77 | C |
| ATOM | 784 | OG | SER | A | 272 | −74.755 | 58.874 | 34.546 | 1.00 | 36.04 | O |
| ATOM | 785 | N | LEU | A | 273 | −75.079 | 62.028 | 34.020 | 1.00 | 25.71 | N |
| ATOM | 786 | CA | LEU | A | 273 | −74.093 | 63.022 | 33.600 | 1.00 | 23.88 | C |
| ATOM | 787 | C | LEU | A | 273 | −74.290 | 64.287 | 34.410 | 1.00 | 22.51 | C |
| ATOM | 788 | O | LEU | A | 273 | −75.405 | 64.625 | 34.845 | 1.00 | 21.40 | O |
| ATOM | 789 | CB | LEU | A | 273 | −74.228 | 63.396 | 32.106 | 1.00 | 23.37 | C |
| ATOM | 790 | CG | LEU | A | 273 | −73.929 | 62.206 | 31.217 | 1.00 | 22.94 | C |

TABLE 23-continued

| ATOM | 791 | CD1 | LEU | A | 273 | −74.238 | 62.437 | 29.793 | 1.00 | 22.67 | C |
| --- | --- | --- | --- | --- | --- | --- | --- | --- | --- | --- | --- |
| ATOM | 792 | CD2 | LEU | A | 273 | −72.517 | 61.683 | 31.326 | 1.00 | 24.37 | C |
| ATOM | 793 | N | PHE | A | 274 | −73.230 | 65.066 | 34.492 | 1.00 | 22.37 | N |
| ATOM | 794 | CA | PHE | A | 274 | −73.401 | 66.466 | 34.990 | 1.00 | 25.17 | C |
| ATOM | 795 | C | PHE | A | 274 | −74.501 | 67.196 | 34.207 | 1.00 | 27.10 | C |
| ATOM | 796 | O | PHE | A | 274 | −74.594 | 67.075 | 32.968 | 1.00 | 21.50 | O |
| ATOM | 797 | CB | PHE | A | 274 | −72.116 | 67.275 | 34.821 | 1.00 | 25.49 | C |
| ATOM | 798 | CG | PHE | A | 274 | −70.909 | 66.724 | 35.528 | 1.00 | 25.96 | C |
| ATOM | 799 | CD1 | PHE | A | 274 | −71.003 | 66.250 | 36.845 | 1.00 | 27.77 | C |
| ATOM | 800 | CD2 | PHE | A | 274 | −69.647 | 66.782 | 34.914 | 1.00 | 26.44 | C |
| ATOM | 801 | CE1 | PHE | A | 274 | −69.867 | 65.841 | 37.534 | 1.00 | 29.91 | C |
| ATOM | 802 | CE2 | PHE | A | 274 | −68.517 | 66.364 | 35.586 | 1.00 | 27.25 | C |
| ATOM | 803 | CZ | PHE | A | 274 | −68.628 | 65.903 | 36.899 | 1.00 | 27.19 | C |
| ATOM | 804 | N | LEU | A | 275 | −75.243 | 68.047 | 34.882 | 1.00 | 22.79 | N |
| ATOM | 805 | CA | LEU | A | 275 | −76.327 | 68.756 | 34.217 | 1.00 | 29.42 | C |

TABLE 24

| ATOM | 806 | C | LEU | A | 275 | −75.856 | 69.660 | 33.071 | 1.00 | 25.86 | C |
| --- | --- | --- | --- | --- | --- | --- | --- | --- | --- | --- | --- |
| ATOM | 807 | O | LEU | A | 275 | −76.477 | 69.695 | 31.995 | 3.00 | 23.37 | O |
| ATOM | 808 | CB | LEU | A | 275 | −77.172 | 69.489 | 35.259 | 1.00 | 29.04 | C |
| ATOM | 809 | CG | LEU | A | 275 | −78.586 | 69.904 | 34.953 | 1.00 | 35.87 | C |
| ATOM | 810 | CD1 | LEU | A | 275 | −79.414 | 68.750 | 34.373 | 1.00 | 36.71 | C |
| ATOM | 811 | CD2 | LEU | A | 275 | −79.206 | 70.471 | 36.233 | 1.00 | 38.69 | C |
| ATOM | 812 | N | ASN | A | 276 | −74.689 | 70.294 | 33.268 | 1.00 | 26.58 | N |
| ATOM | 813 | CA | ASN | A | 276 | −74.067 | 71.089 | 32.242 | 1.00 | 25.96 | C |
| ATOM | 814 | C | ASN | A | 276 | −73.762 | 70.286 | 31.001 | 1.00 | 25.09 | C |
| ATOM | 815 | O | ASN | A | 276 | −73.963 | 70.787 | 29.858 | 1.00 | 21.28 | O |
| ATOM | 816 | CB | ASN | A | 276 | −72.766 | 71.760 | 32.718 | 1.00 | 33.65 | C |
| ATOM | 817 | CG | ASN | A | 276 | −73.011 | 72.964 | 33.626 | 1.00 | 41.49 | C |
| ATOM | 818 | ND2 | ASN | A | 276 | −73.911 | 73.875 | 33.229 | 1.00 | 45.31 | N |
| ATOM | 819 | OD1 | ASN | A | 276 | −72.363 | 73.081 | 34.682 | 1.00 | 56.87 | O |
| ATOM | 820 | N | ASP | A | 277 | −73.259 | 69.054 | 31.202 | 1.00 | 24.56 | N |
| ATOM | 821 | CA | ASP | A | 277 | −73.019 | 68.141 | 30.106 | 1.00 | 22.03 | C |
| ATOM | 822 | C | ASP | A | 277 | −74.276 | 67.709 | 29.404 | 1.00 | 22.69 | C |
| ATOM | 823 | O | ASP | A | 277 | −74.296 | 67.688 | 28.161 | 1.00 | 22.50 | O |
| ATOM | 824 | CB | ASP | A | 277 | −72.188 | 66.961 | 30.534 | 1.00 | 23.66 | C |
| ATOM | 825 | CG | ASP | A | 277 | −70.706 | 67.348 | 30.737 | 1.00 | 26.98 | C |
| ATOM | 326 | OD1 | ASP | A | 277 | −70.264 | 68.503 | 30.342 | 1.00 | 25.55 | O |
| ATOM | 827 | OD2 | ASP | A | 277 | −70.002 | 66.507 | 31.325 | 1.00 | 28.60 | O1− |
| ATOM | 828 | N | GLN | A | 278 | −75.324 | 67.384 | 30.166 | 1.00 | 21.69 | N |
| ATOM | 829 | CA | GLN | A | 278 | −76.596 | 67.085 | 29.544 | 1.00 | 22.92 | C |
| ATOM | 830 | C | GLN | A | 278 | −77.060 | 68.214 | 28.641 | 1.00 | 20.19 | C |
| ATOM | 831 | O | GLN | A | 278 | −77.434 | 67.979 | 27.465 | 1.00 | 18.26 | O |
| ATOM | 832 | CB | GLN | A | 278 | −77.673 | 66.714 | 30.560 | 1.00 | 25.99 | C |
| ATOM | 833 | CG | GLN | A | 278 | −77.374 | 65.494 | 31.445 | 1.00 | 26.28 | C |
| ATOM | 834 | CD | GLN | A | 278 | −78.435 | 65.308 | 32.519 | 1.00 | 29.01 | C |
| ATOM | 835 | NE2 | GLN | A | 278 | −77.985 | 65.071 | 33.764 | 1.00 | 28.55 | N |
| ATOM | 836 | OE1 | GLN | A | 278 | −79.634 | 65.443 | 32.254 | 1.00 | 23.66 | O |
| ATOM | 837 | N | VAL | A | 279 | −76.987 | 69.428 | 29.165 | 1.00 | 19.32 | N |
| ATOM | 838 | CA | VAL | A | 279 | −77.348 | 70.619 | 28.389 | 1.00 | 21.18 | C |
| ATOM | 839 | C | VAL | A | 279 | −76.511 | 70.805 | 27.117 | 1.00 | 21.38 | C |
| ATOM | 840 | O | VAL | A | 279 | −77.046 | 71.051 | 26.020 | 1.00 | 18.26 | O |

TABLE 25

| ATOM | 841 | CB | VAL | A | 279 | −77.356 | 71.878 | 29.268 | 1.00 | 22.27 | C |
| --- | --- | --- | --- | --- | --- | --- | --- | --- | --- | --- | --- |
| ATOM | 842 | CG1 | VAL | A | 279 | −77.634 | 73.150 | 28.422 | 1.00 | 23.34 | C |
| ATOM | 843 | CG2 | VAL | A | 279 | −78.428 | 71.737 | 30.305 | 1.00 | 23.49 | C |
| ATOM | 844 | N | THR | A | 280 | −75.205 | 70.633 | 27.252 | 1.00 | 20.48 | N |
| ATOM | 845 | CA | THR | A | 280 | −74.315 | 70.757 | 26.122 | 1.00 | 20.50 | C |
| ATOM | 848 | C | THR | A | 280 | −74.589 | 69.754 | 25.006 | 1.00 | 20.85 | C |
| ATOM | 847 | O | THR | A | 280 | −74.563 | 70.104 | 23.817 | 1.00 | 18.46 | O |
| ATOM | 848 | CB | THR | A | 280 | −72.876 | 70.622 | 26.620 | 1.00 | 22.81 | C |
| ATOM | 849 | CG2 | THR | A | 280 | −71.895 | 70.624 | 25.503 | 1.00 | 22.64 | C |
| ATOM | 850 | OG1 | THR | A | 280 | −72.570 | 71.725 | 27.464 | 1.00 | 24.03 | O |
| ATOM | 851 | N | LEU | A | 281 | −74.792 | 68.471 | 25.406 | 1.00 | 21.37 | N |
| ATOM | 852 | CA | LEU | A | 281 | −75.085 | 67.455 | 24.473 | 1.00 | 21.63 | C |
| ATOM | 853 | C | LEU | A | 281 | −76.391 | 67.796 | 23.680 | 1.00 | 20.72 | C |
| ATOM | 854 | O | LEU | A | 281 | −76.447 | 67.645 | 22.430 | 1.00 | 20.46 | O |
| ATOM | 855 | CB | LEU | A | 281 | −75.147 | 66.097 | 25.178 | 1.00 | 21.96 | C |
| ATOM | 856 | CG | LEU | A | 281 | −73.837 | 65.487 | 25.736 | 1.00 | 20.61 | C |
| ATOM | 857 | CD1 | LEU | A | 281 | −74.183 | 64.215 | 26.498 | 1.00 | 23.72 | C |
| ATOM | 858 | CD2 | LEU | A | 281 | −72.877 | 65.208 | 24.559 | 1.00 | 21.50 | C |
| ATOM | 859 | N | LEU | A | 282 | −77.426 | 68.223 | 24.370 | 1.00 | 18.08 | N |

TABLE 25-continued

| | | | | | | | | | | | |
|---|---|---|---|---|---|---|---|---|---|---|---|
| ATOM | 860 | CA | LEU | A | 282 | −78.655 | 68.515 | 23.698 | 1.00 | 19.48 | C |
| ATOM | 861 | C | LEU | A | 282 | −78.453 | 69.787 | 22.777 | 1.00 | 22.33 | C |
| ATOM | 862 | O | LEU | A | 282 | −78.831 | 69.790 | 21.563 | 1.00 | 22.17 | O |
| ATOM | 863 | CB | LEU | A | 282 | −79.800 | 68.691 | 24.694 | 1.00 | 20.45 | C |
| ATOM | 864 | CG | LEU | A | 282 | −80.209 | 67.338 | 25.257 | 1.00 | 20.38 | C |
| ATOM | 865 | CD1 | LEU | A | 282 | −80.939 | 67.520 | 26.547 | 1.00 | 20.70 | C |
| ATOM | 866 | CD2 | LEU | A | 282 | −81.114 | 66.618 | 24.275 | 1.00 | 20.57 | C |
| ATOM | 867 | N | LYS | A | 282 | −77.843 | 70.824 | 23.333 | 1.00 | 22.22 | N |
| ATOM | 868 | CA | LYS | A | 283 | −77.566 | 72.061 | 22.544 | 1.00 | 23.13 | C |
| ATOM | 869 | C | LYS | A | 283 | −76.886 | 71.757 | 21.148 | 1.00 | 23.10 | C |
| ATOM | 870 | O | LYS | A | 283 | −77.382 | 72.293 | 20.120 | 1.00 | 20.83 | O |
| ATOM | 871 | CB | LYS | A | 283 | −76.740 | 73.034 | 23.368 | 1.00 | 26.13 | C |
| ATOM | 872 | CG | LYS | A | 283 | −76.298 | 74.328 | 22.662 | 1.00 | 34.37 | C |
| ATOM | 873 | CD | LYS | A | 283 | −75.236 | 75.038 | 23.529 | 1.00 | 37.83 | C |
| ATOM | 874 | CE | LYS | A | 283 | −74.649 | 76.271 | 22.868 | 1.00 | 36.06 | C |
| ATOM | 875 | NZ | LYS | A | 283 | −75.623 | 77.395 | 22.874 | 1.00 | 37.04 | N1+ |

TABLE 26

| | | | | | | | | | | | |
|---|---|---|---|---|---|---|---|---|---|---|---|
| ATOM | 876 | N | TYR | A | 284 | −75.844 | 70.879 | 21.103 | 1.00 | 21.05 | N |
| ATOM | 877 | CA | TYR | A | 284 | −75.096 | 70.637 | 19.874 | 1.00 | 25.09 | C |
| ATOM | 878 | C | TYR | A | 284 | −75.639 | 69.437 | 19.089 | 1.00 | 25.96 | C |
| ATOM | 879 | O | TYR | A | 284 | −75.240 | 69.230 | 17.975 | 1.00 | 27.41 | O |
| ATOM | 880 | CB | TYR | A | 284 | −73.592 | 70.442 | 20.141 | 1.00 | 28.51 | C |
| ATOM | 881 | CG | TYR | A | 284 | −72.908 | 71.712 | 20.518 | 1.00 | 26.70 | C |
| ATOM | 882 | CD1 | TYR | A | 284 | −72.463 | 72.598 | 19.529 | 1.00 | 29.90 | C |
| ATOM | 883 | CD2 | TYR | A | 284 | −72.642 | 72.012 | 21.845 | 1.00 | 28.97 | C |
| ATOM | 884 | CE1 | TYR | A | 284 | −71.833 | 73.808 | 19.892 | 1.00 | 31.05 | C |
| ATOM | 885 | CE2 | TYR | A | 284 | −72.053 | 73.216 | 22.224 | 1.00 | 30.46 | C |
| ATOM | 886 | CZ | TYR | A | 284 | −71.641 | 74.121 | 21.249 | 1.00 | 31.92 | C |
| ATOM | 887 | OH | TYR | A | 284 | −71.035 | 75.327 | 21.678 | 1.00 | 34.89 | O |
| ATOM | 888 | N | GLY | A | 285 | −76.510 | 68.654 | 19.711 | 1.00 | 21.57 | N |
| ATOM | 889 | CA | GLY | A | 235 | −77.076 | 67.439 | 19.141 | 1.00 | 23.64 | C |
| ATOM | 890 | C | GLY | A | 285 | −78.475 | 67.503 | 18.543 | 1.00 | 22.01 | C |
| ATOM | 891 | O | GLY | A | 285 | −78.808 | 66.715 | 17.624 | 1.00 | 19.61 | O |
| ATOM | 892 | N | VAL | A | 286 | −79.297 | 68.418 | 19.041 | 1.00 | 20.76 | N |
| ATOM | 893 | CA | VAL | A | 286 | −80.749 | 68.322 | 18.712 | 1.00 | 20.62 | C |
| ATOM | 894 | C | VAL | A | 286 | −80.991 | 68.575 | 17.196 | 1.00 | 21.05 | C |
| ATOM | 895 | O | VAL | A | 286 | −81.785 | 67.872 | 16.624 | 1.00 | 21.59 | O |
| ATOM | 896 | CB | VAL | A | 286 | −81.697 | 69.157 | 19.613 | 1.00 | 18.67 | C |
| ATOM | 897 | CG1 | VAL | A | 286 | −81.732 | 68.623 | 21.006 | 1.00 | 19.98 | C |
| ATOM | 898 | CG2 | VAL | A | 286 | −81.293 | 70.657 | 19.617 | 1.00 | 17.89 | C |
| ATOM | 899 | N | HIS | A | 297 | −80.291 | 69.500 | 16.577 | 1.00 | 22.17 | N |
| ATOM | 900 | CA | HIS | A | 287 | −80.506 | 69.758 | 15.130 | 1.00 | 22.28 | C |
| ATOM | 901 | C | HIS | A | 287 | −80.044 | 68.646 | 14.217 | 1.00 | 22.53 | C |
| ATOM | 902 | O | HIS | A | 287 | −60.619 | 68.397 | 13.169 | 1.00 | 21.99 | O |
| ATOM | 903 | CB | HIS | A | 287 | −79.898 | 71.111 | 14.729 | 1.00 | 21.60 | C |
| ATOM | 904 | CG | HIS | A | 287 | −80.740 | 72.268 | 35.161 | 1.00 | 24.88 | C |
| ATOM | 905 | CD2 | HIS | A | 287 | −81.795 | 72.866 | 14.543 | 1.00 | 27.99 | C |
| ATOM | 906 | ND1 | HIS | A | 287 | −80.665 | 72.818 | 16.439 | 1.00 | 24.88 | N |
| ATOM | 907 | CE1 | HIS | A | 287 | −81.623 | 73.741 | 16.555 | 1.00 | 29.36 | C |
| ATOM | 908 | NE2 | HIS | A | 287 | −82.317 | 73.796 | 15.418 | 1.00 | 28.46 | N |
| ATOM | 909 | N | GLU | A | 288 | −78.940 | 68.015 | 14.607 | 1.00 | 24.77 | N |
| ATOM | 910 | CA | GLU | A | 288 | −78.441 | 66.873 | 13.908 | 1.00 | 22.59 | C |

TABLE 27

| | | | | | | | | | | | |
|---|---|---|---|---|---|---|---|---|---|---|---|
| ATOM | 911 | C | GLU | A | 288 | −79.506 | 65.813 | 13.935 | 1.00 | 22.49 | C |
| ATOM | 912 | O | GLU | A | 288 | −79.880 | 65.249 | 12.900 | 1.00 | 21.29 | O |
| ATOM | 913 | CB | GLU | A | 288 | −77.122 | 66.343 | 14.515 | 1.00 | 21.63 | C |
| ATOM | 914 | CG | GLU | A | 288 | −75.918 | 67.172 | 14.195 | 1.00 | 24.38 | C |
| ATOM | 915 | CD | GLU | A | 288 | −74.594 | 66.727 | 14.884 | 1.00 | 27.68 | C |
| ATOM | 916 | OE1 | GLU | A | 288 | −74.492 | 65.594 | 15.409 | 1.00 | 28.03 | O |
| ATOM | 917 | OE2 | GLU | A | 288 | −73.580 | 67.480 | 14.835 | 1.00 | 28.04 | O1− |
| ATOM | 918 | N | ALA | A | 239 | −80.014 | 65.549 | 15.113 | 1.00 | 18.55 | N |
| ATOM | 919 | CA | ALA | A | 289 | −81.140 | 64.581 | 15.253 | 1.00 | 19.95 | C |
| ATOM | 920 | C | ALA | A | 289 | −82.401 | 65.009 | 14.515 | 1.00 | 22.31 | C |
| ATOM | 921 | O | ALA | A | 289 | −83.072 | 64.168 | 13.901 | 1.00 | 21.85 | O |
| ATOM | 922 | CB | ALA | A | 289 | −81.503 | 64.365 | 16.699 | 1.00 | 22.63 | C |
| ATOM | 923 | N | ILE | A | 290 | −82.716 | 66.297 | 14.549 | 1.00 | 20.91 | N |
| ATOM | 924 | CA | ILE | A | 290 | −83.903 | 66.799 | 13.850 | 1.00 | 20.12 | C |
| ATOM | 925 | C | ILE | A | 290 | −83.793 | 66.595 | 12.341 | 1.00 | 22.56 | C |
| ATOM | 926 | O | ILE | A | 290 | −84.753 | 66.166 | 11.713 | 1.00 | 21.26 | O |
| ATOM | 927 | CB | ILE | A | 290 | −84.144 | 68.303 | 14.158 | 1.00 | 23.07 | C |
| ATOM | 928 | CG1 | ILE | A | 290 | −84.720 | 68.450 | 15.567 | 1.00 | 22.75 | C |

TABLE 27-continued

| | | | | | | | | | | |
|---|---|---|---|---|---|---|---|---|---|---|
| ATOM | 929 | CG2 | ILE | A | 290 | −85.131 | 68.982 | 13.167 | 1.00 | 23.95 C |
| ATOM | 930 | CD1 | ILE | A | 290 | −84.627 | 69.858 | 16.117 | 1.00 | 24.42 C |
| ATOM | 931 | N | PHE | A | 291 | −82.633 | 66.866 | 11.747 | 1.00 | 20.57 N |
| ATOM | 932 | CA | PHE | A | 291 | −82.505 | 66.682 | 10.294 | 1.00 | 24.21 C |
| ATOM | 933 | C | PHE | A | 291 | −82.431 | 65.224 | 9.817 | 1.00 | 25.75 C |
| ATOM | 934 | O | PHE | A | 291 | −82.874 | 64.929 | 8.718 | 1.00 | 26.46 O |
| ATOM | 935 | CB | PHE | A | 291 | −81.349 | 67.512 | 9.763 | 1.00 | 25.80 C |
| ATOM | 936 | CG | PHE | A | 291 | −81.517 | 69.000 | 10.004 | 1.00 | 25.84 C |
| ATOM | 937 | CD1 | PHE | A | 291 | −82.728 | 69.607 | 9.857 | 1.00 | 26.62 C |
| ATOM | 938 | CD2 | PHE | A | 291 | −80.426 | 69.769 | 10.341 | 1.00 | 27.31 C |
| ATOM | 939 | CE1 | PHE | A | 291 | −82.851 | 70.956 | 10.090 | 1.00 | 28.64 C |
| ATOM | 940 | CE2 | PHE | A | 291 | −80.540 | 71.108 | 10.543 | 1.00 | 27.00 C |
| ATOM | 941 | CZ | PHE | A | 291 | −81.754 | 71.712 | 10.424 | 1.00 | 26.04 C |
| ATOM | 942 | N | ALA | A | 292 | −81.923 | 64.330 | 10.670 | 1.00 | 23.64 N |
| ATOM | 943 | CA | ALA | A | 292 | −82.073 | 62.888 | 10.509 | 1.00 | 24.86 C |
| ATOM | 944 | C | ALA | A | 292 | −83.565 | 62.466 | 10.571 | 1.00 | 26.43 C |
| ATOM | 945 | O | ALA | A | 292 | −83.983 | 61.686 | 9.739 | 1.00 | 28.30 O |

TABLE 28

| | | | | | | | | | | |
|---|---|---|---|---|---|---|---|---|---|---|
| ATOM | 946 | CB | ALA | A | 292 | −81.279 | 62.094 | 11.585 | 1.00 | 24.78 C |
| ATOM | 947 | N | MET | A | 293 | −84.325 | 62.908 | 11.589 | 1.00 | 24.92 N |
| ATOM | 948 | CA | MET | A | 293 | −85.750 | 62.557 | 11.677 | 1.00 | 27.27 C |
| ATOM | 949 | C | MET | A | 293 | −86.592 | 63.172 | 10.570 | 1.00 | 26.44 C |
| ATOM | 950 | O | MET | A | 293 | −87.622 | 62.627 | 10.245 | 1.00 | 23.73 O |
| ATOM | 951 | CB | MET | A | 293 | −86.368 | 62.933 | 13.026 | 1.00 | 26.34 C |
| ATOM | 952 | CG | MET | A | 293 | −85.779 | 62.100 | 14.155 | 1.00 | 31.69 C |
| ATOM | 953 | SD | MET | A | 293 | −86.557 | 62.458 | 15.764 | 1.09 | 35.94 S |
| ATOM | 954 | CE | MET | A | 293 | −85.874 | 64.039 | 16.016 | 1.09 | 29.17 C |
| ATOM | 955 | N | LEU | A | 294 | −86.115 | 64.260 | 9.968 | 1.00 | 25.39 N |
| ATOM | 956 | CA | LEU | A | 294 | −86.838 | 64.967 | 8.906 | 1.00 | 27.32 C |
| ATOM | 957 | C | LEU | A | 294 | −87.003 | 64.080 | 7.686 | 1.00 | 27.45 C |
| ATOM | 958 | O | LEU | A | 294 | −88.034 | 64.124 | 7.003 | 1.00 | 25.25 O |
| ATOM | 959 | CB | LEU | A | 294 | −86.092 | 66.218 | 8.473 | 1.00 | 28.19 C |
| ATOM | 960 | CG | LEU | A | 294 | −86.629 | 66.971 | 7.267 | 1.00 | 31.75 C |
| ATOM | 961 | CD1 | LEU | A | 294 | −88.020 | 67.474 | 7.553 | 1.00 | 35.67 C |
| ATOM | 962 | CD2 | LEU | A | 294 | −85.712 | 68.169 | 6.990 | 1.00 | 33.60 C |
| ATOM | 963 | N | ALA | A | 295 | −85.988 | 63.278 | 7.416 | 1.00 | 25.31 N |
| ATOM | 964 | CA | ALA | A | 295 | −86.087 | 62.292 | 6.327 | 1.00 | 28.44 C |
| ATOM | 965 | C | ALA | A | 295 | −87.312 | 61.393 | 6.393 | 1.00 | 25.92 C |
| ATOM | 966 | O | ALA | A | 295 | −87.972 | 61.081 | 5.359 | 1.00 | 24.71 O |
| ATOM | 967 | CB | ALA | A | 295 | −84.809 | 61.508 | 6.189 | 1.00 | 29.31 C |
| ATOM | 968 | N | SER | A | 296 | −37.714 | 61.049 | 7.604 | 1.00 | 25.75 N |
| ATOM | 969 | CA | SER | A | 296 | −88.881 | 60.182 | 7.766 | 1.00 | 24.04 C |
| ATOM | 970 | C | SER | A | 296 | −90.151 | 60.770 | 7.067 | 1.00 | 24.95 C |
| ATOM | 971 | O | SER | A | 296 | −91.048 | 60.024 | 6.801 | 1.00 | 26.54 O |
| ATOM | 972 | CB | SER | A | 296 | −89.223 | 60.027 | 9.261 | 1.00 | 24.71 C |
| ATOM | 973 | OG | SER | A | 296 | −88.188 | 59.322 | 9.952 | 1.00 | 24.58 O |
| ATOM | 974 | N | ILE | A | 297 | −90.284 | 62.108 | 7.019 | 1.00 | 25.84 N |
| ATOM | 975 | CA | ILE | A | 297 | −91.469 | 62.765 | 6.505 | 1.00 | 26.52 C |
| ATOM | 976 | C | ILE | A | 297 | −91.314 | 63.374 | 5.113 | 1.00 | 26.15 C |
| ATOM | 977 | O | ILE | A | 297 | −92.266 | 64.037 | 4.655 | 1.00 | 26.39 O |
| ATOM | 978 | CB | ILE | A | 297 | −92.065 | 63.816 | 7.482 | 1.00 | 24.20 C |
| ATOM | 979 | CG1 | ILE | A | 297 | −91.076 | 64.901 | 7.838 | 1.00 | 27.94 C |
| ATOM | 980 | CG2 | ILE | A | 297 | −92.558 | 63.111 | 8.714 | 1.00 | 25.71 C |

TABLE 29

| | | | | | | | | | | |
|---|---|---|---|---|---|---|---|---|---|---|
| ATOM | 981 | CD1 | ILE | A | 297 | −91.709 | 66.192 | 8.340 | 1.00 | 29.46 C |
| ATOM | 982 | N | VAL | A | 298 | −90.172 | 63.124 | 4.451 | 1.00 | 24.11 N |
| ATOM | 983 | CA | VAL | A | 298 | −89.777 | 63.778 | 3.216 | 1.00 | 27.33 C |
| ATOM | 984 | C | VAL | A | 298 | −89.801 | 62.746 | 2.100 | 1.00 | 29.01 C |
| ATOM | 985 | O | VAL | A | 298 | −89.520 | 61.595 | 2.346 | 1.00 | 28.72 O |
| ATOM | 986 | CB | VAL | A | 298 | −88.376 | 64.445 | 3.346 | 1.00 | 29.27 C |
| ATOM | 987 | CG1 | VAL | A | 298 | −87.790 | 64.899 | 2.023 | 1.00 | 33.75 C |
| ATOM | 988 | CG2 | VAL | A | 298 | −88.460 | 65.673 | 4.229 | 1.00 | 28.97 C |
| ATOM | 989 | N | ASN | A | 299 | −90.243 | 63.139 | 0.906 | 1.00 | 28.92 N |
| ATOM | 990 | CA | ASN | A | 299 | −89.891 | 62.397 | −0.304 | 1.00 | 30.58 C |
| ATOM | 991 | C | ASN | A | 299 | −89.312 | 63.426 | −1.298 | 1.00 | 32.51 C |
| ATOM | 992 | C | ASN | A | 299 | −89.147 | 64.637 | −0.931 | 1.00 | 28.01 O |
| ATOM | 993 | CB | ASN | A | 299 | −91.055 | 61.502 | −0.793 | 1.00 | 31.13 C |
| ATOM | 994 | CG | ASN | A | 299 | −92.219 | 62.274 | −1.323 | 1.00 | 28.40 C |
| ATOM | 995 | ND2 | ASN | A | 299 | −93.344 | 61.639 | −1.365 | 1.00 | 29.96 N |
| ATOM | 996 | OD1 | ASN | A | 299 | −92.104 | 63.451 | −1.703 | 1.00 | 34.32 O |
| ATOM | 997 | N | LYS | A | 300 | −88.958 | 63.016 | −2.534 | 1.00 | 30.47 N |

TABLE 29-continued

| ATOM | 998 | CA | LYS | A | 300 | −88.235 | 63.969 | −3.401 | 1.00 | 29.89 | C |
| ATOM | 999 | C | LYS | A | 300 | −89.132 | 65.188 | −3.780 | 1.00 | 27.63 | C |
| ATOM | 1000 | O | LYS | A | 300 | −88.667 | 66.223 | −4.250 | 1.00 | 29.06 | O |
| ATOM | 1001 | CB | LYS | A | 300 | −87.687 | 63.285 | −4.659 | 1.00 | 35.59 | C |
| ATOM | 1002 | CG | LYS | A | 300 | −88.750 | 62.747 | −5.570 | 1.00 | 38.65 | C |
| ATOM | 1003 | CD | LYS | A | 300 | −88.136 | 61.929 | −6.702 | 1.00 | 47.73 | C |
| ATOM | 1004 | CE | LYS | A | 300 | −89.131 | 60.885 | −7.220 | 1.00 | 49.64 | C |
| ATOM | 1005 | NZ | LYS | A | 300 | −90.300 | 61.555 | −7.835 | 1.00 | 52.34 | N1+ |
| ATOM | 1006 | N | ASP | A | 301 | −90.426 | 65.020 | −3.614 | 1.00 | 26.61 | N |
| ATOM | 1007 | CA | ASP | A | 301 | −91.418 | 66.023 | −4.043 | 1.00 | 29.63 | C |
| ATOM | 1008 | C | ASP | A | 301 | −91.893 | 66.959 | −2.921 | 1.00 | 26.96 | C |
| ATOM | 1009 | O | ASP | A | 301 | −92.591 | 67.908 | −3.200 | 1.00 | 26.32 | O |
| ATOM | 1010 | CB | ASP | A | 301 | −92.607 | 65.278 | −4.599 | 1.00 | 33.60 | C |
| ATOM | 1011 | CG | ASP | A | 301 | −92.250 | 64.519 | −5.914 | 1.00 | 40.31 | C |
| ATOM | 1012 | OD1 | ASP | A | 301 | −91.302 | 64.917 | −6.630 | 1.00 | 43.22 | O |
| ATOM | 1013 | OD2 | ASP | A | 301 | −92.898 | 63.500 | −6.195 | 1.00 | 44.23 | O1− |
| ATOM | 1014 | N | GLY | A | 302 | −91.551 | 66.693 | −1.650 | 1.00 | 27.44 | N |
| ATOM | 1015 | CA | GLY | A | 302 | −92.019 | 67.536 | −0.541 | 1.00 | 25.67 | C |

TABLE 30

| ATOM | 1016 | C | GLY | A | 302 | −92.089 | 66.826 | 0.805 | 1.00 | 26.48 | C |
| ATOM | 1017 | O | GLY | A | 302 | −91.515 | 65.719 | 0.977 | 1.00 | 24.94 | O |
| ATOM | 1018 | N | LEU | A | 303 | −92.810 | 67.417 | 1.739 | 1.00 | 25.81 | N |
| ATOM | 1019 | CA | LEU | A | 303 | −92.871 | 66.824 | 3.099 | 1.00 | 28.72 | C |
| ATOM | 1020 | C | LEU | A | 303 | −94.223 | 66.934 | 3.779 | 1.00 | 25.52 | C |
| ATOM | 1021 | O | LEU | A | 303 | −94.978 | 67.846 | 3.489 | 1.00 | 26.54 | O |
| ATOM | 1022 | CB | LEU | A | 303 | −91.809 | 67.489 | 4.000 | 1.00 | 33.05 | C |
| ATOM | 1023 | CG | LEU | A | 303 | −92.083 | 68.931 | 4.503 | 1.00 | 37.71 | C |
| ATOM | 1024 | CD1 | LEU | A | 303 | −91.452 | 69.106 | 5.871 | 1.00 | 46.52 | C |
| ATOM | 1025 | CD2 | LEU | A | 303 | −91.519 | 69.933 | 3.526 | 1.00 | 48.79 | C |
| ATOM | 1026 | N | LEU | A | 304 | −94.522 | 65.987 | 4.659 | 1.00 | 25.67 | N |
| ATOM | 1027 | CA | LEU | A | 304 | −95.691 | 65.985 | 5.501 | 1.00 | 26.69 | C |
| ATOM | 1028 | C | LEU | A | 304 | −95.648 | 67.075 | 6.544 | 1.00 | 27.32 | C |
| ATOM | 1029 | O | LEU | A | 304 | −94.589 | 67.349 | 7.110 | 1.00 | 28.79 | O |
| ATOM | 1030 | CB | LEU | A | 304 | −95.835 | 64.672 | 6.232 | 1.00 | 27.60 | C |
| ATOM | 1031 | CG | LEU | A | 304 | −96.280 | 63.556 | 5.390 | 1.00 | 30.36 | C |
| ATOM | 1032 | CD1 | LEU | A | 304 | −96.254 | 62.264 | 6.221 | 1.00 | 32.11 | C |
| ATOM | 1033 | CD2 | LEU | A | 304 | −97.653 | 63.833 | 4.726 | 1.00 | 31.15 | C |
| ATOM | 1034 | N | VAL | A | 305 | −96.789 | 67.715 | 6.735 | 1.00 | 27.58 | N |
| ATOM | 1035 | CA | VAL | A | 305 | −96.998 | 68.713 | 7.785 | 1.00 | 29.03 | C |
| ATOM | 1036 | C | VAL | A | 305 | −98.285 | 68.401 | 8.501 | 1.00 | 30.86 | C |
| ATOM | 1037 | O | VAL | A | 305 | −99.098 | 67.531 | 8.047 | 1.00 | 29.76 | O |
| ATOM | 1038 | CB | VAL | A | 305 | −97.000 | 70.180 | 7.242 | 1.00 | 33.39 | C |
| ATOM | 1039 | CG1 | VAL | A | 305 | −95.640 | 70.512 | 6.669 | 1.00 | 32.65 | C |
| ATOM | 1040 | CG2 | VAL | A | 305 | −98.081 | 70.395 | 6.179 | 1.00 | 34.76 | C |
| ATOM | 1041 | N | ALA | A | 306 | −98.447 | 69.080 | 9.645 | 1.00 | 34.51 | N |
| ATOM | 1042 | CA | ALA | A | 306 | −99.693 | 69.059 | 10.454 | 1.00 | 39.54 | C |
| ATOM | 1043 | C | ALA | A | 306 | −100.179 | 67.667 | 10.754 | 1.00 | 37.23 | C |
| ATOM | 1044 | O | ALA | A | 306 | −101.317 | 67.311 | 10.429 | 1.00 | 37.16 | O |
| ATOM | 1045 | CB | ALA | A | 306 | −100.814 | 69.886 | 9.795 | 1.00 | 41.57 | C |
| ATOM | 1046 | N | ASN | A | 307 | −99.257 | 66.893 | 11.335 | 1.00 | 38.88 | N |
| ATOM | 1047 | CA | ASN | A | 307 | −99.435 | 65.496 | 11.687 | 1.00 | 36.18 | C |
| ATOM | 1048 | C | ASN | A | 307 | −99.849 | 64.610 | 10.518 | 1.00 | 38.54 | C |
| ATOM | 1049 | O | ASN | A | 307 | −100.667 | 63.732 | 10.677 | 1.00 | 43.99 | O |
| ATOM | 1050 | CB | ASN | A | 307 | −100.383 | 65.376 | 12.900 | 1.00 | 44.83 | C |

TABLE 31

| ATOM | 1051 | CG | ASN | A | 307 | −100.159 | 64.078 | 13.703 | 1.00 | 46.49 | C |
| ATOM | 1052 | ND2 | ASN | A | 307 | −101.237 | 63.360 | 13.959 | 1.00 | 48.74 | N |
| ATOM | 1053 | OD1 | ASN | A | 307 | −99.023 | 63.722 | 14.068 | 1.00 | 55.10 | O |
| ATOM | 1054 | N | GLY | A | 308 | −99.262 | 64.829 | 9.336 | 1.00 | 35.63 | N |
| ATOM | 1055 | CA | GLY | A | 308 | −99.594 | 64.057 | 8.150 | 1.00 | 36.15 | C |
| ATOM | 1056 | C | GLY | A | 308 | −100.887 | 64.454 | 7.450 | 1.00 | 35.26 | C |
| ATOM | 1057 | O | GLY | A | 308 | −101.201 | 63.863 | 6.439 | 1.00 | 38.21 | O |
| ATOM | 1058 | N | SER | A | 309 | −101.585 | 65.493 | 7.931 | 1.00 | 40.95 | N |
| ATOM | 1059 | CA | SER | A | 309 | −102.782 | 66.010 | 7.249 | 1.00 | 40.17 | C |
| ATOM | 1060 | C | SER | A | 309 | −102.482 | 66.930 | 6.082 | 1.00 | 39.05 | C |
| ATOM | 1061 | O | SER | A | 309 | −103.366 | 67.111 | 5.266 | 1.00 | 35.55 | O |
| ATOM | 1062 | CB | SER | A | 309 | −103.725 | 66.731 | 8.224 | 1.00 | 41.20 | C |
| ATOM | 1063 | OG | SER | A | 309 | −103.202 | 67.970 | 8.672 | 1.00 | 40.95 | O |
| ATOM | 1064 | N | GLY | A | 310 | −101.256 | 67.488 | 5.987 | 1.00 | 35.81 | N |
| ATOM | 1065 | CA | GLY | A | 310 | −100.831 | 68.262 | 4.794 | 1.00 | 34.10 | C |
| ATOM | 1066 | C | GLY | A | 310 | −99.499 | 67.840 | 4.189 | 1.00 | 34.17 | C |

TABLE 31-continued

| ATOM | 1067 | O   | GLY | A | 310 | -98.680  | 67.191 | 4.847  | 1.00 | 29.87 | O   |
|------|------|-----|-----|---|-----|----------|--------|--------|------|-------|-----|
| ATOM | 1068 | N   | PHE | A | 311 | -99.308  | 68.195 | 2.926  | 1.00 | 27.08 | N   |
| ATOM | 1069 | CA  | PHE | A | 311 | -98.099  | 67.932 | 2.202  | 1.00 | 26.72 | C   |
| ATOM | 1070 | C   | PHE | A | 311 | -97.691  | 69.220 | 1.554  | 1.00 | 27.50 | C   |
| ATOM | 1071 | O   | PHE | A | 311 | -98.437  | 69.744 | 0.699  | 1.00 | 27.00 | O   |
| ATOM | 1072 | CB  | PHE | A | 311 | -98.338  | 66.847 | 1.152  | 1.00 | 25.30 | C   |
| ATOM | 1073 | CG  | PHE | A | 311 | -97.123  | 66.411 | 0.434  | 1.00 | 25.91 | C   |
| ATOM | 1074 | CD1 | PHE | A | 311 | -96.312  | 65.407 | 0.938  | 1.00 | 25.46 | C   |
| ATOM | 1075 | CD2 | PHE | A | 311 | -96.774  | 66.998 | -0.776 | 1.00 | 28.41 | C   |
| ATOM | 1076 | CE1 | PHE | A | 311 | -95.201  | 64.985 | 0.270  | 1.00 | 25.30 | C   |
| ATOM | 1077 | CE2 | PHE | A | 311 | -95.636  | 66.584 | -1.448 | 1.00 | 29.01 | C   |
| ATOM | 1078 | CZ  | PHE | A | 311 | -94.880  | 65.555 | -0.956 | 1.00 | 25.16 | C   |
| ATOM | 1079 | N   | VAL | A | 312 | -96.503  | 69.719 | 1.889  | 1.00 | 25.15 | N   |
| ATOM | 1080 | CA  | VAL | A | 312 | -95.995  | 70.918 | 1.233  | 1.00 | 28.02 | C   |
| ATOM | 1081 | C   | VAL | A | 312 | -95.008  | 70.530 | 0.156  | 1.00 | 26.25 | C   |
| ATOM | 1082 | O   | VAL | A | 312 | -94.114  | 69.693 | 0.415  | 1.00 | 23.84 | O   |
| ATOM | 1083 | CB  | VAL | A | 312 | -95.369  | 71.910 | 2.194  | 1.00 | 28.36 | C   |
| ATOM | 1084 | CG1 | VAL | A | 312 | -94.076  | 71.395 | 2.725  | 1.00 | 36.63 | C   |
| ATOM | 1085 | CG2 | VAL | A | 312 | -95.097  | 73.226 | 1.466  | 1.00 | 28.30 | C   |

TABLE 32

| ATOM | 1086 | N   | THR | A | 313 | -95.158 | 71.105 | -1.060 | 1.00 | 25.88 | N   |
|------|------|-----|-----|---|-----|---------|--------|--------|------|-------|-----|
| ATOM | 1087 | CA  | THR | A | 313 | -94.270 | 70.720 | -2.188 | 1.00 | 23.69 | C   |
| ATOM | 1088 | C   | THR | A | 313 | -92.909 | 71.349 | -2.054 | 1.00 | 24.56 | C   |
| ATOM | 1089 | O   | THR | A | 313 | -92.736 | 72.543 | -1.657 | 1.00 | 22.77 | O   |
| ATOM | 1090 | CB  | THR | A | 313 | -94.863 | 71.029 | -3.616 | 1.00 | 24.89 | C   |
| ATOM | 1091 | CG2 | THR | A | 313 | -96.202 | 70.500 | -3.730 | 1.00 | 28.58 | C   |
| ATOM | 1092 | OG1 | THR | A | 313 | -94.983 | 72.422 | -3.797 | 1.00 | 25.05 | O   |
| ATOM | 1093 | N   | ARG | A | 314 | -91.913 | 70.551 | -2.414 | 1.00 | 26.93 | N   |
| ATOM | 1094 | CA  | ARG | A | 314 | -90.532 | 71.028 | -2.567 | 1.00 | 26.40 | C   |
| ATOM | 1095 | C   | ARG | A | 314 | -90.474 | 72.222 | -3.518 | 1.00 | 27.49 | C   |
| ATOM | 1096 | O   | ARG | A | 314 | -89.771 | 73.198 | -3.257 | 1.00 | 24.83 | O   |
| ATOM | 1097 | CB  | ARG | A | 314 | -89.646 | 69.922 | -3.123 | 1.00 | 30.47 | C   |
| ATOM | 1098 | CG  | ARG | A | 314 | -88.165 | 70.234 | -3.051 | 1.00 | 31.22 | C   |
| ATOM | 1099 | CD  | ARG | A | 314 | -87.436 | 68.980 | -3.396 | 1.00 | 32.57 | C   |
| ATOM | 1100 | NE  | ARG | A | 314 | -86.003 | 69.098 | -3.282 | 1.00 | 31.11 | N   |
| ATOM | 1101 | CZ  | ARG | A | 314 | -85.178 | 68.093 | -3.478 | 1.00 | 30.25 | C   |
| ATOM | 1102 | NH1 | ARG | A | 314 | -85.660 | 66.901 | -3.813 | 1.00 | 29.81 | H1+ |
| ATOM | 1103 | NH2 | ARG | A | 314 | -83.874 | 68.270 | -3.351 | 1.00 | 32.89 | N   |
| ATOM | 1104 | N   | GLU | A | 315 | -91.250 | 72.177 | -4.611 | 1.00 | 26.96 | N   |
| ATOM | 1105 | CA  | GLU | A | 315 | -91.214 | 73.294 | -5.527 | 1.00 | 27.20 | C   |
| ATOM | 1106 | C   | GLU | A | 315 | -91.684 | 74.602 | -4.864 | 1.00 | 24.24 | C   |
| ATOM | 1107 | O   | GLU | A | 315 | -91.045 | 75.647 | -5.012 | 1.00 | 28.17 | O   |
| ATOM | 1108 | CB  | GLU | A | 315 | -92.019 | 72.995 | -6.825 | 1.00 | 32.10 | C   |
| ATOM | 1109 | CG  | GLU | A | 315 | -91.911 | 74.121 | -7.834 | 1.00 | 34.65 | C   |
| ATOM | 1110 | CD  | GLU | A | 315 | -92.958 | 74.111 | -8.954 | 1.00 | 44.98 | C   |
| ATOM | 1111 | OE1 | GLU | A | 315 | -93.171 | 75.216 | -9.516 | 1.00 | 48.23 | O   |
| ATOM | 1112 | OE2 | GLU | A | 315 | -93.544 | 73.060 | -9.286 | 1.00 | 41.82 | O1- |
| ATOM | 1113 | N   | PHE | A | 316 | -92.804 | 74.560 | -4.172 | 1.00 | 26.94 | N   |
| ATOM | 1114 | CA  | PHE | A | 316 | -93.266 | 75.690 | -3.366 | 1.00 | 25.64 | C   |
| ATOM | 1115 | C   | PHE | A | 316 | -92.219 | 76.239 | -2.352 | 1.00 | 26.19 | C   |
| ATOM | 1116 | O   | PHE | A | 316 | -92.005 | 77.437 | -2.251 | 1.00 | 27.22 | O   |
| ATOM | 1117 | CB  | PHE | A | 316 | -94.593 | 75.376 | -2.676 | 1.00 | 25.72 | C   |
| ATOM | 1118 | CG  | PHE | A | 316 | -95.077 | 76.494 | -1.828 | 1.00 | 28.23 | C   |
| ATOM | 1119 | CD1 | PHE | A | 316 | -95.518 | 77.713 | -2.414 | 1.00 | 30.04 | C   |
| ATOM | 1120 | CD2 | PHE | A | 316 | -94.947 | 76.422 | -0.438 | 1.00 | 28.46 | C   |

TABLE 33

| ATOM | 1121 | CE1 | PHE | A | 316 | -95.902 | 78.776 | -1.589 | 1.00 | 29.08 | C |
|------|------|-----|-----|---|-----|---------|--------|--------|------|-------|---|
| ATOM | 1122 | CE2 | PHE | A | 316 | -95.325 | 77.487 | 0.369  | 1.00 | 29.30 | C |
| ATOM | 1123 | CZ  | PHE | A | 316 | -95.841 | 78.626 | -0.187 | 1.00 | 27.55 | C |
| ATOM | 1124 | N   | LEU | A | 317 | -91.552 | 75.372 | -1.637 | 1.00 | 27.97 | N |
| ATOM | 1125 | CA  | LEU | A | 317 | -90.489 | 75.800 | -0.745 | 1.00 | 29.76 | C |
| ATOM | 1126 | C   | LEU | A | 317 | -89.236 | 76.473 | -1.468 | 1.00 | 32.56 | C |
| ATOM | 1127 | O   | LEU | A | 317 | -88.729 | 77.484 | -0.955 | 1.00 | 33.64 | O |
| ATOM | 1128 | CB  | LEU | A | 317 | -90.064 | 74.591 | 0.099  | 1.00 | 29.57 | C |
| ATOM | 1129 | CG  | LEU | A | 317 | -91.143 | 74.037 | 1.025  | 1.00 | 26.60 | C |
| ATOM | 1130 | CD1 | LEU | A | 317 | -90.628 | 72.854 | 1.787  | 1.00 | 30.32 | C |
| ATOM | 1131 | CD2 | LEU | A | 317 | -91.571 | 75.132 | 1.973  | 1.00 | 27.32 | C |
| ATOM | 1132 | N   | ARG | A | 318 | -88.544 | 75.996 | -2.675 | 1.00 | 28.99 | N |
| ATOM | 1133 | CA  | ARG | A | 318 | -87.932 | 76.668 | -3.554 | 1.00 | 30.66 | C |
| ATOM | 1134 | C   | ARG | A | 318 | -88.374 | 77.986 | -4.118 | 1.00 | 29.76 | C |
| ATOM | 1135 | O   | ARG | A | 318 | -87.553 | 78.688 | -4.669 | 1.00 | 30.33 | O |

TABLE 33-continued

| ATOM | 1136 | CB | ARG | A | 318 | −87.548 | 75.803 | −4.787 | 1.00 | 31.20 | C |
|---|---|---|---|---|---|---|---|---|---|---|---|
| ATOM | 1137 | CG | ARG | A | 318 | −86.840 | 74.518 | −4.448 | 1.00 | 32.86 | C |
| ATOM | 1138 | CD | ARG | A | 318 | −86.870 | 73.537 | −5.594 | 1.00 | 38.04 | C |
| ATOM | 1139 | NE | ARG | A | 318 | −85.870 | 72.509 | −5.351 | 1.00 | 40.73 | N |
| ATOM | 1140 | CZ | ARG | A | 318 | −85.633 | 71.482 | −6.161 | 1.00 | 43.75 | C |
| ATOM | 1141 | NH1 | ARG | A | 318 | −86.274 | 71.382 | −7.316 | 1.00 | 50.04 | N1+ |
| ATOM | 1142 | NH2 | ARG | A | 318 | −84.718 | 70.586 | −5.839 | 1.00 | 39.06 | N |
| ATOM | 1143 | N | SER | A | 319 | −89.666 | 78.298 | −4.063 | 1.00 | 30.15 | N |
| ATOM | 1144 | CA | SER | A | 319 | −90.189 | 79.598 | −4.540 | 1.00 | 29.62 | C |
| ATOM | 1145 | C | SER | A | 319 | −90.018 | 80.688 | −3.467 | 1.00 | 31.07 | C |
| ATOM | 1146 | O | SER | A | 319 | −90.237 | 81.861 | −3.717 | 1.00 | 31.84 | O |
| ATOM | 1147 | CB | SER | A | 319 | −91.680 | 79.499 | −4.893 | 1.00 | 30.60 | C |
| ATOM | 1148 | OG | SER | A | 319 | −92.537 | 79.518 | −3.712 | 1.00 | 33.57 | O |
| ATOM | 1149 | N | LEU | A | 320 | −89.613 | 80.328 | −2.269 | 1.00 | 30.91 | N |
| ATOM | 1150 | CA | LEU | A | 320 | −89.473 | 81.357 | −1.199 | 1.00 | 30.30 | C |
| ATOM | 1151 | C | LEU | A | 320 | −88.331 | 82.315 | −1.462 | 1.00 | 30.25 | C |
| ATOM | 1152 | O | LEU | A | 320 | −87.407 | 82.007 | −2.194 | 1.00 | 30.75 | O |
| ATOM | 1153 | CB | LEU | A | 320 | −89.318 | 80.670 | 0.157 | 1.00 | 32.70 | C |
| ATOM | 1154 | CG | LEU | A | 320 | −90.498 | 79.747 | 0.489 | 1.00 | 33.74 | C |
| ATOM | 1155 | CD1 | LEU | A | 320 | −90.253 | 79.051 | 1.816 | 1.00 | 37.75 | C |

TABLE 34

| ATOM | 1156 | CD2 | LEU | A | 320 | −91.841 | 80.461 | 0.517 | 1.00 | 35.95 | C |
|---|---|---|---|---|---|---|---|---|---|---|---|
| ATOM | 1157 | N | ARG | A | 321 | −88.279 | 83.476 | −0.850 | 1.00 | 34.72 | N |
| ATOM | 1158 | CA | ARG | A | 321 | −87.131 | 84.319 | −1.126 | 1.00 | 39.89 | C |
| ATOM | 1159 | C | ARG | A | 321 | −85.852 | 83.746 | −0.512 | 1.00 | 38.94 | C |
| ATOM | 1160 | O | ARG | A | 321 | −85.886 | 82.870 | 0.382 | 1.00 | 38.76 | O |
| ATOM | 1161 | CB | ARG | A | 321 | −87.406 | 85.786 | −0.857 | 1.00 | 44.97 | C |
| ATOM | 1162 | CG | ARG | A | 321 | −87.454 | 86.221 | 0.560 | 1.00 | 51.89 | C |
| ATOM | 1163 | CD | ARG | A | 321 | −87.847 | 87.703 | 0.600 | 1.00 | 52.73 | C |
| ATOM | 1164 | NE | ARG | A | 321 | −88.101 | 88.029 | 1.988 | 1.00 | 61.32 | N |
| ATOM | 1165 | CZ | ARG | A | 321 | −87.164 | 88.291 | 2.905 | 1.00 | 58.38 | C |
| ATOM | 1166 | NH1 | ARG | A | 321 | −85.875 | 88.337 | 2.587 | 1.00 | 55.74 | N1+ |
| ATOM | 1167 | NH2 | ARG | A | 321 | −87.544 | 88.523 | 4.159 | 1.00 | 63.74 | N |
| ATOM | 1168 | N | LYS | A | 322 | −84.735 | 84.234 | −1.037 | 1.00 | 37.36 | N |
| ATOM | 1169 | CA | LYS | A | 322 | −83.456 | 83.546 | −1.055 | 1.00 | 43.64 | C |
| ATOM | 1170 | C | LYS | A | 322 | −82.946 | 83.029 | 0.220 | 1.00 | 44.96 | C |
| ATOM | 1171 | O | LYS | A | 322 | −82.555 | 81.840 | 0.293 | 1.00 | 49.36 | O |
| ATOM | 1172 | CB | LYS | A | 322 | −82.370 | 84.407 | −1.742 | 1.00 | 47.65 | C |
| ATOM | 1173 | CG | LYS | A | 322 | −81.089 | 83.647 | −2.117 | 1.00 | 54.93 | C |
| ATOM | 1174 | CD | LYS | A | 322 | −80.150 | 84.451 | −3.041 | 1.00 | 57.30 | C |
| ATOM | 1175 | CE | LYS | A | 322 | −78.682 | 84.138 | −2.786 | 1.00 | 62.36 | C |
| ATOM | 1176 | NZ | LYS | A | 322 | −78.390 | 82.672 | −2.909 | 1.00 | 63.93 | N1+ |
| ATOM | 1177 | N | PRO | A | 323 | −82.946 | 83.874 | 1.268 | 1.00 | 39.25 | N |
| ATOM | 1178 | CA | PRO | A | 323 | −82.337 | 83.257 | 2.431 | 1.00 | 35.75 | C |
| ATOM | 1179 | C | PRO | A | 323 | −83.086 | 81.977 | 2.862 | 1.00 | 33.66 | C |
| ATOM | 1180 | O | PRO | A | 323 | −82.445 | 80.981 | 3.250 | 1.00 | 36.45 | O |
| ATOM | 1181 | CB | PRO | A | 323 | −82.349 | 84.357 | 3.487 | 1.00 | 41.07 | C |
| ATOM | 1182 | CG | PRO | A | 323 | −82.934 | 85.566 | 2.809 | 1.00 | 41.49 | C |
| ATOM | 1183 | CD | PRO | A | 323 | −83.571 | 85.171 | 1.530 | 1.00 | 39.84 | C |
| ATOM | 1184 | N | PHE | A | 324 | −84.414 | 81.983 | 2.741 | 1.00 | 30.84 | N |
| ATOM | 1185 | CA | PHE | A | 324 | −85.269 | 80.904 | 3.255 | 1.00 | 32.81 | C |
| ATOM | 1186 | C | PHE | A | 324 | −85.244 | 79.687 | 2.309 | 1.00 | 34.96 | C |
| ATOM | 1187 | O | PHE | A | 324 | −84.997 | 78.564 | 2.749 | 1.00 | 31.26 | O |
| ATOM | 1188 | CB | PHE | A | 324 | −86.662 | 81.433 | 3.524 | 1.00 | 29.38 | C |
| ATOM | 1189 | CG | PHE | A | 324 | −86.655 | 82.614 | 4.459 | 1.00 | 28.03 | C |
| ATOM | 1190 | CD1 | PHE | A | 324 | −86.329 | 82.456 | 5.789 | 1.00 | 31.40 | C |

TABLE 35

| ATOM | 1191 | CD2 | PHE | A | 324 | −86.891 | 83.894 | 3.985 | 1.00 | 27.91 | C |
|---|---|---|---|---|---|---|---|---|---|---|---|
| ATOM | 1192 | CE1 | PHE | A | 324 | −86.281 | 83.580 | 6.632 | 1.00 | 29.78 | C |
| ATOM | 1193 | CE2 | PHE | A | 324 | −86.842 | 84.989 | 4.789 | 1.00 | 31.67 | C |
| ATOM | 1194 | CZ | PHE | A | 324 | −86.533 | 84.851 | 6.129 | 1.00 | 30.12 | C |
| ATOM | 1195 | N | SER | A | 325 | −85.375 | 79.909 | 1.006 | 1.00 | 34.91 | N |
| ATOM | 1196 | CA | SER | A | 325 | −85.151 | 78.776 | 0.054 | 1.00 | 35.71 | C |
| ATOM | 1197 | C | SER | A | 325 | −83.806 | 78.107 | 0.270 | 1.00 | 34.34 | C |
| ATOM | 1198 | O | SER | A | 325 | −83.716 | 76.867 | 0.251 | 1.00 | 35.46 | O |
| ATOM | 1199 | CB | SER | A | 325 | −85.293 | 79.241 | −1.398 | 1.00 | 38.23 | C |
| ATOM | 1200 | OG | SER | A | 325 | −84.467 | 80.397 | −1.605 | 1.00 | 38.78 | O |
| ATOM | 1201 | N | ASP | A | 326 | −82.760 | 78.895 | 0.526 | 1.00 | 33.95 | N |
| ATOM | 1202 | CA | ASP | A | 326 | −81.391 | 78.332 | 0.648 | 1.00 | 35.77 | C |
| ATOM | 1203 | C | ASP | A | 326 | −81.186 | 77.525 | 1.920 | 1.00 | 35.75 | C |
| ATOM | 1204 | O | ASP | A | 326 | −80.344 | 76.645 | 1.993 | 1.00 | 34.49 | O |

TABLE 35-continued

| ATOM | 1205 | CB | ASP | A | 326 | −80.310 | 79.424 | 0.589 | 1.00 | 36.49 | C |
| ATOM | 1206 | CG | ASP | A | 326 | −80.116 | 80.010 | −0.839 | 1.00 | 45.20 | C |
| ATOM | 1207 | OD1 | ASP | A | 326 | −80.609 | 79.447 | −1.847 | 1.00 | 44.51 | O |
| ATOM | 1208 | OD2 | ASP | A | 326 | −79.457 | 81.070 | −0.922 | 1.00 | 51.56 | O1− |
| ATOM | 1209 | N | ILE | A | 327 | −81.917 | 77.853 | 2.963 | 1.00 | 35.65 | N |
| ATOM | 1210 | CA | ILE | A | 327 | −81.743 | 77.140 | 4.207 | 1.00 | 32.20 | C |
| ATOM | 1211 | C | ILE | A | 327 | −82.533 | 75.797 | 4.186 | 1.00 | 32.61 | C |
| ATOM | 1212 | O | ILE | A | 327 | −82.168 | 74.827 | 4.850 | 1.00 | 30.41 | O |
| ATOM | 1213 | CB | ILE | A | 327 | −82.098 | 78.098 | 5.354 | 1.00 | 36.21 | C |
| ATOM | 1214 | CG1 | ILE | A | 327 | −81.299 | 77.726 | 6.594 | 1.00 | 38.79 | C |
| ATOM | 1215 | CG2 | ILE | A | 327 | −83.599 | 78.139 | 5.825 | 1.00 | 36.14 | C |
| ATOM | 1216 | CD1 | ILE | A | 327 | −81.490 | 78.705 | 7.707 | 1.00 | 44.53 | C |
| ATOM | 1217 | N | ILE | A | 328 | −83.563 | 75.727 | 3.353 | 1.00 | 27.73 | N |
| ATOM | 1218 | CA | ILE | A | 328 | −84.440 | 74.559 | 3.260 | 1.00 | 28.93 | C |
| ATOM | 1219 | C | ILE | A | 328 | −83.884 | 73.450 | 2.333 | 1.00 | 32.14 | C |
| ATOM | 1220 | O | ILE | A | 328 | −83.926 | 72.263 | 2.708 | 1.00 | 26.34 | O |
| ATOM | 1221 | CB | ILE | A | 328 | −85.867 | 74.998 | 2.817 | 1.00 | 31.22 | C |
| ATOM | 1222 | CG1 | ILE | A | 328 | −86.567 | 75.730 | 4.005 | 1.00 | 33.04 | C |
| ATOM | 1223 | CG2 | ILE | A | 328 | −86.707 | 73.801 | 2.353 | 1.00 | 31.79 | C |
| ATOM | 1224 | CD1 | ILE | A | 328 | −87.856 | 76.463 | 3.628 | 1.00 | 31.93 | C |
| ATOM | 1225 | N | GLU | A | 329 | −83.427 | 73.839 | 1.150 | 1.00 | 27.80 | N |

TABLE 36

| ATOM | 1226 | CA | GLU | A | 329 | −83.094 | 72.864 | 0.076 | 1.00 | 34.00 | C |
| ATOM | 1227 | C | GLU | A | 329 | −82.006 | 71.824 | 0.486 | 1.00 | 31.52 | C |
| ATOM | 1228 | O | GLU | A | 329 | −82.184 | 70.666 | 0.254 | 1.00 | 27.83 | O |
| ATOM | 1229 | CB | GLU | A | 329 | −82.723 | 73.634 | −1.209 | 1.00 | 37.62 | C |
| ATOM | 1230 | CG | GLU | A | 329 | −82.535 | 72.864 | −2.526 | 1.00 | 42.96 | C |
| ATOM | 1231 | CD | GLU | A | 329 | −83.600 | 71.816 | −2.877 | 1.00 | 45.48 | C |
| ATOM | 1232 | OE1 | GLU | A | 329 | −84.786 | 71.843 | −2.476 | 1.00 | 46.26 | O |
| ATOM | 1233 | OE2 | GLU | A | 329 | −83.227 | 70.877 | −3.584 | 1.00 | 48.60 | O1− |
| ATOM | 1234 | N | PRO | A | 330 | −80.935 | 72.235 | 1.179 | 1.00 | 30.91 | N |
| ATOM | 1235 | CA | PRO | A | 330 | −79.948 | 71.258 | 1.598 | 1.00 | 32.27 | C |
| ATOM | 1236 | C | PRO | A | 330 | −80.460 | 70.148 | 2.536 | 1.00 | 31.83 | C |
| ATOM | 1237 | O | PRO | A | 330 | −79.872 | 69.015 | 2.537 | 1.00 | 30.14 | O |
| ATOM | 1238 | CB | PRO | A | 330 | −78.885 | 72.094 | 2.281 | 1.00 | 34.82 | C |
| ATOM | 1239 | CG | PRO | A | 330 | −79.112 | 73.467 | 2.818 | 1.00 | 32.89 | C |
| ATOM | 1240 | CD | PRO | A | 330 | −80.489 | 73.610 | 1.406 | 1.00 | 32.19 | C |
| ATOM | 1241 | N | LYS | A | 331 | −81.563 | 70.427 | 3.245 | 1.00 | 30.14 | N |
| ATOM | 1242 | CA | LYS | A | 331 | −82.286 | 69.397 | 4.125 | 1.00 | 29.88 | C |
| ATOM | 1243 | C | LYS | A | 331 | −82.899 | 68.348 | 3.297 | 1.00 | 33.54 | C |
| ATOM | 1244 | O | LYS | A | 331 | −82.809 | 67.148 | 3.658 | 1.00 | 26.34 | O |
| ATOM | 1245 | CB | LYS | A | 331 | −83.107 | 70.018 | 5.128 | 1.00 | 30.19 | C |
| ATOM | 1246 | CG | LYS | A | 331 | −82.384 | 70.639 | 6.299 | 1.00 | 30.43 | C |
| ATOM | 1247 | CD | LYS | A | 331 | −81.524 | 71.811 | 5.891 | 1.00 | 34.10 | C |
| ATOM | 1248 | CE | LYS | A | 331 | −80.955 | 72.559 | 7.090 | 1.00 | 29.44 | C |
| ATOM | 1249 | NZ | LYS | A | 331 | −80.286 | 73.798 | 6.676 | 1.00 | 27.39 | N1+ |
| ATOM | 1250 | N | PHE | A | 332 | −83.556 | 68.773 | 2.195 | 1.00 | 27.68 | N |
| ATOM | 1251 | CA | PHE | A | 332 | −84.119 | 67.815 | 1.261 | 1.00 | 29.60 | C |
| ATOM | 1252 | C | PHE | A | 332 | −83.042 | 66.992 | 0.631 | 1.00 | 29.15 | C |
| ATOM | 1253 | O | PHE | A | 332 | −83.220 | 65.789 | 0.494 | 1.00 | 31.95 | O |
| ATOM | 1254 | CB | PHE | A | 332 | −84.907 | 68.472 | 0.116 | 1.00 | 34.27 | C |
| ATOM | 1255 | CG | PHE | A | 332 | −86.319 | 68.791 | 0.452 | 1.00 | 33.67 | C |
| ATOM | 1256 | CD1 | PHE | A | 332 | −87.327 | 67.835 | 0.274 | 1.00 | 36.80 | C |
| ATOM | 1257 | CD2 | PHE | A | 332 | −86.658 | 70.046 | 0.919 | 1.00 | 36.26 | C |
| ATOM | 1258 | CE1 | PHE | A | 332 | −88.642 | 68.118 | 0.619 | 1.00 | 33.33 | C |
| ATOM | 1259 | CE2 | PHE | A | 332 | −87.983 | 70.346 | 1.209 | 1.00 | 35.96 | C |
| ATOM | 1260 | CZ | PHE | A | 332 | −88.960 | 69.380 | 1.073 | 1.00 | 35.56 | C |

TABLE 37

| ATOM | 1261 | N | GLU | A | 333 | −81.955 | 67.614 | 0.178 | 1.00 | 30.84 | N |
| ATOM | 1262 | CA | GLU | A | 333 | −80.906 | 66.836 | −0.496 | 1.00 | 33.91 | C |
| ATOM | 1263 | C | GLU | A | 333 | −80.378 | 65.765 | 0.474 | 1.00 | 32.01 | C |
| ATOM | 1264 | O | GLU | A | 333 | −80.221 | 64.638 | 0.098 | 1.00 | 30.20 | O |
| ATOM | 1265 | CB | GLU | A | 333 | −79.752 | 67.708 | −1.015 | 1.00 | 39.71 | C |
| ATOM | 1266 | CG | GLU | A | 333 | −79.906 | 68.234 | −2.451 | 1.00 | 47.09 | C |
| ATOM | 1267 | CD | GLU | A | 333 | −79.504 | 69.720 | −2.661 | 1.00 | 57.65 | C |
| ATOM | 1268 | OE1 | GLU | A | 333 | −80.004 | 70.330 | −3.648 | 1.00 | 59.77 | O |
| ATOM | 1269 | OE2 | GLU | A | 333 | −78.715 | 70.307 | −1.857 | 1.00 | 65.31 | O1− |
| ATOM | 1270 | N | PHE | A | 334 | −80.123 | 66.128 | 1.728 | 1.00 | 27.07 | N |
| ATOM | 1271 | CA | PHE | A | 334 | −79.680 | 65.172 | 2.718 | 1.00 | 23.94 | C |
| ATOM | 1272 | C | PHE | A | 334 | −80.680 | 64.069 | 2.916 | 1.00 | 26.86 | C |
| ATOM | 1273 | O | PHE | A | 334 | −80.331 | 62.864 | 2.899 | 1.00 | 25.41 | O |

TABLE 37-continued

| | | | | | | | | | |
|---|---|---|---|---|---|---|---|---|---|
| ATOM | 1274 | CB | PHE | A | 334 | −79.435 | 65.863 | 4.099 | 1.00 24.87 C |
| ATOM | 1275 | CG | PHE | A | 334 | −79.056 | 64.872 | 5.167 | 1.00 26.47 C |
| ATOM | 1276 | CD1 | PHE | A | 334 | −77.747 | 64.423 | 5.281 | 1.00 28.80 C |
| ATOM | 1277 | CD2 | PHE | A | 334 | −80.034 | 64.250 | 5.934 | 1.00 29.25 C |
| ATOM | 1278 | CE1 | PHE | A | 334 | −77.397 | 63.455 | 6.230 | 1.00 30.11 C |
| ATOM | 1279 | CE2 | PHE | A | 334 | −79.702 | 63.210 | 6.850 | 1.00 28.11 C |
| ATOM | 1280 | CZ | PHE | A | 334 | −78.373 | 62.868 | 7.023 | 1.00 29.58 C |
| ATOM | 1281 | N | ALA | A | 335 | −81.939 | 64.478 | 3.156 | 1.00 25.83 N |
| ATOM | 1282 | CA | ALA | A | 335 | −82.978 | 63.563 | 3.460 | 1.00 27.40 C |
| ATOM | 1283 | C | ALA | A | 335 | −83.240 | 62.532 | 2.354 | 1.00 28.95 C |
| ATOM | 1284 | O | ALA | A | 335 | −83.369 | 61.315 | 2.622 | 1.00 28.87 O |
| ATOM | 1285 | CB | ALA | A | 335 | −84.237 | 64.330 | 3.791 | 1.00 32.76 C |
| ATOM | 1286 | N | VAL | A | 336 | −83.282 | 62.963 | 1.102 | 1.00 30.25 N |
| ATOM | 1287 | CA | VAL | A | 336 | −83.492 | 61.958 | 0.020 | 1.00 30.76 C |
| ATOM | 1288 | C | VAL | A | 336 | −82.391 | 60.918 | −0.046 | 1.00 32.47 C |
| ATOM | 1289 | O | VAL | A | 336 | −82.671 | 59.749 | −0.287 | 1.00 36.43 O |
| ATOM | 1290 | CB | VAL | A | 336 | −83.720 | 62.651 | −1.365 | 1.00 33.20 C |
| ATOM | 1291 | CG1 | VAL | A | 336 | −83.961 | 61.614 | −2.436 | 1.00 35.94 C |
| ATOM | 1292 | CG2 | VAL | A | 336 | −84.994 | 63.444 | −1.309 | 1.00 34.36 C |
| ATOM | 1293 | N | LYS | A | 337 | −81.149 | 61.298 | 0.207 | 1.00 32.94 N |
| ATOM | 1294 | CA | LYS | A | 337 | −80.064 | 60.296 | 0.262 | 1.00 34.09 C |
| ATOM | 1295 | C | LYS | A | 337 | −80.073 | 59.414 | 1.482 | 1.00 33.35 C |

TABLE 38

| | | | | | | | | | |
|---|---|---|---|---|---|---|---|---|---|
| ATOM | 1296 | O | LYS | A | 337 | −79.733 | 58.220 | 1.404 | 1.00 31.09 O |
| ATOM | 1297 | CB | LYS | A | 337 | −78.703 | 60.942 | 0.073 | 1.00 39.33 C |
| ATOM | 1298 | CG | LYS | A | 337 | −78.524 | 61.469 | −1.368 | 1.00 41.68 C |
| ATOM | 1299 | CD | LYS | A | 337 | −77.126 | 61.996 | −1.628 | 1.00 47.73 C |
| ATOM | 1300 | CE | LYS | A | 337 | −76.908 | 63.377 | −1.025 | 1.00 57.47 C |
| ATOM | 1301 | NZ | LYS | A | 337 | −75.490 | 63.826 | −1.218 | 1.00 63.57 N1+ |
| ATOM | 1302 | N | PHE | A | 338 | −80.490 | 59.977 | 2.606 | 1.00 28.72 N |
| ATOM | 1303 | CA | PHE | A | 338 | −80.582 | 59.205 | 3.850 | 1.00 29.56 C |
| ATOM | 1304 | C | PHE | A | 338 | −81.675 | 58.142 | 3.725 | 1.00 26.33 C |
| ATOM | 1305 | O | PHE | A | 338 | −81.496 | 56.982 | 4.196 | 1.00 24.28 O |
| ATOM | 1306 | CB | PHE | A | 338 | −80.893 | 60.157 | 4.987 | 1.00 27.25 C |
| ATOM | 1307 | CG | PHE | A | 338 | −80.789 | 59.572 | 6.335 | 1.00 23.40 C |
| ATOM | 1308 | CD1 | PHE | A | 338 | −79.559 | 59.451 | 6.957 | 1.00 24.14 C |
| ATOM | 1309 | CD2 | PHE | A | 338 | −81.949 | 59.208 | 7.024 | 1.00 23.49 C |
| ATOM | 1310 | CE1 | PHE | A | 338 | −79.432 | 58.998 | 8.295 | 1.00 25.03 C |
| ATOM | 1311 | CE2 | PHE | A | 338 | −81.843 | 58.722 | 8.335 | 1.00 26.26 C |
| ATOM | 1312 | CZ | PHE | A | 338 | −80.565 | 58.572 | 8.962 | 1.00 23.60 C |
| ATOM | 1313 | N | ASN | A | 339 | −82.796 | 58.534 | 3.089 | 1.00 25.99 N |
| ATOM | 1314 | CA | ASN | A | 339 | −83.865 | 57.625 | 2.868 | 1.00 27.86 C |
| ATOM | 1315 | C | ASN | A | 339 | −83.469 | 56.390 | 2.032 | 1.00 28.78 C |
| ATOM | 1316 | O | ASN | A | 339 | −84.102 | 55.363 | 2.224 | 1.00 27.74 O |
| ATOM | 1317 | CB | ASN | A | 339 | −85.121 | 58.245 | 2.289 | 1.00 28.67 C |
| ATOM | 1318 | CG | ASN | A | 339 | −85.923 | 58.984 | 3.332 | 1.00 32.93 C |
| ATOM | 1319 | ND2 | ASN | A | 339 | −86.794 | 59.910 | 2.856 | 1.00 30.47 N |
| ATOM | 1320 | OD1 | ASN | A | 339 | −85.790 | 58.734 | 4.557 | 1.00 29.32 O |
| ATOM | 1321 | N | ALA | A | 340 | −82.403 | 56.471 | 1.234 | 1.00 29.95 N |
| ATOM | 1322 | CA | ALA | A | 340 | −81.920 | 55.301 | 0.450 | 1.00 32.57 C |
| ATOM | 1323 | C | ALA | A | 340 | −81.323 | 54.196 | 3.338 | 1.00 33.57 C |
| ATOM | 1324 | O | ALA | A | 340 | −81.206 | 53.056 | 0.908 | 1.00 35.97 O |
| ATOM | 1325 | CB | ALA | A | 340 | −80.949 | 55.747 | −0.625 | 1.00 35.62 C |
| ATOM | 1326 | N | LEU | A | 341 | −81.050 | 54.506 | 2.610 | 1.00 29.03 N |
| ATOM | 1327 | CA | LEU | A | 341 | −80.643 | 53.525 | 3.566 | 1.00 29.20 C |
| ATOM | 1328 | C | LEU | A | 341 | −81.782 | 52.663 | 4.076 | 1.00 29.94 C |
| ATOM | 1329 | O | LEU | A | 341 | −81.492 | 51.612 | 4.559 | 1.00 34.09 O |
| ATOM | 1330 | CB | LEU | A | 341 | −79.922 | 54.183 | 4.756 | 1.00 29.54 C |

TABLE 39

| | | | | | | | | | |
|---|---|---|---|---|---|---|---|---|---|
| ATOM | 1331 | CG | LEU | A | 341 | −78.657 | 54.963 | 4.438 | 1.00 30.55 C |
| ATOM | 1332 | CD1 | LEU | A | 341 | −77.949 | 55.324 | 5.726 | 1.00 32.49 C |
| ATOM | 1333 | CD2 | LEU | A | 341 | −77.699 | 54.202 | 3.505 | 1.00 34.94 C |
| ATOM | 1334 | N | GLU | A | 342 | −83.045 | 53.110 | 4.007 | 1.00 28.01 N |
| ATOM | 1335 | CA | GLU | A | 342 | −84.188 | 52.297 | 4.329 | 1.00 29.20 C |
| ATOM | 1336 | C | GLU | A | 342 | −84.170 | 51.939 | 5.797 | 1.00 30.98 C |
| ATOM | 1337 | O | GLU | A | 342 | −84.538 | 50.837 | 6.168 | 1.00 27.93 O |
| ATOM | 1338 | CB | GLU | A | 342 | −84.271 | 51.020 | 3.422 | 1.00 33.67 C |
| ATOM | 1339 | CG | GLU | A | 342 | −84.436 | 51.396 | 1.951 | 1.00 40.93 C |
| ATOM | 1340 | CD | GLU | A | 342 | −84.641 | 50.210 | 0.996 | 1.00 51.71 C |
| ATOM | 1341 | OE1 | GLU | A | 342 | −85.155 | 50.443 | −0.127 | 1.00 59.40 O |
| ATOM | 1342 | OE2 | GLU | A | 342 | −84.304 | 49.050 | 1.343 | 1.00 63.85 O1− |

TABLE 39-continued

| | | | | | | | | | | |
|---|---|---|---|---|---|---|---|---|---|---|
| ATOM | 1343 | N | LEU | A | 343 | −83.720 | 52.858 | 6.671 | 1.00 | 25.57 N |
| ATOM | 1344 | CA | LEU | A | 343 | −83.886 | 52.596 | 8.061 | 1.00 | 25.55 C |
| ATOM | 1345 | C | LEU | A | 343 | −85.344 | 52.538 | 8.436 | 1.00 | 27.74 C |
| ATOM | 1346 | O | LEU | A | 343 | −86.157 | 53.182 | 7.841 | 1.00 | 28.31 O |
| ATOM | 1347 | CB | LEU | A | 343 | −83.220 | 53.709 | 8.903 | 1.00 | 28.96 C |
| ATOM | 1348 | CG | LEO | A | 343 | −81.727 | 53.983 | 8.696 | 1.00 | 31.46 C |
| ATOM | 1349 | CD1 | LEU | A | 343 | −81.209 | 54.885 | 9.856 | 1.00 | 33.37 C |
| ATOM | 1350 | CD2 | LEU | A | 343 | −80.941 | 52.709 | 8.626 | 1.00 | 34.61 C |
| ATOM | 1351 | N | ASP | A | 344 | −85.637 | 51.821 | 9.513 | 1.00 | 29.04 N |
| ATOM | 1352 | CA | ASP | A | 344 | −86.914 | 51.879 | 10.183 | 1.00 | 28.97 C |
| ATOM | 1353 | C | ASP | A | 344 | −86.795 | 52.599 | 11.538 | 1.00 | 28.57 C |
| ATOM | 1354 | O | ASP | A | 344 | −85.724 | 53.074 | 11.935 | 1.00 | 26.79 O |
| ATOM | 1355 | CB | ASP | A | 344 | −87.534 | 50.437 | 10.314 | 1.00 | 31.24 C |
| ATOM | 1356 | CG | ASP | A | 344 | −86.814 | 49.528 | 11.308 | 1.00 | 35.96 C |
| ATOM | 1357 | OD1 | ASP | A | 344 | −86.302 | 49.977 | 12.382 | 1.00 | 36.16 O |
| ATOM | 1358 | OD2 | ASP | A | 344 | −86.792 | 48.293 | 11.031 | 1.00 | 39.22 O1- |
| ATOM | 1359 | N | ASP | A | 345 | −87.918 | 52.728 | 12.213 | 1.00 | 25.19 N |
| ATOM | 1360 | CA | ASP | A | 345 | −87.985 | 53.504 | 13.466 | 1.00 | 25.66 C |
| ATOM | 1361 | C | ASP | A | 345 | −87.069 | 52.911 | 14.571 | 1.00 | 26.11 C |
| ATOM | 1362 | O | ASP | A | 345 | −86.457 | 53.688 | 15.373 | 1.00 | 23.67 O |
| ATOM | 1363 | CB | ASP | A | 345 | −89.404 | 53.610 | 13.932 | 1.00 | 26.03 C |
| ATOM | 1364 | CG | ASP | A | 345 | −90.233 | 54.534 | 13.040 | 1.00 | 28.95 C |
| ATOM | 1365 | OD1 | ASP | A | 345 | −89.933 | 55.773 | 12.961 | 1.00 | 28.73 O |

TABLE 40

| | | | | | | | | | | |
|---|---|---|---|---|---|---|---|---|---|---|
| ATOM | 1366 | OD2 | ASP | A | 345 | −91.164 | 54.006 | 12.412 | 1.00 | 29.19 O1- |
| ATOM | 1367 | N | SER | A | 346 | −86.934 | 51.572 | 14.589 | 1.00 | 22.04 N |
| ATOM | 1368 | CA | SER | A | 346 | −86.156 | 50.947 | 15.601 | 1.00 | 24.46 C |
| ATOM | 1369 | C | SER | A | 346 | −84.683 | 51.316 | 15.433 | 1.00 | 24.51 C |
| ATOM | 1370 | O | SER | A | 346 | −83.931 | 51.458 | 16.447 | 1.00 | 26.04 O |
| ATOM | 1371 | CB | SER | A | 346 | −86.340 | 49.372 | 15.630 | 1.00 | 22.35 C |
| ATOM | 1372 | OG | SER | A | 346 | −85.962 | 48.762 | 14.413 | 1.00 | 26.81 O |
| ATOM | 1373 | N | ASP | A | 347 | −84.262 | 51.361 | 14.189 | 1.00 | 23.65 N |
| ATOM | 1374 | CA | ASP | A | 347 | −82.915 | 51.787 | 13.808 | 1.00 | 25.55 C |
| ATOM | 1375 | C | ASP | A | 347 | −82.708 | 53.241 | 14.146 | 1.00 | 25.43 C |
| ATOM | 1376 | O | ASP | A | 347 | −81.659 | 53.605 | 14.673 | 1.00 | 23.57 O |
| ATOM | 1377 | CB | ASP | A | 347 | −82.668 | 51.659 | 12.315 | 1.00 | 24.52 C |
| ATOM | 1378 | CG | ASP | A | 347 | −82.962 | 50.244 | 11.744 | 1.00 | 29.96 C |
| ATOM | 1379 | OD1 | ASP | A | 347 | −82.716 | 49.211 | 12.390 | 1.00 | 26.87 O |
| ATOM | 1380 | OD2 | ASP | A | 347 | −83.366 | 50.185 | 10.554 | 1.00 | 32.36 O1- |
| ATOM | 1381 | N | LEU | A | 348 | −83.666 | 54.082 | 13.744 | 1.00 | 22.88 N |
| ATOM | 1382 | CA | LEU | A | 348 | −83.526 | 55.533 | 13.919 | 1.00 | 23.14 C |
| ATOM | 1383 | C | LEU | A | 348 | −83.418 | 55.906 | 15.392 | 1.00 | 23.29 C |
| ATOM | 1384 | O | LEU | A | 348 | −82.708 | 56.817 | 15.750 | 1.00 | 20.74 O |
| ATOM | 1385 | CB | LEU | A | 348 | −84.733 | 56.249 | 13.298 | 1.00 | 26.01 C |
| ATOM | 1386 | CG | LEU | A | 348 | −84.830 | 56.220 | 11.764 | 1.00 | 27.73 C |
| ATOM | 1387 | CD1 | LEU | A | 348 | −86.220 | 56.657 | 11.283 | 1.00 | 28.83 C |
| ATOM | 1388 | CD2 | LEU | A | 348 | −83.781 | 57.196 | 11.227 | 1.00 | 35.38 C |
| ATOM | 1389 | N | ALA | A | 349 | −84.130 | 55.171 | 16.228 | 1.00 | 21.48 N |
| ATOM | 1390 | CA | ALA | A | 349 | −84.161 | 55.444 | 17.644 | 1.00 | 22.55 C |
| ATOM | 1391 | C | ALA | A | 349 | −82.699 | 55.339 | 18.229 | 1.00 | 21.78 C |
| ATOM | 1392 | O | ALA | A | 349 | −82.229 | 56.231 | 18.918 | 1.00 | 22.46 O |
| ATOM | 1393 | CB | ALA | A | 349 | −85.111 | 54.498 | 18.315 | 1.00 | 22.51 C |
| ATOM | 1394 | N | LEU | A | 350 | −81.998 | 54.253 | 17.905 | 1.00 | 21.46 N |
| ATOM | 1395 | CA | LEU | A | 350 | −80.629 | 54.098 | 18.309 | 1.00 | 24.29 C |
| ATOM | 1396 | C | LEU | A | 350 | −79.702 | 55.144 | 17.615 | 1.00 | 25.71 C |
| ATOM | 1397 | O | LEU | A | 350 | −78.792 | 55.659 | 18.232 | 1.00 | 21.47 O |
| ATOM | 1398 | CB | LEU | A | 350 | −80.105 | 52.719 | 17.939 | 1.00 | 24.44 C |
| ATOM | 1399 | CG | LEU | A | 350 | −80.666 | 51.672 | 18.856 | 1.00 | 24.44 C |
| ATOM | 1400 | CD1 | LEU | A | 350 | −80.655 | 50.328 | 18.218 | 1.00 | 27.61 C |

TABLE 41

| | | | | | | | | | | |
|---|---|---|---|---|---|---|---|---|---|---|
| ATOM | 1401 | CD2 | LEU | A | 350 | −79.946 | 51.679 | 20.177 | 1.00 | 25.21 C |
| ATOM | 1402 | N | PHE | A | 351 | −79.910 | 55.393 | 16.337 | 1.00 | 23.65 N |
| ATOM | 1403 | CA | PHE | A | 351 | −79.095 | 56.396 | 15.645 | 1.00 | 23.35 C |
| ATOM | 1404 | C | PHE | A | 351 | −79.224 | 57.773 | 16.332 | 1.00 | 23.86 C |
| ATOM | 1405 | O | PHE | A | 351 | −78.223 | 58.435 | 16.512 | 1.00 | 24.52 O |
| ATOM | 1406 | CB | PHE | A | 351 | −79.614 | 56.536 | 14.235 | 1.00 | 24.24 C |
| ATOM | 1407 | CG | PHE | A | 351 | −78.862 | 57.412 | 13.357 | 1.00 | 24.31 C |
| ATOM | 1408 | CD1 | PHE | A | 351 | −77.522 | 57.049 | 13.022 | 1.00 | 26.61 C |
| ATOM | 1409 | CD2 | PHE | A | 351 | −79.298 | 58.609 | 12.871 | 1.00 | 26.91 C |
| ATOM | 1410 | CE1 | PHE | A | 351 | −76.758 | 57.849 | 12.196 | 1.00 | 26.41 C |
| ATOM | 1411 | CE2 | PHE | A | 351 | −78.558 | 59.379 | 12.001 | 1.00 | 26.41 C |

TABLE 41-continued

| ATOM | 1412 | CZ  | PHE | A | 351 | −77.296 | 59.009 | 11.659 | 1.00 | 26.29 | C |
| ATOM | 1413 | N   | ILE | A | 352 | −80.443 | 58.217 | 16.645 | 1.00 | 21.10 | N |
| ATOM | 1414 | CA  | ILE | A | 352 | −80.605 | 59.502 | 17.327 | 1.00 | 24.83 | C |
| ATOM | 1415 | C   | ILE | A | 352 | −79.978 | 59.557 | 18.723 | 1.00 | 21.55 | C |
| ATOM | 1416 | O   | ILE | A | 352 | −79.393 | 60.572 | 19.084 | 1.00 | 19.85 | O |
| ATOM | 1417 | CB  | ILE | A | 352 | −82.016 | 60.100 | 17.265 | 1.00 | 29.03 | C |
| ATOM | 1418 | CG1 | ILE | A | 352 | −83.005 | 59.379 | 18.095 | 1.00 | 36.21 | C |
| ATOM | 1419 | CG2 | ILE | A | 352 | −82.504 | 60.161 | 15.776 | 1.00 | 31.79 | C |
| ATOM | 1420 | CD1 | ILE | A | 352 | −84.390 | 59.985 | 17.963 | 1.00 | 39.03 | C |
| ATOM | 1421 | N   | ALA | A | 353 | −80.101 | 58.457 | 19.469 | 1.00 | 20.01 | N |
| ATOM | 1422 | CA  | ALA | A | 353 | −79.389 | 58.293 | 20.747 | 1.00 | 21.50 | C |
| ATOM | 1423 | C   | ALA | A | 353 | −77.869 | 58.496 | 20.609 | 1.00 | 20.07 | C |
| ATOM | 1424 | O   | ALA | A | 353 | −77.246 | 59.208 | 21.417 | 1.00 | 20.35 | O |
| ATOM | 1425 | CB  | ALA | A | 353 | −79.734 | 56.946 | 21.369 | 1.00 | 20.22 | C |
| ATOM | 1426 | N   | ALA | A | 354 | −77.280 | 57.918 | 19.568 | 1.00 | 21.05 | N |
| ATOM | 1427 | CA  | ALA | A | 354 | −75.823 | 58.049 | 19.310 | 1.00 | 21.54 | C |
| ATOM | 1428 | C   | ALA | A | 354 | −75.410 | 59.462 | 18.908 | 1.00 | 24.20 | C |
| ATOM | 1429 | O   | ALA | A | 354 | −74.270 | 59.896 | 19.229 | 1.00 | 25.28 | O |
| ATOM | 1430 | CB  | ALA | A | 354 | −75.366 | 57.100 | 18.228 | 1.00 | 22.04 | C |
| ATOM | 1431 | N   | ILE | A | 355 | −76.270 | 60.154 | 18.163 | 1.00 | 19.97 | N |
| ATOM | 1432 | CA  | ILE | A | 355 | −76.071 | 61.606 | 17.879 | 1.00 | 21.04 | C |
| ATOM | 1433 | C   | ILE | A | 355 | −75.988 | 62.473 | 19.125 | 1.00 | 20.36 | C |
| ATOM | 1434 | O   | ILE | A | 355 | −75.034 | 63.215 | 19.267 | 1.00 | 21.97 | O |
| ATOM | 1435 | CB  | ILE | A | 355 | −77.165 | 62.107 | 16.889 | 1.00 | 19.44 | C |

TABLE 42

| ATOM | 1436 | CG1 | ILE | A | 355 | −76.841 | 61.537 | 15.500 | 1.00 | 20.75 | C |
| ATOM | 1437 | CG2 | ILE | A | 355 | −77.214 | 63.634 | 16.782 | 1.00 | 22.87 | C |
| ATOM | 1438 | CD1 | ILE | A | 355 | −77.870 | 61.812 | 14.475 | 1.00 | 22.49 | C |
| ATOM | 1439 | N   | ILE | A | 356 | −76.949 | 62.321 | 20.016 | 1.00 | 18.50 | N |
| ATOM | 1440 | CA  | ILE | A | 356 | −77.011 | 63.045 | 21.264 | 1.00 | 21.24 | C |
| ATOM | 1441 | C   | ILE | A | 356 | −75.793 | 62.759 | 22.182 | 1.00 | 21.61 | C |
| ATOM | 1442 | O   | ILE | A | 356 | −75.284 | 63.651 | 22.860 | 1.00 | 22.74 | O |
| ATOM | 1443 | CB  | ILE | A | 356 | −78.298 | 62.779 | 22.026 | 1.00 | 22.53 | C |
| ATOM | 1444 | CG1 | ILE | A | 356 | −79.474 | 63.255 | 21.207 | 1.00 | 26.44 | C |
| ATOM | 1445 | CG2 | ILE | A | 356 | −78.400 | 63.637 | 23.310 | 1.00 | 26.07 | C |
| ATOM | 1446 | GD1 | ILE | A | 356 | −80.834 | 62.868 | 21.784 | 1.00 | 28.83 | C |
| ATOM | 1447 | N   | LEU | A | 357 | −75.361 | 61.509 | 22.268 | 1.00 | 23.38 | N |
| ATOM | 1448 | CA  | LEU | A | 357 | −74.235 | 61.135 | 23.122 | 1.00 | 23.00 | C |
| ATOM | 1449 | C   | LEU | A | 357 | −72.830 | 61.320 | 22.432 | 1.00 | 25.58 | C |
| ATOM | 1450 | O   | LEU | A | 357 | −71.901 | 60.605 | 22.667 | 1.00 | 28.10 | O |
| ATOM | 1451 | CB  | LEU | A | 357 | −74.431 | 59.726 | 23.674 | 1.00 | 22.36 | C |
| ATOM | 1452 | CG  | LEU | A | 357 | −75.231 | 59.567 | 24.936 | 1.00 | 24.42 | C |
| ATOM | 1453 | CD1 | LEU | A | 357 | −74.475 | 60.212 | 26.130 | 1.00 | 27.78 | C |
| ATOM | 1454 | CD2 | LEU | A | 357 | −76.610 | 60.180 | 24.795 | 1.00 | 28.12 | C |
| ATOM | 1455 | N   | CYS | A | 358 | −72.664 | 62.386 | 21.663 | 1.00 | 30.54 | N |
| ATOM | 1456 | CA  | CYS | A | 358 | −71.441 | 62.672 | 20.980 | 1.00 | 29.56 | C |
| ATOM | 1457 | C   | CYS | A | 358 | −70.370 | 63.242 | 21.932 | 1.00 | 30.58 | C |
| ATOM | 1458 | O   | CYS | A | 358 | −70.540 | 64.268 | 22.580 | 1.00 | 28.86 | O |
| ATOM | 1459 | CB  | CYS | A | 358 | −71.771 | 63.636 | 19.880 | 1.00 | 36.65 | C |
| ATOM | 1460 | SG  | CYS | A | 358 | −70.315 | 64.123 | 19.048 | 1.00 | 40.83 | S |
| ATOM | 1461 | N   | GLY | A | 359 | −69.236 | 62.554 | 22.022 | 1.00 | 29.82 | N |
| ATOM | 1462 | CA  | GLY | A | 359 | −68.175 | 62.973 | 22.913 | 1.00 | 28.68 | C |
| ATOM | 1463 | C   | GLY | A | 359 | −67.345 | 64.150 | 22.501 | 1.00 | 27.86 | C |
| ATOM | 1464 | O   | GLY | A | 359 | −66.635 | 64.692 | 23.326 | 1.00 | 26.90 | O |
| ATOM | 1465 | N   | ASP | A | 360 | −67.462 | 64.635 | 21.275 | 1.00 | 28.26 | N |
| ATOM | 1466 | CA  | ASP | A | 360 | −66.650 | 65.781 | 20.943 | 1.00 | 33.38 | C |
| ATOM | 1467 | C   | ASP | A | 360 | −67.365 | 67.138 | 20.821 | 1.00 | 32.73 | C |
| ATOM | 1468 | O   | ASP | A | 360 | −66.950 | 67.996 | 20.051 | 1.00 | 36.71 | O |
| ATOM | 1469 | CB  | ASP | A | 360 | −65.722 | 65.483 | 19.795 | 1.00 | 43.49 | C |
| ATOM | 1470 | CG  | ASP | A | 360 | −66.387 | 65.509 | 18.508 | 1.00 | 50.36 | C |

TABLE 43

| ATOM | 1471 | OD1 | ASP | A | 360 | −67.548 | 65.068 | 18.536 | 1.00 | 46.79 | O   |
| ATOM | 1472 | OD2 | ASP | A | 360 | −65.732 | 65.968 | 17.502 | 1.00 | 59.28 | O1− |
| ATOM | 1473 | N   | ARG | A | 361 | −68.375 | 67.359 | 21.646 | 1.00 | 29.07 | N   |
| ATOM | 1474 | CA  | ARG | A | 361 | −69.056 | 68.660 | 21.633 | 1.00 | 25.70 | C   |
| ATOM | 1475 | C   | ARG | A | 361 | −68.204 | 69.687 | 22.382 | 1.00 | 25.12 | C   |
| ATOM | 1476 | O   | ARG | A | 361 | −67.634 | 69.371 | 23.416 | 1.00 | 26.08 | O   |
| ATOM | 1477 | CB  | ARG | A | 361 | −70.434 | 68.538 | 22.286 | 1.00 | 23.65 | C   |
| ATOM | 1478 | CG  | ARG | A | 361 | −71.375 | 67.460 | 21.695 | 1.00 | 24.32 | C   |
| ATOM | 1479 | CD  | ARG | A | 361 | −71.538 | 67.626 | 20.192 | 1.00 | 23.61 | C   |
| ATOM | 1480 | NE  | ARG | A | 361 | −72.640 | 86.855 | 19.664 | 1.00 | 23.03 | N   |

TABLE 43-continued

| ATOM | 1481 | CZ  | ARG | A | 361 | −72.930 | 66.740 | 18.357 | 1.00 | 25.65 | C   |
|------|------|-----|-----|---|-----|---------|--------|--------|------|-------|-----|
| ATOM | 1482 | NH1 | ARG | A | 361 | −72.234 | 67.367 | 17.427 | 1.00 | 23.62 | N1+ |
| ATOM | 1483 | NH2 | ARG | A | 361 | −73.956 | 65.994 | 17.990 | 1.00 | 26.41 | N   |
| ATOM | 1484 | N   | PRO | A | 362 | −68.169 | 70.925 | 21.904 | 1.00 | 26.30 | N   |
| ATOM | 1485 | CA  | PRO | A | 362 | −67.454 | 71.943 | 22.606 | 1.00 | 25.70 | C   |
| ATOM | 1486 | C   | PRO | A | 362 | −67.926 | 72.155 | 24.036 | 1.00 | 25.10 | C   |
| ATOM | 1487 | O   | PRO | A | 362 | −69.088 | 72.307 | 24.278 | 1.00 | 25.35 | O   |
| ATOM | 1488 | CB  | PRO | A | 362 | −67.727 | 73.239 | 21.794 | 1.00 | 27.18 | C   |
| ATOM | 1489 | CG  | PRO | A | 362 | −68.181 | 72.784 | 20.444 | 1.00 | 26.84 | C   |
| ATOM | 1490 | CD  | PRO | A | 362 | −68.723 | 71.386 | 20.611 | 1.00 | 25.25 | C   |
| ATOM | 1491 | N   | GLY | A | 363 | −67.012 | 72.146 | 24.986 | 1.00 | 24.11 | N   |
| ATOM | 1492 | CA  | GLY | A | 363 | −67.379 | 72.537 | 26.369 | 1.00 | 24.36 | C   |
| ATOM | 1493 | C   | GLY | A | 363 | −67.838 | 71.398 | 27.239 | 1.00 | 23.85 | C   |
| ATOM | 1494 | O   | GLY | A | 363 | −68.159 | 71.633 | 28.392 | 1.00 | 26.14 | O   |
| ATOM | 1495 | N   | LEU | A | 364 | −67.887 | 70.185 | 26.674 | 1.00 | 24.65 | N   |
| ATOM | 1496 | CA  | LEU | A | 364 | −68.207 | 68.956 | 27.377 | 1.00 | 23.42 | C   |
| ATOM | 1497 | C   | LEU | A | 364 | −67.102 | 68.663 | 28.380 | 1.00 | 23.38 | C   |
| ATOM | 1498 | O   | LEU | A | 364 | −65.913 | 68.657 | 28.031 | 1.00 | 23.52 | O   |
| ATOM | 1499 | CB  | LEU | A | 364 | −68.359 | 67.799 | 26.403 | 1.00 | 27.51 | C   |
| ATOM | 1500 | CG  | LEU | A | 364 | −69.153 | 66.569 | 26.815 | 1.00 | 31.79 | C   |
| ATOM | 1501 | CD1 | LEU | A | 364 | −70.600 | 66.975 | 27.150 | 1.00 | 29.07 | C   |
| ATOM | 1502 | CD2 | LEU | A | 364 | −69.126 | 65.552 | 25.652 | 1.00 | 33.09 | C   |
| ATOM | 1503 | N   | MET | A | 365 | −67.508 | 68.494 | 29.633 | 1.00 | 23.03 | N   |
| ATOM | 1504 | CA  | MET | A | 365 | −66.580 | 68.245 | 30.745 | 1.00 | 22.95 | C   |
| ATOM | 1505 | C   | MET | A | 365 | −66.144 | 66.761 | 30.857 | 1.00 | 22.88 | C   |

TABLE 44

| ATOM | 1506 | O   | MET | A | 365 | −64.970 | 66.414 | 30.699 | 1.00 | 22.23 | O   |
|------|------|-----|-----|---|-----|---------|--------|--------|------|-------|-----|
| ATOM | 1507 | CB  | MET | A | 365 | −67.161 | 68.756 | 32.074 | 1.00 | 22.80 | C   |
| ATOM | 1508 | CG  | MET | A | 365 | −67.306 | 70.282 | 32.122 | 1.00 | 25.16 | C   |
| ATOM | 1509 | SD  | MET | A | 365 | −65.681 | 71.146 | 32.093 | 1.00 | 26.95 | S   |
| ATOM | 1510 | CE  | MET | A | 365 | −65.685 | 71.755 | 30.366 | 1.00 | 31.57 | C   |
| ATOM | 1511 | N   | ASN | A | 366 | −67.079 | 65.886 | 31.145 | 1.00 | 21.97 | N   |
| ATOM | 1512 | CA  | ASN | A | 366 | −66.672 | 64.480 | 31.383 | 1.00 | 23.05 | C   |
| ATOM | 1513 | C   | ASN | A | 366 | −66.784 | 63.668 | 30.040 | 1.00 | 23.58 | C   |
| ATOM | 1514 | O   | ASN | A | 366 | −67.741 | 62.922 | 29.795 | 1.00 | 23.77 | O   |
| ATOM | 1515 | CB  | ASN | A | 366 | −67.499 | 63.916 | 32.507 | 1.00 | 22.41 | C   |
| ATOM | 1516 | CG  | ASN | A | 366 | −66.996 | 62.556 | 32.991 | 1.00 | 25.52 | C   |
| ATOM | 1517 | ND2 | ASN | A | 366 | −67.666 | 62.001 | 34.020 | 1.00 | 28.47 | N   |
| ATOM | 1518 | OD1 | ASN | A | 366 | −66.080 | 61.993 | 32.427 | 1.00 | 25.40 | O   |
| ATOM | 1519 | N   | VAL | A | 367 | −65.781 | 63.856 | 29.216 | 1.00 | 21.67 | N   |
| ATOM | 1520 | CA  | VAL | A | 367 | −65.688 | 63.253 | 27.860 | 1.00 | 22.09 | C   |
| ATOM | 1521 | C   | VAL | A | 367 | −65.621 | 61.724 | 27.960 | 1.00 | 23.24 | C   |
| ATOM | 1522 | O   | VAL | A | 367 | −66.350 | 61.047 | 27.269 | 1.00 | 23.85 | O   |
| ATOM | 1523 | CB  | VAL | A | 367 | −64.501 | 63.879 | 27.126 | 1.00 | 23.86 | C   |
| ATOM | 1524 | CG1 | VAL | A | 367 | −64.253 | 63.219 | 25.765 | 1.00 | 26.29 | C   |
| ATOM | 1525 | CG2 | VAL | A | 367 | −64.833 | 65.357 | 26.853 | 1.00 | 27.28 | C   |
| ATOM | 1526 | N   | PRO | A | 368 | −64.795 | 61.176 | 28.857 | 1.00 | 26.69 | N   |
| ATOM | 1527 | CA  | PRO | A | 368 | −64.708 | 59.698 | 28.895 | 1.00 | 25.75 | C   |
| ATOM | 1528 | C   | PRO | A | 368 | −66.062 | 59.004 | 29.188 | 1.00 | 24.91 | C   |
| ATOM | 1529 | O   | PRO | A | 368 | −66.386 | 57.959 | 28.627 | 1.00 | 27.21 | O   |
| ATOM | 1530 | CB  | PRO | A | 368 | −63.646 | 59.433 | 30.026 | 1.00 | 27.92 | C   |
| ATOM | 1531 | CG  | PRO | A | 368 | −62.850 | 60.723 | 30.112 | 1.00 | 27.86 | C   |
| ATOM | 1532 | CD  | PRO | A | 368 | −63.858 | 61.828 | 29.823 | 1.00 | 27.07 | C   |
| ATOM | 1533 | N   | ARG | A | 369 | −66.829 | 59.558 | 30.101 | 1.00 | 24.48 | N   |
| ATOM | 1534 | CA  | ARG | A | 369 | −68.110 | 59.014 | 30.423 | 1.00 | 24.27 | C   |
| ATOM | 1535 | C   | ARG | A | 369 | −69.101 | 59.119 | 29.249 | 1.00 | 22.94 | C   |
| ATOM | 1536 | O   | ARG | A | 369 | −69.774 | 58.165 | 28.967 | 1.00 | 23.90 | O   |
| ATOM | 1537 | CB  | ARG | A | 369 | −68.708 | 59.645 | 31.660 | 1.00 | 25.39 | C   |
| ATOM | 1538 | CG  | ARG | A | 369 | −69.898 | 58.924 | 32.175 | 1.00 | 33.11 | C   |
| ATOM | 1539 | CD  | ARG | A | 369 | −70.260 | 59.332 | 33.620 | 1.00 | 39.02 | C   |
| ATOM | 1540 | NE  | ARG | A | 369 | −71.500 | 58.634 | 34.020 | 1.00 | 42.90 | N   |

TABLE 45

| ATOM | 1541 | CO  | ARG | A | 369 | −71.590 | 57.326 | 34.265 | 1.00 | 46.73 | C   |
|------|------|-----|-----|---|-----|---------|--------|--------|------|-------|-----|
| ATOM | 1542 | NH1 | ARG | A | 369 | −70.515 | 56.558 | 34.198 | 1.00 | 47.69 | N1+ |
| ATOM | 1543 | NH2 | ARG | A | 369 | −72.770 | 56.775 | 34.572 | 1.00 | 46.26 | N   |
| ATOM | 1544 | N   | VAL | A | 370 | −69.165 | 80.237 | 28.589 | 1.00 | 21.98 | N   |
| ATOM | 1545 | CA  | VAL | A | 370 | −70.026 | 60.366 | 27.419 | 1.00 | 22.26 | C   |
| ATOM | 1546 | C   | VAL | A | 370 | −69.581 | 59.416 | 26.320 | 1.00 | 21.72 | C   |
| ATOM | 1547 | O   | VAL | A | 370 | −70.412 | 58.787 | 25.703 | 1.00 | 23.73 | O   |
| ATOM | 1548 | CB  | VAL | A | 370 | −70.010 | 61.815 | 26.910 | 1.00 | 21.33 | C   |
| ATOM | 1549 | CG1 | VAL | A | 370 | −70.721 | 61.960 | 25.575 | 1.00 | 21.99 | C   |

TABLE 45-continued

| | | | | | | | | | | |
|---|---|---|---|---|---|---|---|---|---|---|
| ATOM | 1550 | CG2 | VAL | A | 370 | −70.615 | 62.706 | 27.951 | 1.00 | 20.86 C |
| ATOM | 1551 | N | GLU | A | 371 | −68.280 | 59.299 | 26.065 | 1.00 | 21.47 N |
| ATOM | 1552 | CA | GLU | A | 371 | −67.778 | 58.353 | 25.054 | 1.00 | 23.96 C |
| ATOM | 1553 | C | GLU | A | 371 | −68.132 | 56.881 | 25.396 | 1.00 | 24.41 C |
| ATOM | 1554 | O | GLU | A | 371 | −68.518 | 56.126 | 24.480 | 1.00 | 21.17 O |
| ATOM | 1555 | CB | GLU | A | 371 | −66.260 | 58.475 | 24.817 | 1.00 | 24.96 C |
| ATOM | 1556 | CG | GLU | A | 371 | −65.978 | 59.812 | 24.166 | 1.00 | 32.81 C |
| ATOM | 1557 | CD | GLU | A | 371 | −64.566 | 59.971 | 23.628 | 1.00 | 39.02 C |
| ATOM | 1558 | OE1 | GLU | A | 371 | −63.689 | 59.252 | 24.167 | 1.00 | 40.72 O |
| ATOM | 1559 | OE2 | GLU | A | 371 | −64.367 | 60.841 | 22.711 | 1.00 | 46.45 O1− |
| ATOM | 1560 | N | ALA | A | 372 | −68.067 | 56.521 | 26.669 | 1.00 | 23.17 N |
| ATOM | 1561 | CA | ALA | A | 372 | −68.470 | 55.168 | 27.121 | 1.00 | 25.96 C |
| ATOM | 1562 | C | ALA | A | 372 | −69.985 | 54.858 | 26.948 | 1.00 | 27.50 C |
| ATOM | 1563 | O | ALA | A | 372 | −70.382 | 53.729 | 26.543 | 1.00 | 24.51 O |
| ATOM | 1564 | CB | ALA | A | 372 | −68.038 | 54.906 | 28.548 | 1.00 | 26.90 C |
| ATOM | 1565 | N | ILE | A | 373 | −70.828 | 55.850 | 27.210 | 1.00 | 23.63 N |
| ATOM | 1566 | CA | ILE | A | 373 | −72.262 | 55.689 | 26.943 | 1.00 | 22.73 C |
| ATOM | 1567 | C | ILE | A | 373 | −72.473 | 55.621 | 25.396 | 1.00 | 24.64 C |
| ATOM | 1568 | O | ILE | A | 373 | −73.173 | 54.749 | 24.918 | 1.00 | 23.01 O |
| ATOM | 1569 | CB | ILE | A | 373 | −73.039 | 56.819 | 27.540 | 1.00 | 22.89 C |
| ATOM | 1570 | CG1 | ILE | A | 373 | −72.850 | 56.840 | 29.066 | 1.00 | 25.00 C |
| ATOM | 1571 | CG2 | ILE | A | 373 | −74.515 | 56.806 | 27.147 | 1.00 | 22.76 C |
| ATOM | 1572 | CD1 | ILE | A | 373 | −73.288 | 58.149 | 29.652 | 1.00 | 25.70 C |
| ATOM | 1573 | N | GLN | A | 374 | −71.817 | 56.488 | 24.625 | 1.00 | 22.07 N |
| ATOM | 1574 | CA | GLN | A | 374 | −71.956 | 56.435 | 23.142 | 1.00 | 23.40 C |
| ATOM | 1575 | C | GLN | A | 374 | −71.552 | 55.082 | 22.558 | 1.00 | 22.83 C |

TABLE 46

| | | | | | | | | | | |
|---|---|---|---|---|---|---|---|---|---|---|
| ATOM | 1576 | O | GLN | A | 374 | −72.215 | 54.525 | 21.693 | 1.00 | 22.35 O |
| ATOM | 1577 | CB | GLN | A | 374 | −71.233 | 57.551 | 22.412 | 1.00 | 23.14 C |
| ATOM | 1578 | CG | GLN | A | 374 | −71.749 | 57.654 | 20.938 | 1.00 | 23.59 C |
| ATOM | 1570 | CD | GLN | A | 374 | −70.908 | 58.520 | 20.053 | 1.00 | 26.27 C |
| ATOM | 1580 | NE2 | GLN | A | 374 | −71.540 | 59.443 | 19.261 | 1.00 | 22.90 N |
| ATOM | 1581 | OE1 | GLN | A | 374 | −69.696 | 58.399 | 20.094 | 1.00 | 25.56 O |
| ATOM | 1582 | N | ASP | A | 375 | −70.477 | 54.533 | 23.075 | 1.00 | 25.96 N |
| ATOM | 1583 | CA | ASP | A | 375 | −70.011 | 53.219 | 22.648 | 1.00 | 24.82 C |
| ATOM | 1584 | C | ASP | A | 375 | −71.028 | 52.137 | 22.875 | 1.00 | 25.19 C |
| ATOM | 1585 | O | ASP | A | 375 | −71.224 | 51.324 | 21.976 | 1.00 | 25.31 O |
| ATOM | 1586 | CB | ASP | A | 375 | −68.719 | 52.845 | 23.394 | 1.00 | 28.10 C |
| ATOM | 1587 | CO | ASP | A | 375 | −67.537 | 53.667 | 22.980 | 1.00 | 29.79 C |
| ATOM | 1588 | OD1 | ASP | A | 375 | −67.590 | 54.233 | 21.882 | 1.00 | 32.18 O |
| ATOM | 1589 | OD2 | ASP | A | 375 | −66.522 | 53.690 | 23.727 | 1.00 | 33.07 O1− |
| ATOM | 1590 | N | THR | A | 376 | −71.639 | 52.092 | 24.075 | 1.00 | 23.06 N |
| ATOM | 1591 | CA | THR | A | 376 | −72.751 | 51.169 | 24.336 | 1.00 | 24.01 C |
| ATOM | 1592 | C | THR | A | 376 | −73.927 | 51.281 | 23.342 | 1.00 | 24.51 C |
| ATOM | 1593 | O | TKR | A | 376 | −74.398 | 50.312 | 22.856 | 1.00 | 22.48 O |
| ATOM | 1594 | CB | THR | A | 376 | −73.319 | 51.420 | 25.708 | 1.00 | 28.77 C |
| ATOM | 1595 | CG2 | THR | A | 376 | −74.453 | 50.453 | 26.017 | 1.00 | 27.76 C |
| ATOM | 1596 | OG1 | THR | A | 376 | −72.273 | 51.265 | 26.669 | 1.00 | 32.71 O |
| ATOM | 1597 | N | ILE | A | 377 | −74.366 | 52.510 | 23.044 | 1.00 | 23.15 N |
| ATOM | 1598 | CA | ILE | A | 377 | −75.373 | 52.768 | 22.047 | 1.00 | 22.26 C |
| ATOM | 1599 | C | ILR | A | 377 | −74.935 | 52.286 | 20.662 | 1.00 | 21.93 C |
| ATOM | 1600 | O | ILE | A | 377 | −75.688 | 51.607 | 19.964 | 1.00 | 22.09 O |
| ATOM | 1601 | CB | ILE | A | 377 | −75.676 | 54.280 | 21.954 | 1.00 | 23.90 C |
| ATOM | 1602 | CG1 | ILE | A | 377 | −76.197 | 54.815 | 23.307 | 1.00 | 24.70 C |
| ATOM | 1603 | CG2 | ILE | A | 377 | −76.692 | 54.543 | 20.864 | 1.00 | 25.87 C |
| ATOM | 1604 | CD1 | ILE | A | 377 | −76.264 | 56.331 | 23.373 | 1.00 | 26.10 C |
| ATOM | 1605 | N | LEU | A | 378 | −73.712 | 52.619 | 20.281 | 1.00 | 22.56 N |
| ATOM | 1606 | CA | LEU | A | 378 | −73.210 | 52.194 | 19.002 | 1.00 | 24.21 C |
| ATOM | 1607 | C | LEU | A | 378 | −73.055 | 50.672 | 18.857 | 1.00 | 24.14 C |
| ATOM | 1608 | O | LEU | A | 378 | −73.281 | 50.136 | 17.796 | 1.00 | 22.82 O |
| ATOM | 1609 | CB | LEU | A | 378 | −71.914 | 52.893 | 18.683 | 1.00 | 29.61 C |
| ATOM | 1610 | CG | LEU | A | 378 | −72.061 | 54.354 | 18.311 | 1.00 | 29.55 C |

TABLE 47

| | | | | | | | | | | |
|---|---|---|---|---|---|---|---|---|---|---|
| ATOM | 1611 | CD1 | LEU | A | 378 | −70.680 | 55.054 | 18.063 | 1.00 | 32.08 C |
| ATOM | 1612 | CD2 | LEU | A | 378 | −72.946 | 54.465 | 17.087 | 1.00 | 32.66 C |
| ATOM | 1613 | N | ARG | A | 379 | −72.646 | 49.984 | 19.907 | 1.00 | 25.21 N |
| ATOM | 1614 | CA | ARG | A | 379 | −72.591 | 48.484 | 19.883 | 1.00 | 25.30 C |
| ATOM | 1615 | C | ARG | A | 379 | −74.007 | 47.901 | 19.699 | 1.00 | 26.76 C |
| ATOM | 1616 | O | ARG | A | 379 | −74.195 | 46.888 | 18.960 | 1.00 | 27.40 O |
| ATOM | 1617 | CB | ARG | A | 379 | −71.877 | 47.941 | 21.131 | 1.00 | 27.61 C |
| ATOM | 1618 | CG | ARG | A | 379 | −70.377 | 48.349 | 21.083 | 1.00 | 27.10 C |

TABLE 47-continued

| ATOM | 1619 | CD  | ARG | A | 379 | −69.395 | 47.763 | 22.099 | 1.00 | 33.04 | C   |
|------|------|-----|-----|---|-----|---------|--------|--------|------|-------|-----|
| ATOM | 1620 | NE  | ARG | A | 379 | −69.356 | 48.394 | 23.346 | 1.00 | 35.36 | N   |
| ATOM | 1621 | CZ  | ARG | A | 379 | −68.411 | 49.150 | 23.920 | 1.00 | 32.49 | C   |
| ATOM | 1622 | NH1 | ARG | A | 379 | −67.193 | 49.476 | 23.463 | 1.00 | 34.96 | N1+ |
| ATOM | 1623 | NH2 | ARG | A | 379 | −68.777 | 49.617 | 25.060 | 1.00 | 32.64 | N   |
| ATOM | 1624 | N   | ALA | A | 380 | −74.977 | 48.532 | 20.352 | 1.00 | 24.60 | N   |
| ATOM | 1625 | CA  | ALA | A | 380 | −76.383 | 48.132 | 20.183 | 1.00 | 23.29 | C   |
| ATOM | 1626 | C   | ALA | A | 380 | −76.880 | 48.407 | 18.790 | 1.00 | 24.65 | C   |
| ATOM | 1627 | O   | ALA | A | 380 | −77.542 | 47.537 | 13.223 | 1.00 | 24.36 | O   |
| ATOM | 1628 | CB  | ALA | A | 380 | −77.269 | 48.757 | 21.197 | 1.00 | 22.00 | C   |
| ATOM | 1629 | N   | LEU | A | 381 | −76.558 | 49.571 | 18.248 | 1.00 | 23.87 | N   |
| ATOM | 1630 | CA  | LEU | A | 381 | −76.915 | 49.888 | 16.866 | 1.00 | 25.43 | C   |
| ATOM | 1631 | C   | LEU | A | 381 | −76.324 | 48.885 | 15.883 | 1.00 | 28.15 | C   |
| ATOM | 1632 | O   | LEU | A | 381 | −76.995 | 48.413 | 14.977 | 1.00 | 27.26 | O   |
| ATOM | 1633 | CB  | LEU | A | 381 | −76.481 | 51.294 | 16.512 | 1.00 | 26.61 | C   |
| ATOM | 1634 | CG  | LEU | A | 381 | −76.660 | 51.771 | 15.082 | 1.00 | 26.84 | C   |
| ATOM | 1635 | CD1 | LEU | A | 381 | −78.122 | 51.687 | 14.713 | 1.00 | 27.00 | C   |
| ATOM | 1636 | CD2 | LEU | A | 381 | −76.190 | 53.210 | 14.983 | 1.00 | 30.28 | C   |
| ATOM | 1637 | N   | GLU | A | 382 | −75.026 | 48.645 | 16.000 | 1.00 | 31.12 | N   |
| ATOM | 1638 | CA  | GLU | A | 382 | −74.364 | 47.669 | 15.133 | 1.00 | 30.35 | C   |
| ATOM | 1639 | C   | GLU | A | 382 | −75.028 | 46.289 | 15.191 | 1.00 | 29.03 | C   |
| ATOM | 1640 | O   | GLU | A | 382 | −75.232 | 45.669 | 14.160 | 1.00 | 31.24 | O   |
| ATOM | 1641 | CB  | GLU | A | 382 | −72.851 | 47.583 | 15.464 | 1.00 | 33.36 | C   |
| ATOM | 1642 | CG  | GLU | A | 382 | −72.126 | 46.427 | 14.819 | 1.00 | 39.35 | C   |
| ATOM | 1643 | CD  | GLU | A | 382 | −70.620 | 46.465 | 15.101 | 1.00 | 45.14 | C   |
| ATOM | 1644 | OE1 | GLU | A | 382 | −70.168 | 46.336 | 16.287 | 1.00 | 48.21 | O   |
| ATOM | 1645 | OE2 | GLU | A | 382 | −69.906 | 46.647 | 14.114 | 1.00 | 56.89 | O1− |

TABLE 48

| ATOM | 1646 | N   | PHE | A | 383 | −75.364 | 45.835 | 16.378 | 1.00 | 27.04 | N |
| ATOM | 1647 | CA  | PHE | A | 383 | −76.008 | 44.560 | 16.565 | 1.00 | 31.77 | C |
| ATOM | 1648 | C   | PHE | A | 383 | −77.452 | 44.538 | 16.012 | 1.00 | 32.97 | C |
| ATOM | 1649 | O   | PHE | A | 383 | −77.863 | 43.594 | 15.328 | 1.00 | 27.70 | O |
| ATOM | 1650 | CB  | PHE | A | 383 | −76.078 | 44.218 | 18.036 | 1.00 | 31.21 | C |
| ATOM | 1651 | CG  | PHE | A | 383 | −77.033 | 43.106 | 18.310 | 1.00 | 39.96 | C |
| ATOM | 1652 | CD1 | PHE | A | 383 | −76.664 | 41.781 | 18.031 | 1.00 | 40.89 | C |
| ATOM | 1653 | CD2 | PHE | A | 383 | −78.325 | 43.376 | 18.788 | 1.00 | 39.47 | C |
| ATOM | 1654 | CE1 | PHE | A | 383 | −77.579 | 40.758 | 18.251 | 1.00 | 46.44 | C |
| ATOM | 1655 | CE2 | PHE | A | 388 | −79.237 | 42.360 | 18.993 | 1.00 | 41.69 | C |
| ATOM | 1656 | CZ  | PHE | A | 383 | −78.857 | 41.051 | 18.736 | 1.00 | 46.86 | C |
| ATOM | 1657 | N   | HIS | A | 384 | −78.188 | 45.609 | 16.317 | 1.00 | 30.88 | N |
| ATOM | 1658 | CA  | HIS | A | 384 | −79.553 | 45.814 | 15.842 | 1.00 | 32.42 | C |
| ATOM | 1659 | C   | HIS | A | 384 | −79.672 | 45.825 | 14.321 | 1.00 | 29.76 | C |
| ATOM | 1660 | O   | HIS | A | 384 | −80.626 | 45.246 | 13.809 | 1.00 | 34.18 | O |
| ATOM | 1661 | CB  | HIS | A | 384 | −80.151 | 47.089 | 16.400 | 1.00 | 31.32 | C |
| ATOM | 1662 | CG  | HIS | A | 384 | −81.590 | 47.247 | 16.086 | 1.00 | 34.28 | C |
| ATOM | 1663 | CD2 | HIS | A | 384 | −82.219 | 48.045 | 15.183 | 1.00 | 33.92 | C |
| ATOM | 1664 | ND1 | HIS | A | 384 | −82.575 | 46.527 | 16.726 | 1.00 | 32.34 | N |
| ATOM | 1665 | CE1 | HIS | A | 384 | −83.756 | 46.871 | 16.224 | 1.00 | 33.77 | C |
| ATOM | 1666 | NE2 | HIS | A | 384 | −83.566 | 47.785 | 15.286 | 1.00 | 34.10 | N |
| ATOM | 1667 | N   | LEU | A | 385 | −78.753 | 46.488 | 13.635 | 1.00 | 27.91 | N |
| ATOM | 1668 | CA  | LEU | A | 385 | −78.803 | 46.635 | 12.186 | 1.00 | 31.02 | C |
| ATOM | 1669 | C   | LEU | A | 385 | −78.566 | 45.309 | 11.473 | 1.00 | 40.36 | C |
| ATOM | 1670 | O   | LEU | A | 385 | −79.283 | 44.953 | 10.517 | 1.00 | 39.50 | O |
| ATOM | 1671 | CB  | LEU | A | 385 | −77.757 | 47.604 | 11.709 | 1.00 | 30.41 | C |
| ATOM | 1672 | CG  | LEU | A | 385 | −78.016 | 49.104 | 11.921 | 1.00 | 31.38 | C |
| ATOM | 1673 | CD1 | LEU | A | 385 | −76.734 | 49.827 | 11.543 | 1.00 | 30.60 | C |
| ATOM | 1674 | CD2 | LEU | A | 385 | −79.200 | 49.639 | 11.091 | 1.00 | 29.78 | C |
| ATOM | 1675 | N   | GLN | A | 386 | −77.542 | 44.606 | 11.937 | 1.00 | 43.61 | N |
| ATOM | 1676 | CA  | GLN | A | 386 | −77.183 | 43.282 | 11.408 | 1.00 | 55.03 | C |
| ATOM | 1677 | C   | GLN | A | 386 | −78.395 | 42.374 | 11.603 | 1.00 | 45.90 | C |
| ATOM | 1678 | O   | GLN | A | 386 | −78.865 | 41.754 | 10.639 | 1.00 | 52.92 | O |
| ATOM | 1679 | CB  | GLN | A | 386 | −75.871 | 42.744 | 12.079 | 1.00 | 54.20 | C |
| ATOM | 1680 | CG  | GLN | A | 386 | −75.213 | 41.553 | 11.390 | 1.00 | 63.42 | C |

TABLE 49

| ATOM | 1681 | CD  | GLN | A | 386 | −76.038 | 40.284 | 11.555 | 1.00 | 70.69 | C |
| ATOM | 1682 | NE2 | GLN | A | 386 | −76.317 | 39.594 | 10.448 | 1.00 | 69.88 | N |
| ATOM | 1683 | OE1 | GLN | A | 386 | −76.462 | 39.960 | 12.665 | 1.00 | 76.95 | O |
| ATOM | 1684 | N   | ALA | A | 387 | −78.952 | 42.373 | 12.809 | 1.00 | 42.99 | N |
| ATOM | 1688 | CA  | ALA | A | 337 | −80.151 | 41.569 | 13.122 | 1.00 | 44.81 | C |
| ATOM | 1686 | C   | ALA | A | 387 | −81.277 | 41.916 | 12.162 | 1.00 | 47.01 | C |
| ATOM | 1687 | O   | ALA | A | 387 | −81.801 | 41.074 | 11.436 | 1.00 | 54.11 | O |

TABLE 49-continued

| ATOM | 1688 | CB  | ALA | A | 387 | −80.602 | 41.803 | 14.570 | 1.00 | 41.95 | C   |
| ATOM | 1689 | N   | ASN | A | 388 | −81.582 | 43.197 | 12.114 | 1.00 | 48.33 | N   |
| ATOM | 1690 | CA  | ASN | A | 388 | −82.710 | 43.718 | 11.376 | 1.00 | 44.38 | C   |
| ATOM | 1691 | C   | ASN | A | 388 | −82.557 | 43.793 | 9.805  | 1.00 | 40.56 | C   |
| ATOM | 1692 | O   | ASN | A | 388 | −83.560 | 43.707 | 9.103  | 1.00 | 44.07 | O   |
| ATOM | 1693 | CB  | ASN | A | 388 | −83.049 | 45.100 | 12.025 | 1.00 | 46.83 | C   |
| ATOM | 1694 | GG  | ASN | A | 388 | −84.420 | 45.668 | 11.600 | 1.00 | 56.78 | C   |
| ATOM | 1695 | NP2 | ASN | A | 388 | −84.589 | 47.009 | 11.776 | 1.00 | 43.52 | N   |
| ATOM | 1696 | OD1 | ASN | A | 388 | −85.323 | 44.917 | 11.127 | 1.00 | 50.08 | O   |
| ATOM | 1697 | N   | HIS | A | 389 | −81.342 | 43.998 | 9.273  | 1.00 | 36.28 | N   |
| ATOM | 1698 | CA  | HIS | A | 389 | −81.080 | 44.195 | 7.826  | 1.00 | 36.61 | C   |
| ATOM | 1699 | C   | HIS | A | 389 | −79.933 | 43.232 | 7.438  | 1.00 | 43.24 | C   |
| ATOM | 1700 | O   | HIS | A | 389 | −78.866 | 43.693 | 7.037  | 1.00 | 39.40 | O   |
| ATOM | 1701 | CB  | HIS | A | 389 | −80.584 | 45.637 | 7.477  | 1.00 | 41.48 | C   |
| ATOM | 1702 | CG  | HIS | A | 389 | −81.486 | 46.758 | 7.920  | 1.00 | 42.12 | C   |
| ATOM | 1703 | CD2 | HIS | A | 389 | −81.666 | 47.330 | 9.132  | 1.00 | 41.68 | C   |
| ATOM | 1704 | ND1 | HIS | A | 389 | −82.335 | 47.415 | 7.061  | 1.00 | 49.03 | N   |
| ATOM | 1705 | CE1 | HIS | A | 389 | −82.991 | 48.356 | 7.722  | 1.00 | 52.40 | C   |
| ATOM | 1706 | NE2 | HIS | A | 389 | −82.625 | 48.305 | 8.989  | 1.00 | 43.14 | N   |
| ATOM | 1707 | N   | PRO | A | 390 | −80.128 | 41.887 | 7.549  | 1.00 | 49.76 | N   |
| ATOM | 1708 | CA  | PRO | A | 390 | −78.923 | 41.035 | 7.366  | 1.00 | 50.61 | C   |
| ATOM | 1709 | C   | PRO | A | 390 | −78.281 | 41.183 | 8.965  | 1.00 | 49.25 | C   |
| ATOM | 1710 | O   | PRO | A | 390 | −77.064 | 41.210 | 5.828  | 1.00 | 50.40 | O   |
| ATOM | 1711 | CB  | PRO | A | 380 | −79.415 | 39.588 | 7.674  | 1.00 | 49.35 | C   |
| ATOM | 1712 | CG  | PRO | A | 390 | −80.861 | 39.666 | 7.893  | 1.00 | 51.85 | C   |
| ATOM | 1713 | CD  | PRO | A | 390 | −81.274 | 41.114 | 8.077  | 1.00 | 53.39 | C   |
| ATOM | 1714 | N   | ASP | A | 391 | −79.098 | 41.436 | 4.965  | 1.00 | 52.37 | N   |
| ATOM | 1715 | CA  | ASP | A | 391 | −78.592 | 41.599 | 3.623  | 1.00 | 57.91 | C   |

TABLE 50

| ATOM | 1716 | C   | ASP | A | 391 | −77.830 | 42.908 | 3.369 | 1.00 | 61.02  | C   |
| ATOM | 1717 | O   | ASP | A | 391 | −77.303 | 43.061 | 2.256 | 1.00 | 53.48  | O   |
| ATOM | 1718 | CB  | ASP | A | 391 | −79.753 | 41.496 | 2.629 | 1.00 | 60.11  | C   |
| ATOM | 1719 | CG  | ASP | A | 391 | −80.583 | 40.253 | 2.840 | 1.00 | 60.88  | C   |
| ATOM | 1720 | OD1 | ASP | A | 391 | −80.012 | 39.180 | 3.120 | 1.00 | 65.09  | O   |
| ATOM | 1721 | OD2 | ASP | A | 391 | −81.813 | 40.362 | 2.749 | 1.00 | 69.00  | O1− |
| ATOM | 1722 | N   | ALA | A | 392 | −77.767 | 43.834 | 4.344 | 1.00 | 53.30  | N   |
| ATOM | 1723 | CA  | ALA | A | 392 | −77.197 | 45.184 | 4.106 | 1.00 | 54.52  | C   |
| ATOM | 1724 | C   | ALA | A | 392 | −75.796 | 45.310 | 4.721 | 1.00 | 58.71  | C   |
| ATOM | 1725 | O   | ALA | A | 392 | −75.588 | 45.671 | 5.930 | 1.00 | 48.19  | O   |
| ATOM | 1726 | CB  | ALA | A | 392 | −78.142 | 46.262 | 4.642 | 1.00 | 54.46  | C   |
| ATOM | 1727 | N   | GLN | A | 393 | −74.808 | 44.949 | 3.918 | 1.00 | 60.15  | N   |
| ATOM | 1728 | CA  | GLN | A | 393 | −73.426 | 45.011 | 4.422 | 1.00 | 71.87  | C   |
| ATOM | 1729 | C   | GLN | A | 393 | −73.008 | 46.475 | 4.326 | 1.00 | 69.85  | C   |
| ATOM | 1730 | O   | GLN | A | 393 | −73.469 | 47.230 | 3.442 | 1.00 | 72.69  | O   |
| ATOM | 1731 | CB  | GLN | A | 393 | −72.441 | 44.055 | 3.699 | 1.00 | 73.80  | C   |
| ATOM | 1732 | CG  | GLN | A | 393 | −71.089 | 43.858 | 4.414 | 1.00 | 76.08  | C   |
| ATOM | 1733 | CD  | GLN | A | 393 | −71.200 | 43.125 | 5.752 | 1.00 | 81.05  | C   |
| ATOM | 1734 | NE2 | GLN | A | 393 | −70.926 | 43.833 | 6.841 | 1.00 | 74.51  | N   |
| ATOM | 1735 | OE1 | GLN | A | 393 | −71.518 | 41.934 | 5.796 | 1.00 | 87.90  | O   |
| ATOM | 1736 | N   | TYR | A | 394 | −72.163 | 46.868 | 5.266 | 1.00 | 60.68  | N   |
| ATOM | 1737 | CA  | TYR | A | 394 | −71.626 | 48.201 | 5.328 | 1.00 | 58.14  | C   |
| ATOM | 1738 | C   | TYR | A | 394 | −72.698 | 49.233 | 5.756 | 1.00 | 46.03  | C   |
| ATOM | 1739 | O   | TYR | A | 394 | −72.455 | 50.436 | 5.590 | 1.00 | 43.17  | O   |
| ATOM | 1740 | CB  | TYR | A | 394 | −70.965 | 48.628 | 3.970 | 1.00 | 69.18  | C   |
| ATOM | 1741 | CG  | TYR | A | 394 | −69.910 | 47.684 | 3.402 | 1.00 | 77.03  | C   |
| ATOM | 1742 | CD1 | TYR | A | 394 | −70.267 | 46.549 | 2.666 | 1.00 | 82.29  | C   |
| ATOM | 1743 | CD2 | TYR | A | 394 | −68.551 | 47.954 | 3.564 | 1.00 | 87.23  | C   |
| ATOM | 1744 | CE1 | TYR | A | 394 | −69.314 | 45.691 | 2.145 | 1.00 | 84.59  | C   |
| ATOM | 1745 | CE2 | TYR | A | 394 | −67.585 | 47.104 | 3.037 | 1.00 | 94.30  | C   |
| ATOM | 1746 | CZ  | TYR | A | 394 | −67.977 | 45.975 | 2.329 | 1.00 | 92.67  | C   |
| ATOM | 1747 | OH  | TYR | A | 394 | −67.032 | 45.128 | 1.807 | 1.00 | 102.03 | O   |
| ATOM | 1748 | N   | LEU | A | 395 | −73.857 | 48.798 | 6.282 | 1.00 | 38.11  | N   |
| ATOM | 1749 | CA  | LEU | A | 395 | −74.900 | 49.738 | 6.645 | 1.00 | 35.94  | C   |
| ATOM | 1750 | C   | LEU | A | 395 | −74.387 | 50.554 | 7.861 | 1.00 | 31.05  | C   |

TABLE 51

| ATOM | 1751 | O   | LEU | A | 395 | −74.544 | 51.750 | 7.892 | 1.00 | 29.03 | O |
| ATOM | 1752 | CB  | LEU | A | 395 | −76.267 | 49.038 | 6.865 | 1.00 | 35.47 | C |
| ATOM | 1753 | CG  | LEU | A | 395 | −77.471 | 49.905 | 7.289 | 1.00 | 35.99 | C |
| ATOM | 1754 | CD1 | LEU | A | 395 | −77.721 | 51.043 | 6.300 | 1.00 | 38.61 | C |
| ATOM | 1755 | CD2 | LEU | A | 395 | −78.733 | 49.066 | 7.407 | 1.00 | 33.86 | C |
| ATOM | 1756 | N   | PHE | A | 396 | −73.696 | 49.909 | 8.790 | 1.00 | 29.46 | N |

TABLE 51-continued

| ATOM | 1757 | CA | PHE | A | 396 | −73.213 | 50.578 | 10.005 | 1.00 | 30.43 | C |
|---|---|---|---|---|---|---|---|---|---|---|---|
| ATOM | 1758 | C | PHE | A | 396 | −72.160 | 51.670 | 9.689 | 1.00 | 34.51 | C |
| ATOM | 1759 | O | PHE | A | 396 | −72.368 | 52.815 | 10.073 | 1.00 | 32.82 | O |
| ATOM | 1760 | CB | PHE | A | 396 | −72.728 | 49.564 | 10.982 | 1.00 | 30.07 | C |
| ATOM | 1761 | CG | PHE | A | 396 | −72.214 | 50.125 | 12.233 | 1.00 | 29.62 | C |
| ATOM | 1762 | CD1 | PHE | A | 396 | −73.070 | 50.683 | 13.154 | 1.00 | 29.80 | C |
| ATOM | 1763 | CD2 | PHE | A | 396 | −70.864 | 50.093 | 12.502 | 1.00 | 29.69 | C |
| ATOM | 1764 | CE1 | PHE | A | 396 | −72.568 | 51.247 | 14.335 | 1.00 | 31.86 | C |
| ATOM | 1765 | CE2 | PHE | A | 396 | −70.362 | 50.634 | 13.683 | 1.00 | 33.35 | C |
| ATOM | 1766 | CZ | PHE | A | 396 | −71.226 | 51.185 | 14.621 | 1.00 | 31.57 | C |
| ATOM | 1767 | N | PRO | A | 397 | −71.115 | 51.359 | 8.883 | 1.00 | 36.63 | N |
| ATOM | 1768 | CA | PRO | A | 397 | −70.219 | 52.470 | 8.497 | 1.00 | 34.78 | C |
| ATOM | 1769 | C | PRO | A | 397 | −70.848 | 53.557 | 7.663 | 1.00 | 28.84 | C |
| ATOM | 1770 | O | PRO | A | 397 | −70.445 | 54.675 | 7.798 | 1.00 | 30.67 | O |
| ATOM | 1771 | CB | PRO | A | 397 | −69.037 | 51.796 | 7.723 | 1.00 | 39.59 | C |
| ATOM | 1772 | CG | PRO | A | 397 | −69.530 | 50.383 | 7.508 | 1.00 | 41.58 | C |
| ATOM | 1773 | CD | PRO | A | 397 | −70.510 | 50.042 | 8.589 | 1.00 | 35.62 | C |
| ATOM | 1774 | N | LYS | A | 398 | −71.780 | 53.250 | 6.780 | 1.00 | 30.76 | N |
| ATOM | 1775 | CA | LYS | A | 398 | −72.474 | 54.289 | 6.014 | 1.00 | 34.97 | C |
| ATOM | 1776 | C | LYS | A | 398 | −73.254 | 55.233 | 6.938 | 1.00 | 33.02 | C |
| ATOM | 1777 | O | LYS | A | 398 | −73.292 | 56.431 | 6.727 | 1.00 | 32.65 | O |
| ATOM | 1778 | CB | LYS | A | 398 | −73.473 | 53.685 | 5.051 | 1.00 | 37.65 | C |
| ATOM | 1779 | CG | LYS | A | 398 | −72.873 | 53.014 | 3.844 | 1.00 | 40.10 | C |
| ATOM | 1780 | CD | LYS | A | 398 | −73.997 | 52.351 | 3.075 | 1.00 | 46.51 | C |
| ATOM | 1781 | CE | LYS | A | 398 | −73.532 | 51.798 | 1.755 | 1.00 | 53.01 | C |
| ATOM | 1782 | NZ | LYS | A | 398 | −74.562 | 50.826 | 1.280 | 1.00 | 56.91 | N1+ |
| ATOM | 1783 | N | LEU | A | 399 | −73.839 | 54.668 | 7.971 | 1.00 | 32.88 | N |
| ATOM | 1784 | CA | LEU | A | 399 | −74.566 | 55.457 | 8.954 | 1.00 | 37.65 | C |
| ATOM | 1785 | C | LEU | A | 399 | −73.625 | 56.305 | 9.828 | 1.00 | 36.37 | C |

TABLE 52

| ATOM | 1786 | O | LEU | A | 399 | −73.989 | 57.454 | 10.164 | 1.00 | 32.54 | O |
|---|---|---|---|---|---|---|---|---|---|---|---|
| ATOM | 1787 | CB | LEU | A | 399 | −75.462 | 54.561 | 9.839 | 1.00 | 40.16 | C |
| ATOM | 1788 | CG | LEU | A | 399 | −76.932 | 54.332 | 9.481 | 1.00 | 40.74 | C |
| ATOM | 1789 | CD1 | LEU | A | 399 | −77.573 | 53.483 | 10.567 | 1.00 | 40.82 | C |
| ATOM | 1790 | CD2 | LEU | A | 399 | −77.705 | 55.644 | 9.381 | 1.00 | 40.84 | C |
| ATOM | 1791 | N | LEU | A | 400 | −72.441 | 55.757 | 10.166 | 1.00 | 35.29 | N |
| ATOM | 1792 | CA | LEU | A | 400 | −71.371 | 56.528 | 10.810 | 1.00 | 33.69 | C |
| ATOM | 1793 | C | LEU | A | 400 | −70.948 | 57.732 | 9.956 | 1.00 | 32.60 | C |
| ATOM | 1794 | O | LEU | A | 400 | −70.721 | 58.820 | 10.496 | 1.00 | 29.48 | O |
| ATOM | 1795 | CB | LEU | A | 400 | −70.166 | 55.626 | 11.146 | 1.00 | 38.44 | C |
| ATOM | 1796 | CG | LEU | A | 400 | −70.322 | 54.633 | 12.320 | 1.00 | 39.28 | C |
| ATOM | 1797 | CD1 | LEU | A | 400 | −68.963 | 54.045 | 12.677 | 1.00 | 41.77 | C |
| ATOM | 1798 | CD2 | LEU | A | 400 | −70.903 | 55.269 | 13.561 | 1.00 | 40.93 | C |
| ATOM | 1799 | N | GLN | A | 401 | −70.891 | 57.565 | 8.634 | 1.00 | 28.99 | N |
| ATOM | 1800 | CA | GLN | A | 401 | −70.632 | 58.683 | 7.756 | 1.00 | 28.21 | C |
| ATOM | 1801 | C | GLN | A | 401 | −71.802 | 59.721 | 7.742 | 1.00 | 28.34 | C |
| ATOM | 1802 | O | GLN | A | 401 | −71.539 | 60.949 | 7.658 | 1.00 | 29.06 | O |
| ATOM | 1803 | CB | GLN | A | 401 | −70.324 | 58.183 | 6.329 | 1.00 | 33.09 | C |
| ATOM | 1804 | CG | GLN | A | 401 | −69.562 | 59.231 | 5.286 | 1.00 | 33.74 | C |
| ATOM | 1805 | CD | GLN | A | 401 | −68.758 | 60.048 | 5.688 | 1.00 | 36.66 | C |
| ATOM | 1806 | NE2 | GLN | A | 401 | −68.888 | 61.388 | 5.659 | 1.00 | 31.14 | N |
| ATOM | 1807 | OE1 | GLN | A | 401 | −67.733 | 59.488 | 6.068 | 1.00 | 39.63 | O |
| ATOM | 1808 | N | LYS | A | 402 | −73.070 | 59.264 | 7.797 | 1.00 | 25.96 | N |
| ATOM | 1809 | CA | LYS | A | 402 | −74.209 | 60.199 | 7.909 | 1.00 | 25.95 | C |
| ATOM | 1810 | C | LYS | A | 402 | −74.077 | 61.033 | 9.154 | 1.00 | 23.94 | C |
| ATOM | 1811 | O | LYS | A | 402 | −74.447 | 62.187 | 9.128 | 1.00 | 26.38 | O |
| ATOM | 1812 | CB | LYS | A | 402 | −75.552 | 59.490 | 7.934 | 1.00 | 28.50 | C |
| ATOM | 1813 | CG | LYS | A | 402 | −75.879 | 58.714 | 6.657 | 1.00 | 26.31 | C |
| ATOM | 1814 | CD | LYS | A | 402 | −75.772 | 59.517 | 5.388 | 1.00 | 28.54 | C |
| ATOM | 1815 | CE | LYS | A | 402 | −76.303 | 58.718 | 4.190 | 1.00 | 27.64 | C |
| ATOM | 1816 | NZ | LYS | A | 402 | −76.102 | 59.461 | 2.930 | 1.00 | 29.00 | N1+ |
| ATOM | 1817 | N | MET | A | 403 | −73.544 | 60.488 | 10.232 | 1.00 | 23.90 | N |
| ATOM | 1818 | CA | MET | A | 403 | −73.350 | 61.299 | 11.454 | 1.00 | 30.10 | C |
| ATOM | 1819 | C | MET | A | 403 | −72.378 | 62.437 | 11.180 | 1.00 | 28.49 | C |
| ATOM | 1820 | O | MET | A | 403 | −72.597 | 63.543 | 11.639 | 1.00 | 28.00 | O |

TABLE 53

| ATOM | 1821 | CB | MET | A | 403 | −72.844 | 60.472 | 12.638 | 1.00 | 28.20 | C |
|---|---|---|---|---|---|---|---|---|---|---|---|
| ATOM | 1822 | CG | MET | A | 403 | −73.860 | 59.483 | 13.161 | 1.00 | 31.77 | C |
| ATOM | 1823 | SD | MET | A | 403 | −73.214 | 58.354 | 14.434 | 1.00 | 35.49 | S |
| ATOM | 1824 | CE | MET | A | 403 | −73.028 | 59.555 | 15.771 | 1.00 | 31.96 | C |
| ATOM | 1825 | N | ALA | A | 404 | −71.301 | 62.157 | 10.453 | 1.00 | 27.71 | N |

TABLE 53-continued

| ATOM | 1826 | CA | ALA | A | 404 | −70.361 | 63.232 | 10.058 | 1.00 | 27.46 | C |
| ATOM | 1827 | C | ALA | A | 404 | −71.032 | 64.242 | 9.088 | 1.00 | 25.78 | C |
| ATOM | 1828 | O | ALA | A | 404 | −70.881 | 65.480 | 9.243 | 1.00 | 24.01 | O |
| ATOM | 1829 | CB | AAA | A | 404 | −69.091 | 62.624 | 9.437 | 1.00 | 28.74 | C |
| ATOM | 1830 | N | ASP | A | 405 | −71.760 | 63.728 | 8.080 | 1.00 | 27.41 | N |
| ATOM | 1831 | CA | ASP | A | 405 | −72.509 | 64.591 | 7.159 | 1.00 | 28.82 | C |
| ATOM | 1832 | C | ASP | A | 405 | −73.501 | 65.493 | 7.913 | 1.00 | 27.63 | C |
| ATOM | 1833 | O | ASP | A | 405 | −73.618 | 66.675 | 7.576 | 1.00 | 23.81 | O |
| ATOM | 1834 | CB | ASP | A | 405 | −73.290 | 63.818 | 6.102 | 1.00 | 30.66 | C |
| ATOM | 1835 | CG | ASP | A | 405 | −72.432 | 62.877 | 5.308 | 1.00 | 34.80 | C |
| ATOM | 1836 | OD1 | ASP | A | 405 | −71.214 | 63.111 | 5.266 | 1.00 | 35.46 | O |
| ATOM | 1837 | OD2 | ASP | A | 405 | −72.998 | 61.904 | 4.729 | 1.00 | 36.84 | O1− |
| ATOM | 1838 | N | LEU | A | 406 | −74.197 | 64.936 | 8.913 | 1.00 | 24.47 | N |
| ATOM | 1839 | CA | LEU | A | 406 | −75.100 | 65.752 | 9.726 | 1.00 | 26.31 | C |
| ATOM | 1840 | C | LEU | A | 406 | −74.418 | 66.918 | 10.481 | 1.00 | 27.81 | C |
| ATOM | 1841 | O | LEU | A | 406 | −74.951 | 68.060 | 10.530 | 1.00 | 25.13 | O |
| ATOM | 1842 | CB | LEU | A | 406 | −75.882 | 64.991 | 10.737 | 1.00 | 26.02 | C |
| ATOM | 1843 | CG | LEU | A | 406 | −77.054 | 64.187 | 10.067 | 1.00 | 25.97 | C |
| ATOM | 1844 | CD1 | LEU | A | 406 | −77.586 | 63.066 | 10.943 | 1.00 | 27.40 | C |
| ATOM | 1845 | CD2 | LEU | A | 406 | −78.173 | 65.203 | 9.749 | 1.00 | 28.95 | C |
| ATOM | 1846 | N | ARG | A | 407 | −73.284 | 66.625 | 11.096 | 1.00 | 28.99 | N |
| ATOM | 1847 | CA | ARG | A | 407 | −72.489 | 67.682 | 11.750 | 1.00 | 31.04 | C |
| ATOM | 1848 | C | ARG | A | 407 | −72.159 | 68.857 | 10.827 | 1.00 | 30.99 | C |
| ATOM | 1849 | O | ARG | A | 407 | −72.317 | 70.029 | 11.207 | 1.00 | 27.68 | O |
| ATOM | 1850 | CB | ARG | A | 407 | −71.190 | 67.134 | 12.303 | 1.00 | 34.80 | C |
| ATOM | 1851 | CG | ARG | A | 407 | −70.461 | 68.197 | 13.129 | 1.00 | 43.33 | C |
| ATOM | 1852 | CD | ARG | A | 407 | −69.122 | 67.691 | 13.542 | 1.00 | 51.25 | C |
| ATOM | 1853 | NE | ARG | A | 407 | −69.321 | 66.561 | 14.439 | 1.00 | 57.12 | N |
| ATOM | 1854 | CZ | ARG | A | 407 | −68.864 | 66.458 | 15.682 | 1.00 | 59.61 | C |
| ATOM | 1855 | NH1 | ARG | A | 407 | −68.124 | 67.403 | 16.249 | 1.00 | 64.83 | N1− |

TABLE 54

| ATOM | 1856 | NH2 | ARG | A | 407 | −69.141 | 65.347 | 16.356 | 1.00 | 66.29 | N |
| ATOM | 1857 | N | GLN | A | 408 | −71.786 | 68.527 | 9.588 | 1.00 | 31.95 | N |
| ATOM | 1858 | CA | GLN | A | 408 | −71.521 | 69.528 | 8.578 | 1.00 | 33.21 | C |
| ATOM | 1859 | C | GLN | A | 408 | −72.785 | 70.287 | 8.165 | 1.00 | 30.84 | C |
| ATOM | 1860 | O | GLN | A | 408 | −72.720 | 71.491 | 8.021 | 1.00 | 28.93 | O |
| ATOM | 1862 | CB | GLN | A | 408 | −70.844 | 68.919 | 7.329 | 1.00 | 31.28 | C |
| ATOM | 1862 | CG | GLN | A | 408 | −70.323 | 69.898 | 6.269 | 1.00 | 39.38 | C |
| ATOM | 1863 | CD | GLN | A | 408 | −69.468 | 71.054 | 6.819 | 1.00 | 48.21 | C |
| ATOM | 1864 | NE2 | GLN | A | 408 | −69.571 | 72.230 | 6.176 | 1.00 | 52.23 | N |
| ATOM | 1865 | OE1 | GLN | A | 408 | −68.721 | 70.902 | 7.792 | 1.00 | 54.34 | O |
| ATOM | 1866 | N | LEU | A | 409 | −73.869 | 69.565 | 7.889 | 1.00 | 26.13 | N |
| ATOM | 1867 | CA | LEU | A | 409 | −75.142 | 70.190 | 7.625 | 1.00 | 27.05 | C |
| ATOM | 1868 | C | LEU | A | 409 | −75.568 | 71.182 | 8.693 | 1.00 | 24.72 | C |
| ATOM | 1669 | O | LEU | A | 409 | −76.069 | 72.279 | 8.359 | 1.00 | 24.70 | O |
| ATOM | 1870 | CB | LEU | A | 409 | −76.246 | 69.138 | 7.451 | 1.00 | 29.77 | C |
| ATOM | 1871 | CG | LEU | A | 409 | −77.575 | 69.537 | 6.833 | 1.00 | 29.39 | C |
| ATOM | 1872 | CD1 | LEU | A | 409 | −77.431 | 69.753 | 5.317 | 1.00 | 31.31 | C |
| ATOM | 1873 | CD2 | LEU | A | 409 | −78.652 | 68.478 | 7.150 | 1.00 | 30.11 | C |
| ATOM | 1874 | N | VAL | A | 410 | −75.394 | 70.812 | 9.964 | 1.00 | 22.17 | N |
| ATOM | 1875 | CA | VAL | A | 410 | −75.784 | 71.666 | 11.009 | 1.00 | 22.63 | C |
| ATOM | 1876 | C | VAL | A | 410 | −74.872 | 72.886 | 11.176 | 1.00 | 29.03 | C |
| ATOM | 1877 | O | VAL | A | 410 | −75.337 | 74.043 | 11.498 | 1.00 | 24.83 | O |
| ATOM | 1878 | CB | VAL | A | 410 | −75.967 | 70.878 | 12.348 | 1.00 | 24.73 | C |
| ATOM | 1879 | CG1 | VAL | A | 410 | −76.122 | 71.823 | 13.542 | 1.00 | 25.10 | C |
| ATOM | 1880 | CG2 | VAL | A | 410 | −77.207 | 69.957 | 12.230 | 1.00 | 23.96 | C |
| ATOM | 1881 | N | THR | A | 411 | −73.577 | 72.668 | 10.993 | 1.00 | 28.16 | N |
| ATOM | 1882 | CA | THR | A | 411 | −72.654 | 73.739 | 10.950 | 1.00 | 29.59 | C |
| ATOM | 1883 | C | THR | A | 411 | −73.014 | 74.791 | 9.875 | 1.00 | 27.22 | C |
| ATOM | 1884 | O | THR | A | 411 | −73.030 | 75.987 | 10.117 | 1.00 | 30.48 | O |
| ATOM | 1885 | CB | THR | A | 411 | −71.186 | 73.265 | 10.750 | 1.00 | 32.40 | C |
| ATOM | 1886 | CG2 | THR | A | 411 | −70.219 | 74.386 | 10.803 | 1.00 | 30.16 | C |
| ATOM | 1887 | OG1 | THR | A | 411 | −70.894 | 72.374 | 11.832 | 1.00 | 33.61 | O |
| ATOM | 1888 | N | GLU | A | 412 | −73.337 | 74.323 | 8.686 | 1.00 | 26.93 | N |
| ATOM | 1889 | CA | GLU | A | 412 | −73.772 | 75.236 | 7.631 | 1.00 | 30.29 | C |
| ATOM | 1890 | C | GLU | A | 412 | −75.121 | 75.933 | 8.006 | 1.00 | 31.12 | C |

TABLE 55

| ATOM | 1891 | O | GLU | A | 412 | −75.300 | 77.150 | 7.885 | 1.00 | 30.51 | O |
| ATOM | 1892 | CB | GLU | A | 412 | −73.861 | 74.455 | 6.317 | 1.00 | 33.75 | C |
| ATOM | 1893 | CG | GLU | A | 412 | −72.457 | 74.039 | 5.822 | 1.00 | 40.20 | C |
| ATOM | 1894 | CD | GLU | A | 412 | −72.465 | 73.001 | 4.698 | 1.00 | 47.08 | C |

TABLE 55-continued

| ATOM | 1895 | OE1 | GLU | A | 412 | −73.554 | 72.617 | 4.233 | 1.00 | 54.41 | O |
|---|---|---|---|---|---|---|---|---|---|---|---|
| ATOM | 1896 | OE2 | GLU | A | 412 | −71.365 | 72.546 | 4.285 | 1.00 | 49.65 | O1− |
| ATOM | 1897 | N | HIS | A | 413 | −76.047 | 75.148 | 8.528 | 1.00 | 29.49 | N |
| ATOM | 1898 | CA | HIS | A | 413 | −77.315 | 75.699 | 8.977 | 1.00 | 26.39 | C |
| ATOM | 1899 | C | HIS | A | 413 | −77.109 | 76.805 | 9.993 | 1.00 | 25.11 | C |
| ATOM | 1990 | O | HIS | A | 413 | −77.722 | 77.876 | 9.860 | 1.00 | 26.38 | O |
| ATOM | 1901 | CB | HIS | A | 413 | −78.188 | 74.580 | 9.560 | 1.00 | 23.12 | C |
| ATOM | 1902 | CG | HIS | A | 413 | −79.522 | 75.046 | 9.984 | 1.00 | 23.11 | C |
| ATOM | 1903 | CD2 | HIS | A | 413 | −80.026 | 75.273 | 11.221 | 1.00 | 21.55 | C |
| ATOM | 1904 | ND1 | HIS | A | 413 | −80.532 | 75.312 | 9.089 | 1.00 | 24.68 | N |
| ATOM | 1905 | CE1 | HIS | A | 413 | −81.586 | 75.745 | 9.763 | 1.00 | 26.14 | C |
| ATOM | 1906 | NE2 | HIS | A | 413 | −81.315 | 75.686 | 11.064 | 1.00 | 22.15 | N |
| ATOM | 1907 | N | ALA | A | 414 | −76.242 | 76.571 | 10.967 | 1.00 | 26.07 | N |
| ATOM | 1908 | CA | ALA | A | 414 | −76.002 | 77.519 | 12.049 | 1.00 | 28.84 | C |
| ATOM | 1909 | C | ALA | A | 414 | −75.500 | 78.868 | 11.514 | 1.00 | 35.11 | C |
| ATOM | 1910 | O | ALA | A | 414 | −75.861 | 79.953 | 12.016 | 1.00 | 32.56 | O |
| ATOM | 1911 | CB | ALA | A | 414 | −75.030 | 76.929 | 13.067 | 1.00 | 29.01 | C |
| ATOM | 1912 | N | GLN | A | 415 | −74.678 | 78.794 | 10.483 | 1.00 | 36.20 | N |
| ATOM | 1913 | CA | GLN | A | 415 | −74.135 | 79.967 | 9.872 | 1.00 | 37.44 | C |
| ATOM | 1914 | C | GLN | A | 415 | −75.207 | 80.700 | 9.101 | 1.00 | 33.89 | C |
| ATOM | 1915 | O | GLN | A | 415 | −75.237 | 81.917 | 9.156 | 1.00 | 31.76 | O |
| ATOM | 1916 | CB | GLN | A | 415 | −72.961 | 79.619 | 8.942 | 1.00 | 42.32 | C |
| ATOM | 1917 | CG | GLN | A | 415 | −71.739 | 79.097 | 9.696 | 1.00 | 48.89 | C |
| ATOM | 1918 | CD | GLN | A | 415 | −70.750 | 78.337 | 8.794 | 1.00 | 53.99 | C |
| ATOM | 1919 | NE2 | GLN | A | 415 | −69.698 | 77.808 | 9.413 | 1.00 | 53.75 | N |
| ATOM | 1920 | OE1 | GLN | A | 415 | −70.929 | 78.224 | 7.568 | 1.00 | 52.41 | O |
| ATOM | 1921 | N | MET | A | 416 | −76.017 | 79.984 | 8.320 | 1.00 | 33.05 | N |
| ATOM | 1922 | CA | MET | A | 416 | −77.150 | 80.589 | 7.624 | 1.00 | 34.79 | C |
| ATOM | 1923 | C | MET | A | 416 | −78.164 | 81.280 | 8.596 | 1.00 | 34.33 | C |
| ATOM | 1924 | O | MET | A | 416 | −78.642 | 82.392 | 8.313 | 1.00 | 30.58 | O |
| ATOM | 1925 | CB | MET | A | 416 | −77.845 | 79.572 | 6.747 | 1.00 | 32.26 | C |

TABLE 56

| ATOM | 1926 | CG | MET | A | 416 | −77.055 | 79.242 | 5.502 | 1.00 | 40.07 | C |
|---|---|---|---|---|---|---|---|---|---|---|---|
| ATOM | 1927 | SD | MET | A | 416 | −77.961 | 78.233 | 4.300 | 1.00 | 43.33 | S |
| ATOM | 1928 | CE | MET | A | 416 | −77.903 | 76.610 | 5.083 | 1.00 | 44.36 | C |
| ATOM | 1929 | N | MET | A | 417 | −78.450 | 80.622 | 9.731 | 1.00 | 35.67 | N |
| ATOM | 1930 | CA | MET | A | 417 | −79.346 | 81.182 | 10.760 | 1.00 | 35.07 | C |
| ATOM | 1931 | C | MET | A | 417 | −78.753 | 82.490 | 11.291 | 1.00 | 40.63 | C |
| ATOM | 1932 | O | MET | A | 417 | −79.468 | 83.481 | 11.416 | 1.00 | 32.87 | O |
| ATOM | 1933 | CB | MET | A | 417 | −79.535 | 80.196 | 11.909 | 1.00 | 30.27 | C |
| ATOM | 1934 | CG | MET | A | 417 | −80.411 | 78.925 | 11.468 | 1.00 | 29.12 | C |
| ATOM | 1935 | SD | MET | A | 417 | −82.097 | 79.317 | 10.974 | 1.00 | 27.51 | S |
| ATOM | 1936 | CE | MET | A | 417 | −82.697 | 79.803 | 12.592 | 1.00 | 26.14 | C |
| ATOM | 1937 | N | GLN | A | 418 | −77.453 | 82.501 | 11.554 | 1.00 | 40.22 | N |
| ATOM | 1938 | CA | GLN | A | 418 | −76.812 | 83.728 | 12.067 | 1.00 | 46.89 | C |
| ATOM | 1939 | C | GLN | A | 418 | −76.914 | 84.889 | 11.083 | 1.00 | 40.56 | C |
| ATOM | 1940 | O | GLN | A | 418 | −77.210 | 85.995 | 11.502 | 1.00 | 38.83 | O |
| ATOM | 1941 | CB | GLN | A | 418 | −75.360 | 83.513 | 12.493 | 1.00 | 51.33 | C |
| ATOM | 1942 | CG | GLN | A | 418 | −74.894 | 84.615 | 13.454 | 1.00 | 64.12 | C |
| ATOM | 1943 | CD | GLN | A | 418 | −75.706 | 84.655 | 14.761 | 1.00 | 75.41 | C |
| ATOM | 1944 | NE2 | GLN | A | 418 | −75.754 | 83.512 | 15.479 | 1.00 | 70.14 | N |
| ATOM | 1945 | OE1 | GLN | A | 418 | −76.304 | 85.695 | 15.106 | 1.00 | 82.82 | O |
| ATOM | 1946 | N | ARG | A | 419 | −76.759 | 84.623 | 9.787 | 1.00 | 37.57 | N |
| ATOM | 1947 | CA | ARG | A | 419 | −77.018 | 85.608 | 8.785 | 1.00 | 39.41 | C |
| ATOM | 1948 | C | ARG | A | 419 | −78.448 | 86.137 | 8.731 | 1.00 | 42.52 | C |
| ATOM | 1949 | O | ARG | A | 419 | −78.655 | 87.349 | 8.509 | 1.00 | 40.64 | O |
| ATOM | 1950 | CB | ARG | A | 419 | −76.605 | 85.094 | 7.406 | 1.00 | 49.15 | C |
| ATOM | 1951 | CG | ARG | A | 419 | −75.085 | 85.231 | 7.162 | 1.00 | 63.02 | C |
| ATOM | 1952 | CD | ARG | A | 419 | −74.635 | 85.012 | 5.704 | 1.00 | 68.99 | C |
| ATOM | 1953 | NE | ARG | A | 419 | −75.476 | 85.695 | 4.694 | 1.00 | 77.28 | N |
| ATOM | 1954 | CZ | ARG | A | 419 | −75.563 | 87.019 | 4.484 | 1.00 | 74.70 | C |
| ATOM | 1955 | NH1 | ARG | A | 419 | −74.881 | 87.905 | 5.217 | 1.00 | 80.67 | N1+ |
| ATOM | 1956 | NH2 | ARG | A | 419 | −76.366 | 87.471 | 3.525 | 1.00 | 75.19 | N |
| ATOM | 1957 | N | ILE | A | 420 | −79.434 | 85.244 | 8.893 | 1.00 | 37.33 | N |
| ATOM | 1958 | CA | ILE | A | 420 | −80.842 | 85.642 | 8.903 | 1.00 | 35.66 | C |
| ATOM | 1959 | C | ILE | A | 420 | −81.054 | 86.502 | 10.133 | 1.00 | 36.93 | C |
| ATOM | 1960 | O | ILE | A | 420 | −81.709 | 87.557 | 10.052 | 1.00 | 36.22 | O |

TABLE 57

| ATOM | 1961 | CB | ILE | A | 420 | −81.817 | 84.419 | 8.864 | 1.00 | 36.90 | C |
|---|---|---|---|---|---|---|---|---|---|---|---|
| ATOM | 1962 | CG1 | ILE | A | 420 | −81.766 | 83.780 | 7.454 | 1.00 | 35.07 | C |
| ATOM | 1963 | CG2 | ILE | A | 420 | −83.271 | 84.828 | 9.183 | 1.00 | 36.40 | C |

TABLE 57-continued

| ATOM | 1964 | CD1 | ILE | A | 420 | −82.362 | 82.379 | 7.393 | 1.00 | 38.25 | C |
| ATOM | 1965 | N | LYS | A | 421 | −80.500 | 86.034 | 11.257 | 1.00 | 39.35 | N |
| ATOM | 1966 | CA | LYS | A | 421 | −80.686 | 86.883 | 12.457 | 1.00 | 47.01 | C |
| ATOM | 1967 | C | LYS | A | 421 | −80.216 | 88.337 | 12.251 | 1.00 | 50.25 | C |
| ATOM | 1968 | O | LYS | A | 421 | −80.980 | 89.261 | 12.521 | 1.00 | 48.27 | O |
| ATOM | 1969 | CB | LYS | A | 421 | −80.004 | 86.250 | 13.646 | 1.00 | 53.65 | C |
| ATOM | 1970 | CG | LYS | A | 421 | −80.390 | 86.947 | 14.932 | 1.00 | 58.38 | C |
| ATOM | 1971 | CD | LYS | A | 421 | −80.467 | 86.006 | 16.116 | 1.00 | 60.16 | C |
| ATOM | 1972 | CE | LYS | A | 421 | −80.092 | 86.751 | 17.394 | 1.00 | 65.92 | C |
| ATOM | 1973 | NZ | LYS | A | 421 | −73.606 | 86.913 | 17.398 | 1.00 | 65.71 | N1+ |
| ATOM | 1974 | N | LYS | A | 422 | −79.024 | 88.544 | 11.676 | 1.00 | 53.97 | N |
| ATOM | 1975 | CA | LYS | A | 422 | −78.508 | 89.921 | 11.459 | 1.00 | 56.84 | C |
| ATOM | 1976 | C | LYS | A | 422 | −79.177 | 90.701 | 10.334 | 1.00 | 49.14 | C |
| ATOM | 1977 | O | LYS | A | 422 | −79.312 | 91.903 | 10.452 | 1.00 | 48.85 | O |
| ATOM | 1978 | CB | LYS | A | 422 | −76.969 | 89.965 | 11.349 | 1.00 | 57.20 | C |
| ATOM | 1979 | CG | LYS | A | 422 | −76.376 | 89.343 | 12.601 | 1.00 | 67.73 | C |
| ATOM | 1980 | CD | LYS | A | 422 | −74.963 | 89.745 | 12.960 | 1.00 | 72.93 | C |
| ATOM | 1981 | CE | LYS | A | 422 | −74.532 | 88.920 | 14.175 | 1.00 | 72.23 | C |
| ATOM | 1982 | NZ | LYS | A | 422 | −73.070 | 88.994 | 14.433 | 1.00 | 76.51 | N1+ |
| ATOM | 1983 | N | THR | A | 423 | −79.635 | 90.046 | 9.281 | 1.00 | 41.52 | N |
| ATOM | 1984 | CA | THR | A | 423 | −80.119 | 90.778 | 8.131 | 1.00 | 38.98 | C |
| ATOM | 1985 | C | THR | A | 423 | −81.668 | 90.835 | 7.934 | 1.00 | 41.51 | C |
| ATOM | 1986 | O | THR | A | 423 | −82.165 | 91.703 | 7.203 | 1.00 | 44.20 | O |
| ATOM | 1987 | CB | THR | A | 423 | −79.503 | 90.197 | 6.860 | 1.00 | 43.81 | C |
| ATOM | 1988 | CG2 | THR | A | 423 | −77.959 | 90.314 | 6.900 | 1.00 | 44.09 | C |
| ATOM | 1989 | OG1 | THR | A | 423 | −79.886 | 88.814 | 6.752 | 1.00 | 46.10 | O |
| ATOM | 1990 | N | GLU | A | 424 | −82.420 | 89.900 | 8.507 | 1.00 | 37.39 | N |
| ATOM | 1991 | CA | GLU | A | 424 | −83.872 | 89.821 | 8.284 | 1.00 | 37.32 | C |
| ATOM | 1992 | C | GLU | A | 424 | −84.493 | 90.382 | 9.554 | 1.00 | 38.93 | C |
| ATOM | 1993 | O | GLU | A | 424 | −84.763 | 89.637 | 10.437 | 1.00 | 35.52 | O |
| ATOM | 1994 | CB | GLU | A | 424 | −84.304 | 88.367 | 8.089 | 1.00 | 38.32 | C |
| ATOM | 1995 | CG | GLU | A | 424 | −83.875 | 87.720 | 6.807 | 1.00 | 36.39 | C |

TABLE 58

| ATOM | 1996 | CD | GLU | A | 424 | −84.428 | 88.447 | 5.617 | 1.00 | 42.27 | C |
| ATOM | 1997 | OE1 | GLU | A | 424 | −85.530 | 89.054 | 5.688 | 1.00 | 44.21 | O |
| ATOM | 1998 | OE2 | GLU | A | 424 | −83.755 | 88.429 | 4.584 | 1.00 | 42.57 | O1− |
| ATOM | 1999 | N | THR | A | 425 | −84.735 | 91.692 | 9.557 | 1.00 | 33.28 | N |
| ATOM | 2000 | CA | THR | A | 425 | −85.046 | 92.404 | 10.771 | 1.00 | 36.06 | C |
| ATOM | 2001 | C | THR | A | 425 | −86.535 | 92.273 | 11.058 | 1.00 | 33.78 | C |
| ATOM | 2002 | O | THR | A | 425 | −36.962 | 92.617 | 12.140 | 1.00 | 35.79 | O |
| ATOM | 2003 | CB | THR | A | 425 | −84.693 | 93.888 | 10.667 | 1.00 | 36.18 | C |
| ATOM | 2004 | CG2 | THR | A | 425 | −83.180 | 94.077 | 10.557 | 1.00 | 45.18 | C |
| ATOM | 2005 | OG1 | THR | A | 425 | −85.263 | 94.412 | 9.484 | 1.00 | 40.54 | O |
| ATOM | 2006 | N | GLU | A | 426 | −87.308 | 91.740 | 10.111 | 1.00 | 28.03 | N |
| ATOM | 2007 | CA | GLU | A | 426 | −88.702 | 91.358 | 10.401 | 1.00 | 28.81 | C |
| ATOM | 2008 | C | GLU | A | 426 | −88.887 | 89.927 | 10.908 | 1.00 | 26.50 | C |
| ATOM | 2009 | O | GLU | A | 426 | −90.049 | 89.498 | 11.134 | 1.00 | 27.64 | O |
| ATOM | 2010 | CB | GLU | A | 426 | −89.590 | 91.676 | 9.178 | 1.00 | 31.39 | C |
| ATOM | 2011 | CG | GLU | A | 426 | −89.490 | 93.134 | 8.729 | 1.00 | 37.17 | C |
| ATOM | 2012 | CD | GLU | A | 426 | −90.436 | 93.456 | 7.573 | 1.00 | 41.18 | C |
| ATOM | 2013 | OE1 | GLU | A | 428 | −91.004 | 92.520 | 6.968 | 1.00 | 43.10 | O |
| ATOM | 2014 | OE2 | GLU | A | 426 | −90.593 | 94.641 | 7.289 | 1.00 | 48.02 | O1− |
| ATOM | 2015 | N | THR | A | 427 | −87.789 | 89.211 | 11.198 | 1.00 | 24.14 | N |
| ATOM | 2016 | CA | THR | A | 427 | −87.833 | 87.855 | 11.789 | 1.00 | 25.42 | C |
| ATOM | 2017 | C | THR | A | 427 | −87.072 | 87.891 | 13.119 | 1.00 | 27.29 | C |
| ATOM | 2018 | O | THR | A | 427 | −86.379 | 88.852 | 13.372 | 1.00 | 25.89 | O |
| ATOM | 2019 | CB | THR | A | 427 | −87.213 | 86.806 | 10.872 | 1.00 | 28.91 | C |
| ATOM | 2020 | CG2 | THR | A | 427 | −87.688 | 86.976 | 9.496 | 1.00 | 27.62 | C |
| ATOM | 2021 | OG1 | THR | A | 427 | −85.779 | 86.911 | 10.853 | 1.00 | 32.19 | O |
| ATOM | 2022 | N | SER | A | 428 | −87.350 | 86.932 | 13.984 | 1.00 | 23.04 | N |
| ATOM | 2023 | CA | SER | A | 428 | −86.653 | 86.655 | 15.246 | 1.00 | 24.42 | C |
| ATOM | 2024 | C | SER | A | 428 | −86.608 | 85.144 | 15.357 | 1.00 | 25.83 | C |
| ATOM | 2025 | O | SER | A | 428 | −87.149 | 84.387 | 14.451 | 1.00 | 24.95 | O |
| ATOM | 2026 | CB | SER | A | 428 | −87.386 | 87.236 | 16.455 | 1.00 | 25.64 | C |
| ATOM | 2027 | OG | SER | A | 428 | −87.487 | 88.641 | 16.271 | 1.60 | 33.94 | O |
| ATOM | 2028 | N | LEU | A | 429 | −85.989 | 84.713 | 16.445 | 1.00 | 25.40 | N |
| ATOM | 2029 | CA | LEU | A | 429 | −86.058 | 83.357 | 16.904 | 1.00 | 27.19 | C |
| ATOM | 2030 | C | LEU | A | 429 | −86.785 | 83.184 | 18.183 | 1.00 | 28.22 | C |

TABLE 59

| ATOM | 2031 | O | LEU | A | 429 | −86.598 | 83.980 | 19.109 | 1.00 | 24.64 | O |
| ATOM | 2032 | CB | LEU | A | 429 | −84.623 | 82.866 | 17.131 | 1.00 | 30.15 | C |

TABLE 59-continued

| ATOM | 2033 | CG | LEU | A | 429 | −83.726 | 82.738 | 15.906 | 1.09 | 34.00 | C |
|---|---|---|---|---|---|---|---|---|---|---|---|
| ATOM | 2034 | CD1 | LEU | A | 429 | −82.352 | 82.206 | 16.315 | 1.00 | 37.07 | C |
| ATOM | 2035 | CD2 | LEU | A | 429 | −84.271 | 81.744 | 14.985 | 1.00 | 33.70 | C |
| ATOM | 2036 | N | HIS | A | 430 | −87.474 | 82.032 | 18.293 | 1.00 | 25.38 | N |
| ATOM | 2037 | CA | HIS | A | 430 | −88.078 | 81.564 | 19.523 | 1.00 | 25.37 | C |
| ATOM | 2038 | C | HIS | A | 430 | −86.980 | 81.514 | 20.600 | 1.00 | 24.20 | C |
| ATOM | 2039 | O | HIS | A | 430 | −85.832 | 81.192 | 20.289 | 1.00 | 24.18 | O |
| ATOM | 2040 | CB | HIS | A | 430 | −88.690 | 80.175 | 19.316 | 1.00 | 25.72 | C |
| ATOM | 2041 | CG | HIS | A | 430 | −89.483 | 79.663 | 20.470 | 1.00 | 26.51 | C |
| ATOM | 2042 | CD2 | HIS | A | 430 | −90.822 | 79.599 | 20.670 | 1.00 | 31.13 | C |
| ATOM | 2043 | ND1 | HIS | A | 430 | −88.898 | 79.140 | 21.608 | 1.00 | 24.62 | N |
| ATOM | 2044 | CE1 | HIS | A | 430 | −89.825 | 78.789 | 22.472 | 1.00 | 28.44 | C |
| ATOM | 2045 | NE2 | HIS | A | 430 | −91.012 | 79.072 | 21.942 | 1.00 | 30.35 | N |
| ATOM | 2046 | N | PRO | A | 431 | −87.316 | 81.822 | 21.852 | 1.00 | 24.22 | N |
| ATOM | 2047 | CA | PRO | A | 431 | −86.234 | 81.861 | 22.871 | 1.00 | 26.27 | C |
| ATOM | 2048 | C | PRO | A | 431 | −85.456 | 80.546 | 23.072 | 1.00 | 24.41 | C |
| ATOM | 2049 | O | PRO | A | 431 | −84.279 | 80.571 | 23.389 | 1.00 | 24.67 | O |
| ATOM | 2050 | CB | PRO | A | 431 | −86.953 | 82.253 | 24.184 | 1.00 | 28.01 | C |
| ATOM | 2051 | CG | PRO | A | 431 | −88.387 | 82.417 | 23.844 | 1.00 | 30.68 | C |
| ATOM | 2052 | CD | PRO | A | 431 | −88.625 | 82.247 | 22.383 | 1.00 | 26.76 | C |
| ATOM | 2053 | N | LEU | A | 432 | −86.122 | 79.389 | 22.943 | 1.00 | 24.66 | N |
| ATOM | 2054 | CA | LEU | A | 432 | −85.424 | 78.157 | 23.006 | 1.00 | 24.56 | C |
| ATOM | 2055 | C | LEU | A | 432 | −84.352 | 78.015 | 21.919 | 1.00 | 26.38 | C |
| ATOM | 2056 | O | LEU | A | 432 | −83.231 | 77.514 | 22.186 | 1.00 | 24.65 | O |
| ATOM | 2057 | CB | LEU | A | 432 | −86.395 | 76.988 | 22.951 | 1.00 | 26.50 | C |
| ATOM | 2058 | CG | LEU | A | 432 | −85.756 | 75.588 | 22.999 | 1.00 | 30.72 | C |
| ATOM | 2059 | CD1 | LEU | A | 432 | −84.950 | 75.447 | 24.293 | 1.00 | 30.92 | C |
| ATOM | 2060 | CC2 | LEU | A | 432 | −86.847 | 74.513 | 22.889 | 1.00 | 33.22 | C |
| ATOM | 2061 | N | LEU | A | 433 | −84.705 | 78.404 | 20.682 | 1.00 | 23.00 | N |
| ATOM | 2062 | CA | LEU | A | 433 | −83.713 | 78.388 | 19.597 | 1.00 | 23.15 | C |
| ATOM | 2063 | C | LEU | A | 433 | −82.637 | 79.414 | 19.830 | 1.00 | 24.87 | C |
| ATOM | 2064 | O | LEU | A | 433 | −81.473 | 79.173 | 19.541 | 1.00 | 23.68 | O |
| ATOM | 2065 | CB | LEU | A | 433 | −84.396 | 78.595 | 18.221 | 1.00 | 23.49 | C |

TABLE 60

| ATOM | 2065 | CG | LEU | A | 433 | −85.464 | 77.588 | 17.854 | 1.00 | 22.17 | C |
|---|---|---|---|---|---|---|---|---|---|---|---|
| ATOM | 2067 | CD1 | LEU | A | 433 | −86.067 | 77.876 | 16.457 | 1.00 | 25.22 | C |
| ATOM | 2068 | CD2 | LEU | A | 433 | −84.916 | 76.155 | 17.851 | 1.00 | 24.45 | C |
| ATOM | 2069 | N | GLN | A | 434 | −83.013 | 80.573 | 20.372 | 1.00 | 27.89 | N |
| ATOM | 2070 | CA | GLN | A | 434 | −82.031 | 81.542 | 20.744 | 1.00 | 30.08 | C |
| ATOM | 2071 | C | GLN | A | 434 | −80.977 | 80.942 | 21.626 | 1.00 | 31.49 | C |
| ATOM | 2072 | O | GLN | A | 434 | −79.800 | 81.173 | 21.411 | 1.00 | 27.37 | O |
| ATOM | 2073 | CB | GLN | A | 434 | −82.648 | 82.731 | 21.472 | 1.00 | 35.38 | C |
| ATOM | 2074 | CG | GLN | A | 434 | −83.253 | 83.747 | 20.529 | 1.00 | 43.02 | C |
| ATOM | 2075 | CD | GLN | A | 434 | −83.772 | 84.985 | 21.253 | 1.00 | 45.98 | C |
| ATOM | 2076 | NE2 | GLN | A | 434 | −84.840 | 85.550 | 20.753 | 1.00 | 37.28 | N |
| ATOM | 2077 | OE2 | GLN | A | 434 | −83.205 | 85.419 | 22.238 | 1.00 | 52.64 | O |
| ATOM | 2078 | N | GLU | A | 435 | −81.424 | 80.218 | 22.644 | 1.00 | 30.28 | N |
| ATOM | 2079 | CA | GLU | A | 435 | −80.540 | 79.620 | 23.629 | 1.00 | 33.08 | C |
| ATOM | 2080 | C | GLU | A | 435 | −79.659 | 78.568 | 22.944 | 1.00 | 29.56 | C |
| ATOM | 2081 | O | GLU | A | 435 | −78.475 | 78.487 | 23.218 | 1.00 | 31.31 | O |
| ATOM | 2082 | CH | GLU | A | 435 | −71.375 | 78.991 | 24.792 | 1.00 | 32.24 | C |
| ATOM | 2083 | CG | GLU | A | 435 | −80.552 | 78.283 | 25.851 | 1.00 | 37.81 | C |
| ATOM | 2084 | CD | GLU | A | 435 | −81.439 | 77.735 | 26.964 | 1.00 | 39.56 | C |
| ATOM | 2085 | OE1 | GLU | A | 435 | −82.154 | 78.550 | 27.599 | 1.00 | 33.75 | O |
| ATOM | 2086 | OE2 | GLU | A | 435 | −81.478 | 76.482 | 27.161 | 1.00 | 37.57 | O1− |
| ATOM | 2087 | N | ILE | A | 436 | −80.221 | 77.763 | 22.054 | 1.00 | 27.00 | N |
| ATOM | 2088 | CA | ILE | A | 436 | −79.421 | 76.759 | 21.383 | 1.00 | 28.05 | C |
| ATOM | 2089 | C | ILE | A | 436 | −78.345 | 77.415 | 20.476 | 1.00 | 28.60 | C |
| ATOM | 2090 | O | ILE | A | 436 | −77.173 | 77.000 | 20.504 | 1.00 | 28.23 | O |
| ATOM | 2091 | CB | ILE | A | 436 | −80.308 | 75.755 | 20.610 | 1.00 | 29.27 | C |
| ATOM | 2092 | CG1 | ILE | A | 436 | −81.154 | 74.945 | 21.616 | 1.00 | 29.22 | C |
| ATOM | 2093 | CG2 | ILE | A | 436 | −79.510 | 74.905 | 19.624 | 1.00 | 26.42 | C |
| ATOM | 2094 | CD1 | ILE | A | 436 | −82.322 | 74.256 | 20.982 | 1.00 | 32.89 | C |
| ATOM | 2095 | N | TYR | A | 437 | −78.719 | 78.424 | 19.689 | 1.00 | 28.08 | N |
| ATOM | 2096 | CA | TYR | A | 437 | −77.777 | 79.039 | 18.763 | 1.00 | 29.60 | C |
| ATOM | 2097 | C | TYR | A | 437 | −76.717 | 79.960 | 19.410 | 1.00 | 33.35 | C |
| ATOM | 2098 | O | TYR | A | 437 | −75.689 | 80.254 | 18.821 | 1.00 | 36.32 | O |
| ATOM | 2099 | CB | TYR | A | 437 | −78.521 | 79.786 | 17.623 | 1.00 | 31.05 | C |
| ATOM | 2100 | CG | TYR | A | 437 | −79.132 | 78.814 | 16.679 | 1.00 | 29.90 | C |
| ATOM | 2101 | CD1 | TYR | A | 437 | −78.312 | 77.953 | 15.952 | 1.00 | 30.45 | C |
| ATOM | 2102 | CD2 | TYR | A | 437 | −80.519 | 78.674 | 16.550 | 1.00 | 33.02 | C |
| ATOM | 2103 | CE1 | TYR | A | 437 | −78.835 | 76.957 | 15.136 | 1.00 | 31.07 | C |
| ATOM | 2104 | CE2 | TYR | A | 437 | −81.040 | 77.728 | 15.673 | 1.00 | 32.36 | C |
| ATOM | 2105 | CZ | TYR | A | 437 | −80.174 | 76.885 | 14.959 | 1.00 | 33.29 | C |
| ATOM | 2106 | OH | TYR | A | 437 | −80.617 | 75.894 | 14.108 | 1.00 | 30.56 | O |

TABLE 60-continued

| | | | | | | | | | | | |
|---|---|---|---|---|---|---|---|---|---|---|---|
| ATOM | 2107 | N | LYS | A | 438 | −77.000 | 80.453 | 20.600 | 1.00 | 37.60 | N |
| ATOM | 2108 | CA | LYS | A | 438 | −76.123 | 81.401 | 21.251 | 1.00 | 39.75 | C |
| ATOM | 2109 | C | LYS | A | 438 | −74.796 | 80.720 | 21.465 | 1.00 | 38.00 | C |
| ATOM | 2110 | O | LYS | A | 438 | −74.729 | 79.623 | 22.071 | 1.00 | 38.03 | O |
| ATOM | 2111 | CB | LYS | A | 438 | −76.718 | 31.793 | 22.612 | 1.00 | 42.46 | C |
| ATOM | 2112 | CG | LYS | A | 438 | −76.254 | 83.122 | 23.159 | 1.00 | 51.86 | C |
| ATOM | 2113 | CD | LYS | A | 438 | −77.234 | 83.525 | 24.268 | 1.00 | 58.95 | C |
| ATOM | 2114 | CE | LYS | A | 438 | −76.733 | 84.712 | 25.064 | 1.00 | 65.81 | C |
| ATOM | 2115 | NZ | LYS | A | 438 | −75.394 | 84.406 | 25.647 | 1.00 | 62.26 | N1+ |
| ATOM | 2116 | N | ASP | A | 439 | −73.742 | 81.365 | 21.029 | 1.00 | 44.04 | N |
| ATOM | 2117 | CA | ASP | A | 439 | −72.388 | 80.934 | 21.395 | 1.00 | 49.58 | C |
| ATOM | 2118 | C | ASP | A | 439 | −72.078 | 79.534 | 20.870 | 1.00 | 55.28 | C |
| ATOM | 2119 | O | ASP | A | 439 | −71.323 | 78.795 | 21.499 | 1.00 | 64.49 | O |
| ATOM | 2120 | CB | ASP | A | 439 | −72.187 | 80.982 | 22.951 | 1.00 | 49.50 | C |
| ATOM | 2121 | CG | ASP | A | 439 | −72.214 | 82.378 | 23.502 | 1.00 | 51.51 | C |
| ATOM | 2122 | OD1 | ASP | A | 439 | −71.786 | 83.305 | 22.792 | 1.00 | 54.56 | O |
| ATOM | 2123 | OD2 | ASP | A | 439 | −72.655 | 82.568 | 24.654 | 1.00 | 55.70 | O1− |
| ATOM | 2124 | N | MET | A | 440 | −72.638 | 79.198 | 19.708 | 1.00 | 56.46 | N |
| ATOM | 2125 | CA | MET | A | 440 | −72.558 | 77.857 | 19.135 | 1.00 | 59.32 | C |
| ATOM | 2126 | C | MET | A | 440 | −71.533 | 77.799 | 17.991 | 1.00 | 60.65 | C |
| ATOM | 2127 | O | MET | A | 440 | −70.714 | 78.708 | 17.818 | 1.00 | 75.07 | O |
| ATOM | 2128 | CB | MET | A | 440 | −73.951 | 77.429 | 18.628 | 1.00 | 54.21 | C |
| ATOM | 2129 | CG | MET | A | 440 | −73.981 | 75.993 | 18.131 | 1.00 | 57.89 | C |
| ATOM | 2130 | SD | MET | A | 440 | −75.366 | 75.444 | 17.097 | 1.00 | 44.85 | S |
| ATOM | 2131 | CE | MET | A | 440 | −76.330 | 74.727 | 18.421 | 1.00 | 46.57 | C |
| TER | 2132 | | MET | A | 440 | | | | | | |
| HETATM | 2133 | C01 | MF8 | C | 181 | −85.170 | 73.923 | 10.756 | 1.00 | 52.79 A | C |
| HETATM | 2134 | N02 | MF8 | C | 181 | −85.289 | 75.323 | 10.348 | 1.00 | 42.65 A | N |
| HETATM | 2135 | C03 | MF8 | C | 181 | −85.285 | 75.440 | 8.852 | 1.00 | 40.00 A | C |

TABLE 62

| | | | | | | | | | | | |
|---|---|---|---|---|---|---|---|---|---|---|---|
| HETATM | 2136 | C04 | MF8 | C | 181 | −85.397 | 76.452 | 11.325 | 1.00 | 34.99 A | C |
| HETATM | 2137 | N05 | MF8 | C | 181 | −85.502 | 77.620 | 10.870 | 1.00 | 55.93 A | N |
| HETATM | 2138 | N06 | MF8 | C | 181 | −85.440 | 76.490 | 12.785 | 1.00 | 35.76 A | N |
| HETATM | 2139 | C07 | MF8 | C | 183 | −84.265 | 76.024 | 13.505 | 1.00 | 28.27 A | C |
| HETATM | 2140 | N08 | MF8 | C | 131 | −83.041 | 76.223 | 13.080 | 1.00 | 28.33 A | N |
| HETATM | 2141 | N09 | MF8 | C | 181 | −84.537 | 75.301 | 14.632 | 1.00 | 23.77 A | N |
| HETATM | 2142 | C01 | LIG | E | 2 | −94.683 | 67.061 | −9.236 | 1.00 | 65.08 A | C |
| HETATM | 2143 | C02 | LIG | E | 2 | −95.038 | 68.145 | −8.216 | 1.00 | 68.98 A | C |
| HETATM | 2144 | C03 | LIG | E | 2 | −94.468 | 67.851 | −6.824 | 1.00 | 72.22 A | C |
| HETATM | 2145 | C04 | LIG | E | 2 | −95.527 | 67.671 | −5.740 | 1.00 | 74.19 A | C |
| HETATM | 2146 | C05 | LIG | E | 2 | −96.313 | 66.354 | −5.786 | 1.00 | 72.54 A | C |
| HETATM | 2147 | C06 | LIG | E | 2 | −97.830 | 66.572 | −5.923 | 1.00 | 76.99 A | C |
| HETATM | 2148 | C07 | LIG | E | 2 | −98.580 | 66.325 | −4.598 | 1.00 | 76.56 A | C |
| HETATM | 2149 | O08 | LIG | E | 2 | −98.974 | 64.973 | −4.421 | 1.00 | 82.85 A | O |
| HETATM | 2150 | C09 | LIG | E | 2 | −98.344 | 64.301 | −3.373 | 1.00 | 82.20 A | C |
| HETATM | 2151 | O10 | LIG | E | 2 | −97.243 | 63.407 | −3.921 | 1.00 | 89.30 A | C |
| HETATM | 2152 | C11 | LIG | E | 2 | −96.605 | 62.459 | −2.968 | 1.00 | 79.70 A | C |
| HETATM | 2153 | C12 | LIG | E | 2 | −95.845 | 61.429 | −3.751 | 1.00 | 76.49 A | C |
| HETATM | 2154 | O13 | LIG | E | 2 | −94.981 | 62.130 | −4.602 | 1.00 | 76.49 A | O |
| HETATM | 2155 | C14 | LIG | E | 2 | −97.626 | 61.796 | −2.015 | 1.00 | 77.56 A | C |
| HETATM | 2156 | O15 | LIG | E | 2 | −96.896 | 61.145 | −0.986 | 1.00 | 92.84 A | O |
| HETATM | 2157 | C16 | LIG | E | 2 | −98.445 | 62.865 | −1.374 | 1.00 | 69.52 A | C |
| HETATM | 2158 | O17 | LIG | E | 2 | −99.200 | 62.390 | −0.206 | 1.00 | 62.74 A | O |
| HETATM | 2159 | C18 | LIG | E | 2 | −99.279 | 63.567 | −2.369 | 1.00 | 68.74 A | C |
| HETATM | 2160 | O19 | LIG | E | 2 | −100.097 | 64.494 | −1.626 | 1.00 | 68.99 A | O |

TABLE 63

CONECT 2133 2134
CONECT 2134 2133 2135 2136
CONECT 2135 2134
CONECT 2136 2134 2137 2138
CONECT 2137 2136
CONECT 2138 2136 2139
CONECT 2139 2138 2140 2141
CONECT 2140 2139
CONECT 2141 2139
CONECT 2142 2143
CONECT 2143 2142 2144
CONECT 2144 2143 2145
CONECT 2145 2144 2146
CONECT 2146 2145 2147
CONECT 2147 2146 2148
CONECT 2148 2147 2149
CONECT 2149 2148 2150
CONECT 2150 2149 2151 2159
CONECT 2151 2150 2152
CONECT 2152 2151 2153 2155
CONECT 2153 2152 2154
CONECT 2154 2153
CONECT 2155 2152 2156 2157
CONECT 2156 2155
CONECT 2157 2155 2158 2159
CONECT 2158 2157
CONECT 2159 2150 2157 2160
CONECT 2160 2159
END

Example 6

A final exercise tolerance test was performed in mice to verify whether metformin could improve exercise tolerance.

Metformin was administered by intraperitoneal injection of metformin/PBS solution (solution of metformin dissolved in PBS) so that the dose of metformin per body weight of mice was 25 mg/kg. For the metformin-non-administered group, an equal volume of PBS was intraperitoneally administered instead of the metformin/PBS solution.

The training for the final exercise tolerance test, in which the speed at start was 15 m/min and increased by 1 m/min every 10 minutes, and the running time after the speed reached 20 m/min was 10 minutes (1 hour in total), was performed 5 times a week for a total of 4 weeks using a treadmill device. Metformin administration was performed at 10 pm each time, and the training was performed by a protocol starting 12 hours later (10 am).

First, twenty 10-week-old male C57BL/6 mice were divided into 4 groups (5 mice per group). Among these 4 groups, for one group, neither training nor metformin administration was performed (hereinafter, referred to as "control group"), for another group, only training was performed without metformin administration (hereinafter, referred to as "training group"), for another group, only metformin administration was performed without training (hereinafter, referred to as "metformin administration group"), and for the remaining group, both metformin administration and training were performed (hereinafter, referred to as "training+metformin administration group"). In addition, in order to average the motivation for exercise and exercise preference of individual mice in each group, the first exercise tolerance test was performed after training acclimatization to rank the mice, and the mice were divided into 4 groups so that the test results were even. Furthermore, in the test after the training period, the exercise tolerance was evaluated in such a manner that the running time was set as the time until the number of electrode contacts during the test reached 50 (number of shocks: NOS50), the speed at the start was set as 15 m/min and increased by 1 m/min every 10 minutes, and when the speed reached the maximum speed of 30 m/min, the running at the maximum speed was performed until NOS50 was reached.

Figure 19:
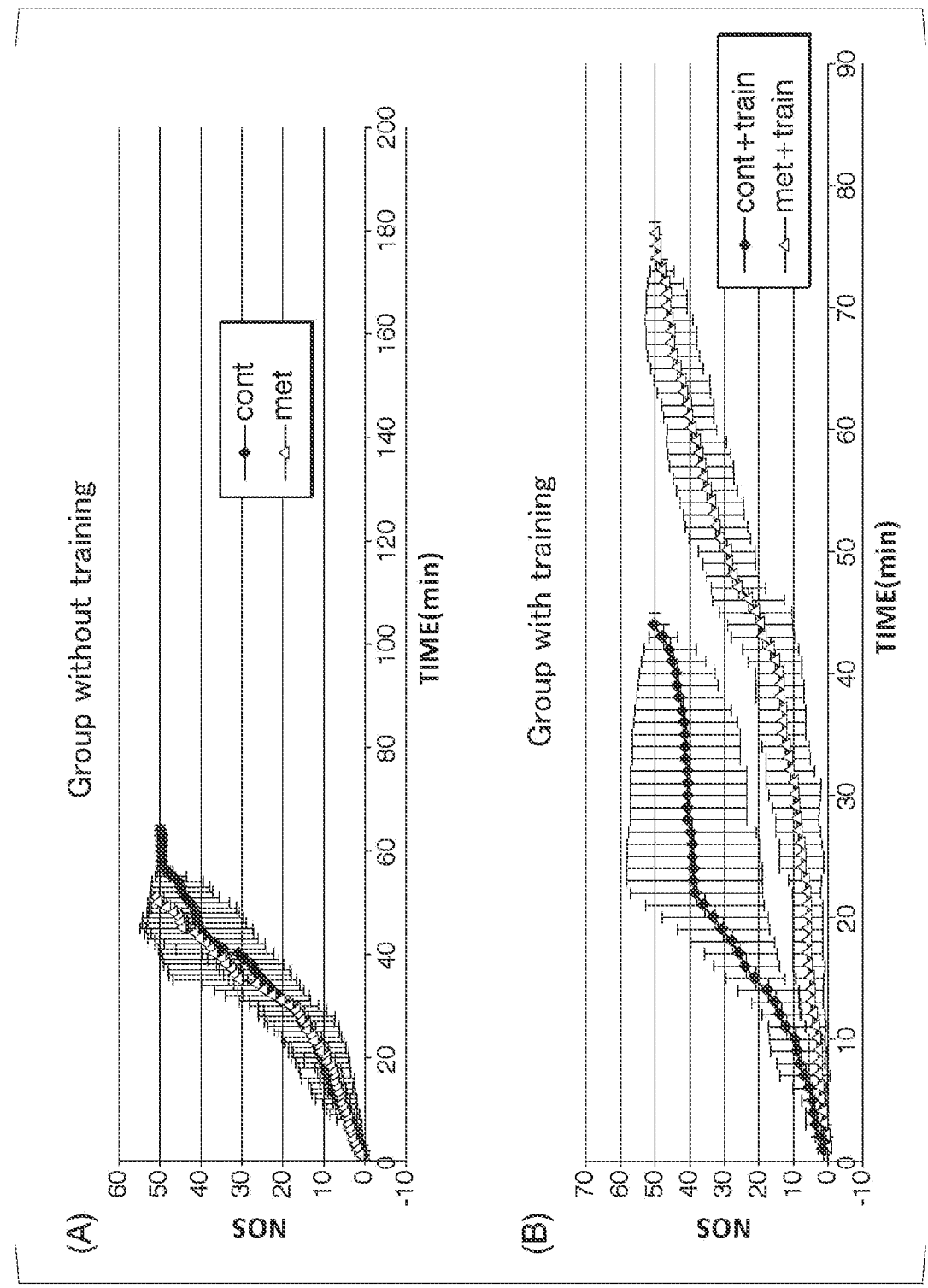
FIG. 19 is a diagram showing the measurement results of the number of shocks (NOS) in each elapsed time from the start of training in each group in Example 6.

FIG. 19 shows the measurement results of the number of shocks (NOS) in each elapsed time from the start of training in each group. FIG. 19A shows the results of the control group ("cont" in the figure) and the metformin administration group ("met" in the figure), and FIG. 19B shows the results of the training group ("cont+train" in the figure) and the results of the training+metformin administration group ("met+train" in the figure). As shown in FIG. 19(A), the metformin administration group did not show an improvement in exercise tolerance as compared with the control group, and showed a slight decreasing tendency. On the other hand, as shown in FIG. 19(B), the training+metformin administration group showed higher exercise tolerance than the training group. From these results, it was found that metformin alone does improve exercise tolerance, but the combination of metformin administration and training improves exercise tolerance.

Example 7

A new PPARδ activator was searched for using the structure data of the co-crystal of metformin/PPARδ.

Specifically, guanidine derivatives or biguanidine derivatives capable of fitting within the ligand binding pocket similar to metformin were searched for by performing a docking mode analysis between metformin and PPARδ based on the structure data of the co-crystal of metformin/PPARδ and performing a docking mode prediction calculation considering the solvent effects for known guanidine derivatives and biguanidine derivatives. In the prediction, the binding free energy was calculated based on the thermodynamic cycle, and the accuracy was improved by using a trajectory of molecular dynamics calculation (MM-PBSA: Molecular Mechanic/Poisson Boltzmann Surface Area, MM-GBSA: Molecular Mechanic/Generalized Born Surface Area).

Figure 20:
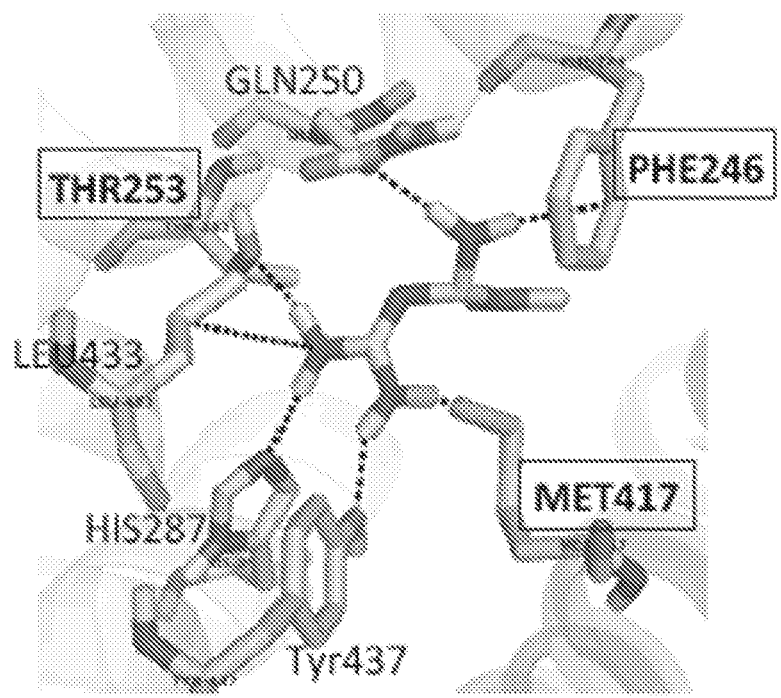
FIG. 20 is a diagram showing the interaction between the guanidino group of metformin and the amino acid residue on the interior surface of the PPARδ ligand binding pocket in the structure of the complex crystal of PPARδ and metformin in Example 7.
Figure 21:
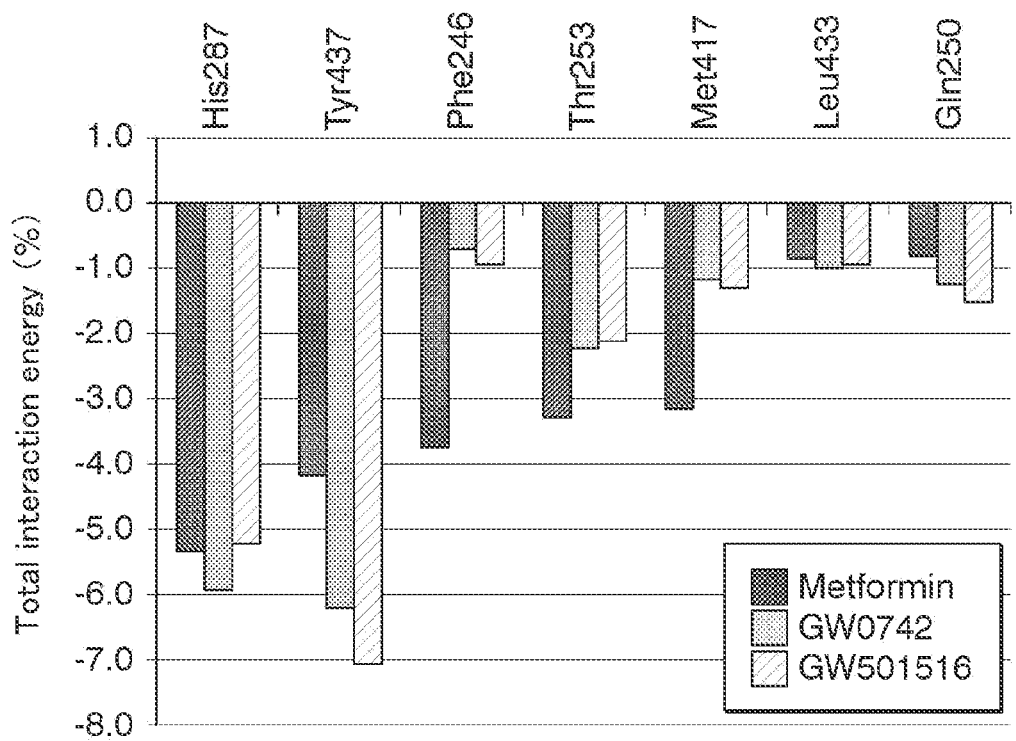
FIG. 21 is a diagram showing the calculation results of the interaction energy of metformin, GW0742, or GW501516 with seven amino acid residues (Tyr437, Leu433, Met417, His287, Thr253, Grn250, Ph246) in the hPPARδ ligand binding pocket in Example 7.

As shown in FIG. 20, the guanidino group of metformin interacts with and binds to an amino acid residue in the ligand binding pocket of hPPARδ (Tyr437, Leu433, Met417, His287, Thr253, Grn250, Ph246 are shown in the figure). His413 is not shown because it is located in front of the drawing. In addition, as a result of calculation of molecular dynamics, it was found that the guanidino group of metformin can interact with amino acid residues more than the amino acid residues shown in FIG. 2 depending on the solvent conditions and the like. The energy of interaction with each amino acid was calculated and the results of comparison with GW501516 and GW0742 (CAS No.: 317318-84-6) among the GW medicines which are known as PPARδ synthetic agonists are shown in FIG. 21. As shown in FIG. 21, similar to GW agonists, metformin can bind to the seven amino acid residues in the ligand binding pocket of hPPARδ with the illustrated binding energy. In particular, the binding energies with Met417 and Ph246 were apparently higher in metformin than in GW agonists. This indicates that metformin is more stably immobilized at the entrance of the ligand-binding pocket, has higher tilting-down activity of helix-12, and has higher activity as an agonist than GW agonists.

By the docking mode analysis, compounds having a guanidino group or a biguanidino group at the molecular end were selected in which the entire molecule entered into the ligand binding pocket of hPPARδ in a state where the guanidino group and the like form hydrogen bonds with His413, His287, Thr253 and Tyr437 of hPPARδ. The selected compounds are candidate compounds for the PPARδ activator.

Example 8

Among the compounds (1-1-4), the effects of compound (B-1), compound (B-2), and compound (B-3) on the transcriptional regulation of PPARδ were investigated. The effects on the transcriptional activity of PPARδ were measured by performing a luciferase assay on the cells treated with 10 μM of each compound dissolved in DMSO.

Specifically, CV1 cells, which are cultured cells derived from African green monkey kidneys, were seeded on a 24-well plate (1×105 cells/well) and cultured until they became 70% confluent. DMEM containing 10% fetal bovine serum and 1% antibiotic was used as the culture medium. After reaching the desired cell density, the entire medium was removed, and a mixture obtained by mixing 2 μL of MH2004 (plasmid encoding a firefly luciferase gene having a Gal4 activation sequence upstream: 100 ng/μL), 1 μL of pRL-CMV (plasmid encoding the *Renilla reniformis* luciferase gene directly under the CMV promoter: 100 ng/μL), 2 μL of GAL4-Ppard (plasmid encoding Gal4-DNA binding region fused with PPARδ gene: 100 ng/μL) and 1.5 μL of PEI (polyethylenimine: manufactured by Invitrogen) with 45 μL culture medium "Opti-MEM" (registered trademark)

(manufactured by Thermo Fisher Scientific) was added to each well, and the cells were cultured for about 36 hours. Then, the entire medium was replaced with a medium containing a test substance to be examined for the transcriptional activation ability of PPARδ such as metformin, and then cultured for 12 hours.

Then, the collected cells were lysed in a cell lysis buffer, suspended with a luminescent substrate (firefly luciferin), and the luminescence of the suspension was measured with a luminometer. In addition, the remaining suspension was mixed with *Renilla* luciferin and the amount of luminescence was measured with a luminometer. The result of the amount of light emitted by *Renilla* luciferin was used as the intrinsic control of gene transfer. Finally, the amount of luminescence of firefly luciferin was calculated as a light emission intensity (RLU) by dividing by the amount of luminescence of *Renilla* luciferin.

The results of the luciferase assay (n=3) are shown in Table 64. The relative emission intensity of the reaction solution treated with each compound was determined as the transcriptional activation ability of PPARδ in each compound treatment, where the light emission intensity of the reaction solution to which an equal amount of DMSO was added (control) was defined as 1. The relative emission intensities were all 1.1 or more in the reaction solutions to which the compounds were added, and the transcriptional activity of PPARδ was increased. From this result, it was found that these compounds can be PPARδ activators.

TABLE 64

| Compound | Light emission intensity (RLU) | | Relative emission intensity | |
|---|---|---|---|---|
| | Average | SD | Average | SD |
| No addition | 223550 | — | 1.00 | — |
| B-1 | 250467 | 6573 | 1.12 | 0.03 |
| B-2 | 265600 | 1652 | 1.19 | 0.01 |
| B-3 | 457033 | 10308 | 2.04 | 0.05 |

Example 9

Among the compounds (1-1-2), compound (A-4) (1-{4-[({2-[3-fluoro-4-(trifluoromethyl) phenyl]4-methylthiazole-5-yl}methyl) thio]-2-methylbenzyl}guanidine) was synthesized and its effect on the transcriptional regulation of PPARδ was investigated.

Synthesis of Compound (A-4)

(1) Synthesis of S-(4-cyano-3-methylphenyl)ethanethioate

Chemical Formula 14

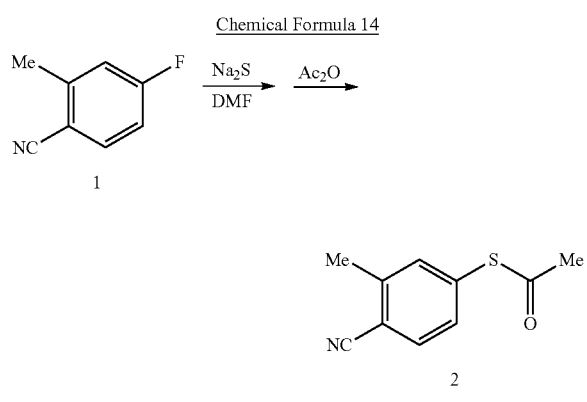

Na$_2$S (5.08 g, 65.1 mmol) was added at once to a solution obtained by dissolving 4-fluoro-2-methylbenzonitrile (CAS No.: 147754-12-9, Compound 1) (8 g, 59.2 mmol) in DMF (9 mL) at room temperature and in a nitrogen atmosphere. The reaction mixture was stirred overnight. The resulting mixture was cooled to 0° C., acetic anhydride (9 mL) was added dropwise, and the mixture was then stirred at room temperature for 1 hour. Subsequently, ethyl acetate (100 mL) and water (30 mL) were added to the mixture. The entire amount was layer-separated, and the organic layer was washed with saturated brine (30 mL×2) and then dried over anhydrous sodium sulfate. The solvent was then removed under reduced pressure and the residue was purified by column chromatography (silica gel, eluted with 3% to 40% ethyl acetate in hexane) to obtain the above compound (1.4 g, 12.4% yield) as a brown oil.

$^1$H NMR (400 MHz, CDCl$_3$) δ 7.62 (d, J=8.0 Hz, 1H), 7.39 (s, 1H), 7.33 (dd, J=8.0, 1.1 Hz, 1H), 2.56 (s, 3H), 2.45 (s, 3H).

(2) Synthesis of 4-[({2-[3-fluoro-4-(trifluoromethyl) phenyl]-4-methylthiazole-5-yl}methyl) thio]-2-methylbenzonitrile Chemical formula 15

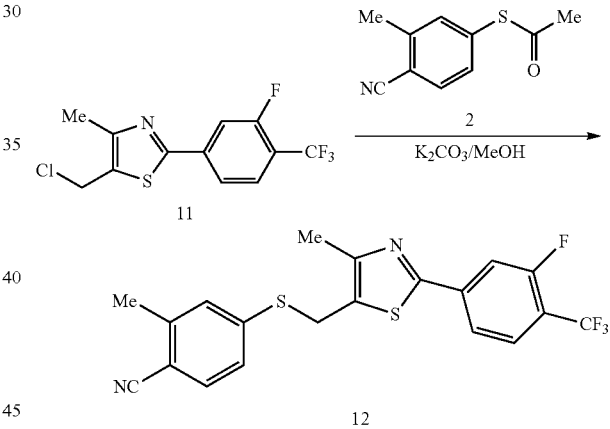

A mixture of 5-(chloromethyl)-2-[3-fluoro-4-(trifluoromethyl) phenyl]-4-methylthiazole (CAS No. 317319-33-8, US Patent Publication 2003/0203947A1, Compound 11) (2.23 g, 7.22 mmol), S-(4-cyano-3-methylphenyl) ethanethioate (Compound 2) (1.38 g, 7.22 mmol) and a solution obtained by dissolving potassium carbonate (1.22 g, 8.66 mmol) in methanol (20 mL) was stirred at room temperature for 1 hour. The resulting mixture was filtered under vacuum and the filter cake was collected and dissolved in dichloromethane (200 mL). The obtained organic matter was washed with water (30 mL) and brine (30 mL), dried over anhydrous sodium sulfate and concentrated under reduced pressure to obtain the above compound (1.8 g, yield 59.1%) as a white solid.

$^1$H NMR (400 MHz, CDCl$_3$) δ 7.72 (dd, J=13.8, 9.8 Hz, 2H), 7.67-7.61 (m, 1H), 7.51 (d, J=8.1 Hz, 1H), 7.22 (s, 1H), 7.17 (d, J=8.2 Hz, 1H), 4.32 (s, 2H), 2.51 (s, 3H), 2.43 (s, 3H).

MS-ESI (m/z) 423.1 [M+H]$^+$.

(3) Synthesis of 4-[({2-[3-fluoro-4-(trifluoromethyl)phenyl]-4-methylthiazole-5-yl}methyl)thio]-2-methylbenzaldehyde Chemical formula 16

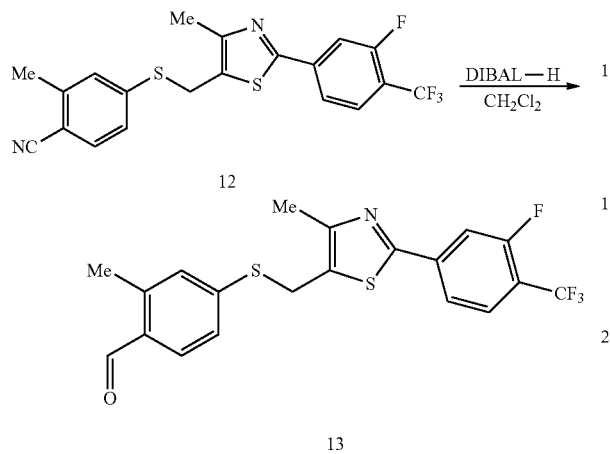

DIBAL-H (1.5 M toluene solution, 4.69 mL, 7.04 mmol) was added dropwise to a solution obtained by dissolving 4-[({2-[3-fluoro-4-(trifluoromethyl) phenyl]-4-methylthiazole-5-yl}methyl) thio]-2-methylbenzonitrile (Compound 12) (1.98 g, 4.69 mmol) in dichloromethane (20 mL) at 0° C. The obtained reaction mixture was stirred at 0° C. for 1 hour and then quenched with 10% hydrochloric acid (34 mL). The resulting mixture was vigorously stirred for 30 minutes. The resulting mixture was then treated with 20% sodium potassium tartrate (34 mL) and the resulting mixture was vigorously stirred for an additional 30 minutes. The reaction mixture was basified to pH 9 with 15% sodium hydroxide and then extracted with dichloromethane (60 mL×3). All the obtained organic layers were combined, washed with brine (40 mL), dried over anhydrous sodium sulfate and concentrated under reduced pressure. The residue was purified by column chromatography (silica gel, eluted with 2% to 10% ethyl acetate in hexane) to obtain the above compound (1.28 g, yield 64.0%) as a pale yellow solid.

$^1$H NMR (400 MHz, CDCl$_3$) δ 10.19 (s, 1H), 7.72 (dd, J=15.8, 7.6 Hz, 3H), 7.63 (t, J=7.6 Hz, 1H), 7.24 (s, 1H), 7.16 (s, 1H), 4.35 (s, 2H), 2.64 (s, 3H), 2.45 (s, 3H).

MS-ESI (m/z) 426.1 [M+H]$^+$.

(4) Synthesis of {4-[({2-[3-fluoro-4-(trifluoromethyl) phenyl]-4-methylthiazole-5-yl}methyl}thio)-2-methylphenyl}methanol Chemical formula 17

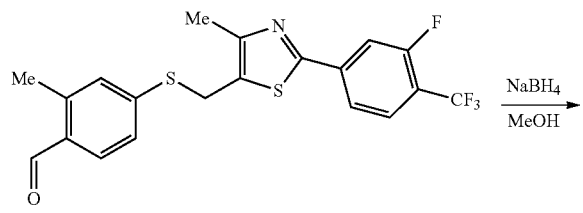

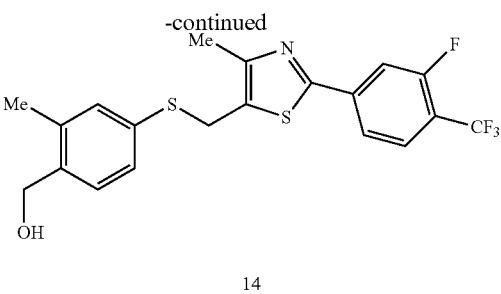

Sodium borohydride (NaBH$_4$) (295 mg, 7.76 mmol) was added in small portions to a solution obtained by dissolving 4-[({2-[3-fluoro-4-(trifluoromethyl) phenyl]-4-methylthiazole-5-yl}methyl)thio}-2-methylbenzaldehyde (Compound 13) (1.5 g, 3.53 mmol) in methanol (15 mL) at 0° C. The resulting mixture was stirred at 0° C. for 30 minutes. An aqueous ammonium chloride solution (20 mL) was added to the mixture, and the mixture was extracted with ethyl acetate (60 mL×2). The organic layers were combined, washed with brine (20 mL), dried over anhydrous sodium sulfate and concentrated under reduced pressure to obtain the above compound (1.45 g, 96.0% yield) as a pale yellow solid.

$^1$H NMR (400 MHz, CDCl$_3$) δ 7.75-7.67 (m, 2H), 7.65-7.59 (m, 1H), 7.30 (d, J=7.7 Hz, 1H), 7.19 (d, J=8.5 Hz, 2H), 4.68 (d, J=5.4 Hz, 2H), 4.21 (s, 2H), 2.30 (s, 6H).

MS-ESI (m/z) 428.1 [M+H]$^+$.

(5) Synthesis of 5-({[4-(chloromethyl)-3-methylphenyl]thio]methyl}-2-[3-fluoro-4-(trifluoromethyl) phenyl]-4-methylthiazole Chemical formula 18

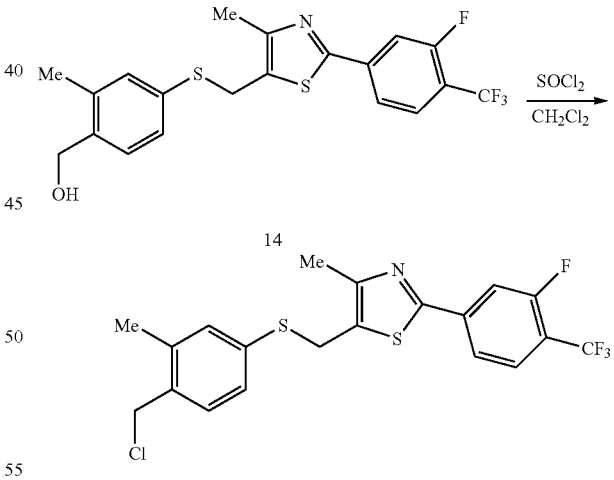

DMF (1 drop) and thionyl chloride (0.37 mL, 5.09 mmol) were added dropwise to a solution obtained by dissolving {4-[({2-[3-fluoro-4-(trifluoromethyl) phenyl]-4-methylthiazole-5-yl}methyl) thio]-2-methylphenyl}methanol (Compound 14) (1.45 g, 3.39 mmol) in dichloromethane (14 mL) at 0° C. The resulting mixture was stirred at 0° C. for 1 hour. Water (10 mL) was added to the mixture and then the organic layer was separated. The recovered organic layer was washed with brine, dried over anhydrous sodium sulfate and concentrated under reduced pressure to obtain the above compound (1.47 g, 97.0% yield) as a yellow solid.

¹H NMR (400 MHz, CDCl₃) δ 7.76-7.67 (m, 2H), 7.62 (t, J=7.6 Hz, 1H), 7.24 (d, J=7.9 Hz, 1H), 7.19-7.12 (m, 2H), 4.57 (s, 2H), 4.23 (s, 2H), 2.38 (s, 3H), 2.32 (s, 3H)).

MS-ESI (m/z) 446.0 [M+H]⁺.

(6) Synthesis of 1,3-di-Boc-2-{4-[({2-[3-fluoro-4-(trifluoromethyl)phenyl]-4-methylthiazole-5-yl]methyl}thio)-2-methyl benzyl]guanidine Chemical formula 19

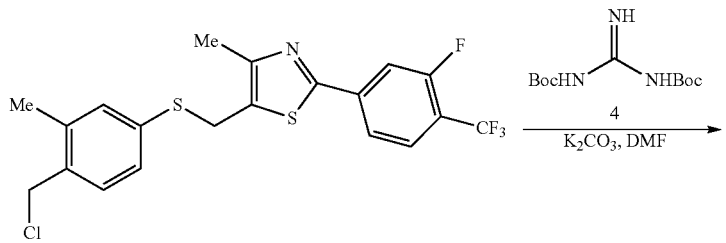

15

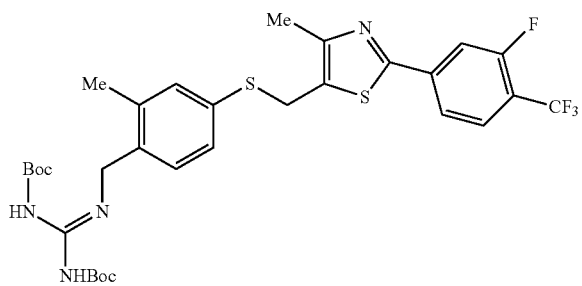

16

A mixture containing 5-({[4-(chloromethyl)-3-methylphenyl) thio]methyl}-2-[3-fluoro-4-(trifluoromethyl) phenyl]-4-methylthiazole (Compound 15) (1.47 g, 3.3 mmol), 1,3-bis (tert-butoxycarbonyl) guanidine (CAS No. 154476-57-0, Compound 4) (1.28 g, 4.95 mmoL) and potassium carbonate (685 mg, 4.95 mmol) dissolved in DMF (15 mL) was heated at 75° C. for 1 hour in a nitrogen atmosphere. The mixture was then diluted with water (60 mL). The entire amount was extracted with ethyl acetate (60 mL×3). All of the recovered organic layers were combined, washed with brine (30 mL×2), dried over anhydrous sodium sulfate and concentrated under reduced pressure. The residue was purified by column chromatography (silica gel, eluted with 1% to 10% ethyl acetate in hexane) to obtain the above compound (1.6 g, yield 73%) as a pale green solid.

¹H NMR (400 MHz, CDCl₃) δ 9.50 (s, 1H), 9.35 (s, 1H), 7.70 (t, J=10.1 Hz, 2H), 7.62 (t, J)=7.5 Hz, 1H), 7.14-7.16 (m, 2H), 6.90 (d, J=7.8 Hz, 1H), 5.12 (s, 2H), 4.19 (s, 2H), 2.30 (s, 3H), 2.25 (s, 3H), 1.46 (s, 9H), 1.22 (s, 9H).

MS-ESI (m/z) 669.3 [M+H]⁺.

(7) Synthesis of 1-{4-[({2-[3-fluoro-4-(trifluoromethyl) phenyl]4-methylthiazole-5-yl}methyl) thio]-2-methylbenzyl}guanidine Chemical formula 20

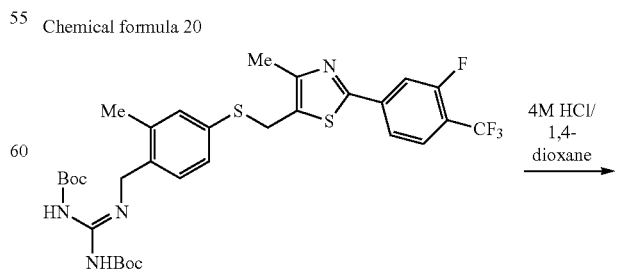

16

-continued

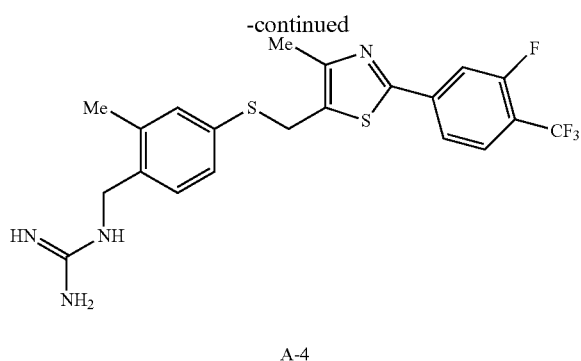

A-4

A mixture of a solution obtained by dissolving 1,3-di-Boc-2-{4-[({2-[3-fluoro-4-(trifluoromethyl) phenyl]-4-methylthiazole-5-yl}methyl) thio]-2-methyl benzyl}guanidine (Compound 16) (800 mg, 1.2 mmol) in 1,4-dioxane (8 mL) with HCl/1,4-dioxane (4.0M, 3.0 mL) was stirred at 50° C. for 2 hours. Next, the solvent was removed under reduced pressure, the residue was dissolved in methanol (6 mL), and the pH was adjusted to 8 to 9 with an aqueous sodium carbonate solution. Water (15 mL) was added to the obtained mixture, and the mixture was vacuum filtered. The resulting filter cake was washed with water (10 mL) and dried in high vacuum to obtain the above compound (A-4) (350 mg, 62% yield) as a white solid.

$^1$H NMR (300 MHz, DMSO-d6): δ 7.92-7.84 (m, 3H), 7.55-7.00 (m, 5H), 4.48 (s, 2H), 4.20 (S, 2H), 2.31 (s, 3H), 2.22 (s, 3H).

MS-ESI (m/z) 469.2 [M+H]$^+$.

Figure 22:
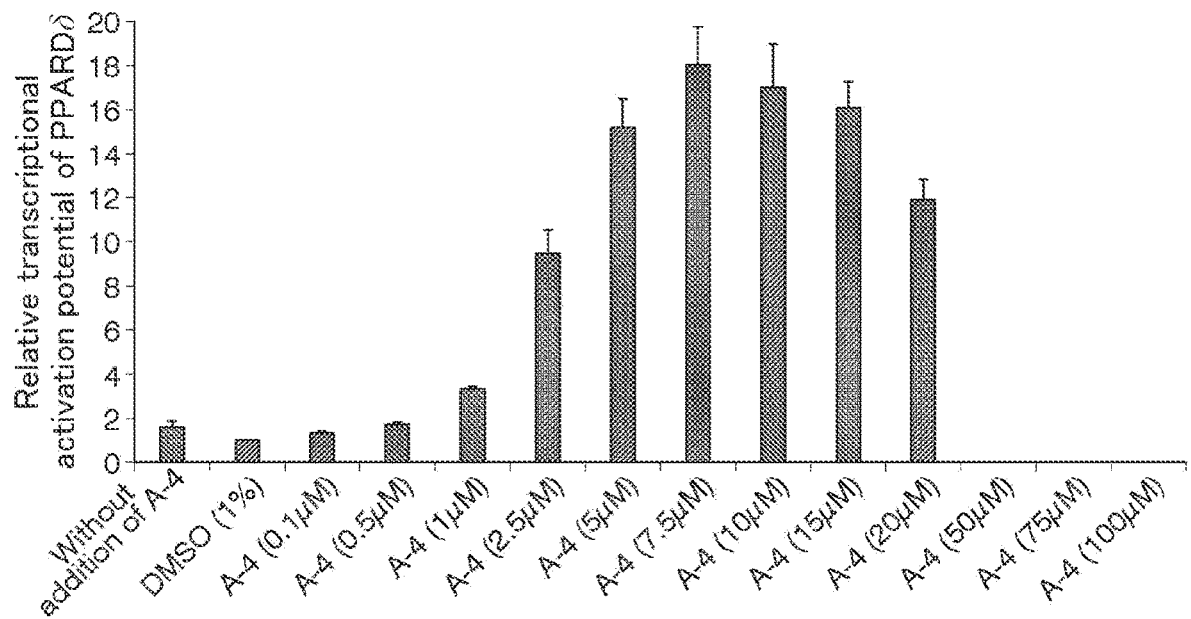
FIG. 22 is a diagram showing the results of a luciferase assay using PPREx2-tk-luciferase in the cells treated with compound (A-4) in Example 9.

The effect of the obtained compound (A-4) on PPARδ activity was investigated. Specifically, a luciferase assay was carried out in the same manner as in Example 8 except that compound (A-4) dissolved in DMSO (0.1%) was added to the reaction system as a test substance (n=3). The measurement result of the relative transcriptional activation ability obtained by the luciferase assay is shown in FIG. 22. As a result, it was observed that the transcriptional activity of PPARδ tended to increase depending on the amount of compound (A-4) added. However, when the addition amount was 50 μM or more, the cells died and it was impossible to measure the transcription activity of PPARδ. From these results, it was found that compound (A-4) can be used as a PPARδ activator.

Example 10

The effect of compound (A-4) on the expression of the gene whose expression is induced by PPARδ was investigated. Specifically, compound (A-4) was added to mouse skeletal muscle-derived myoblast cell line C2C12 cells, and the expression levels of the angptl4, pdk4 and the cpt1a genes, whose expression is induced by PPARδ (NPL 12), were measured. In addition, the Hprt gene was used as an endogenous control, and GW0742 was used as a positive control for PPARδ activation.

First, C2C12 cells were seeded on a 24-well plate (1×10$^5$ cells/well) and cultured until 80-90% confluent. DMEM containing 10% bovine serum and 1% antibiotic was used as the culture medium. After culturing for 36 hours, when the target cell density was reached, the entire medium was replaced with a serum-free DMEM medium containing each concentration of compound (A-4), and the cells were cultured for 16 hours (n=3). After culturing, the medium was discarded, a trizol reagent (manufactured by Invitrogen) for RNA extraction was directly added to each well to lyse the cells, and then the total RNA was extracted by ethanol precipitation. Using the obtained total RNA as a template, cDNA was synthesized using the reverse transcriptase "Superscript" (manufactured by Biorad).

Quantitative PCR was performed using the obtained cDNA as a template. The cDNA of the template, the primer that amplifies each gene to be measured, and the polymerase mix "ssoFast EvaGreen Supermix" (manufactured by Biorad) for quantitative PCR were mixed. Analysis was performed using a real-time PCR detection system "CFX connect (registered trademark)" (manufactured by Biorad).

From the obtained gene expression data, the expression level of each gene was divided by the expression level of the endogenous control gene to calculate the relative expression level.

Figure 23A:
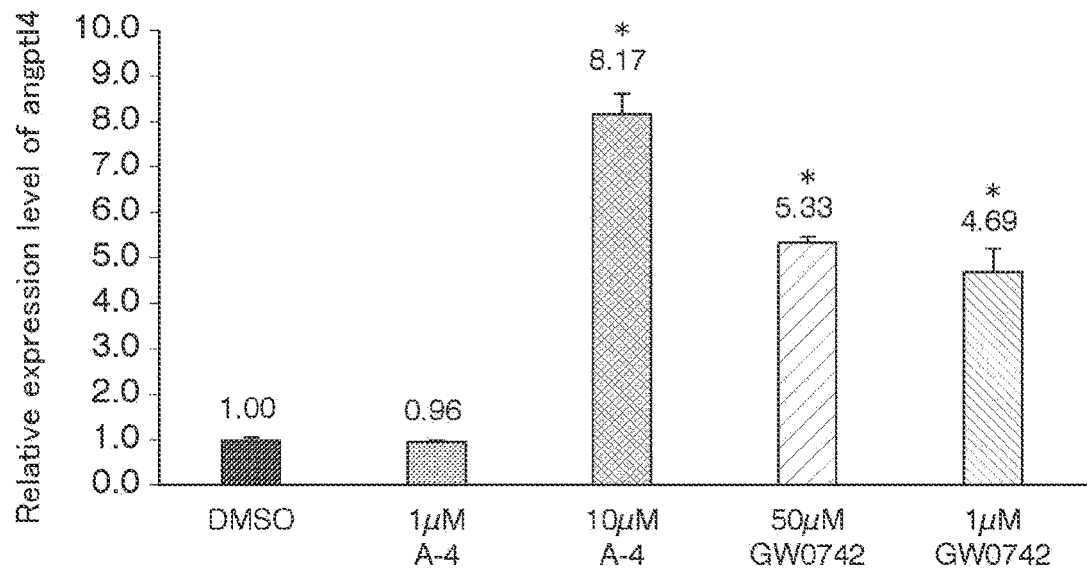
FIG. 23A is a diagram showing the measurement results of the relative expression level of the angptl4 gene in the cells treated with compound (A-4) or GW0742 in Example 10.
Figure 23B:
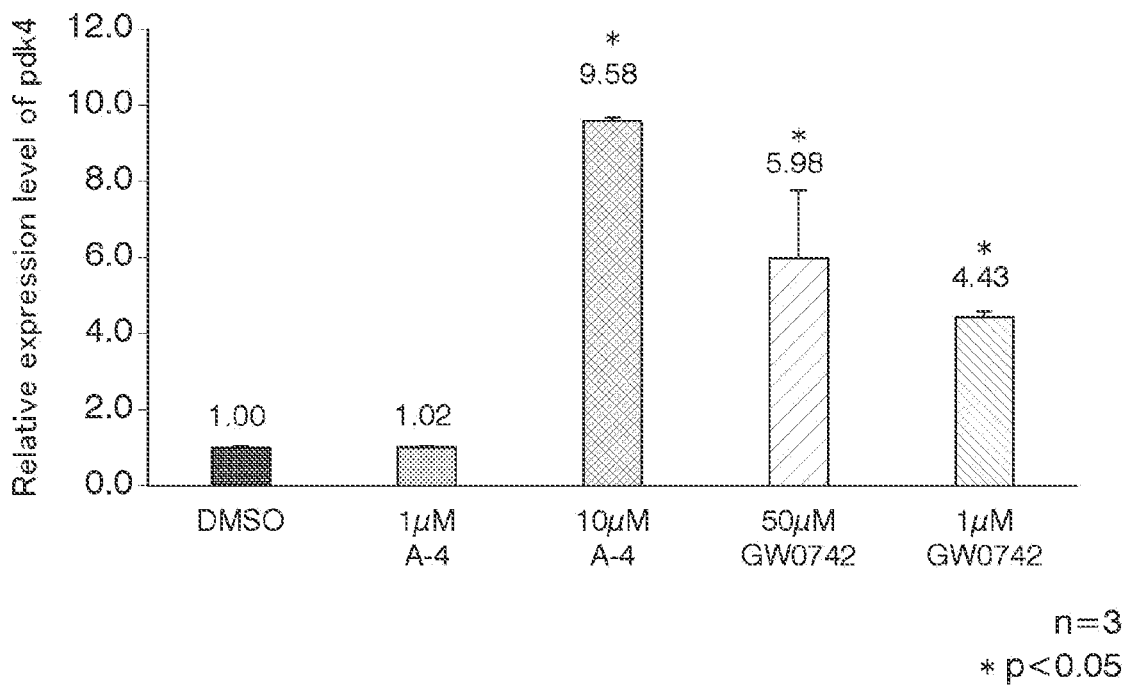
FIG. 23B is a diagram showing the measurement results of the relative expression level of the pdk4 gene in the cells treated with compound (A-4) or GW0742 in Example 10.
Figure 23C:
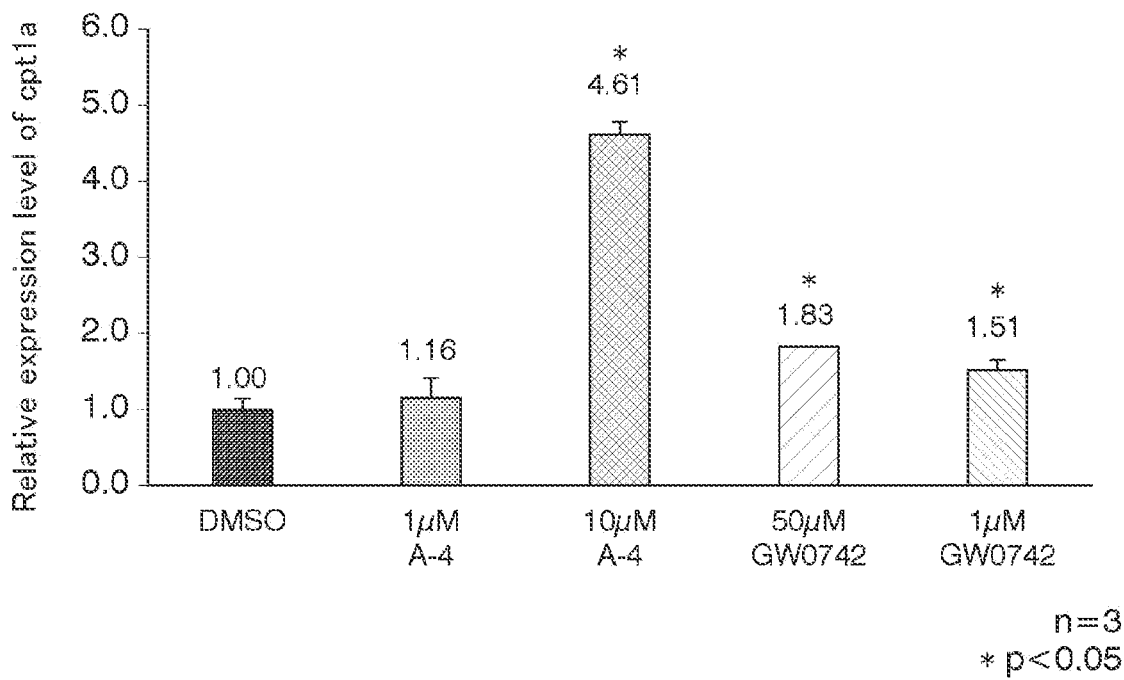
FIG. 23C is a diagram showing the measurement results of the relative expression level of the cpt1a gene in the cells treated with compound (A-4) or GW0742 in Example 10.

The results are shown in FIGS. 23A-C. As a result, in the cells to which 10 μM of compound (A-4) was added, the expression levels of the angptl4 gene, pdk4 gene, and the cpt1a gene were increased, as in the cells to which the GW0742 was added. From the results, it was confirmed that compound (A-4) has an ability to activate the transcriptional activity of PPARδ.

The invention claimed is:
1. A PPARδ agonist comprising a guanidine derivative as an active ingredient, wherein
the PPARδ agonist activates transcriptional activity of PPARδ (peroxisome proliferator-activated receptor δ); and
the guanidine derivative is a compound represented by any of the following formulas (A-1) to (A-4), (B-1) to (B-3),

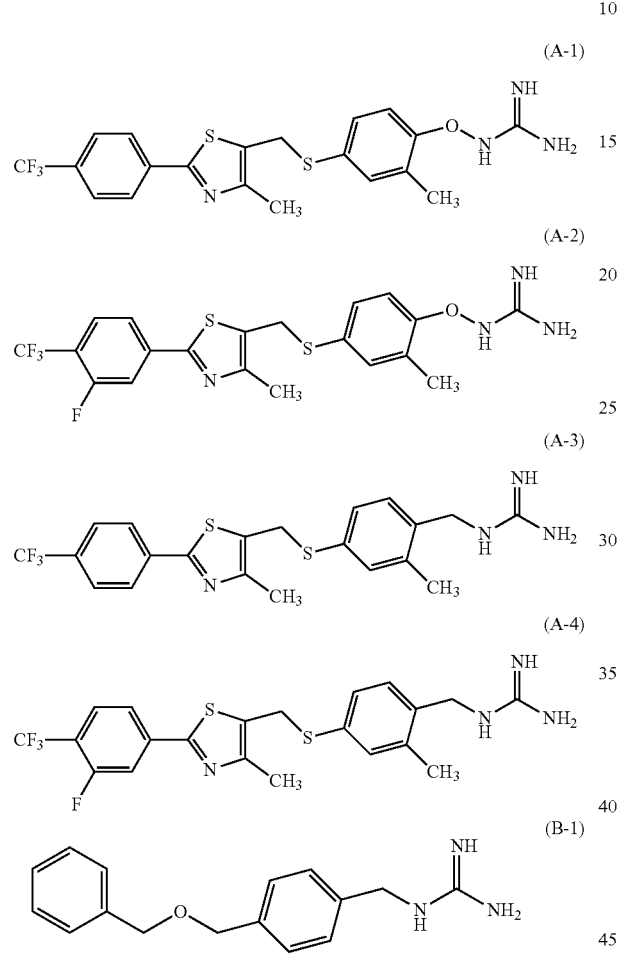

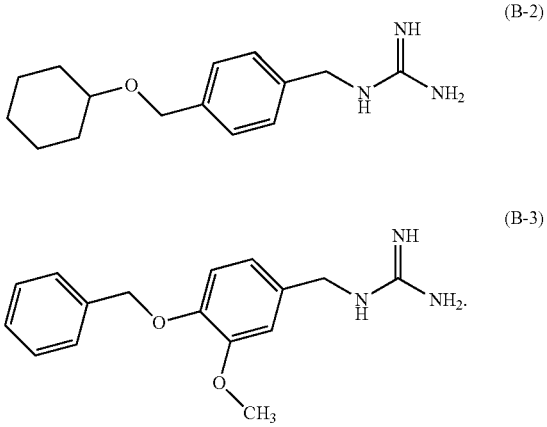

2. The PPARδ agonist according to claim 1, wherein
the guanidine derivative is capable of fitting within a ligand binding pocket of PPARδ, in a state where a guanidino group form a hydrogen bond with amino acid residues corresponding to each of the 413th histidine, 287th histidine, 253rd threonine and the 437th tyrosine of human PPARδ, among amino acid residues constituting an interior surface of the ligand binding pocket.

3. An exercise tolerance-improving agent comprising the PPARδ agonist defined in claim 1 as an active ingredient.

4. A pharmaceutical composition containing the PPARδ agonist according to claim 1, wherein
the pharmaceutical composition is for treating or preventing a disease for which a therapeutic effect can be obtained by activating a transcriptional activity of PPARδ.

5. The pharmaceutical composition according to claim 4, wherein the disease is diabetes, obesity, cardiomyopathy, or liver fibrosis.

6. The pharmaceutical composition according to claim 4, wherein the pharmaceutical composition is for immunotherapy.

* * * * *